US011358952B2

(12) United States Patent
Alexander et al.

(10) Patent No.: US 11,358,952 B2
(45) Date of Patent: Jun. 14, 2022

(54) SUBSTITUTED 4-AMINOISOINDOLINE-1,3-DIONE COMPOUNDS, COMPOSITIONS THEREOF, AND METHODS OF TREATMENT THEREWITH

(71) Applicant: Celgene Corporation, Summit, NJ (US)

(72) Inventors: Matthew D. Alexander, San Diego, CA (US); Soraya Carranclo, San Diego, CA (US); Matthew D. Correa, San Diego, CA (US); Virginia Heather Sharron Grant, San Diego, CA (US); Joshua Hansen, La Jolla, CA (US); Roy L. Harris, San Diego, CA (US); Dehua Huang, San Diego, CA (US); Timothy S. Kercher, San Diego, CA (US); Antonia Lopez-Girona, San Diego, CA (US); Mark A. Nagy, Encinitas, CA (US); Veronique Plantevin-Krenitsky, San Diego, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/390,815

(22) Filed: Apr. 22, 2019

(65) Prior Publication Data

US 2019/0322647 A1 Oct. 24, 2019

Related U.S. Application Data

(60) Provisional application No. 62/661,525, filed on Apr. 23, 2018.

(51) Int. Cl.

| | |
|---|---|
| *C07D 403/14* | (2006.01) |
| *C07D 407/14* | (2006.01) |
| *C07D 491/10* | (2006.01) |
| *C07D 401/04* | (2006.01) |
| *C07D 401/14* | (2006.01) |
| *C07D 417/14* | (2006.01) |
| *C07D 491/08* | (2006.01) |
| *C07D 491/107* | (2006.01) |
| *C07D 498/08* | (2006.01) |
| *A61P 35/00* | (2006.01) |

(52) U.S. Cl.

CPC ............ *C07D 403/14* (2013.01); *A61P 35/00* (2018.01); *C07D 407/14* (2013.01)

(58) Field of Classification Search

CPC .................................................... C07D 401/04

USPC ...................................... 544/358; 514/253.09

See application file for complete search history.

(56) References Cited

U.S. PATENT DOCUMENTS

| | | | |
|---|---|---|---|
| 7,091,353 B2 | 8/2006 | Robarge et al. | |
| 8,518,972 B2 | 8/2013 | Man et al. | |
| 8,957,065 B2 * | 2/2015 | Cha | A61K 45/06 514/210.21 |
| 9,090,585 B2 | 7/2015 | Dewitt | |
| 9,598,669 B2 | 3/2017 | Edinger et al. | |
| 10,357,489 B2 * | 7/2019 | Alexander | A61K 31/573 |
| 2004/0087546 A1 | 5/2004 | Zeldis | |
| 2005/0143344 A1 | 6/2005 | Zeldis et al. | |
| 2006/0154880 A1 | 7/2006 | Hensel | |
| 2007/0004920 A1 | 1/2007 | Ge et al. | |
| 2008/0064876 A1 | 3/2008 | Muller et al. | |
| 2009/0232776 A1 | 9/2009 | Moutouh-de Parseval | |
| 2011/0196150 A1 | 8/2011 | Man et al. | |
| 2011/0312996 A1 | 12/2011 | Buckman et al. | |
| 2012/0122865 A1 | 5/2012 | Muller et al. | |
| 2012/0252844 A1 | 10/2012 | DeWitt | |
| 2014/0206629 A1 | 7/2014 | Blaine | |
| 2018/0015087 A1 | 1/2018 | Liu et al. | |
| 2018/0099940 A1 | 4/2018 | Crew et al. | |
| 2018/0215731 A1 | 8/2018 | Crew et al. | |

(Continued)

FOREIGN PATENT DOCUMENTS

| | | |
|---|---|---|
| CN | 1597680 A | 7/2008 |
| CN | 107056772 A | 8/2017 |
| CN | 107698575 A | 2/2018 |

(Continued)

OTHER PUBLICATIONS

Hulikal, Deuterium Labeled Compounds in Drug Discovery Process, Abstract (Year: 2010).*

Pimlott, PubMed Abstract (Nucl. Med. Commmun., 26(3), 183-5. (Year: 2005).*

Patani et al., "Bioisosterism: A Rational, etc.," Chem. Rev., 96, 3147-3176. (Year: 1996).*

*Primary Examiner* — John M Mauro

(74) *Attorney, Agent, or Firm* — Jones Day

(57) ABSTRACT

Provided herein are 4-aminoisoindoline-1,3-dione compounds having the following structure:

(I)

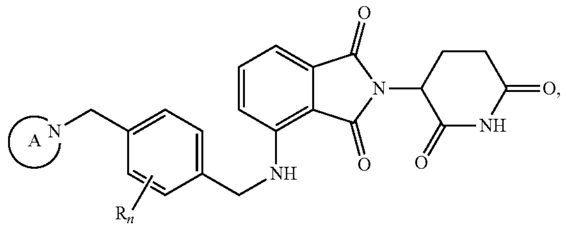

wherein R, Ring A, and n are as defined herein, compositions comprising an effective amount of a 4-aminoisoindoline-1,3-dione compound, and methods for treating or preventing disorders.

21 Claims, No Drawings

(56) References Cited

U.S. PATENT DOCUMENTS

| | | | |
|---|---|---|---|
| 2018/0237418 A1 | 8/2018 | Qian et al. | |
| 2021/0139466 A1 | 5/2021 | You et al. | |

FOREIGN PATENT DOCUMENTS

| | | | | |
|---|---|---|---|---|
| CN | 108690020 A | 10/2018 | | |
| CN | 108794453 A | 11/2018 | | |
| WO | WO 2002/059106 A1 | 8/2002 | | |
| WO | WO 2003/097052 A2 | 11/2003 | | |
| WO | WO 2006/028964 A1 | 3/2006 | | |
| WO | WO 2007/027527 A2 | 3/2007 | | |
| WO | WO 2008/027542 A2 | 3/2008 | | |
| WO | WO 2008/033567 A1 | 3/2008 | | |
| WO | WO 2008/115516 A2 | 9/2008 | | |
| WO | WO 2009/145899 A1 | 12/2009 | | |
| WO | WO 2016/040449 A1 | 3/2016 | | |
| WO | WO 2016/105518 A1 | 6/2016 | | |
| WO | WO 2017/007612 A1 | 1/2017 | | |
| WO | WO 2017/024317 A2 | 2/2017 | | |
| WO | WO 2017/067530 A2 | 4/2017 | | |
| WO | WO 2017/161028 A1 | 9/2017 | | |
| WO | WO 2017/176957 A1 | 10/2017 | | |
| WO | WO 2017/197056 A1 | 11/2017 | | |
| WO | WO 2017223415 A1 | 12/2017 | | |
| WO | WO 2017223452 A1 | 12/2017 | | |
| WO | WO 2018081530 A1 | 5/2018 | | |
| WO | WO 2018085247 A1 | 5/2018 | | |
| WO | WO 2018098280 A1 | 5/2018 | | |
| WO | WO 2018102725 A1 | 6/2018 | | |
| WO | WO 2018106870 A1 | 6/2018 | | |
| WO | WO-2018214796 A1 * | 11/2018 | ........... | C07D 417/14 |
| WO | WO 2019014429 A1 | 1/2019 | | |
| WO | WO 2019/206853 | 10/2019 | | |

* cited by examiner

SUBSTITUTED 4-AMINOISOINDOLINE-1,3-DIONE COMPOUNDS, COMPOSITIONS THEREOF, AND METHODS OF TREATMENT THEREWITH

This application claims priority to U.S. Provisional Application No. 62/661,525, filed Apr. 23, 2018, the entirety of which is incorporated herein by reference.

FIELD

Provided herein are certain 4-aminoisoindoline-1,3-dione compounds, compositions comprising an effective amount of such compounds, and methods for treating or preventing Diffuse Large B-Cell Lymphoma (DLBCL), comprising administering an effective amount of such 4-aminoisoindoline-1,3-dione compounds to a subject in need thereof.

BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and metastasis. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Current cancer therapy may involve surgery, chemotherapy, hormonal therapy and/or radiation treatment to eradicate neoplastic cells in a patient. Recent advances in cancer therapeutics are discussed by Rajkumar et al. in *Nature Reviews Clinical Oncology* 11, 628-630 (2014).

All of the current cancer therapy approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells.

With respect to chemotherapy, there are a variety of chemotherapeutic agents available for treatment of cancer. A majority of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Diffuse large B-cell lymphoma (DLBCL) accounts for approximately one-third of non-Hodgkin's lymphoma (NHL). NHL is the fifth most common cancer for both men and women in the United States. An estimated 385,700 patients worldwide were diagnosed with NHL in 2012 and approximately 199,700 patients died as a result of the disease. (Torre, L. A. et al. Global cancer statistics, 2012; *CA Cancer J. Clin.* 65, 87-108 (2015)). DLBCL, the most common form of B-cell NHL, had an estimated 27,650 new cases in the USA in 2016, accounting for approximately 26% of all mature B-cell NHL neoplasms diagnosed. (Teras, L. R. et al. 2016 US lymphoid malignancy statistics by World Health Organization subtypes; *CA Cancer J. Clin.* 66, 443-459 (2016)). While some DLBCL patients are cured with traditional chemotherapy, the remainder die from the disease.

There remains a significant need for safe and effective methods of treating, preventing and managing DLBCL, particularly for DLBCL that is refractory to standard treatments, such as surgery, radiation therapy, chemotherapy and hormonal therapy, while reducing or avoiding the toxicities and/or side effects associated with conventional therapies.

Citation or identification of any reference in this section of this application is not to be construed as an admission that the reference is prior art to the present application.

SUMMARY

Provided herein are compounds having the following formula (I):

(I)

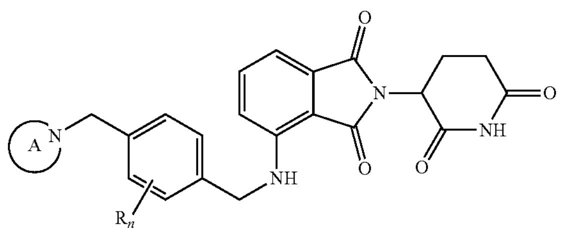

or a pharmaceutically acceptable salt, tautomer, isotopolog, or stereoisomer thereof, wherein R, Ring A and n are as defined herein.

A compound of formula (I) or a pharmaceutically acceptable salt, tautomer, isotopolog, or stereoisomer thereof (each being referred to herein as an "Isoindolinedione Compound") is useful for treating or preventing DLBCL.

In one aspect, provided herein are Isoindolinedione Compounds as described in the instant disclosure, such as, for example, in Table 1.

In one aspect, provided herein are pharmaceutical compositions comprising an effective amount of an Isoindolinedione Compound as described herein, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing DLBCL, comprising administering to a subject in need thereof an effective amount of an Isoindolinedione Compound as described herein. In another aspect, provided herein are methods for treating or preventing DLBCL, comprising administering to a subject in need thereof an effective amount of a pharmaceutical composition described herein. In another aspect, provided herein are Isoindolinedione Compounds as described herein for use in the treatment of DLBCL. In another aspect, provided herein are pharmaceutical compositions as described herein for use in the treatment of DLBCL.

In another aspect provided herein are methods for preparing Isoindolinedione Compounds as described herein.

The present embodiments can be understood more fully by reference to the detailed description and examples, which are intended to exemplify non-limiting embodiments.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein and unless otherwise specified, an "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, 2-methylpentyl, 3-methylpentyl, -4-methylpentyl, -2,3-dimethylbutyl and the like. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, $-C{\equiv}CH$, $-C{\equiv}C(CH_3)$, $-C{\equiv}C(CH_2CH_3)$, $-CH_2C{\equiv}CH$, $-CH_2C{\equiv}C(CH_3)$ and $-CH_2C{\equiv}C(CH_2CH_3)$, among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy, aryloxy, heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); amino, alkylamino, cycloalkylamino, arylamino, heterocyclylamino, heteroarylamino, heterocycloalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or $-B(OH)_2$.

As used herein and unless otherwise specified, a "cycloalkyl" group is a saturated, or partially saturated cyclic alkyl group of from 3 to 10 carbon atoms having a single cyclic ring or multiple condensed or bridged rings which can be optionally substituted. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. Examples of unsaturared cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

As used herein and unless otherwise specified, an "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryl groups include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

As used herein and unless otherwise specified, a "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indol-2-onyl), isoindolin-1-onyl, azaindolyl, pyrrolopyridyl (e.g., 1H-pyrrolo[2,3-b]pyridyl), indazolyl, benzimidazolyl (e.g., 1H-benzo[d]imidazolyl), azabenzimidazolyl, imidazopyridyl (e.g., 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl, 3,4-dihydroisoquinolin-1(2H)-onyl, tetrahydroquinolinyl, quinoxalinyl, and quinazolinyl groups. A heteroaryl group can be substituted or unsubstituted.

As used herein and unless otherwise specified, a "heterocyclyl" is an aromatic ring system (also referred to as heteroaryl) or non-aromatic cycloalkyl (also referred to as heterocycloalkyl) in which one to four of the ring carbon atoms are independently replaced with a heteroatom. Suitable heteroatoms include oxygen, sulfur and nitrogen. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-onyl or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indol-2-onyl), isoindolin-1-onyl, indolinyl, isoindolyl, isoindolinyl, azaindolyl, pyrrolopyridyl (e.g, 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (e.g., benzo[d]oxazolyl), benzothiazolyl, benzothiadiazolyl, benzo[1,3]dioxolyl, pyrazolopyridyl (e.g., 1H-pyrazolo[3,4-b]pyridyl, 1H-pyrazolo[4,3-b]-pyridyl), azabenzimidazolyl, imidazopyridyl (e.g., 1H-imidazo[4,5-b]pyridyl), triazolopyridyl, isoxazolopyridyl, purinyl, xanthinyl, adeninyl, guaninyl, quinolinyl, isoquinolinyl, 3,4-dihydroisoquinolin-1(2H)-onyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

As used herein, the following heterocyclyl names refer to the structures in the table below. In some embodiments, the point of attachment is via the ring nitrogen atom.

| Heterocyclyl Name | Heterocyclyl Structure |
|---|---|
| azetidyl | 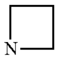 |
| 5-azaspiro[2,3]hexyl | 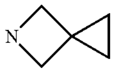 |
| 2-azaspiro[3.3]heptyl | 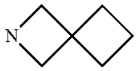 |
| 2,6-diazaspiro[3.3]heptyl | 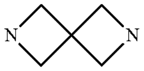 |
| 2-oxa-6-azaspiro[3.3]heptyl | 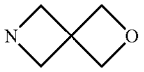 |
| 2-azaspiro[3.4]octyl | 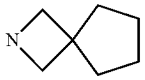 |
| 5-oxa-2-azaspiro[3.4]octyl | 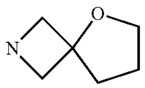 |
| 6-oxa-2-azaspiro[3.4]octyl | 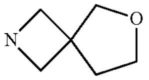 |
| 2-azaspiro[3.5]nonyl | 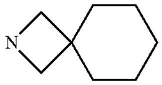 |
| 2,7-diazaspiro[3.5]nonyl | 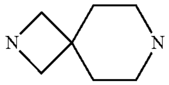 |
| 7-oxa-2-azaspiro[3.5]nonyl | 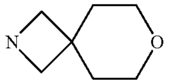 |

-continued

| Heterocyclyl Name | Heterocyclyl Structure |
|---|---|
| 8'-azaspiro[azetidine-3,3'-bicyclo[3.2.1]octyl] | 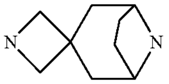 [SMILES: C1CC2CC3(CNC3)CC1N2] |
| pyrrolidyl | 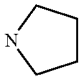 |
| isothiazolidinyl | 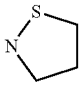 |
| 6-azaspiro[3.4]octyl | 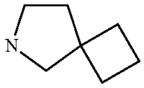 |
| 2-oxa-6-azaspiro[3.4]octyl | 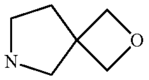 |
| octahydrocyclopenta[c]pyrrolyl | 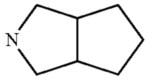 |
| 1,2,3,3a,4,5-hexahydrocyclopenta[c]pyrrolyl | 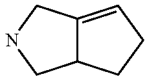 |
| 1,2,3,3a,4,6a-hexahydrocyclopenta[c]pyrrolyl | 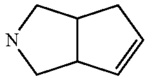 |
| isoindolinyl | 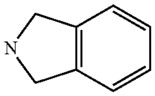 |
| piperidyl | 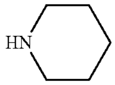 |
| piperazinyl | 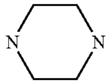 |
| morpholinyl | 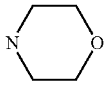 |
| thiomorpholinyl | 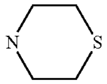 |
| thiomorpholine 1,1-dioxidyl | 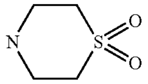 |
| 5-azaspiro[2.5]octyl | 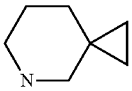 |
| 6-azaspiro[2.5]octyl | 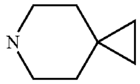 |

-continued

| Heterocyclyl Name | Heterocyclyl Structure |
|---|---|
| 7-azaspiro[3.5]nonyl | 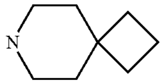 |
| 1-oxa-8-azaspiro[4.5]decanyl | 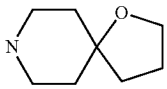 |
| 2-oxa-8-azaspiro[4.5]decanyl | 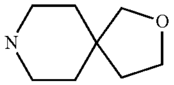 |
| 2,8-diazaspiro[4.5]decan-1-onyl | 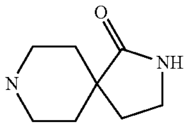 [SMILES: O=C1NCCC12CCNCC2] |
| 3-oxa-9-azaspiro[5.5]undecanyl | 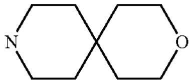 [SMILES: C1CC2(CCN1)CCOCC2] |
| 5,6,7,8-tetrahydro-[1,2,4]triazolo[1,5-a]pyrazinyl | 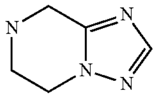 |
| 1,2,3,4-tetrahydroisoquinolyl | 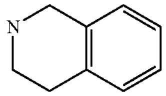 |
| 8-oxa-3-azabicyclo[3.2.1]octyl | 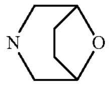 |
| 3-oxa-8-azabicyclo[3.2.1]octyl | 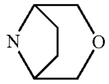 |
| 1,4-oxazepanyl | 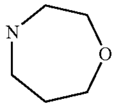 |
| 8-azabicyclo[3.2.1]octyl | 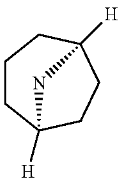 |

As used herein and unless otherwise specified, a "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopropylmethyl, cyclobutylmethyl, cyclopentylmethyl, cyclohexylmethyl, cyclopropylethyl, cyclobutylethyl, cyclopentylethyl, cyclohexylethyl, cyclopentylpropyl, cyclohexylpropyl and the like.

As used herein and unless otherwise specified, an "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and aralkyl groups wherein the aryl group is fused to a cycloalkyl group such as indan-4-yl ethyl.

As used herein and unless otherwise specified, a "heterocyclylalkyl" group is a radical of the formula: -alkyl-heterocyclyl, wherein alkyl and heterocyclyl are defined above. A "heteroarylalkyl" group is a radical of the formula: -alkyl-heteroaryl, wherein alkyl and heteroaryl are defined above. A "heterocycloalkylalkyl" group is a radical of the formula: -alkyl-heterocycloalkyl, wherein alkyl and heterocycloalkyl are defined above. Substituted heterocyclylalkyl groups may be substituted at the alkyl, the heterocyclyl, or both the alkyl and the heterocyclyl portions of the group. Representative heterocylylalkyl groups include but are not limited to morpholin-4-yl ethyl, morpholin-4-yl propyl, furan-2-yl methyl, furan-3-yl methyl, pyridin-3-yl methyl, tetrahydrofuran-2-yl ethyl, and indol-2-yl propyl.

As used herein and unless otherwise specified, a "halogen" is fluorine, chlorine, bromine or iodine.

As used herein and unless otherwise specified, a "hydroxyalkyl" group is an alkyl group as described above substituted with one or more hydroxy groups.

As used herein and unless otherwise specified, an "alkoxy" group is —O-(alkyl), wherein alkyl is defined above. An "alkylthio" group is —S-(alkyl), wherein alkyl is defined above.

As used herein and unless otherwise specified, an "alkoxyalkyl" group is -(alkyl)-O-(alkyl), wherein alkyl is defined above.

As used herein and unless otherwise specified, a "cycloalkyloxy" group is —O-(cycloalkyl), wherein cycloalkyl is defined above.

As used herein and unless otherwise specified, an "aryloxy" group is —O-(aryl), wherein aryl is defined above.

As used herein and unless otherwise specified, a "heterocyclyloxy" group is —O-(heterocyclyl), wherein heterocyclyl is defined above. A "heteroaryloxy" group is —O-(heteroaryl), wherein heteroaryl is defined above. A "heterocycloalkyloxy" group is —O-(heterocycloalkyl), wherein heterocycloalkyl is defined above.

As used herein and unless otherwise specified, an "amino" group is a radical of the formula: —$NH_2$, —NH($R^\#$), or —N($R^\#$)$_2$, wherein each $R^\#$ is independently an alkyl, cycloalkyl, cycloalkylalkyl, aryl, aralkyl, heterocyclyl (e.g., heteroaryl or heterocycloalkyl), or heterocyclylalkyl (e.g., heteroarylalkyl or heterocycloalkylalkyl) group defined above, each of which is independently substituted or unsubstituted.

In one embodiment, an "amino" group is an "alkylamino" group, which is a radical of the formula: —NH-alkyl or —N(alkyl)$_2$, wherein each alkyl is independently defined above. The term "cycloalkylamino", "arylamino", "heterocyclylamino", "heteroarylamino", "heterocycloalkylamino", or the like, mirrors the above description for "alkylamino" where the term "alkyl" is replaced with "cycloalkyl", "aryl", "heterocyclyl", "heteroaryl", "heterocycloalkyl", or the like, respectively.

As used herein and unless otherwise specified, a "carboxy" group is a radical of the formula: —C(O)OH.

As used herein and unless otherwise specified, an "acyl" group is a radical of the formula: —C(O)($R^\#$) or —C(O)H, wherein $R^\#$ is defined above. A "formyl" group is a radical of the formula: —C(O)H.

As used herein and unless otherwise specified, an "amido" group is a radical of the formula: —C(O)—$NH_2$, —C(O)—NH($R^\#$), —C(O)—N($R^\#$)$_2$, —NH—C(O)H, —NH—C(O)—($R^\#$), —N($R^\#$)—C(O)H, or —N($R^\#$)—C(O)—($R^\#$), wherein each $R^\#$ is independently defined above.

In one embodiment, an "amido" group is an "aminocarbonyl" group, which is a radical of the formula: —C(O)—$NH_2$, —C(O)—NH($R^\#$), —C(O)—N($R^\#$)$_2$, wherein each $R^\#$ is independently defined above.

In one embodiment, an "amido" group is an "acylamino" group, which is a radical of the formula: —NH—C(O)H, —NH—C(O)—($R^\#$), —N($R^\#$)—C(O)H, or —N($R^\#$)—C(O)—($R^\#$), wherein each $R^\#$ is independently defined above.

As used herein and unless otherwise specified, a "sulfonylamino" group is a radical of the formula: —$NHSO_2$($R^\#$) or —N($R^\#$)$SO_2$($R^\#$), wherein each $R^\#$ is defined above.

As used herein and unless otherwise specified, an "ester" group is a radical of the formula: —C(O)—O—($R^\#$) or —O—C(O)—($R^\#$), wherein $R^\#$ is defined above.

In one embodiment, an "ester" group is an "alkoxycarbonyl" group, which is a radical of the formula: —C(O)—O-(alkyl), wherein alkyl is defined above. The term "cycloalkyloxycarbonyl", "aryloxycarbonyl", "heterocyclyloxycarbonyl", "heteroaryloxycarbonyl", "heterocycloalkyloxycarbonyl", or the like, mirrors the above description for "alkoxycarbonyl" where the term "alkoxy" is replaced with "cycloalkyloxy", "aryloxy", "heterocyclyloxy", "heteroaryloxy", "heterocycloalkyloxy", or the like, respectively.

As used herein and unless otherwise specified, a "carbamate" group is a radical of the formula: —O—C(O)—$NH_2$, —O—C(O)—NH($R^\#$), —O—C(O)—N($R^\#$)$_2$, —NH—C(O)—O—($R^\#$), or —N($R^\#$)—C(O)—O—($R^\#$), wherein each W is independently defined above.

As used herein and unless otherwise specified, a "urea" group is a radical of the formula: —NH(CO)$NH_2$, —NHC(O)NH($R^\#$), —NHC(O)N($R^\#$)$_2$, —N($R^\#$)C(O)$NH_2$, —N($R^\#$)C(O)NH($R^\#$), or —N($R^\#$)C(O)N($R^\#$)$_2$, wherein each W is independently defined above.

As used herein and unless otherwise specified, a "sulfinyl" group is a radical of the formula: —S(O)$_2R^\#$, wherein $R^\#$ is defined above.

As used herein and unless otherwise specified, a "sulfonyl" group is a radical of the formula: —S(O)$_2R^\#$, wherein $R^\#$ is defined above.

As used herein and unless otherwise specified, an "aminosulfonyl" group is a radical of the formula: —$SO_2NH_2$, —$SO_2$NH($R^\#$), or —$SO_2$N($R^\#$)$_2$, wherein each $R^\#$ is independently defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen; alkyl, alkenyl, alkynyl, cycloalkyl, aryl, heterocyclyl, heteroaryl, heterocycloalkyl, cycloalkylalkyl, aralkyl, heterocyclylalkyl, heteroarylalkyl, heterocycloalkylalkyl, optionally further substituted; hydroxy; alkoxy; cycloalkyloxy, aryloxy, heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); oxide (e.g., a nitrogen atom substituted with an oxide is called N-oxide); amino, alkylamino, cycloalkylamino, arylamino, heterocyclylamino, heteroarylamino, heterocycloalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or $—B(OH)_2$.

As used herein, the term "Isoindolinedione Compound" refers to compounds of formula (I) as well as to further embodiments provided herein. In one embodiment, an "Isoindolinedione Compound" is a compound set forth in Table 1. The term "Isoindolinedione Compound" includes pharmaceutically acceptable salts, tautomers, isotopologues, and stereoisomers of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences,* $18^{th}$ eds., Mack Publishing, Easton Pa. (1990) or *Remington: The Science and Practice of Pharmacy,* $19^{th}$ eds., Mack Publishing, Easton Pa. (1995).

As used herein and unless otherwise indicated, the term "stereoisomer" or "stereomerically pure" means one stereoisomer of an Isoindolinedione Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Isoindolinedione Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Isoindolinedione Compounds, as well as the use of mixtures of those forms, are encompassed by the embodiments disclosed herein. For example, mixtures comprising equal or unequal amounts of the enantiomers of a particular Isoindolinedione Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, Ind., 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

It should also be noted the Isoindolinedione Compounds can include E and Z isomers, or a mixture thereof, and cis and trans isomers or a mixture thereof. In certain embodiments, the Isoindolinedione Compounds are isolated as either the E or Z isomer. In other embodiments, the Isoindolinedione Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

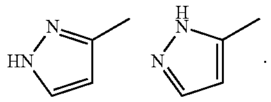

As readily understood by one skilled in the art, a wide variety of functional groups and other structures may exhibit tautomerism and all tautomers of compounds of formula (I) are within the scope of the present invention.

It should also be noted the Isoindolinedione Compounds can contain unnatural proportions of atomic isotopes at one or more of the atoms. For example, the compounds may be radiolabeled with radioactive isotopes, such as for example tritium ($^3H$), iodine-125 ($^{125}I$) sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition"

refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the Isoindolinedione Compounds as described herein, whether radioactive or not, are intended to be encompassed within the scope of the embodiments provided herein. In some embodiments, there are provided isotopologues of the Isoindolinedione Compounds, for example, the isotopologues are deuterium, carbon-13, and/or nitrogen-15 enriched Isoindolinedione Compounds. As used herein, "deuterated", means a compound wherein at least one hydrogen (H) has been replaced by deuterium (indicated by D or $^{2}H$), that is, the compound is enriched in deuterium in at least one position.

It is understood that, independently of stereomerical or isotopic composition, each Isoindolinedione Compound referred to herein can be provided in the form of any of the pharmaceutically acceptable salts discussed herein. Equally, it is understood that the isotopic composition may vary independently from the stereomerical composition of each Isoindolinedione Compound referred to herein. Further, the isotopic composition, while being restricted to those elements present in the respective Isoindolinedione Compound or salt thereof, may otherwise vary independently from the selection of the pharmaceutically acceptable salt of the respective Isoindolinedione Compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is DLBCL as described herein or a symptoms thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is DLBCL, as described herein, or symptoms thereof.

The term "effective amount" in connection with an Isoindolinedione Compound means an amount capable of treating or preventing a disorder, disease or condition, or symptoms thereof, disclosed herein.

The term "subject" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having DLBCL, or a symptom thereof.

In general, the technical teaching of one embodiment can be combined with that described in other embodiments provided herein.

Isoindolinedione Compounds

Provided herein are compounds having the following formula (I):

(I)

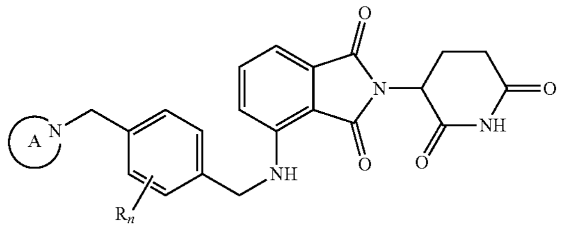

or a pharmaceutically acceptable salt, tautomer, isotopolog, or stereoisomer thereof, wherein:

Ring A is an optionally substituted non-aromatic heterocyclyl (with the point of attachment on the ring nitrogen atom);

each R is independently substituted or unsubstituted $C_{1-3}$ alkyl, or halogen;

and n is 0, 1, 2, 3 or 4.

In some embodiments, the compound is a compound of formula (II)

(II)

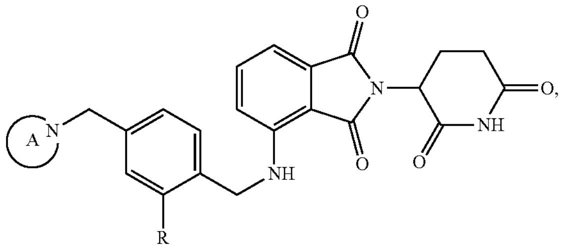

or a pharmaceutically acceptable salt, tautomer, isotopolog, or stereoisomer thereof, wherein Ring A and R are as defined herein.

In some embodiments, the compound is a compound of formula (III)

(III)

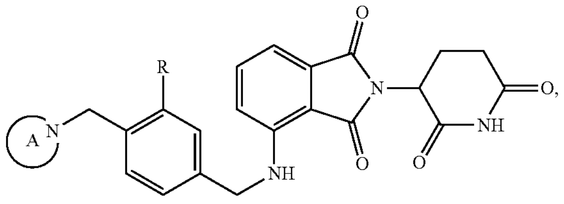

or a pharmaceutically acceptable salt, tautomer, isotopolog, or stereoisomer thereof, wherein Ring A and R are as defined herein.

In some embodiments, the compound is a compound of formula (IV)

(IV)

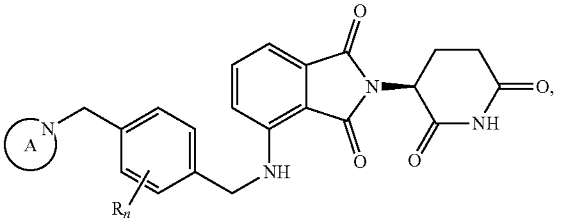

or a pharmaceutically acceptable salt, tautomer, or isotopolog thereof, wherein Ring A, n and R are as defined herein.

In some embodiments, the compound is a compound of formula (V)

(V)

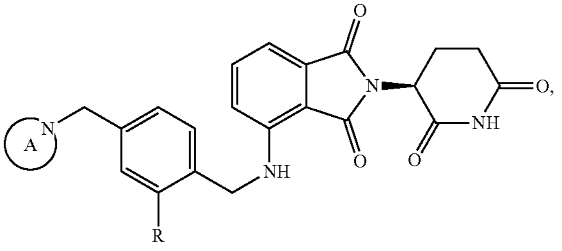

or a pharmaceutically acceptable salt, tautomer, or isotopolog thereof, wherein Ring A and R are as defined herein.

In some embodiments, the compound is a compound of formula (VI)

(VI)

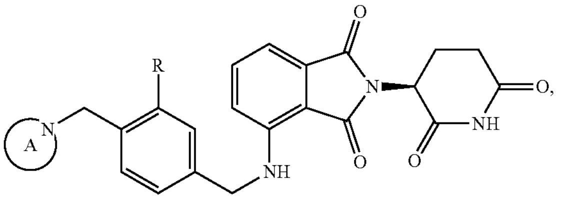

or a pharmaceutically acceptable salt, tautomer, or isotopolog thereof, wherein Ring A and R are as defined herein.

In some embodiments, the compound is a compound of formula (VII)

(VII)

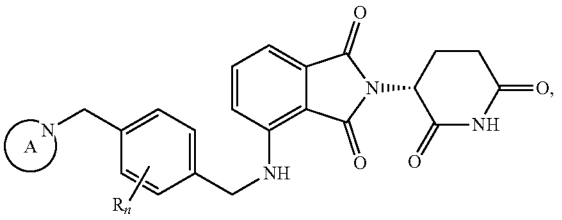

or a pharmaceutically acceptable salt, tautomer, or isotopolog thereof, wherein Ring A, n and R are as defined herein.

In some embodiments, the compound is a compound of formula (VIII)

(VIII)

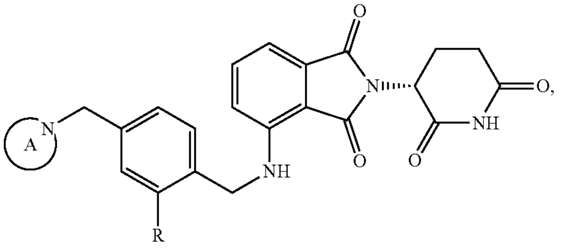

or a pharmaceutically acceptable salt, tautomer, or isotopolog thereof, wherein Ring A and R are as defined herein.

In some embodiments, the compound is a compound of formula (IX)

(IX)

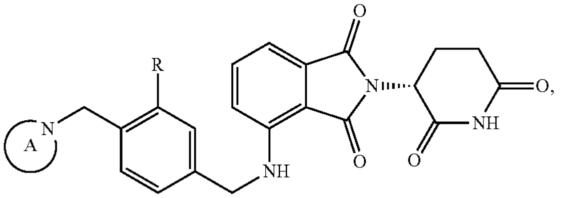

or a pharmaceutically acceptable salt, tautomer, or isotopolog thereof, wherein Ring A and R are as defined herein.

In some embodiments of compounds of formulas (I), (II), (III), (IV), (V), (VI), (VII), (VIII), or (IX), Ring A is an optionally substituted non-aromatic heterocyclyl selected from azetidyl; piperidyl; piperazinyl; morpholinyl; 5-azaspiro[2,3]hexyl; 2-azaspiro[3.3]heptyl; 2-oxa-6-azaspiro[3.3]heptyl; 2-azaspiro[3.4]octyl; 5-oxa-2-azaspiro[3.4]octyl; 6-oxa-2-azaspiro[3.4]octyl; 2-azaspiro[3.5]nonyl; 7-oxa-2-azaspiro[3.5]nonyl; octahydrocyclopenta[c]pyrrolyl; 1,2,3,3a,4,6a-hexahydrocyclopenta[c]pyrrolyl; 6-azaspiro[3.4]octyl; 2-oxa-6-azaspiro[3.4]octyl; 6-azaspiro[2.5]octyl; 7-azaspiro[3.5]nonyl; 1-oxa-8-azaspiro[4.5]decanyl; 2-oxa-8-azaspiro[4.5]decanyl; 2,8-diazaspiro[4.5]decan-1-onyl; 3-oxa-9-azaspiro[5.5]undecanyl; 1,4-oxazepanyl; 8-azabicyclo[3.2.1]octyl; and isoindolinyl. In one embodiment, Ring A is an optionally substituted non-aromatic heterocyclyl selected from azetidyl; piperidyl; piperazinyl; 5-azaspiro[2,3]hexyl; 2-azaspiro[3.3]heptyl; 2-oxa-6-azaspiro[3.3]heptyl; 2-azaspiro[3.4]octyl; 5-oxa-2-azaspiro[3.4]octyl; 6-oxa-2-azaspiro[3.4]octyl; 2-azaspiro[3.5]nonyl; 7-oxa-2-azaspiro[3.5]nonyl; octahydrocyclopenta[c]pyrrolyl; 1,2,3,3a,4,6a-hexahydrocyclopenta[c]pyrrolyl; 6-azaspiro[3.4]octyl; 2-oxa-6-azaspiro[3.4]octyl; 6-azaspiro[2.5]octyl; 7-azaspiro[3.5]nonyl; 1-oxa-8-azaspiro[4.5]decanyl; 2-oxa-8-azaspiro[4.5]decanyl; 2,8-diazaspiro[4.5]decan-1-onyl; 3-oxa-9-azaspiro[5.5]undecanyl; 1,4-oxazepanyl; 8-azabicyclo[3.2.1]octyl; and isoindolinyl. In another embodiment, Ring A is an optionally substituted non-aromatic heterocyclyl selected from azetidyl; piperidyl; piperazinyl; 2-azaspiro[3.3]heptyl; 2-azaspiro[3.4]octyl; 5-oxa-2-azaspiro[3.4]octyl; 7-oxa-2- azaspiro[3.5]nonyl; 1-oxa-8-azaspiro[4.5]decanyl; and 2,8-diazaspiro[4.5]decan-1-onyl. In another embodiment, Ring A is an optionally substituted non-aromatic heterocyclyl selected from azetidyl; piperidyl; piperazinyl; and morpholinyl. In another embodiment, Ring A is an optionally substituted azetidyl. In another embodiment, Ring A is an optionally substituted piperidyl. In another embodiment, Ring A is an optionally substituted piperazinyl. In another embodiment, Ring A is an optionally substituted morpholinyl.

In some embodiments of compounds of formulas (I), (II), (III), (IV), (V), (VI), (VII), (VIII), or (IX), Ring A is substituted with one or more substituents independently selected from halogen, $C_{1-6}$ alkyl, $OR^1$, $CON(R^2)_2$, $SO_2(C_{1-4}$ alkyl), $N(R^2)SO_2(C_{1-4}$ alkyl), —($C_{0-3}$ alkyl)-($C_{3-7}$ cycloalkyl), (non-aromatic heterocyclyl), aryl, heteroaryl, O-aryl, O-heteroaryl, and C(O)aryl; wherein the alkyl, cycloalkyl, heterocyclyl, aryl, or heteroaryl are optionally substituted; wherein $R^1$ is H, optionally substituted $C_{1-6}$ alkyl, or optionally substituted —($C_{0-3}$ alkyl)-($C_{3-7}$ cycloalkyl); and each $R^2$ is independently H, or $C_{1-6}$ alkyl. In other embodiments, Ring A is substituted with one or more substituents independently selected from F, Cl, Br, $CH_3$, $CH_2CH_3$, n-propyl, isopropyl, n-butyl, sec-butyl, isobutyl, t-butyl, n-pentyl, isopentyl, $CH_2F$, $CHF_2$, $CF_3$, $CH_2CH_2F$, $CH_2CHF_2$, $CH_2CF_3$, $CH(CH_3)CF_3$, $CH_2CH_2CF_3$, OH, $OCH_3$, $OCH_2CH_3$, O-isopropyl, O-n-propyl, O-n-butyl, O-isobutyl, O-t-butyl, $OCF_3$, O-cyclopropyl, O-cyclobutyl, $OCH_2$-cyclopropyl, $OCH_2$-cyclobutyl, $CONH_2$, $CONH(CH_3)$, $CON(CH_3)_2$, $SO_2CH_3$, $SO_2CH_2CH_3$, $SO_2$-isopropyl, cyclopropyl, cyclobutyl, $CH_2$-cyclopropyl, $CH_2$-cyclobutyl; (non-aromatic heterocyclyl) selected from azetidyl, pyrrolidyl, pyrrolidonyl, isothiazolidyl, isothiazolidine 1,1-dioxidyl, piperidyl, piperazinyl, morpholinyl, 3-oxa-8-azabicyclo[3.2.1]octyl, or 8-oxa-3-azabicyclo[3.2.1]octyl, wherein the heterocyclyl is optionally substituted with one or more substituents independently selected from $CH_3$, $CH_2CH_3$, or $CF_3$, phenyl, O-phenyl or C(O)-phenyl, wherein the phenyl is optionally substituted with one or more substituents independently selected from F, Cl, $CH_3$, CN, or $CONH_2$; heteroaryl selected from pyrazolyl, imidazolyl, oxazolyl, isoxazolyl, oxadiazolyl, thiadiazolyl, pyridyl, pyrazinyl, pyridazinyl, pyrimidyl, or benzoisoxazolyl, wherein the heteroaryl is optionally substituted with one or more substituents independently selected from F, Cl, $CF_3$, CN, $CONH_2$, $CONH(CH_3)_2$ or $CON(CH_3)_2$; O-pyridyl, and O-pyrimidyl. In some embodiments, Ring A is substituted with one or more substituents independently selected from F, $CH_3$, $CH_2CH_3$, isopropyl, t-butyl, $CH_2F$, $CF_3$, $CH(CH_3)CF_3$, OH, $OCH_3$, $OCH_2CH_3$, O-isopropyl, O-n-propyl, O-isobutyl, O-t-butyl, $OCF_3$, O-cyclobutyl, $OCH_2$-cyclopropyl, $CON(CH_3)_2$, $SO_2CH_2CH_3$, $SO_2$-isopropyl, cyclopropyl, cyclobutyl, $CH_2$-cyclopropyl; (non-aromatic heterocyclyl) selected from pyrrolidyl, pyrrolidonyl, isothiazolidine 1,1-dioxidyl, morpholinyl, 3-oxa-8-azabicyclo[3.2.1]octyl, or 8-oxa-3-azabicyclo[3.2.1]octyl, wherein the heterocyclyl is optionally substituted with one or more substituents independently selected from $CH_3$; phenyl, O-phenyl or C(O)-phenyl, wherein the phenyl is optionally substituted with one or more substituents independently selected from F, Cl, $CH_3$, CN, or $CONH_2$; heteroaryl selected from pyrazolyl, oxazolyl, oxadiazolyl, thiadiazolyl, pyridyl, pyrazinyl, pyrimidyl or benzoisoxazolyl, wherein the heteroaryl is optionally substituted with one or more substituents independently selected from F, Cl, $CF_3$, CN, $CONH_2$, $CON(CH_3)_2$; O-pyridyl, and O-pyrimidyl.

In some embodiments of compounds of formulas (I), (II), (III), (IV), (V), (VI), (VII), (VIII), or (IX), Ring A is azetidyl, substituted with one or more substituents independently selected from $C_{1-6}$ alkyl, (non-aromatic heterocyclyl), aryl, heteroaryl, O-aryl, and O-heteroaryl; wherein the alkyl, cycloalkyl, heterocyclyl, aryl, or heteroaryl are optionally substituted. In some such embodiments, Ring A is azetidyl, substituted with one or more substituents independently selected from $CH_2CH_3$, n-propyl, isopropyl, n-butyl, sec-butyl, isobutyl, t-butyl; $CF_3$; pyrrolidyl; pyrolidonyl; piperidyl; piperazinyl; morpholinyl, optionally substituted with one or more $CH_3$; 3-oxa-8-azabicyclo[3.2.1]octyl; 8-oxa-3-azabicyclo[3.2.1]octyl; pyrazolyl; 2-pyridyl; 3-pyridyl; 4-pyridyl, phenyl; and O-phenyl; wherein the phenyl optionally is substituted with one or more substituents selected from F or CN. In other embodiments, Ring A is azetidyl, substituted with one or more substituents independently selected from $CH_2CH_3$, isopropyl, t-butyl; $CF_3$; pyrrolidyl; pyrolidonyl; morpholinyl, optionally substituted with one or more $CH_3$; 3-oxa-8-azabicyclo[3.2.1]octyl; 8-oxa-3-azabicyclo[3.2.1]octyl; pyrazolyl; 2-pyridyl; 3-pyridyl; phenyl; and O-phenyl; wherein the phenyl optionally is substituted with one or more substituents selected from F or CN. In one embodiment, Ring A is azetidyl, substituted with morpholinyl. In some such embodiments, R is F and n is 1. In some such embodiments, the compound is a compound of formula (II), and R is F. In other such embodiments, the compound is a compound of formula (III) and R is F. In yet other such embodiments, the compound is a compound of formula (IV), R is F and n is 1. In other such embodiments, the compound is a compound of formula (V) and R is F. In still other such embodiments, the compound is a compound of formula (VI) and R is F. In yet other such embodiments, the compound is a compound of formula (VII), R is F and n is 1. In other such embodiments, the compound is a compound of formula (VIII) and R is F. In still other such embodiments, the compound is a compound of formula (IX) and R is F. In some such embodiments, the compound is a compound of formula (II), and R is $CH_3$. In other such embodiments, the compound is a compound of formula (III) and R is $CH_3$. In yet other such embodiments, the compound is a compound of formula (IV), R is $CH_3$ and n is 1. In other such embodiments, the compound is a compound of formula (V) and R is $CH_3$. In still other such embodiments, the compound is a compound of formula (VI) and R is $CH_3$. In yet other such embodiments, the compound is a compound of formula (VII), R is $CH_3$ and n is 1. In other such embodiments, the compound is a compound of formula (VIII) and R is $CH_3$. In still other such embodiments, the compound is a compound of formula (IX) and R is $CH_3$.

In some embodiments of compounds of formulas (I), (II), (III), (IV), (V), (VI), (VII), (VIII), or (IX), Ring A is

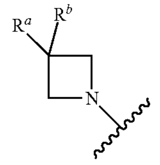

wherein $R^a$ is H, and $R^b$ is $C_{1-6}$ alkyl, non-aromatic heterocyclyl, aryl, heteroaryl, or O-aryl; or $R^a$ and $R^b$ together with the carbon to which they are attached form a 3-6 membered cycloalkyl, or a 4-6 membered non-aromatic heterocyclyl; wherein the alkyl, cycloalkyl, heterocyclyl, aryl, or heteroaryl are optionally substituted with one or more halogen, $C_{1-3}$ alkyl, or CN.

In some such embodiments, $R^a$ is H, and $R^b$ is $CH_2CH_3$, n-propyl, isopropyl, n-butyl, sec-butyl, isobutyl, t-butyl; $CF_3$; pyrrolidyl; pyrolidonyl; piperidyl; piperazinyl; morpholinyl, optionally substituted with one or more $CH_3$; 3-oxa-8-azabicyclo[3.2.1]octyl; 8-oxa-3-azabicyclo[3.2.1]octyl; pyrazolyl; 2-pyridyl; 3-pyridyl; phenyl; or O-phenyl; wherein the phenyl optionally is substituted with one or more substituents selected from F or CN. In some such embodiments, $R^a$ is H, and $R^b$ is $CH_2CH_3$, isopropyl, t-butyl, $CF_3$, pyrrolidyl; pyrolidonyl; piperidyl; piperazinyl; morpholinyl, optionally substituted with one or more $CH_3$; 3-oxa-8-azabicyclo[3.2.1]octyl; 8-oxa-3-azabicyclo[3.2.1]octyl; pyrazolyl; 2-pyridyl; 3-pyridyl; phenyl; or O-phenyl; wherein the phenyl optionally is substituted with one or more substituents selected from F or CN. In some such embodiments, $R^a$ is H, and $R^b$ is $CH_2CH_3$, isopropyl, t-butyl, $CF_3$, pyrrolidyl; pyrrolidonyl, morpholinyl, 2,2-dimethylmorpholinyl, 3,3-dimethylmorpholinyl, 2,6-dimethylmorpholinyl, 3,5-dimethylmorpholinyl, 3-oxa-8-azabicyclo[3.2.1]octyl, 8-oxa-3-azabicyclo[3.2.1]octyl, pyrazolyl, 2-pyridyl, 3-pyridyl, phenyl, 3-fluorophenyl, 4-fluorophenyl, 3-cyanophenyl, 4-cyanophenyl, O-phenyl, or O-4-cyanophenyl. In one embodiment, $R^a$ and $R^b$ together with the carbon to which they are attached form a cyclopropyl, cyclobutyl, 3,3-difluorocyclobutyl, cyclopentyl, cyclohexyl, oxetanyl, tetrahydrofuranyl, or tetrahydropyranyl. In some such embodiments, the compound is a compound of formula (II), and R is F. In other such embodiments, the compound is a compound of formula (III) and R is F. In yet other such embodiments, the compound is a compound of formula (IV), R is F and n is 1. In other such embodiments, the compound is a compound of formula (V) and R is F. In still other such embodiments, the compound is a compound of formula (VI) and R is F. In yet other such embodiments, the compound is a compound of formula (VII), R is F and n is 1. In other such embodiments, the compound is a compound of formula (VIII) and R is F. In still other such embodiments, the compound is a compound of formula (IX) and R is F. In some such embodiments, the compound is a compound of formula (II), and R is $CH_3$. In other such embodiments, the compound is a compound of formula (III) and R is $CH_3$. In yet other such embodiments, the compound is a compound of formula (IV), R is $CH_3$ and n is 1. In other such embodiments, the compound is a compound of formula (V) and R is $CH_3$. In still other such embodiments, the compound is a compound of formula (VI) and R is $CH_3$. In yet other such embodiments, the compound is a compound of formula (VII), R is $CH_3$ and n is 1. In other such embodiments, the compound is a compound of formula (VIII) and R is $CH_3$. In still other such embodiments, the compound is a compound of formula (IX) and R is $CH_3$.

In some embodiments of compounds of formulas (I), (II), (III), (IV), (V), (VI), (VII), (VIII), or (IX), Ring A is piperidyl, substituted with one or more substituents independently selected from halogen, $C_{1-6}$ alkyl, $OR^1$, $CON(R^2)_2$, $SO_2(C_{1-4}$ alkyl), $C_{3-7}$ cycloalkyl, non-aromatic heterocyclyl, aryl, heteroaryl and O-heteroaryl; wherein the alkyl, cycloalkyl, heterocyclyl, aryl, or heteroaryl are optionally substituted; wherein $R^1$ is H, optionally substituted $C_{1-6}$ alkyl, or optionally substituted —($C_{0-3}$ alkyl)-($C_{3-7}$ cycloalkyl); and each $R^2$ is independently H, or $C_{1-6}$ alkyl. In other embodiments, Ring A is piperidyl, substituted with one or more substituents independently selected from F, Cl, $CH_3$, $CH_2CH_3$, n-propyl, isopropyl, n-butyl, sec-butyl, isobutyl, t-butyl, $CH_2F$, $CHF_2$, $CF_3$, OH, $OCH_3$, $OCH_2CH_3$, O-n-propyl, O-isopropyl, O-n-butyl, O-isobutyl, O-t-butyl, $OCF_3$, O-cyclopropyl, O-cyclobutyl, $OCH_2$-cyclopropyl, $OCH_2$-cyclobutyl, $CONH_2$, $CONH(CH_3)$, $CON(CH_3)_2$, $SO_2CH_3$, $SO_2CH_2CH_3$, $SO_2$-isopropyl, cyclopropyl, cyclobutyl, pyrrolidonyl, isothiazolidine 1,1-dioxidyl, morpholinyl; tetrahydrofuranyl, tetrahydropyranyl, pyrazolyl; oxadiazolyl, optionally substituted with $CH_3$; phenyl, optionally substituted with one or more F; 2-pyridyl, 3-pyridyl, 4-pyridyl, O-2-pyridyl, O-3-pyridyl, and O-4-pyridyl. In some embodiments, Ring A is piperidyl, substituted with one or more substituents independently selected from F, $CH_3$, $CH_2CH_3$, isopropyl, t-butyl, $CHF_2$, $CF_3$, OH, $OCH_3$, $OCH_2CH_3$, O-isopropyl, O-isobutyl, O-t-butyl, $OCF_3$, O-cyclobutyl, $OCH_2$-cyclopropyl, $CON(CH_3)_2$, $SO_2CH_2CH_3$, $SO_2$-isopropyl, cyclopropyl, pyrrolidonyl, isothiazolidine 1,1-dioxidyl, morpholinyl; tetrahydropyranyl, pyrazolyl, oxadiazolyl, substituted with $CH_3$; phenyl, substituted with one or more F; 2-pyridyl, and O-2-pyridyl. In some such embodiments, the compound is a compound of formula (II), and R is F. In other such embodiments, the compound is a compound of formula (III) and R is F. In yet other such embodiments, the compound is a compound of formula (IV), R is F and n is 1. In other such embodiments, the compound is a compound of formula (V) and R is F. In still other such embodiments, the compound is a compound of formula (VI) and R is F. In yet other such embodiments, the compound is a compound of formula (VII), R is F and n is 1. In other such embodiments, the compound is a compound of formula (VIII) and R is F. In still other such embodiments, the compound is a compound of formula (IX) and R is F. In some such embodiments, the compound is a compound of formula (II), and R is $CH_3$. In other such embodiments, the compound is a compound of formula (III) and R is $CH_3$. In yet other such embodiments, the compound is a compound of formula (IV), R is $CH_3$ and n is 1. In other such embodiments, the compound is a compound of formula (V) and R is $CH_3$. In still other such embodiments, the compound is a compound of formula (VI) and R is $CH_3$. In yet other such embodiments, the compound is a compound of formula (VII), R is $CH_3$ and n is 1. In other such embodiments, the compound is a compound of formula (VIII) and R is $CH_3$. In still other such embodiments, the compound is a compound of formula (IX) and R is $CH_3$.

In some embodiments of compounds of formulas (I), (II), (III), (IV), (V), (VI), (VII), (VIII), or (IX), Ring A is

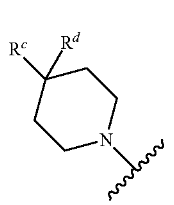

wherein $R^c$ is H, halogen, OH, or ($C_{1-3}$ alkyl); and $R^d$ is optionally substituted ($C_{1-3}$ alkyl), $OR^1$, $C(O)N(R^2)_2$, $SO_2(C_{1-4}$ alkyl), $C_{3-7}$ cycloalkyl, non-aromatic heterocyclyl, aryl, heteroaryl, or O-heteroaryl; or $R^c$ and $R^d$ together with the carbon to which they are attached form a 3-6 membered cycloalkyl, or a 4-6 membered non-aromatic heterocyclyl; wherein $R^1$ is H, optionally substituted $C_{1-6}$ alkyl, or optionally substituted —($C_{0-3}$ alkyl)-($C_{3-7}$ cycloalkyl); each $R^2$ is independently H, or $C_{1-6}$ alkyl; and wherein the alkyl, cycloalkyl, heterocyclyl, aryl, or heteroaryl are optionally substituted with one or more halogen, $C_{1-3}$ alkyl, or CN.

In some such embodiments, $R^c$ is H, OH, F, $CH_3$, or $CH_2CH_3$. In other such embodiments, $R^d$ is $CH_3$, $CH_2CH_3$, n-propyl, isopropyl, n-butyl, sec-butyl, isobutyl, t-butyl, $CH_2F$, $CHF_2$, $CF_3$, $OCH_3$, $OCH_2CH_3$, O-n-propyl, O-isopropyl, O-n-butyl, O-isobutyl, O-t-butyl, $OCF_3$, O-cyclopropyl, O-cyclobutyl, $OCH_2$-cyclopropyl, $OCH_2$-cyclobutyl, $CONH_2$, $CONH(CH_3)$, $CON(CH_3)_2$, $SO_2CH_3$, $SO_2CH_2CH_3$, $SO_2$-isopropyl, cyclopropyl, cyclobutyl, pyrrolidonyl, isothiazolidine 1,1-dioxidyl, morpholinyl, tetrahydrofuranyl, tetrahydropyranyl, pyrazolyl; oxadiazolyl, optionally substituted with $CH_3$; phenyl, optionally substituted with one or more F; 2-pyridyl, 3-pyridyl, 4-pyridyl, O-2-pyridyl, O-3-pyridyl, or O-4-pyridyl. In other embodiments, $R^d$ is $CH_3$, $CH_2CH_3$, isopropyl, t-butyl, $CHF_2$, $CF_3$, $OCH_3$, $OCH_2CH_3$, O-isopropyl, O-isobutyl, O-t-butyl, $OCF_3$, O-cyclobutyl, $OCH_2$-cyclopropyl, $CON(CH_3)_2$, $SO_2CH_2CH_3$, $SO_2$-isopropyl, cyclopropyl, pyrrolidonyl, isothiazolidine 1,1-dioxidyl, morpholinyl, tetrahydropyranyl, pyrazolyl, 2-methyl-1,3,4-oxadiazolyl, 3,5-difluorophenyl, 2-pyridyl, or O-2-pyridyl. In one embodiment, $R^a$ and $R^b$ together with the carbon to which they are attached form a cyclopropyl, cyclobutyl, 3,3-difluorocyclobutyl, pyrrolidonyl, 1-methylpyrrolidonyl, tetrahydrofuranyl, 2,2-dimethyltetrahydrofuranyl, or tetrahydropyranyl. In some such embodiments, the compound is a compound of formula (II), and R is F. In other such embodiments, the compound is a compound of formula (III) and R is F. In yet other such embodiments, the compound is a compound of formula (IV), R is F and n is 1. In other such embodiments, the compound is a compound of formula (V) and R is F. In still other such embodiments, the compound is a compound of formula (VI) and R is F. In yet other such embodiments, the compound is a compound of formula (VII), R is F and n is 1. In other such embodiments, the compound is a compound of formula (VIII) and R is F. In still other such embodiments, the compound is a compound of formula (IX) and R is F. In some such embodiments, the compound is a compound of formula (II), and R is $CH_3$. In other such embodiments, the compound is a compound of formula (III) and R is $CH_3$. In yet other such embodiments, the compound is a compound of formula (IV), R is $CH_3$ and n is 1. In other such embodiments, the compound is a compound of formula (V) and R is $CH_3$. In still other such embodiments, the compound is a compound of formula (VI) and R is $CH_3$. In yet other such embodiments, the compound is a compound of formula (VII), R is $CH_3$ and n is 1. In other such embodiments, the compound is a compound of formula (VIII) and R is $CH_3$. In still other such embodiments, the compound is a compound of formula (IX) and R is $CH_3$.

In some embodiments of compounds of formulas (I), (II), (III), (IV), (V), (VI), (VII), (VIII), or (IX), Ring A is piperazinyl, substituted with one or more substituents independently selected from $C_{1-6}$ alkyl, $SO_2(C_{1-4}$ alkyl), —($C_{0-3}$ alkyl)-($C_{3-7}$ cycloalkyl), aryl, heteroaryl and CO-aryl; wherein the alkyl, cycloalkyl, aryl, or heteroaryl are optionally substituted. In other embodiments, Ring A is piperazinyl, substituted with one or more substituents independently selected from $CH_3$, $CH_2CH_3$, n-propyl, isopropyl, n-butyl, sec-butyl, isobutyl, t-butyl, $CF_3$, $CH_2CF_3$, $CH(CH_3)CF_3$, $SO_2CH_3$, $SO_2CH_2CH_3$, $SO_2$-isopropyl, cyclopropyl, cyclobutyl, $(CH_2)$cyclopropyl, $(CH_2)$cyclobutyl, phenyl, optionally substituted with one or more Cl, F, CN, $CH_3$, $CONH_2$; pyrazolyl, optionally substituted with $CH_3$ or $CH_2CH_3$; oxazolyl, optionally substituted with $CH_3$ or $CH_2CH_3$; oxadiazolyl, optionally substituted with $CH_3$ or $CH_2CH_3$; thiadiazolyl, optionally substituted with $CH_3$, $CH_2CH_3$, or $CF_3$; 2-pyridyl, 3-pyridyl, or 4-pyridyl, each optionally substituted with Cl, F, $CF_3$, CN, $CONH_2$, $CONH(CH_3)$ or $CON(CH_3)_2$; pyrazinyl, optionally substituted with $CH_3$ or $CH_2CH_3$; pyrimidyl, optionally substituted with $OCH_3$; benzoisoxazolyl; and CO(phenyl), wherein the phenyl is optionally fluorinated. In other embodiments, Ring A is piperazinyl, substituted with one or more substituents independently selected from $CH_3$, isopropyl, t-butyl, $CH(CH_3)CF_3$, $SO_2CH_2CH_3$, $SO_2$-isopropyl, cyclopropyl, cyclobutyl, $(CH_2)$cyclopropyl, phenyl, optionally substituted with one or more Cl, F, CN, $CH_3$, $CONH_2$; pyrazolyl, optionally substituted with $CH_3$; oxazolyl, optionally substituted with $CH_3$; oxadiazolyl, optionally substituted with $CH_2CH_3$; thiadiazolyl, optionally substituted with $CH_3$, or $CH_2CH_3$; 2-pyridyl, optionally substituted with Cl, F, $CF_3$, CN, or $CONH_2$; 3-pyridyl, optionally substituted with $CF_3$, CN, $CONH_2$, or $CON(CH_3)_2$; 4-pyridyl, optionally substituted with $CONH_2$; pyrazinyl, optionally substituted with $CH_3$; pyrimidyl, optionally substituted with $OCH_3$; benzoisoxazolyl; and CO(phenyl), wherein the phenyl is optionally fluorinated. In other embodiments, A is piperazinyl, substituted with t-butyl or pyridyl, wherein the pyridyl is optionally substituted with $C(O)NH_2$. In some such embodiments, R is F and n is 1. In some such embodiments, the compound is a compound of formula (II), and R is F. In other such embodiments, the compound is a compound of formula (III) and R is F. In yet other such embodiments, the compound is a compound of formula (IV), R is F and n is 1. In other such embodiments, the compound is a compound of formula (V) and R is F. In still other such embodiments, the compound is a compound of formula (VI) and R is F. In yet other such embodiments, the compound is a compound of formula (VII), R is F and n is 1. In other such embodiments, the compound is a compound of formula (VIII) and R is F. In still other such embodiments, the compound is a compound of formula (IX) and R is F. In some such embodiments, the compound is a compound of formula (II), and R is $CH_3$. In other such embodiments, the compound is a compound of formula (III) and R is $CH_3$. In yet other such embodiments, the compound is a compound of formula (IV), R is $CH_3$ and n is 1. In other such embodiments, the compound is a compound of formula (V) and R is $CH_3$. In still other such embodiments, the compound is a compound of formula (VI) and R is $CH_3$. In yet other such embodiments, the compound is a compound of formula (VII), R is $CH_3$ and n is 1. In other such embodiments, the compound is a compound of formula (VIII) and R is $CH_3$. In still other such embodiments, the compound is a compound of formula (IX) and R is $CH_3$.

In some embodiments of compounds of formulas (I), (II), (III), (IV), (V), (VI), (VII), (VIII), or (IX), Ring A is

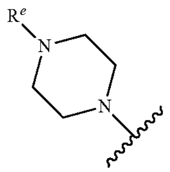

wherein $R^e$ is $C_{1-6}$ alkyl, $SO_2(C_{1-4}$ alkyl), —($C_{0-3}$ alkyl)-($C_{3-7}$ cycloalkyl), aryl, heteroaryl or CO-aryl; wherein the alkyl, cycloalkyl, aryl, or heteroaryl are optionally substituted.

In some such embodiments, $R^e$ is $CH_3$, $CH_2CH_3$, n-propyl, isopropyl, n-butyl, sec-butyl, isobutyl, t-butyl, $CH_2CF_3$, $CH(CH_3)CF_3$, $SO_2CH_3$, $SO_2CH_2CH_3$, $SO_2$-isopropyl, cyclopropyl, cyclobutyl, $(CH_2)$cyclopropyl, $(CH_2)$cyclobutyl, phenyl, optionally substituted with one or more Cl, F, CN, $CH_3$, $CONH_2$; pyrazolyl, optionally substituted with $CH_3$ or $CH_2CH_3$; oxazolyl, optionally substituted with $CH_3$ or $CH_2CH_3$; oxadiazolyl, optionally substituted with $CH_3$ or $CH_2CH_3$; thiadiazolyl, optionally substituted with $CH_3$, $CH_2CH_3$, or $CF_3$; 2-pyridyl, 3-pyridyl, or 4-pyridyl, each optionally substituted with Cl, F, $CF_3$, CN, $CONH_2$, CONH$(CH_3)$ or $CON(CH_3)_2$; pyrazinyl, optionally substituted with $CH_3$ or $CH_2CH_3$; pyrimidyl, optionally substituted with $OCH_3$; benzoisoxazolyl; or CO(phenyl), wherein the phenyl is optionally fluorinated. In some embodiments, $R^e$ is isopropyl, t-butyl, $CH(CH_3)CF_3$, $SO_2CH_2CH_3$, $SO_2$-isopropyl, cyclopropyl, cyclobutyl, $(CH_2)$cyclopropyl, phenyl, optionally substituted with one or more Cl, F, CN, $CH_3$, $CONH_2$; pyrazolyl, optionally substituted with $CH_3$; oxazolyl, optionally substituted with $CH_3$; oxadiazolyl, optionally substituted with $CH_2CH_3$; thiadiazolyl, optionally substituted with $CH_3$, or $CH_2CH_3$; 2-pyridyl, optionally substituted with Cl, F, $CF_3$, CN, or $CONH_2$; 3-pyridyl, optionally substituted with $CF_3$, CN, $CONH_2$, or $CON(CH_3)_2$; 4-pyridyl, optionally substituted with $CONH_2$; pyrazinyl, optionally substituted with $CH_3$; pyrimidyl, optionally substituted with $OCH_3$; benzoisoxazolyl; or CO(phenyl), wherein the phenyl is optionally fluorinated. In some such embodiments, R is F or $CH_3$, and n is 1. In some such embodiments, the compound is a compound of formula (II), and R is F. In other such embodiments, the compound is a compound of formula (III) and R is F. In yet other such embodiments, the compound is a compound of formula (IV), R is F and n is 1. In other such embodiments, the compound is a compound of formula (V) and R is F. In still other such embodiments, the compound is a compound of formula (VI) and R is F. In yet other such embodiments, the compound is a compound of formula (VII), R is F and n is 1. In other such embodiments, the compound is a compound of formula (VIII) and R is F. In still other such embodiments, the compound is a compound of formula (IX) and R is F. In some such embodiments, the compound is a compound of formula (II), and R is $CH_3$. In other such embodiments, the compound is a compound of formula (III) and R is $CH_3$. In yet other such embodiments, the compound is a compound of formula (IV), R is $CH_3$ and n is 1. In other such embodiments, the compound is a compound of formula (V) and R is $CH_3$. In still other such embodiments, the compound is a compound of formula (VI) and R is $CH_3$. In yet other such embodiments, the compound is a compound of formula (VII), R is $CH_3$ and n is 1. In other such embodiments, the compound is a compound of formula (VIII) and R is $CH_3$. In still other such embodiments, the compound is a compound of formula (IX) and R is $CH_3$.

In some embodiments of compounds of formulas (I), (IV) or (VII), Ring A is morpholinyl, and R is F or $CH_3$, and n is 1. In other embodiments of compounds of formulas (II), (III), (V), (VI), (VIII), or (IX), Ring A is morpholinyl, and R is F or $CH_3$. In some such embodiments, the compound is a compound of formula (II), and R is F. In other such embodiments, the compound is a compound of formula (III) and R is F. In yet other such embodiments, the compound is a compound of formula (IV), R is F and n is 1. In other such embodiments, the compound is a compound of formula (V) and R is F. In still other such embodiments, the compound is a compound of formula (VI) and R is F. In yet other such embodiments, the compound is a compound of formula (VII), R is F and n is 1. In other such embodiments, the compound is a compound of formula (VIII) and R is F. In still other such embodiments, the compound is a compound of formula (IX) and R is F. In some such embodiments, the compound is a compound of formula (II), and R is $CH_3$. In other such embodiments, the compound is a compound of formula (III) and R is $CH_3$. In yet other such embodiments, the compound is a compound of formula (IV), R is $CH_3$ and n is 1. In other such embodiments, the compound is a compound of formula (V) and R is $CH_3$. In still other such embodiments, the compound is a compound of formula (VI) and R is $CH_3$. In yet other such embodiments, the compound is a compound of formula (VII), R is $CH_3$ and n is 1. In other such embodiments, the compound is a compound of formula (VIII) and R is $CH_3$. In still other such embodiments, the compound is a compound of formula (IX) and R is $CH_3$.

In other embodiments of compounds of formulas (I), (II), (III), (IV), (V), (VI), (VII), (VIII), or (IX), Ring A is selected from 5-azaspiro[2,3]hexyl; 2-azaspiro[3.3]heptyl; 2-oxa-6-azaspiro[3.3]heptyl; 2-azaspiro[3.4]octyl; 5-oxa-2-azaspiro[3.4]octyl; 6-oxa-2-azaspiro[3.4]octyl; 2-azaspiro[3.5]nonyl; 7-oxa-2-azaspiro[3.5]nonyl; octahydrocyclopenta[c]pyrrolyl; 1,2,3,3a,4,6a-hexahydrocyclopenta[c]pyrrolyl; 6-azaspiro[3.4]octyl; 2-oxa-6-azaspiro[3.4]octyl; 6-azaspiro[2.5]octyl; 7-azaspiro[3.5]nonyl; 1-oxa-8-azaspiro[4.5]decanyl; 2-oxa-8-azaspiro[4.5]decanyl; 2,8-diazaspiro[4.5]decan-1-onyl; 3-oxa-9-azaspiro[5.5]undecanyl; 1,4-oxazepanyl; 8-azabicyclo[3.2.1]octyl; and isoindolinyl; each optionally substituted with one or more $CH_3$ or F.

In some embodiments of compounds of formulas (I), (II), (III), (IV), (V), (VI), (VII), (VIII), or (IX), R is $CH_3$ or F. In some embodiments of compounds of formula (I), R is $CH_3$ or F. In some embodiments of compounds of formula (II), R is $CH_3$ or F. In some embodiments of compounds of formula (III), R is $CH_3$ or F. In some embodiments of compounds of formula (IV), R is $CH_3$ or F. In some embodiments of compounds of formula (V), R is $CH_3$ or F. In some embodiments of compounds of formula (VI), R is $CH_3$ or F. In some embodiments of compounds of formula (VII), R is $CH_3$ or F. In some embodiments of compounds of formula (VIII), R is $CH_3$ or F. In some embodiments of compounds of formula (IX), R is $CH_3$ or F. In some embodiments of compounds of formula (I), R is $CH_3$. In some embodiments of compounds of formula (II), R is $CH_3$. In some embodiments of compounds of formula (III), R is $CH_3$. In some embodiments of compounds of formula (IV), R is $CH_3$. In some embodiments of compounds of formula (V), R is $CH_3$. In some embodiments of compounds of formula (VI), R is $CH_3$. In some embodiments of compounds of formula (VII), R is $CH_3$. In some embodiments of compounds of formula (VIII), R is $CH_3$. In some embodiments of compounds of formula (IX), R is $CH_3$. In some embodiments of compounds of formula (I), R is F. In some embodiments of compounds of formula (II), R is F. In some embodiments of compounds of formula (III), R is F. In some embodiments of compounds of formula (IV), R is F. In some embodiments of compounds of formula (V), R is F. In some embodiments of compounds of formula (VI), R is F. In some embodiments of compounds of formula (VII), R is F. In some embodiments of compounds of formula (VIII), R is F. In some embodiments of compounds of formula (IX), R is F.

In some embodiments of compounds of formulas (I), (II), (III), (IV), (V), (VI), (VII), (VIII), or (IX), R is substituted or unsubstituted $C_{1-3}$ alkyl. In one embodiment, R is methyl. In one embodiment, R is ethyl. In one embodiment, R is n-propyl. In one embodiment, R is isopropyl.

In some embodiments of compounds of formulas (I), (II), (III), (IV), (V), (VI), (VII), (VIII), or (IX), R is halogen. In one embodiment, R is F. In one embodiment, R is Cl. In one embodiment, R is Br. In one embodiment, R is I.

In some embodiments of compounds of formulas (I), (IV) or (VII), n is 0.

In other embodiments, n is 1. In other embodiments, n is 2. In other embodiments, n is 3. In other embodiments, n is 4. In some embodiments of compounds of formula (I), n is 0. In other embodiments, n is 1. In other embodiments, n is 2. In other embodiments, n is 3. In other embodiments, n is 4. In some embodiments of compounds of formula (IV), n is 0. In other embodiments, n is 1. In other embodiments, n is 2. In other embodiments, n is 3. In other embodiments, n is 4. In some embodiments of compounds of formula (VII), n is 0. In other embodiments, n is 1. In other embodiments, n is 2. In other embodiments, n is 3. In other embodiments, n is 4.

In some embodiments of compounds of formulas (I), (IV) or (VII), R is $CH_3$ or F and n is 1. In some embodiments of compounds of formulas (I), (IV) or (VII), R is $CH_3$ and n is 1. In some embodiments of compounds of formulas (I), (IV) or (VII), R is F and n is 1.

Isoindolinedione Compounds set forth in Table 1 were tested in DLBCL assays described herein and were found to have activity therein. In one embodiment, the Isoindolinedione Compound is a compound as described herein, wherein the compound at a concentration of 1 μM inhibits DLBCL cell growth, for example SU-DHL-4 cell line growth, by at least about 50% or more.

Methods for Making Isoindolinedione Compounds

The Isoindolinedione Compounds can be made using conventional organic syntheses and commercially available starting materials. By way of example and not limitation, Isoindolinedione Compounds of formula (I) can be prepared as outlined in Schemes 1 and 2 shown below as well as in the examples set forth herein. It should be noted that one skilled in the art would know how to modify the procedures set forth in the illustrative schemes and examples to arrive at the desired products.

Scheme 1

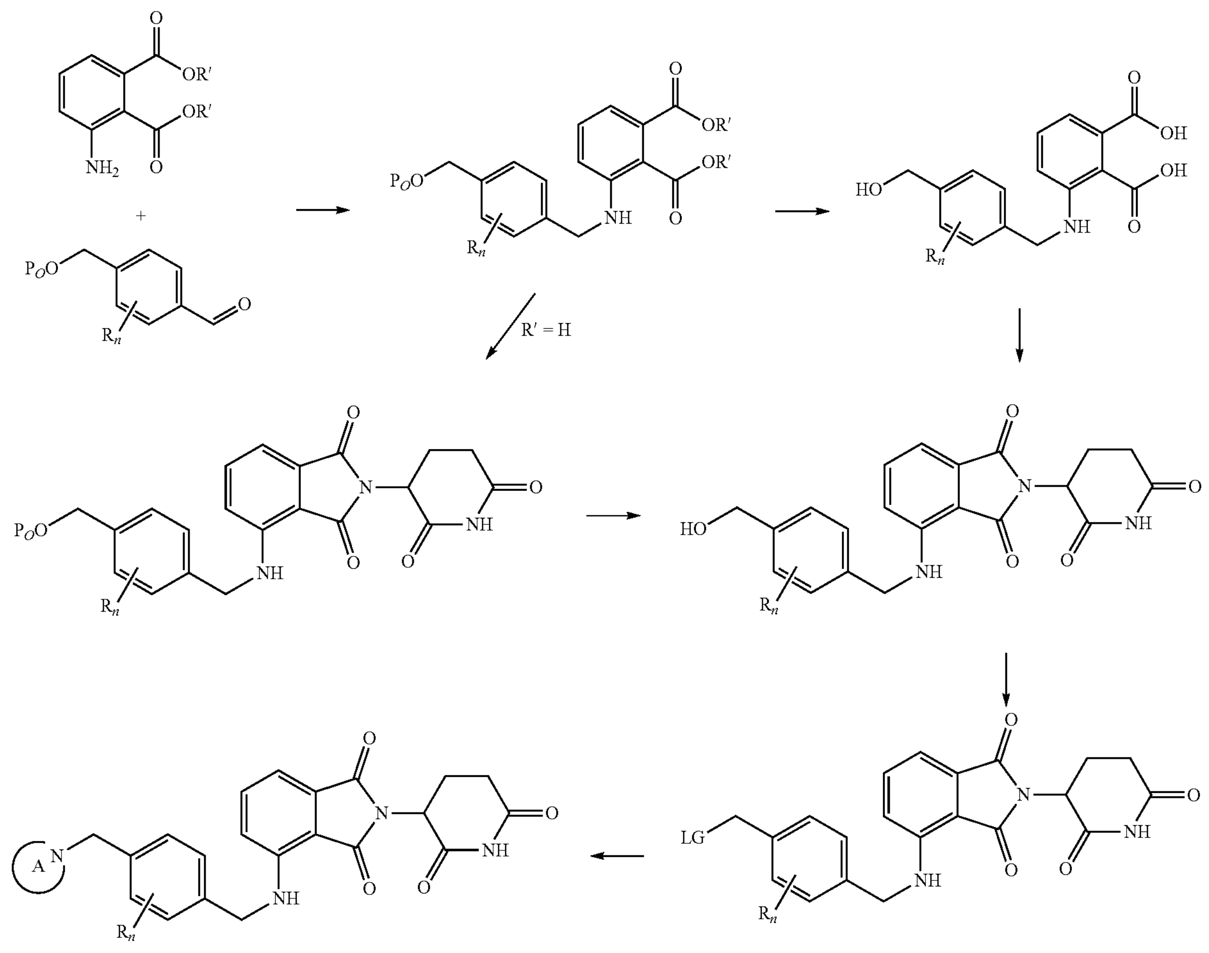

(I)

Further embodiments provided herein include combinations of one or more of the particular embodiments set forth above.

Representative compounds of formulas (I), (II), (III), (IV), (V), (VI), (VII), (VIII), or (IX) are set forth in Table 1.

As shown in Scheme 1, compounds of formula (I), wherein Ring A, n and R are as defined herein, can be prepared starting with reductive amination of an appropriately derivatized and protected 4-hydroxymethylbenzaldehyde (wherein Po is a hydroxyl protecting group), with 3-aminophthalic acid (wherein R' is H) or dialkyl-3-aminophthalate (wherein R' is $C_{1-2}$ alkyl), using a reductive amination agent, such as $BH_3$.2-methylpyridine, $B_{10}H_{14}$, or $NaBH(OAc)_3$, in a solvent, such as MeOH, dioxane, DCM, 1,2-dichloroethane, $CH_3CN$, THF or mixtures thereof, in the presence of an acid, such as acetic acid or TFA, optionally at a temperature between about 0 and 25° C. In a first approach, when R' is H, the intermediate is subjected to cyclo-dehydration, by treatment with 3-aminopiperidine-2,6-dione and a base, such as pyridine, at elevated temperature, for example, at about 120° C. Subsequently, the hydroxyl protecting group is removed, for example, when Po is a silyl ether, Po can be removed by treatment with an acid, such as $H_2SO_4$ or HCl, or a reagent such as TBAF, in a solvent, such as THF or aqueous THF. In a second approach, the protecting groups are removed (for example, when R' is $C_{1-2}$ alkyl, the carboxylates are deprotected, for example by saponification with a base, such as NaOH, in a solvent, such as aqueous THF, and the protecting group Po, such as a silyl ether, is simultaneously removed), followed by cyclo-dehydration as described above. Subsequently a leaving group LG is introduced into the resulting intermediate (wherein LG is OMs, OTs, or a halogen such as Cl or Br), for example when LG is Cl, by reaction with $CH_3SO_2C_1$, $SOCl_2$ or $Ph_3P—CCl_4$, or when LG is Br, by reaction with $SOBr_2$, $Ph_3P—Br_2$, or $PBr_3$, or when LG is OMs, by reaction with $CH_3SO_2Cl$ or methanesulfonic anhydride, or when LG is OTs, by reaction with TsCl, in a solvent, such as DCM, ether or toluene, at a temperature between about 0 and 25° C. Displacement of the leaving group LG with Ring A, as defined herein, in the presence of a base, such as DIEA, TEA, $Na_2CO_3$, $K_2CO_3$, or $Cs_2CO_3$, in a solvent, such as DMSO, DMF, DMA, NMP, or $CH_3CN$, at a temperature between about 25 and 80° C., provides the target molecules of formula (I).

Scheme 2

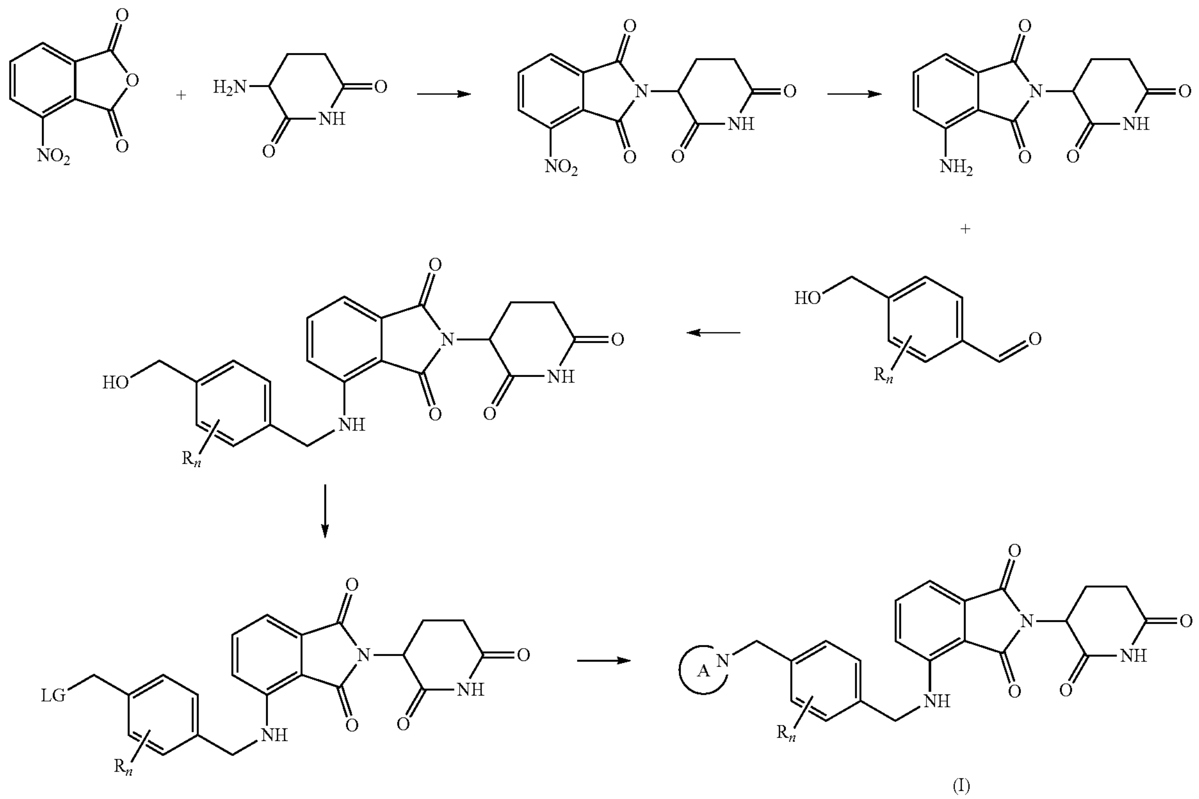

(I)

An alternative route to compounds of formula (I) is shown in Scheme 2. 4-Nitroisobenzofuran-1,3-dione is treated with 3-aminopiperidine-2,6-dione, in the presence of an acid, such as acetic acid, at elevated temperature, for example 130° C. Reduction of the nitro group is achieved by treatment with a reducing agent, for example, hydrogen gas, in the presence of a catalyst, for example Pd/C, Ni or Pt, or Fe or Zn in the presence of HCl, acetic acid, or $NH_4Cl$, or $SnCl_2$, in a solvent, for example, DMA, EtOH, water, EtOAc, DMF or EtOAc/DMF mixtures. The amine containing intermediate is subjected to reductive amination by reaction with an appropriately derivatized 4-hydroxymethylbenzaldehyde, in the presence of a reducing agent, for example, $B_{10}H_{14}$, in a solvent, such as MeOH or dioxane or mixtures thereof, at a temperature between about 0 and 25° C. As before, a leaving group LG is then introduced in the intermediate (LG is OMs, OTs, Cl or Br), for example when LG is Cl, by reaction with $CH_3SO_2Cl$, $SOCl_2$ or $Ph_3P—CCl_4$, or when LG is Br, by reaction with $SOBr_2$, $Ph_3P—Br_2$, or $PBr_3$, or when LG is OMs, by reaction with $CH_3SO_2Cl$ or methanesulfonic anhydride, or when LG is OTs, by reaction with TsCl, in a solvent, such as dichloromethane, ether or toluene, at a temperature between about 0 and 25° C. As in Scheme 1, displacement of the leaving group LG with a heterocycle Ring A in the presence of a base, such as DIEA, TEA, $Na_2CO_3$, $K_2CO_3$, $Cs_2CO_3$, in a solvent, such as DMSO, DMF, DMA, NMP, or $CH_3CN$, at a temperature between about 25 and 80° C., provides the target molecules of formula (I).

In some embodiments, chiral separation (by standard methods and as described herein) of the enantiomers of compounds of formula (I) provides compounds of formula (IV) and formula (VII)

(IV)

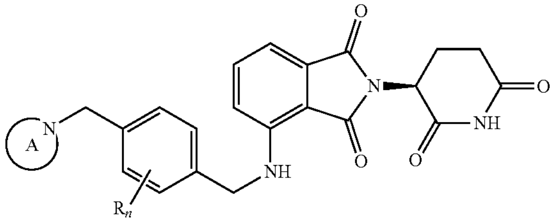

(VII)

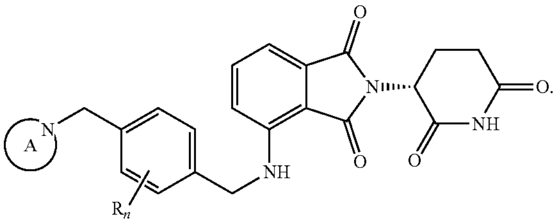

The term "protected" with respect to hydroxyl groups, refers to forms of these functionalities which are protected from undesirable reaction with a protecting group known to those skilled in the art, such as those set forth in Protective Groups in Organic Synthesis, Greene, T. W.; Wuts, P. G. M., John Wiley & Sons, New York, N.Y., ($5^{th}$ Edition, 2014), which can be added or removed using the procedures set forth therein. Examples of protected hydroxyl groups include, but are not limited to, silyl ethers such as those obtained by reaction of a hydroxyl group with a reagent such as, but not limited to, t-butyldiphenylchlorosilane, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate.

In one aspect, provided herein are methods for preparing a compound of formula (I):

(I)

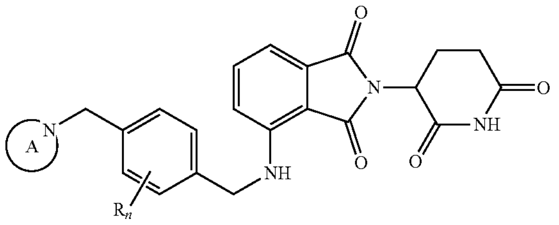

the methods comprising contacting a compound of formula (Ia)

(Ia)

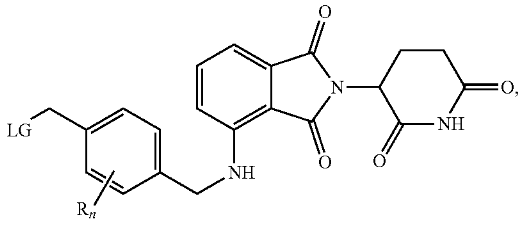

with 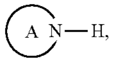

in the presence of a base, in a solvent, under conditions suitable to provide a compound of formula (I), wherein Ring A is an optionally substituted non-aromatic heterocyclyl (with the point of attachment on the ring nitrogen atom);

each R is independently substituted or unsubstituted $C_{1-3}$ alkyl, or halogen;

n is 0, 1, 2, 3 or 4; and

LG is OMs, OTs, or halogen.

In some embodiments, Ring A is an optionally substituted non-aromatic heterocyclyl selected from azetidyl; piperidyl; piperazinyl; morpholinyl; 5-azaspiro[2,3]hexyl; 2-azaspiro[3.3]heptyl; 2-oxa-6-azaspiro[3.3]heptyl; 2-azaspiro[3.4]octyl; 5-oxa-2-azaspiro[3.4]octyl; 6-oxa-2-azaspiro[3.4]octyl; 2-azaspiro[3.5]nonyl; 7-oxa-2-azaspiro[3.5]nonyl; octahydrocyclopenta[c]pyrrolyl; 1,2,3,3a,4,6a-hexahydrocyclopenta[c]pyrrolyl; 6-azaspiro[3.4]octyl; 2-oxa-6-azaspiro[3.4]octyl; 6-azaspiro[2.5]octyl; 7-azaspiro[3.5]nonyl; 1-oxa-8-azaspiro[4.5]decanyl; 2-oxa-8-azaspiro[4.5]decanyl; 2,8-diazaspiro[4.5]decan-1-onyl; 3-oxa-9-azaspiro[5.5]undecanyl; 1,4-oxazepanyl; 8-azabicyclo[3.2.1]octyl; or isoindolinyl. In one embodiment, Ring A is an optionally substituted non-aromatic heterocyclyl selected from azetidyl; piperidyl; piperazinyl; 2-azaspiro[3.3]heptyl; 2-azaspiro[3.4]octyl; 5-oxa-2-azaspiro[3.4]octyl; 7-oxa-2-azaspiro[3.5]nonyl; 1-oxa-8-azaspiro[4.5]decanyl; or 2,8-diazaspiro[4.5]decan-1-onyl. In one embodiment, LG is Cl. In another, LG is Br. In one embodiment, the base is DIEA, TEA, $Na_2CO_3$, $K_2CO_3$, or $Cs_2CO_3$. In another embodiment, the solvent is DMSO, DMF, DMA, NMP, or $CH_3CN$. In some embodiments the contacting is performed at a temperature of about 25 to about 80° C.

In some embodiments, the methods further comprise preparing a compound of formula (Ia):

(Ia)

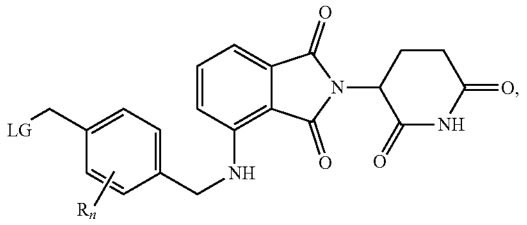

the methods comprising contacting a compound of formula (Ib)

(Ib)

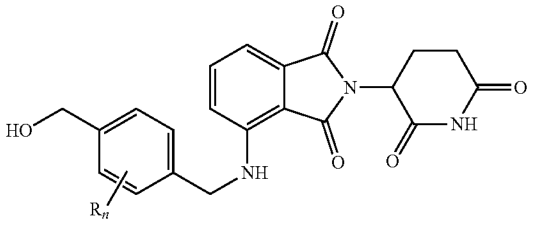

(a) when LG is Cl, with $CH_3SO_2C_1$, $SOCl_2$, or $Ph_3P—CCl_4$;

(b) when LG is Br, with $SOBr_2$, $Ph_3P—Br_2$, or $PBr_3$;

(c) when LG is OMs, with $CH_3SO_2Cl$, or methanesulfonic anhydride;

(d) when LG is OTs, with TsCl;

in a solvent, under conditions suitable to provide a compound of formula (Ia).

In one embodiment, the solvent is DCM, ether or toluene. In some embodiments the contacting is performed at a temperature of about 0 to about 25° C.

In some embodiments, the methods further comprise preparing a compound of formula (Ib):

(Ib)

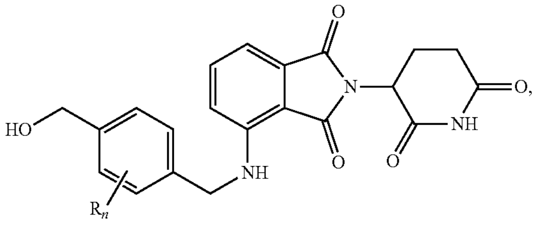

the methods comprising deprotecting a compound of formula (Ic)

(Ic)

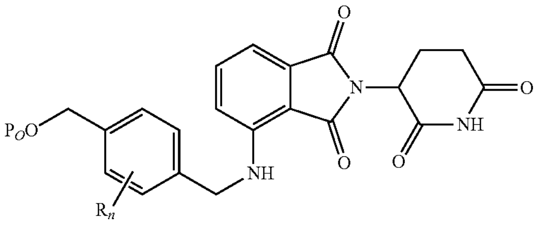

in a solvent, under conditions suitable to provide a compound of formula (Ib), wherein Po is a hydroxyl protecting group.

In one embodiment, Po is a silyl ether and the deprotection is treatment with an acid or with TBAF. In some such embodiments, the acid is $H_2SO_4$ or HCl. In other embodiments, the solvent is THF or aqueous THF. In some embodiments, the deprotecting is performed at a temperature of about 0 to about 60° C.

In some embodiments, the methods further comprise preparing a compound of formula (Ic):

(Ic)

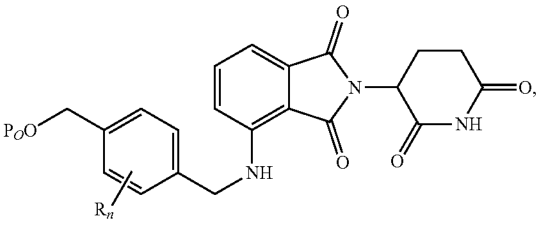

the methods comprising contacting a compound of formula (Id)

(Id)

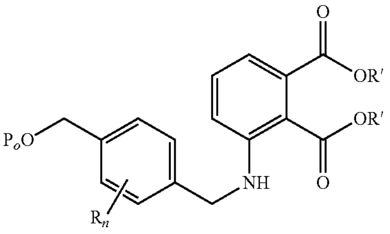

with 3-aminopiperidine-2,6-dione and a base, under conditions suitable to provide a compound of formula (Ic), wherein R' is H.

In some embodiments, the base is pyridine. In some embodiments, the contacting is performed at a temperature of about 25 to about 130° C.

In some other embodiments, the methods further comprise preparing a compound of formula (Ib):

(Ib)

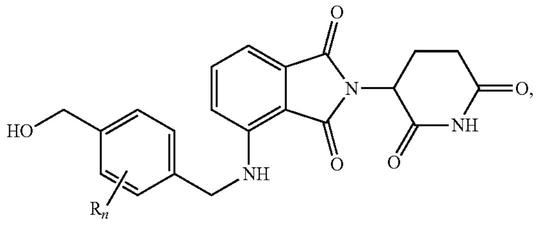

the methods comprising contacting a compound of formula (Ie)

(Ie)

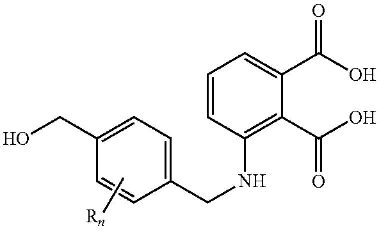

with 3-aminopiperidine-2,6-dione and a base, under conditions suitable to provide a compound of formula (Ib).

In some embodiments, the base is pyridine. In some embodiments, the contacting is performed at a temperature of about 25 to about 120° C.

In some such embodiments, the methods further comprise preparing a compound of formula (Ie):

(Ie)

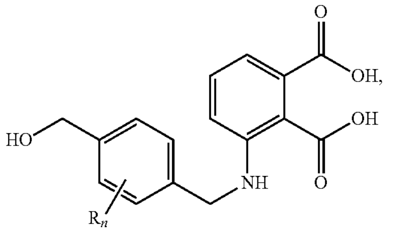

the methods comprising deprotecting a compound of formula (Id)

(Id)

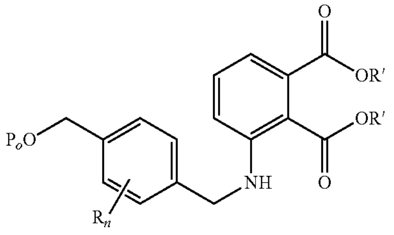

under conditions suitable to provide a compound of formula (Ie), wherein R' is $C_{1-2}$ alkyl and Po is a hydroxyl protecting group.

In one embodiment, Po is a silyl ether and the deprotection is treatment with a base in a solvent. In one embodiment, the base is NaOH. In another embodiment the solvent is aqueous THF. In some embodiments, the contacting is performed at a temperature of about 0 to about 60° C.

In some embodiments, the methods further comprise preparing a compound of formula (Id):

(Id)

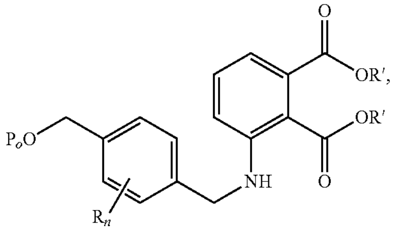

the methods comprising contacting a compound of formula (If)

(If)

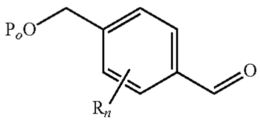

with a compound of formula (Ig)

(Ig)

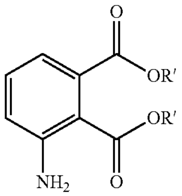

in the presence of a reductive amination agent, and an acid, in a solvent, under conditions suitable to provide a compound of formula (Id), wherein R' is H or $C_{1-2}$ alkyl.

In some embodiments, the reductive amination agent is $BH_3$.2-methylpyridine, $B_{10}H_{14}$, or $NaBH(OAc)_3$. In some embodiments, the solvent is MeOH, dioxane, DCM, 1,2-dichloroethane, $CH_3CN$, THF or mixtures thereof. In other embodiments, the acid is acetic acid or TFA. In some embodiments, the contacting is performed at a temperature of about 0 to about 25° C.

In some other embodiments, the methods further comprise preparing a compound of formula (Ib):

(Ib)

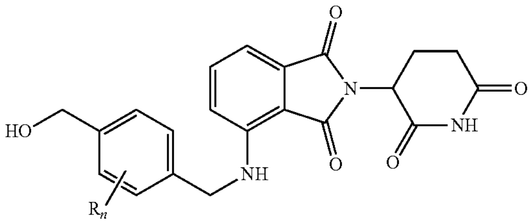

the methods comprising contacting a compound of formula (Ih)

(Ih)

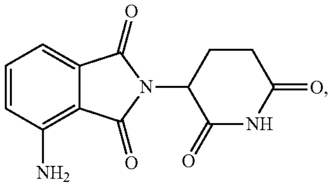

with a compound of formula (Ii)

(Ii)

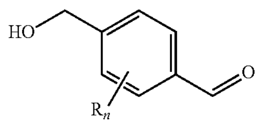

in the presence of a reducing agent, in a solvent, under conditions suitable to provide a compound of formula (Ib).

In one embodiment, the reducing agent is $B_{10}H_{14}$. In another embodiment, the solvent is MeOH, dioxane or mixtures thereof. In some embodiments the contacting is performed at a temperature of about 0 to about 25° C.

In some embodiments, the methods further comprise preparing a compound of formula (Ih):

(Ih)

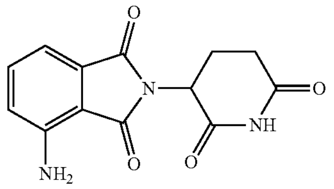

the methods comprising reducing a compound of formula (Ij)

(Ij)

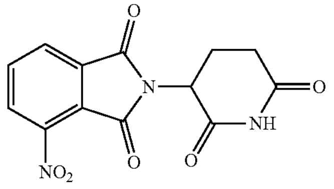

In the presence of a reducing agent, in a solvent, under conditions suitable to provide a compound of formula (Ih).

In some embodiments, the reducing agent is hydrogen gas, in the presence of a catalyst. In some such embodiments the catalyst is Pd/C, Ni or Pt. In other embodiments, the reducing agent is Fe or Zn in the presence of HCl, acetic acid, or $NH_4C_1$. In yet other embodiments, the reducing agent is $SnCl_2$. In some embodiments, the solvent is DMA, EtOH, water, EtOAc, DMF or EtOAc/DMF. In some embodiments, the contacting is performed at a temperature of about 0 to about 60° C.

Methods of Use

The Isoindolinedione Compounds have utility as pharmaceuticals to treat, prevent or improve conditions in animals or humans. Accordingly, provided herein are many uses of the Isoindolinedione Compounds, including the treatment or prevention of those diseases set forth below. The methods provided herein comprise the administration of an effective amount of one or more Isoindolinedione Compound(s) to a subject in need thereof.

In one aspect provided herein are methods for treating or preventing DLBCL, comprising administering to a subject in need thereof an effective amount of an Isoindolinedione Compound as described herein. In one aspect provided herein are methods for treating DLBCL, comprising administering to a subject in need thereof an effective amount of an Isoindolinedione Compound as described herein. In one aspect provided herein are methods for preventing DLBCL, comprising administering to a subject in need thereof an effective amount of an Isoindolinedione Compound as described herein. For example, the Isoindolinedione Compound is a compound from Table 1.

In another aspect provided herein are compounds for use in the treatment or prevention of DLBCL, comprising administering to a subject in need thereof an effective amount of an Isoindolinedione Compound. In some embodiments, provided herein are compounds for use in the treatment of DLBCL, comprising administering to a subject in need thereof an effective amount of an Isoindolinedione Compound as described herein. In some embodiments, provided herein are compounds for use in the prevention of DLBCL, comprising administering to a subject in need thereof an effective amount of an Isoindolinedione Compound as described herein. For example, the Isoindolinedione. Compound is a compound from Table 1.

In some embodiments, the DLBCL is activated B-cell-like DLBCL (ABC-DLBCL). In others, the DLBCL is germinal center B-cell-like DLBCL (GCB-DLBCL). In yet others, the DLBCL is unclassified DLBCL. In still others the DLBCL is primary mediastinal B-cell type DLBCL (PMBL DLBCL). In other embodiments, the DLBCL is double-hit DLBCL (DHIT DLBCL), also referred to as cMyc/Bcl-2 mutant DLBCL. In some embodiments, the DLBCL is triple-hit DLBCL (THIT DLBCL) also referred to as cMyc/Bcl2/Bcl6 rearrangement DLBCL.

In some embodiments, the DLBCL is newly diagnosed DLBCL. In some embodiments, the DLBCL is primary DLBCL. In others, the DLBCL is relapsed DLBCL. In still others, the DLBCL is refractory DLBCL. In some embodiments the DLBCL is relapsed or refractory DLBCL. In some embodiments the DLBCL is relapsed/refractory DLBCL. In one embodiment, the DLBCL is refractory to one or more of rituximab, cyclophosphamide, doxorubicin, vincristine, prednisone, etoposide, Bendamustine (Treanda), lenalidomide, or gemcitabine.

In some embodiments of the methods described herein the methods further include administration of one or more of rituximab, cyclophosphamide, doxorubicin, vincristine, prednisone, etoposide, Bendamustine (Treanda), lenalidomide, or gemcitabine. In some embodiments of the methods described herein the methods further include administration of one or more of rituximab, cyclophosphamide, doxorubicin, vincristine, prednisone, etoposide, Bendamustine (Treanda), or gemcitabine. In some embodiments of the methods described herein, the treatment further includes treatment with one or more of RCHOP (rituximab plus cyclophosphamide, doxorubicin, vincristine, and prednisone), R-EPOCH (etoposide, rituximab plus cyclophosphamide, doxorubicin, vincristine, and prednisone), stem cell transplant, Bendamustine (Treanda) plus rituximab, rituximab, lenalidomide plus rituximab, or gemcitabine-based combinations. In some embodiments of the methods described herein, the treatment further includes treatment with one or more of RCHOP (rituximab plus cyclophosphamide, doxorubicin, vincristine, and prednisone), R-EPOCH (etoposide, rituximab plus cyclophosphamide, doxorubicin, vincristine, and prednisone), stem cell transplant, Bendamustine (Treanda) plus rituximab, rituximab, or gemcitabine-based combinations Pharmaceutical Compositions and Routes of Administration The Isoindolinedione Compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Isoindolinedione Compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of an Isoindolinedione Compound to be administered to a subject is rather widely variable and can be subject to the judgment of a health-care practitioner. In general, the Isoindolinedione Compounds can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the Isoindolinedione Compound administered will depend on such factors as the solubility of the active component, the formulation used and the route of administration.

In another embodiment, provided herein are methods for the treatment or prevention of a disease or disorder comprising the administration of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day of an Isoindolinedione Compound to a subject in need thereof.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of an Isoindolinedione Compound.

In a particular embodiment, provided herein are unit dosage formulations comprising about 0.1 mg or 100 mg of an Isoindolinedione Compound.

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of an Isoindolinedione Compound.

An Isoindolinedione Compound can be administered once, twice, three, four or more times daily. In a particular embodiment, doses of 100 mg or less are administered as a once daily dose and doses of more than 100 mg are administered twice daily in an amount equal to one half of the total daily dose.

An Isoindolinedione Compound can be administered orally for reasons of convenience. In one embodiment, when administered orally, an Isoindolinedione Compound is administered with a meal and water. In another embodiment, the Isoindolinedione Compound is dispersed in a liquid, such as water or juice (e.g., apple juice or orange juice) and administered orally as a solution or a suspension.

The Isoindolinedione Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing an Isoindolinedione Compound without an additional carrier, excipient or vehicle.

In another embodiment, provided herein are compositions comprising an effective amount of an Isoindolinedione Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing an Isoindolinedione Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer an Isoindolinedione Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Isoindolinedione Compound can be delayed or prolonged by proper formulation. For example, a slowly soluble pellet of the Isoindolinedione Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Isoindolinedione Compound in oily or emulsified vehicles that allow it to disperse slowly in the serum.

EXAMPLES

The following examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations used:

| | |
|---|---|
| Ac | Acetyl |
| nBuLi | n-Butyllithium |
| DCM | Dichloromethane |
| DEA | Diethylamine |
| DIEA | N,N-Diisopropylethylamine |
| DMA | N,N-Dimethylacetamide |
| DMAP | 4-Dimethylaminopyridine |

-continued

| | |
|---|---|
| DMF | N,N-Dimethylformamide |
| DMSO | Dimethylsulfoxide |
| ESI | Electrospray ionization |
| EtOH | Ethanol |
| EtOAc | Ethyl acetate |
| HPLC | High performance liquid chromatography |
| HTRF | Homogeneous time resolved fluorescence |
| LCMS | Liquid chromatography mass spectrometry |
| MeOH | Methanol |
| Ms | Methanesulfonyl or mesyl |
| MsCl | Methanesulfonyl chloride or mesyl chloride |
| MS | Mass spectrometry |
| NMP | N-Methylpyrrolidone |
| NMR | Nuclear magnetic resonance |
| TBAF | Tetra-n-butylammonium fluoride |
| TEA | Triethylamine |
| TFA | Trifluoracetic acid |
| THF | Tetrahydrofuran |
| TLC | Thin layer chromatography |
| Ts | 4-Toluenesulfonyl or tosyl |
| TsCl | 4-Toluenesulfonyl chloride or tosyl chloride |

Compound Synthesis

Example 1: 4-((4-((4-(tert-Butyl)piperazin-1-yl)methyl)-3-methylbenzyl)amino)-2-(2,6-dioxopiperidin-3-yl)isoindoline-1,3-dione

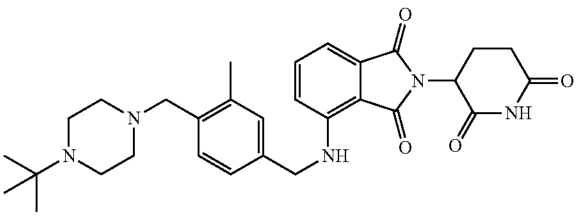 [SMILES: Cc1cc(CNc2cccc3c2C(=O)N(C2CCC(=O)NC2=O)C3=O)ccc1CN1CCN(C(C)(C)C)CC1]

2-(2,6-Dioxo-3-piperidyl)-4-nitro-isoindoline-1,3-dione: A mixture of 4-nitroisobenzofuran-1,3-dione (70.4 g, 365 mmol) and 3-aminopiperidine-2,6-dione hydrochloride (50.0 g, 304 mmol) in acetic acid (1 L) was stirred at 130° C. for 16 hours under a nitrogen atmosphere. The solvent was removed under reduced pressure and the residual solid was washed with ethyl acetate (500 mL) and dried in vacuum to afford 2-(2,6-dioxo-3-piperidyl)-4-nitro-isoindoline-1,3-dione as a gray solid (130 g, 70.6% yield). $^1H$ NMR (400 MHz DMSO-$d_6$) δ ppm 11.15 (s, 1H), 8.32 (d, J=8.0 Hz, 1H), 8.21 (d, J=7.6 Hz, 1H), 8.09 (t, J=7.6 Hz, 1H), 5.20-5.15 (m, 1H), 2.89-2.81 (m, 1H), 2.60-2.47 (m, 2H), 2.04 (t, J=5.6 Hz, 1H).

4-Amino-2-(2,6-dioxo-3-piperidyl)isoindoline-1,3-dione

To a solution of 2-(2,6-dioxo-3-piperidyl)-4-nitro-isoindoline-1,3-dione (43.0 g, 142 mmol) in DMA (1.5 L) was added Pd/C (15.0 g, 14.1 mmol, 10% Pd) under a blanket of $N_2$. The mixture was degassed under vacuum and purged with $H_2$ (3×). The purged mixture was stirred at 40° C. under an atmosphere of $H_2$ (40 psi) for 16 hours. The reaction mixture was purged with $N_2$, filtered and the filtrate was concentrated under vacuum. The residual solid was washed with ethyl acetate (200 mL) and dried under vacuum to give 4-amino-2-(2,6-dioxo-3-piperidyl)isoindoline-1,3-dione as a yellow solid (75 g, 64.5% yield). $^1$H NMR (400 MHz DMSO-$d_6$) δ ppm 11.07 (s, 1H), 7.46 (d, J=6.4 Hz, 1H), 7.00 (t, J=7.0 Hz, 2H), 6.51 (br s, 2H), 5.06-5.01 (m, 1H), 2.93-2.89 (m, 1H), 2.60-2.49 (m, 2H), 2.03-2.00 (m, 1H).

(4-Bromo-2-methyl-phenyl)methoxy-tert-butyl-diphenyl-silane

To a solution of (4-bromo-2-methyl-phenyl)methanol (80.0 g, 398 mmol) in $CH_2Cl_2$ (800 mL) was added imidazole (32.5 g, 477 mmol), DMAP (2.43 g, 20.0 mmol) and tert-butyl-diphenyl-silyl chloride (164 g, 597 mmol). The mixture was stirred at ambient temperature for 16 hours and was diluted with saturated ammonium chloride (1.00 L). The mixture was extracted with ethyl acetate (800 mL×2) and the combined organic fractions were washed with water (600 mL) and saturated NaCl (500 mL). The solution was dried over anhydrous $MgSO_4$, filtered and concentrated. The crude residue was purified by silica gel column chromatography (petroleum ether) to give (4-bromo-2-methyl-phenyl) methoxy-tert-butyl-diphenyl-silane (147 g, 84.1% yield) as light yellow oil. $^1$H NMR (400 MHz $CDCl_3$) δ ppm 7.59 (t, J=6.4 Hz, 4H), 7.36-7.28 (m, 9H), 4.58 (s, 2H), 2.06 (s, 3H), 1.01 (s, 9H).

4-(Hydroxymethyl)-3-methyl-benzaldehyde

A solution of (4-bromo-2-methyl-phenyl)methoxy-tert-butyl-diphenyl-silane (147 g, 334 mmol) in THF (2.0 L) was cooled to −78° C. and n-BuLi (201 mL, 502 mmol, 2.5 M in hexane) was added dropwise, while keeping the temperature below −65° C. After the addition, the reaction mixture was stirred at −65° C. for 30 minutes and DMF (73.4 g, 1.00 mol) was added dropwise keeping the temperature below −60° C. The reaction mixture was stirred at this temperature for 2 hours and was quenched with saturated $NH_4C_1$ (800 mL) below −40° C. Water (800 mL) and ethyl acetate (800 mL) were added and the mixture was stirred for 10 minutes reaching ambient temperature. The organic layer was removed, washed with saturated NaCl (800 mL) and dried over $Na_2SO_4$. The solution was filtered and concentrated to give crude 4-[[tert-butyl(diphenyl)silyl]oxymethyl]-3-methyl-benzaldehyde (130 g) as light yellow oil which was used into next step without any further purification.

To a solution of crude 4-[[tert-butyl(diphenyl)silyl]oxymethyl]-3-methyl-benzaldehyde (130 g, 334 mmol) in THF (2.0 L) was added TBAF-$3H_2O$ (52.3 g, 167 mmol) and the reaction mixture was stirred at ambient temperature for 16 hours. The reaction mixture was diluted with water (800 mL) and extracted with ethyl acetate (500 mL×2). The organic layers were combined, washed with saturated NaCl (800 mL) and dried over anhydrous $Na_2SO_4$. The solution was filtered, concentrated and the residue was purified by silica gel column chromatography (10-20% petroleum ether/ethyl acetate) to give 4-(hydroxymethyl)-3-methyl-benzaldehyde (41.0 g, 81.6% yield) as light yellow oil. $^1$H NMR (400 MHz $CDCl_3$) δ ppm 9.97 (s, 1H), 7.73-7.60 (m, 3H), 4.78 (s, 2H), 2.38 (s, 3H).

4-((4-(Chloromethyl)-3-methylbenzyl)amino)-2-(2,6-dioxopiperidin-3-yl)isoindoline-1,3-dione A solution of 4-amino-2-(2,6-dioxo-3-piperidyl)isoindoline-1,3-dione (30.0 g, 110 mmol) in 20% MeOH/dioxane (725 mL) was cooled to 0° C. and 4-(hydroxymethyl)-3-methyl-benzaldehyde (33.0 g, 220 mmol) and $B_{10}H_{14}$ (26.8 g, 220 mmol) were added sequentially. The mixture was allowed to reach ambient temperature and was stirred for 2 hours. The reaction mixture was concentrated and the residue was treated with EtOH (500 mL). The mixture was stirred for 1 hour and the resulting slurry was filtered. The collected solid cake was washed with ethyl acetate (200 mL) and dried in vacuum to give crude 2-(2,6-dioxopiperidin-3-yl)-4-((4-(hydroxymethyl)-3-methylbenzyl)amino)isoindoline-1,3-dione (39.0 g) as a yellow solid which was used in the next step without further purification.

A solution of 2-(2,6-dioxopiperidin-3-yl)-4-((4-(hydroxymethyl)-3-methylbenzyl)amino)isoindoline-1,3-dione (38.0 g, 93.3 mmol) and DIEA (25.3 g, 196 mmol) in NMP (400 mL) was cooled to 0° C. and methane sulfonyl chloride (21.4 g, 187 mmol) was added over 3 minutes. The ice bath was removed and the reaction was stirred at ambient temperature for 16 hours. The reaction mixture was added dropwise to stirred saturated $NaHCO_3$ (800 mL) diluted with water (800 mL). The resulting slurry was filtered and the product cake was dissolved in $CH_2Cl_2$ (500 mL). The solution was washed with saturated NaCl (200 mL), dried over $Na_2SO_4$, filtered and concentrated. The residue was purified by silica gel column chromatography (20-50% petroleum ether/ethyl acetate). The purified solid was washed with acetonitrile (500 mL) and dried in vacuum to give 4-((4-(chloromethyl)-3-methylbenzyl)amino)-2-(2,6-dioxopiperidin-3-yl)isoindoline-1,3-dione (24.0 g, 60.5% yield) as a yellow solid. $^1$H NMR (400 MHz DMSO-$d_6$) δ ppm 11.08 (s, 1H), 7.47 (d, J=7.2 Hz, 1H), 7.31 (d, J=8.0 Hz, 1H), 7.21-7.16 (m, 3H), 7.00 (d, J=6.8 Hz, 1H), 6.91 (d, J=8.8 Hz, 1H), 5.07-5.03 (m, 1H), 4.73 (s, 2H), 4.50 (d, J=6.4 Hz, 2H), 2.87-2.61 (m, 1H), 2.60-2.47 (m, 2H), 2.33 (s, 3H), 2.05-2.04 (m, 1H). LCMS (ESI) m/z 426.2 $[M+H]^+$.

4-((4-((4-(tert-Butyl)piperazin-1-yl)methyl)-3-methylbenzyl)amino)-2-(2,6-dioxopiperidin-3-yl)isoindoline-1,3-dione 4-((4-(Chloromethyl)-3-methylbenzyl)amino)-2-(2,6-dioxopiperidin-3-yl)isoindoline-1,3-dione (0.075 g, 0.176 mmol), 1-(tert-butyl)piperazine (0.025 g, 0.176 mmol), and DIEA (0.092 mL, 0.528 mmol) were dissolved in DMF (1.0 mL) and the resulting solution was stirred at ambient temperature for 48 hours. The reaction mixture was purified by standard methods to afford 4-((4-((4-(tert-butyl)piperazin-1-yl)methyl)-3-methylbenzyl)amino)-2-(2,6-dioxopiperidin-3-yl)isoindoline-1,3-dione (56.9 mg, 60.8% yield). $^1$H NMR (400 MHz, DMSO-$d_6$) δ ppm 11.10 (s, 1H), 8.20 (s, 1H), 7.52 (dd, J=8.44, 7.21 Hz, 1H), 7.08-7.20 (m, 4H), 7.00 (dd, J=17.85, 7.83 Hz, 2H), 5.07 (dd, J=12.84, 5.26 Hz, 1H), 4.49 (d, J=6.11 Hz, 2H), 3.35 (s, 3H), 2.84-2.98 (m, 1H), 2.54-2.63 (m, 2H), 2.40-2.48 (m, 3H), 2.32-2.39 (m, 3H), 2.28 (s, 3H), 1.96-2.14 (m, 1H), 0.98 (s, 9H). LCMS (ESI) m/z 532.4 $[M+H]^+$.

Example 2: 2-(2,6-Dioxopiperidin-3-yl)-4-((3-((4-ethylpiperidin-1-yl)methyl)-4-methylbenzyl)amino)isoindoline-1,3-dione Hydrochloride

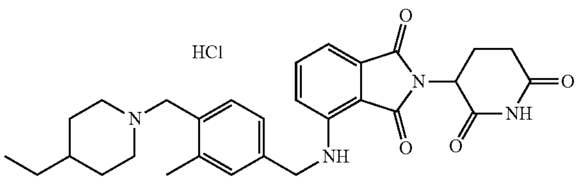 [SMILES: CCC1CCN(Cc2ccc(CNc3cccc4c3C(=O)N(C3CCC(=O)NC3=O)C4=O)cc2C)CC1 ; Cl]

To a solution of 4-((4-(chloromethyl)-3-methylbenzyl)amino)-2-(2,6-dioxopiperidin-3-yl)isoindoline-1,3-dione (0.080 g, 0.188 mmol) (prepared as described herein) and 4-ethylpiperidine (0.040 g, 0.188 mmol) in dry DMSO (0.30 mL) was added DIEA (0.115 mL, 0.657 mmol) and the reaction mixture was stirred at ambient temperature for 24 hours. The reaction was diluted with DMSO (1.5 mL), filtered through a membrane syringe filter (0.45 μm nylon) and the solution was purified by standard methods to afford 2-(2,6-dioxopiperidin-3-yl)-4-((3-((4-ethylpiperidin-1-yl)methyl)-4-methylbenzyl)amino)isoindoline-1,3-dione hydrochloride (56.4 mg, 55.7% yield). LCMS (ESI) m/z 503.6 $[M+H]^+$.

Example 3: 5-(4-(4-(((2-(2,6-Dioxopiperidin-3-yl)-1,3-dioxoisoindolin-4-yl)amino)methyl)-2-methylbenzyl)piperazin-1-yl)picolinamide Hydrochloride

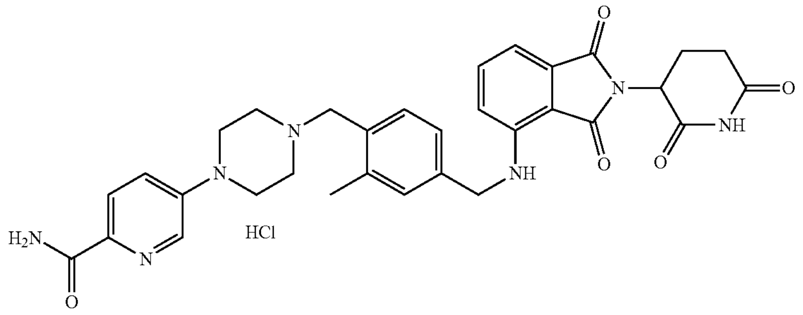 [SMILES: Cc1cc(CNc2cccc3c2C(=O)N(C2CCC(=O)NC2=O)C3=O)ccc1CN1CCN(c2ccc(C(N)=O)nc2)CC1 ; Cl]

To a solution of 4-((4-(chloromethyl)-3-methylbenzyl)amino)-2-(2,6-dioxopiperidin-3-yl)isoindoline-1,3-dione (0.080 g, 0.188 mmol) (prepared as described herein) and 5-(piperazin-1-yl)picolinamide (0.039 g, 0.188 mmol) in dry DMF (0.30 mL) was added DIEA (0.115 mL, 0.657 mmol) and the reaction mixture was stirred at ambient temperature for 24 hours. The reaction was diluted with DMSO (1.5 mL), filtered through a membrane syringe filter (0.45 μm nylon) and the solution was purified by standard methods to afford 5-(4-(4-(((2-(2,6-dioxopiperidin-3-yl)-1,3-dioxoisoindolin-4-yl)amino)methyl)-2-methylbenzyl)piperazin-1-yl)picolinamide hydrochloride (35.0 mg, 29.5% yield). LCMS (ESI) m/z 596.6 $[M+H]^+$.

Example 4: 4-((4-((6-Azaspiro[2.5]octan-6-yl)methyl)-3-methylbenzyl)amino)-2-(2,6-dioxopiperidin-3-yl)isoindoline-1,3-dione Hydrochloride

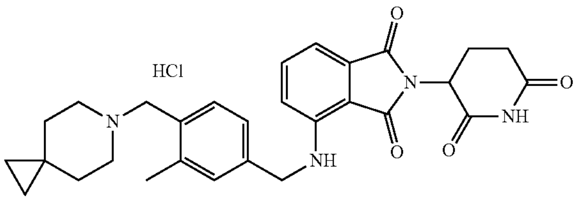 [SMILES: Cc1cc(CNc2cccc3c2C(=O)N(C2CCC(=O)NC2=O)C3=O)ccc1CN1CCC2(CC1)CC2 ; Cl]

To a solution of 4-((4-(chloromethyl)-3-methylbenzyl)amino)-2-(2,6-dioxopiperidin-3-yl)isoindoline-1,3-dione (0.080 g, 0.188 mmol) and 6-azaspiro[2.5]octane (0.021 g, 0.188 mmol) in dry DMF (0.600 mL) was added DIEA (0.115 mL, 0.657 mmol) and the reaction mixture was stirred at ambient temperature for 24 hours. The reaction was diluted with DMSO (1.0 mL), filtered through a membrane syringe filter (0.45 μm nylon) and the solution was purified using standard methods to afford 4-((4-((6-azaspiro[2.5]octan-6-yl)methyl)-3-methylbenzyl)amino)-2-(2,6-dioxopiperidin-3-yl)isoindoline-1,3-dione hydrochloride (76.1 mg, 75.3% yield). LCMS (ESI) m/z 501.6 [M+H]+.

Example 5: 2-(2,6-Dioxopiperidin-3-yl)-4-((4-((4-isopropoxypiperidin-1-yl)methyl)-3-methylbenzyl)amino)isoindoline-1,3-dione

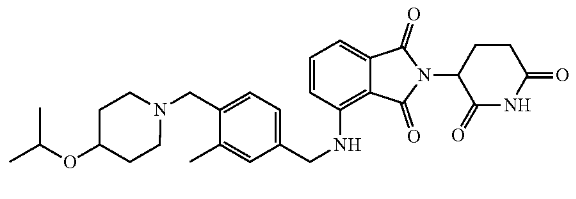 [SMILES: Cc1cc(CNc2cccc3c2C(=O)N(C2CCC(=O)NC2=O)C3=O)ccc1CN1CCC(OC(C)C)CC1]

To a solution of 4-((4-(chloromethyl)-3-methylbenzyl)amino)-2-(2,6-dioxopiperidin-3-yl)isoindoline-1,3-dione (0.080 g, 0.188 mmol) and 4-isopropoxypiperidine (0.027 g, 0.188 mmol) in dry DMF (0.600 mL) was added DIEA (0.115 mL, 0.657 mmol) and the reaction mixture was stirred at ambient temperature for 24 hours. The reaction was diluted with DMSO (1.0 mL), filtered through a membrane syringe filter (0.45 μm nylon) and the solution was purified using standard methods to afford 2-(2,6-dioxopiperidin-3-yl)-4-((4-((4-isopropoxypiperidin-1-yl)methyl)-3-methylbenzyl)amino)isoindoline-1,3-dione (18.9 mg, 18.8%). LCMS (ESI) m/z 533.6 [M+H]+.

Example 6: 4-(4-(4-(((2-(2,6-Dioxopiperidin-3-yl)-1,3-dioxoisoindolin-4-yl)amino)methyl)-2-methylbenzyl)piperazin-1-yl)-3-methylbenzonitrile Hydrochloride

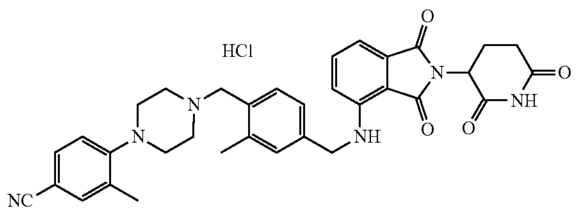 [SMILES: Cc1cc(CNc2cccc3c2C(=O)N(C2CCC(=O)NC2=O)C3=O)ccc1CN1CCN(c2ccc(C#N)cc2C)CC1 ; Cl]

To a mixture of 3-methyl-4-piperazin-1-yl-benzonitrile hydrochloride (0.100 g, 0.420 mmol) in DMF (4.0 mL) was added diisopropylethylamine (0.370 mL, 2.10 mmol) followed by 4-((4-(chloromethyl)-3-methylbenzyl)amino)-2-(2,6-dioxopiperidin-3-yl)isoindoline-1,3-dione (0.179 g, 0.420 mmol). The reaction mixture was stirred at 50° C. for 2 hours, cooled to ambient temperature and diluted with MeOH (1 mL). The mixture was filtered and the filtrate was purified using standard methods to give 4-(4-(4-(((2-(2,6-dioxopiperidin-3-yl)-1,3-dioxoisoindolin-4-yl)amino)methyl)-2-methylbenzyl)piperazin-1-yl)-3-methylbenzonitrile hydrochloride (53.0 mg, 18.9% yield). LCMS (ESI) m/z 591.3 $[M+1]^+$.

Example 7: 5-(4-(4-(((2-(2,6-Dioxopiperidin-3-yl)-1,3-dioxoisoindolin-4-yl)amino)methyl)benzyl)piperazin-1-yl)picolinamide 2-(2,6-Dioxopiperidin-3-yl)-4-((4-(hydroxymethyl)benzyl)amino)isoindoline-1,3-dione To a solution of 4-amino-2-(2,6-dioxo-3-piperidyl)isoindoline-1,3-dione (25.0 g, 91.5 mmol) in 20% MeOH-dioxane (600 mL) was added 4-(hydroxymethyl)benzaldehyde (25.0 g, 184 mmol) and $B_{10}H_{14}$ (22.5 g, 184 mmol). The mixture was stirred at ambient temperature for 2 hours with venting (pressure) and was concentrated. The residue was diluted with ethanol (500 mL) and the mixture stirred for 1 hour. The resulting suspension was filtered, the collected solid cake was washed with ethyl acetate (200 mL) and dried in vacuum to give crude 2-(2,6-dioxopiperidin-3-yl)-4-((4-(hydroxymethyl)benzyl)amino)isoindoline-1,3-dione (28.0 g) as a yellow-green solid which was used in next step without further purification. LCMS (ESI) m/z 376.2 $[MH-18]^+$.

4-((4-(Chloromethyl)benzyl)amino)-2-(2,6-dioxopiperidin-3-yl)isoindoline-1,3-dione A solution of crude 2-(2,6-dioxo-3-piperidyl)-4-[[4-(hydroxymethyl)phenyl]methylamino]isoindo line-1,3-dione (28.0 g, 71.2 mmol) and DIEA (26.1 mL, 150 mmol) in NMP (285 mL) was purged with a nitrogen atmosphere and cooled to 0° C. Methane sulfonyl chloride (16.3 g, 142 mmol) was added dropwise over 5 minutes and the mixture was allowed to reach ambient temperature. The mixture was stirred at ambient temperature for 16 hours and was added dropwise to stirred saturated $NaHCO_3$ (800 mL) diluted with $H_2O$ (800 mL). The resulting suspension was filtered and the collected solid cake washed with $H_2O$ (500 mL) and acetonitrile (500 mL). The solid was dried in vacuum to give 4-((4-(chloromethyl)benzyl)amino)-2-(2,6-dioxopiperidin-3-yl)isoindoline-1,3-dione as a yellow solid (22.7 g, 77.5% yield). $^1H$ NMR (400 MHz DMSO-$d_6$) δ ppm 11.12 (s, 1H), 7.51-7.28 (m, 6H), 7.03 (d, J=6.8 Hz, 1H), 6.94 (d, J=8.0 Hz, 1H), 5.11-5.06 (m, 1H), 4.74 (s, 2H), 4.58 (d, J=6.0 Hz, 2H), 2.94-2.86 (m, 1H), 2.63-2.51 (m, 2H), 2.08-2.05 (m, 1H). LCMS (ESI) m/z 412.1 $[M+H]^+$.

5-(4-(4-(((2-(2,6-Dioxopiperidin-3-yl)-1,3-dioxoisoindolin-4-yl)amino)methyl)benzyl)piperazin-1-yl)picolinamide To a solution of 4-((4-(chloromethyl)benzyl)amino)-2-(2,6-dioxopiperidin-3-yl)isoindoline-1,3-dione (300 mg, 0.619

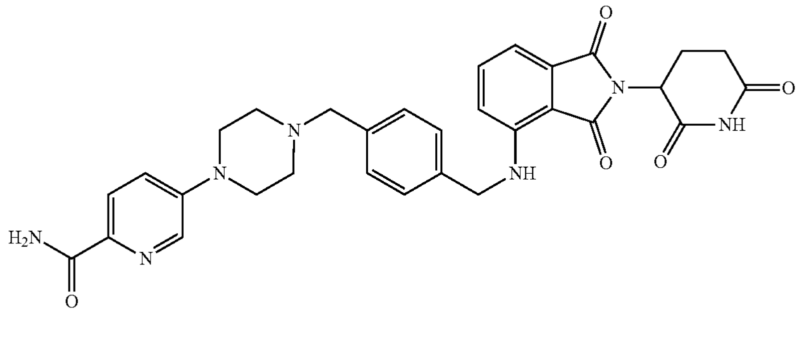 [SMILES: NC(=O)c1ccc(N2CCN(Cc3ccc(CNc4cccc5c4C(=O)N(C4CCC(=O)NC4=O)C5=O)cc3)CC2)cn1]

mmol) in anhydrous DMSO (3.0 mL) were sequentially added 5-(piperazin-1-yl)picolinamide (153 mg, 0.743 mmol) and DIEA (108 μL, 0.619 mmol). The reaction mixture was stirred at ambient temperature for 16 hours and was diluted with 15% formic acid in DMSO (3 mL). The mixture was filtered through a membrane syringe filter (0.45 μm nylon) and the solution was purified using standard methods to provide 5-(4-(4-(((2-(2,6-dioxopiperidin-3-yl)-1,3-dioxoisoindolin-4-yl)amino)methyl)benzyl)piperazin-1-yl)picolinamide (255 mg, 70.8%). LCMS (ESI) m/z 582.2 $[M+H]^+$.

Example 8: 4-(1-(4-(((2-(2,6-Dioxopiperidin-3-yl)-1,3-dioxoisoindolin-4-yl)amino)methyl)benzyl)azetidin-3-yl)benzonitrile Hydrochloride

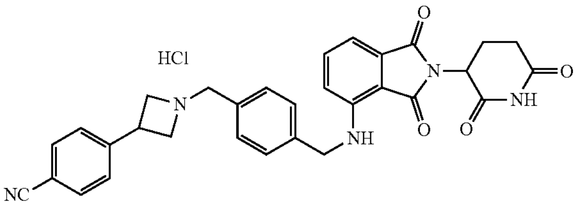 [SMILES: N#Cc1ccc(C2CN(Cc3ccc(CNc4cccc5c4C(=O)N(C4CCC(=O)NC4=O)C5=O)cc3)C2)cc1 ; Cl]

To a solution of 4-((4-(chloromethyl)benzyl)amino)-2-(2,6-dioxopiperidin-3-yl)isoindoline-1,3-dione (0.062 g, 0.150 mmol) and 4-(azetidin-3-yl)benzonitrile hydrochloride (0.031 g, 0.180 mmol) in dry DMF (0.30 mL) was added DIEA (0.079 mL, 0.450 mmol) and the reaction mixture was stirred at ambient temperature for 24 hours. The reaction was quenched with chilled 10% formic acid in DMSO (1.5 mL), filtered through a membrane syringe filter (0.45 μm nylon) and the solution was purified using standard methods to afford 4-(1-(4-(((2-(2,6-dioxopiperidin-3-yl)-1,3-dioxoisoindolin-4-yl)amino)methyl)benzyl)azetidin-3-yl)benzonitrile hydrochloride (31.0 mg, 36.3% yield). LCMS (ESI) m/z 534.2 $[M+H]^+$.

Example 9: 2-(2,6-Dioxopiperidin-3-yl)-4-((4-((4-(5-fluoropyridin-2-yl)piperazin-1-yl)methyl)benzyl)amino)isoindoline-1,3-dione

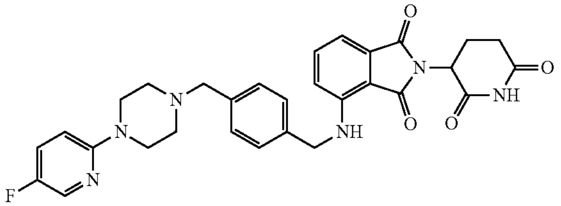 [SMILES: O=C1CCC(N2C(=O)c3cccc(NCc4ccc(CN5CCN(c6ccc(F)cn6)CC5)cc4)c3C2=O)C(=O)N1]

A mixture of 4-((4-(chloromethyl)benzyl)amino)-2-(2,6-dioxopiperidin-3-yl)isoindoline-1,3-dione (0.20 g, 0.487 mmol), DIEA (0.296 mL, 1.70 mmol), and 1-(5-fluoro-2-pyridyl)piperazine (153.7 mg, 0.848 mmol) in DMF (3.00 mL) was stirred at 50° C. for 24 hours under $N_2$ atmosphere. The reaction mixture was diluted with $H_2O$ (30 mL) and extracted with ethyl acetate (3×30 mL). The combined organic layers were washed with saturated sodium chloride (3×20 mL), dried over $Na_2SO_4$, filtered and concentrated under reduced pressure. The residue was purified by standard methods to give 2-(2,6-dioxopiperidin-3-yl)-4-((4-((4-(5-fluoropyridin-2-yl)piperazin-1-yl)methyl)benzyl)amino)isoindoline-1,3-dione hydrochloride (238 mg, 97.6% yield). LCMS (ESI) m/z 557.3 $[M+H]^+$.

Example 10: 6-(4-(4-(((2-(2,6-Dioxopiperidin-3-yl)-1,3-dioxoisoindolin-4-yl)amino)methyl)benzyl)piperazin-1-yl)nicotinamide

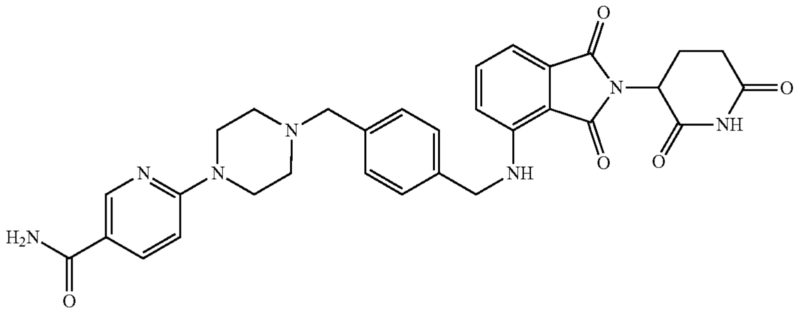 [SMILES: NC(=O)c1ccc(N2CCN(Cc3ccc(CNc4cccc5c4C(=O)N(C4CCC(=O)NC4=O)C5=O)cc3)CC2)nc1]

4-((4-(Chloromethyl)benzyl)amino)-2-(2,6-dioxopiperidin-3-yl)isoindoline-1,3-dione (0.216 g, 0.524 mmol), 6-(piperazin-1-yl)nicotinamide (0.108 g, 0.524 mmol), and DIEA (0.275 mL, 1.57 mmol) were dissolved in DMF (2.9 mL) and the mixture was stirred for 16 hours at ambient temperature. The mixture was purified using standard methods to afford 6-(4-(4-(((2-(2,6-dioxopiperidin-3-yl)-1,3-dioxoisoindolin-4-yl)amino)methyl)benzyl)piperazin-1-yl)

nicotinamide (125 mg, 41.0% yield). $^{1}$H NMR (400 MHz, DMSO-$d_6$) δ ppm 11.10 (s, 1H), 8.59 (d, J=2.20 Hz, 1H), 7.94 (dd, J=9.05, 2.45 Hz, 1H), 7.74 (br d, J=1.96 Hz, 1H), 7.44-7.56 (m, 1H), 7.32 (q, J=8.23 Hz, 4H), 7.20 (br t, J=6.24 Hz, 1H), 7.05-7.15 (m, 1H), 7.00 (dd, J=15.65, 7.83 Hz, 2H), 6.80 (d, J=9.05 Hz, 1H), 5.07 (dd, J=12.84, 5.26 Hz, 1H), 4.55 (br d, J=6.36 Hz, 2H), 3.56 (br d, J=4.65 Hz, 4H), 3.48 (s, 2H), 2.81-2.99 (m, 1H), 2.54-2.64 (m, 2H), 2.42 (br t, J=4.77 Hz, 4H), 1.96-2.10 (m, 1H). LCMS (ESI) m/z 582.2 [M+H]$^+$.

Example 11: 5-(4-(4-(((2-(2,6-Dioxopiperidin-3-yl)-1,3-dioxoisoindolin-4-yl)amino)methyl)benzyl)piperazin-1-yl)-N,N-dimethylpicolinamide

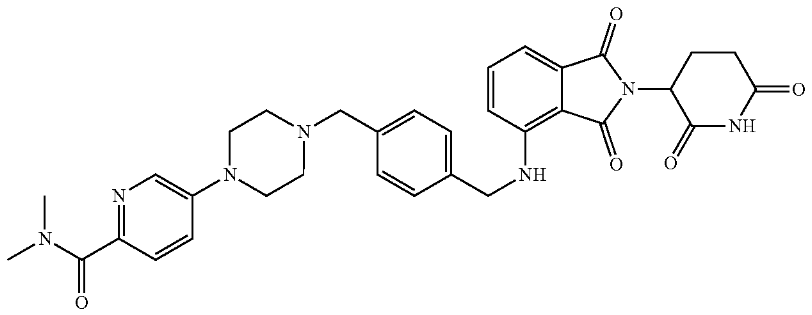 [SMILES: CN(C)C(=O)c1ccc(N2CCN(Cc3ccc(CNc4cccc5c4C(=O)N(C4CCC(=O)NC4=O)C5=O)cc3)CC2)cn1]

4-((4-(Chloromethyl)benzyl)amino)-2-(2,6-dioxopiperidin-3-yl)isoindoline-1,3-dione (0.450 g, 1.09 mmol), N,N-dimethyl-5-(piperazin-1-yl)picolinamide hydrochloride (0.444 g, 1.64 mmol), and DIEA (0.954 mL, 5.46 mmol) were dissolved in DMF (6.0 mL) and the mixture was stirred at ambient temperature for 72 hours. The mixture was purified using standard methods to afford 5-(4-(4-(((2-(2,6-dioxopiperidin-3-yl)-1,3-dioxoisoindolin-4-yl)amino)methyl)benzyl)piperazin-1-yl)-N,N-dimethylpicolinamide (177 mg, 26.6% yield). $^{1}$H NMR (400 MHz, DMSO-$d_6$) δ ppm 11.10 (s, 1H), 8.22 (br d, J=1.96 Hz, 1H), 7.42-7.59 (m, 2H), 7.27-7.39 (m, 5H), 7.21 (br t, J=5.62 Hz, 1H), 7.00 (br dd, J=15.53, 7.70 Hz, 2H), 5.07 (br dd, J=12.59, 5.01 Hz, 1H), 4.55 (br d, J=5.87 Hz, 2H), 3.50 (s, 2H), 3.27 (br s, 4H), 2.80-3.10 (m, 7H), 2.54-2.64 (m, 2H), 2.39-2.48 (m, 4H), 2.05 (br dd, J=10.51, 4.89 Hz, 1H). LCMS (ESI) m/z 610.4 [M+H]$^+$.

Example 12: 4-((4-((4-(1H-Pyrazol-1-yl)piperidin-1-yl)methyl)benzyl)amino)-2-(2,6-dioxopiperidin-3-yl)isoindoline-1,3-dione Hydrochloride

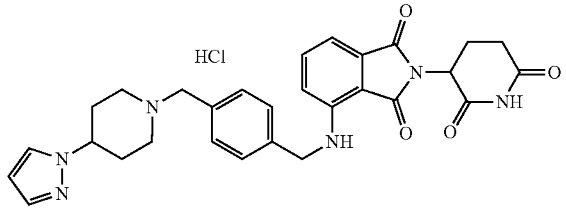 [SMILES: O=C1CCC(N2C(=O)c3cccc(NCc4ccc(CN5CCC(n6cccn6)CC5)cc4)c3C2=O)C(=O)N1 ; Cl]

To a solution of 4-((4-(chloromethyl)benzyl)amino)-2-(2,6-dioxopiperidin-3-yl)isoindoline-1,3-dione (0.200 g, 0.486 mmol) and 4-(1H-pyrazol-1-yl)piperidine (0.073 g, 0.486 mmol) in dry DMF (1.50 mL) was added DIEA (0.297 mL, 1.70 mmol) and the reaction mixture was stirred at ambient temperature for 24 hours. The reaction was diluted with DMSO (2.0 mL), filtered through a membrane syringe filter (0.45 μm nylon) and the solution was purified using standard methods to afford 4-((4-((4-(1H-pyrazol-1-yl)piperidin-1-yl)methyl)benzyl)amino)-2-(2,6-dioxopiperidin-3-yl)isoindoline-1,3-dione hydrochloride (69.9 mg, 25.6%). LCMS (ESI) m/z 527.6 [M+H]$^+$.

Example 13: 4-(4-(4-(((2-(2,6-Dioxopiperidin-3-yl)-1,3-dioxoisoindolin-4-yl)amino)methyl)benzyl)piperazin-1-yl)benzamide

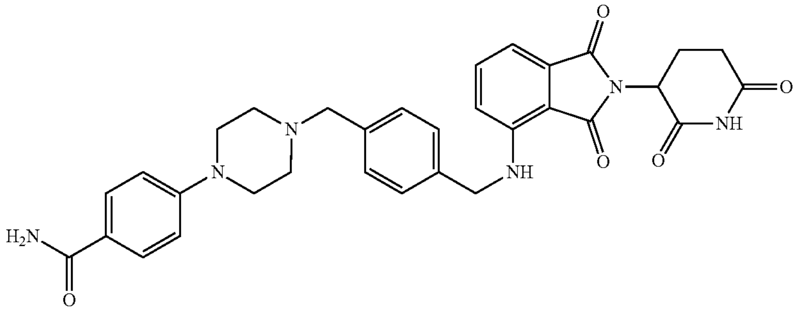 [SMILES: NC(=O)c1ccc(N2CCN(Cc3ccc(CNc4cccc5c4C(=O)N(C4CCC(=O)NC4=O)C5=O)cc3)CC2)cc1]

4-((4-(Chloromethyl)benzyl)amino)-2-(2,6-dioxopiperidin-3-yl)isoindoline-1,3-dione (0.075 g, 0.182 mmol), 4-(piperazin-1-yl)benzamide hydrochloride (0.044 g, 0.182 mmol), and DIEA (0.127 mL, 0.728 mmol) were dissolved in DMF (1.0 mL) and the resulting solution was stirred for 16 hours at ambient temperature. The reaction was stirred at 50° C. for an additional 5 hours and was cooled to ambient temperature. The mixture was purified using standard methods to afford 4-(4-(4-(((2-(2,6-dioxopiperidin-3-yl)-1,3-dioxoisoindolin-4-yl)amino)methyl)benzyl)piperazin-1-yl) benzamide (71.4 mg, 67.5% yield). $^1$H NMR (400 MHz, DMSO-$d_6$) δ ppm 11.11 (s, 1H), 7.65-7.79 (m, 3H), 7.52 (t, J=7.83 Hz, 1H), 7.27-7.40 (m, 4H), 7.21 (br t, J=6.36 Hz, 1H), 7.01 (dd, J=15.65, 7.82 Hz, 3H), 6.91 (d, J=8.80 Hz, 2H), 5.08 (dd, J=12.96, 5.38 Hz, 1H), 4.56 (br d, J=6.36 Hz, 2H), 3.49 (s, 2H), 3.23 (br s, 4H), 2.84-2.96 (m, 1H), 2.55 (s, 2H), 2.48 (br s, 4H), 2.06 (br dd, J=10.64, 5.50 Hz, 1H). LCMS (ESI) m/z 581.4 $[M+H]^+$.

Example 14: (S)-6-(4-(4-(((2-(2,6-Dioxopiperidin-3-yl)-1,3-dioxoisoindolin-4-yl)amino)methyl)benzyl) piperazin-1-yl)nicotinamide

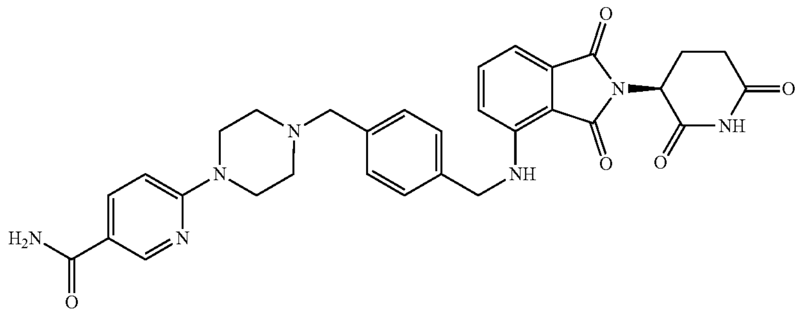 [SMILES: NC(=O)c1ccc(N2CCN(Cc3ccc(CNc4cccc5c4C(=O)N([C@H]4CCC(=O)NC4=O)C5=O)cc3)CC2)nc1]

(S)-2-(2,6-Dioxopiperidin-3-yl)-4-((4-(hydroxymethyl)benzyl)amino)isoindoline-1,3-dione A suspension of (S)-4-amino-2-(2,6-dioxopiperidin-3-yl) isoindoline-1,3-dione (1.37 g, 5.00 mmol) (prepared as described in U.S. patent publication US 2007/0004920) and 4-(hydroxymethyl)benzaldehyde (0.817 g, 6.00 mmol) in dry 2:1 dioxane-MeOH (25 mL) was cooled to 0° C. and decaborane (1.34 g, 9.90 mmol) was added in small portions over 2 minutes. The reaction flask was fitted with a septum and needle vent and the mixture was stirred vigorously for 10 minutes. The resulting solution was allowed to reach ambient temperature and stirred for 3 hours. The mixture was concentrated and the residual yellow foam was purified on a silica gel column (Biotage KP-Sil 50 g, 0-10% MeOH—$CH_2Cl_2$ gradient). The product was suspended in MTBE (75 mL) and stirred vigorously for 16 hours. The suspension was collected, washed with MTBE and dried in vacuum to provide (S)-2-(2,6-dioxopiperidin-3-yl)-4-((4-(hydroxymethyl)benzyl)amino)isoindoline-1,3-dione (1.82 g, 93% yield) as a yellow solid. LCMS (ESI) m/z 394.0 $[M+H]^+$.

(S)-4-((4-(Chloromethyl)benzyl)amino)-2-(2,6-dioxopiperidin-3-yl)isoindoline-1,3-dione A solution of (S)-2-(2,6-dioxopiperidin-3-yl)-4-((4-(hydroxymethyl)benzyl)amino)isoindoline-1,3-dione (1.50 g, 3.81 mmol) in dry NMP (12 mL) was cooled to 0° C. and methane sulfonyl chloride (0.594 mL, 7.63 mmol) and DIEA (1.33 mL, 7.63 mmol) were added sequentially. The mixture was stirred for 7 hours during which time the temperature slowly reached ambient temperature over 2 hours. Additional methane sulfonyl chloride (0.120 mL) and DIEA (0.260 mL) were added and the mixture was stirred for 15 hours. The reaction mixture was slowly added to $H_2O$ (60 mL) cooled to 0° C. with vigorous mixing. The resulting yellow slurry was stirred for 10 minutes and the precipitate was collected by vacuum filtration. The collected solid was washed with $H_2O$ and $Et_2O$ and dissolved in EtOAc. The solution was dried over $MgSO_4$, filtered and concentrated to give crude (S)-4-((4-(chloromethyl)benzyl)amino)-2-(2,6-dioxopiperidin-3-yl)isoindoline-1,3-dione as a yellow solid that was used in the next step without further purification. LCMS (ESI) m/z 412.0 $[M+H]^+$.

(S)-6-(4-(4-(((2-(2,6-Dioxopiperidin-3-yl)-1,3-dioxoisoindolin-4-yl)amino)methyl)benzyl)piperazin-1-yl)nicotinamide To a solution of crude (S)-4-((4-(chloromethyl)benzyl) amino)-2-(2,6-dioxopiperidin-3-yl)isoindoline-1,3-dione (242 mg, 0.500 mmol) in dry DMSO (1.5 mL) was added 6-(piperazin-1-yl)nicotinamide (113 mg, 0.550 mmol) and the mixture stirred for 15 minutes. To the resulting solution DIEA (0.087 mL, 0.500 mmol) was added and the mixture was stirred at ambient temperature for 16 hours. The reaction mixture was diluted with 20% formic acid in DMSO (3 mL) and filtered (nylon, 45 μm). The solution was purified by standard methods to yield (S)-6-(4-(4-(((2-(2,6-dioxopiperidin-3-yl)-1,3-dioxoisoindolin-4-yl)amino)methyl)benzyl)piperazin-1-yl)nicotinamide (156 mg, 54%). LCMS (ESI) m/z 582.2 $[M+H]^+$. 88% ee by chiral HPLC.

Example 15: (R)-6-(4-(4-(((2-(2,6-Dioxopiperidin-3-yl)-1,3-dioxoisoindolin-4-yl)amino)methyl)benzyl)piperazin-1-yl)nicotinamide

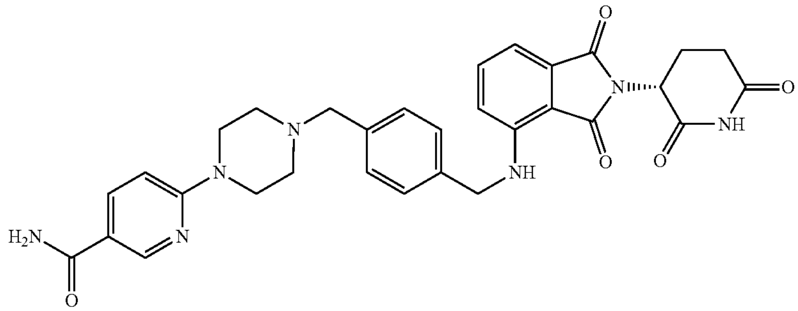 [SMILES: NC(=O)c1ccc(N2CCN(Cc3ccc(CNc4cccc5c4C(=O)N([C@@H]4CCC(=O)NC4=O)C5=O)cc3)CC2)nc1]

The material obtained in example 14 was further purified by chiral reverse-phase chromatography to yield (S)-6-(4-(4-(((2-(2,6-dioxopiperidin-3-yl)-1,3-dioxoisoindolin-4-yl)amino)methyl)benzyl)piperazin-1-yl)nicotinamide (119 mg, >99% ee), LCMS (ESI) m/z 582.2 $[M+H]^+$, and (R)-6-(4-(4-(((2-(2,6-dioxopiperidin-3-yl)-1,3-dioxoisoindolin-4-yl)amino)methyl)benzyl)piperazin-1-yl)nicotinamide (6 mg, >99% ee), LCMS (ESI) m/z 582.2 $[M+H]^+$.

Example 16: 4-(4-(4-(((2-(2,6-Dioxopiperidin-3-yl)-1,3-dioxoisoindolin-4-yl)amino)methyl)benzyl)piperazin-1-yl)picolinamide

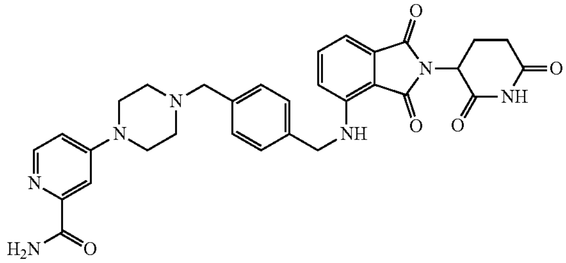 [SMILES: NC(=O)c1cc(N2CCN(Cc3ccc(CNc4cccc5c4C(=O)N(C4CCC(=O)NC4=O)C5=O)cc3)CC2)ccn1]

To a solution of 4-((4-(chloromethyl)benzyl)amino)-2-(2,6-dioxopiperidin-3-yl)isoindoline-1,3-dione (0.080 g, 0.194 mmol) and 6-(piperazin-1-yl)picolinamide (0.040 g, 0.188 mmol) in dry DMSO (0.30 mL) was added DIEA (0.102 mL, 0.583 mmol) and the reaction mixture was stirred at ambient temperature for 24 hours. The reaction was diluted with DMSO (1.5 mL), filtered through a membrane syringe filter (0.45 μm nylon) and the solution was purified using standard methods to afford 6-(4-(4-(((2-(2,6-dioxopiperidin-3-yl)-1,3-dioxoisoindolin-4-yl)amino)methyl)benzyl)piperazin-1-yl)picolinamide (41.0 mg, 36.3% yield). LCMS (ESI) m/z 582.6 $[M+H]^+$.

Example 17: 2-(2,6-Dioxopiperidin-3-yl)-4-((4-((4-ethylpiperidin-1-yl)methyl)benzyl)amino)isoindoline-1,3-dione Hydrochloride

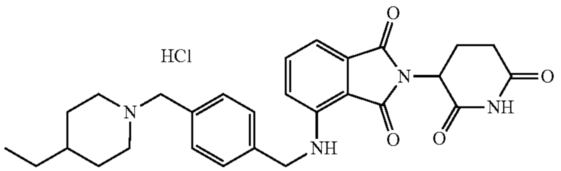 [SMILES: CCC1CCN(Cc2ccc(CNc3cccc4c3C(=O)N(C3CCC(=O)NC3=O)C4=O)cc2)CC1 ; Cl]

To a solution of 4-((4-(chloromethyl)benzyl)amino)-2-(2,6-dioxopiperidin-3-yl)isoindoline-1,3-dione (0.200 g, 0.486 mmol) and 4-ethylpiperidine (0.055 g, 0.486 mmol) in dry DMF (1.50 mL) was added DIEA (0.297 mL, 1.70 mmol) and the reaction mixture was stirred at ambient temperature for 24 hours. The reaction was diluted with DMSO (2.0 mL), filtered through a membrane syringe filter (0.45 μm nylon) and the solution was purified using standard methods to afford 2-(2,6-dioxopiperidin-3-yl)-4-((4-((4-ethylpiperidin-1-yl)methyl)benzyl)amino)isoindoline-1,3-dione hydrochloride (127.4 mg, 50.0% yield). LCMS (ESI) m/z 489.6 $[M+H]^+$.

Example 18: 4-((4-((2-Azaspiro[3.3]heptan-2-yl)methyl)-2-fluorobenzyl)amino)-2-(2,6-dioxopiperidin-3-yl)isoindoline-1,3-dione

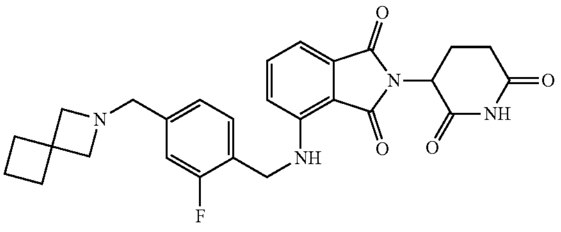 [SMILES: O=C1CCC(N2C(=O)c3cccc(NCc4ccc(CN5CC6(CCC6)C5)cc4F)c3C2=O)C(=O)N1]

(4-Bromo-3-fluorophenyl)methanol

A solution of 4-bromo-3-fluoro-benzoic acid (15.0 g, 68.5 mmol) in THF (150 mL) was cooled to 0° C. and borane-dimethyl sulfide complex (13.7 mL, 137 mmol, 10 M in THF) was added dropwise under nitrogen atmosphere. The cooling bath was removed and the mixture was stirred at ambient temperature for 12 hours. The mixture was cooled to 0° C., quenched with MeOH (50 mL) and poured into water (30 mL). The mixture was concentrated under vacuum and the residual aqueous mixture was diluted with ethyl acetate (150 mL) and water (150 mL) and stirred for 15 minutes. The organic phase was removed and the aqueous phase was extracted with ethyl acetate (150 mL×2). The organic fractions were combined, dried with anhydrous sodium sulfate, filtered, and concentrated under vacuum. The residue was purified by silica gel column chromatography (2-10% ethyl acetate in petroleum ether) to give 4-bromo-3-fluoro-phenyl)methanol (13.1 g, 93.3% yield) as a colorless liquid. LCMS (ESI) m/z 187.0 [MH−18⁻]. $^1$H NMR (400 MHz, $CDCl_3$) δ ppm 7.54-7.45 (m, 1H), 7.14 (d, J=9.2 Hz, 1H), 7.00 (d, J=7.9 Hz, 1H), 4.64 (d, J=4.6 Hz, 2H), 2.20 (br s, 1H).

(4-Bromo-3-fluoro-phenyl)methoxy-tert-butyl-dimethyl-silane

A solution of (4-bromo-3-fluoro-phenyl)methanol (13.1 g, 63.9 mmol) and imidazole (12.2 g, 179 mmol) in DMF (150 mL) was cooled to 0° C. and tert-butylchlorodimethylsilane (14.4 g, 95.8 mmol) was added. The cooling bath was removed and the mixture was stirred at ambient temperature for 16 hours. The reaction was poured into chilled water (30 mL), diluted with ethyl acetate (100 mL) and water (100 mL) and stirred for 15 minutes. The organic phase was removed and the aqueous phase was extracted with ethyl acetate (150 mL×2). The organic fractions were combined, washed with saturated NaCl (50 mL×2), dried with anhydrous sodium sulfate, filtered and concentrated under vacuum. The residue was purified by silica gel column chromatography (0-10% ethyl acetate in petroleum ether) to give (4-bromo-3-fluoro-phenyl)methoxy-tert-butyl-dimethyl-silane (18.6 g, 91.2% yield) as a colorless liquid. $^1$H NMR (400 MHz, $CDCl_3$) δ ppm 7.49 (dd, J=7.1, 8.1 Hz, 1H), 7.18-7.08 (m, 1H), 7.01-6.92 (m, 1H), 4.69 (s, 2H), 0.96 (s, 9H), 0.12 (s, 6H).

4-[[tert-Butyl(dimethyl)silyl]oxymethyl]-2-fluoro-benzaldehyde

Under an atmosphere of nitrogen a solution of (4-bromo-3-fluoro-phenyl)methoxy-tert-butyl-dimethyl-silane (18.6 g, 58.3 mmol) in THF (150 mL) was cooled to −78° C. and n-BuLi (25.6 mL, 64.0 mmol, 2.5 M in hexane) was added dropwise. The mixture was stirred at −78° C. for 5 minutes and DMF (5.83 mL, 75.7 mmol) was added. The mixture was stirred at −78° C. for 2 hours and allowed to warm to ambient temperature. The reaction mixture was cooled to 0° C. and quenched with saturated ammonium chloride (60 mL) and water (30 mL). The mixture was extracted with ethyl acetate (2×150 mL) and the combined extracts were dried over sodium sulfate, filtered and concentrated. The residue was purified by silica gel column chromatography (0-2% ethyl acetate in petroleum ether) to give 4-[[tert-butyl(dimethyl)silyl]oxymethyl]-2-fluoro-benzaldehyde (11.5 g, 73.5% yield) as a yellow liquid. MS (ESI) m/z: 269.1 [M+1]$^+$.

3-((4-(((tert-Butyldimethylsilyl)oxy)methyl)-2-fluorobenzyl)amino)phthalic acid

A solution of 4-[[tert-butyl(dimethyl)silyl]oxymethyl]-2-fluoro-benzaldehyde (7.50 g, 27.9 mmol) and 3-aminophthalic acid (5.06 g, 27.9 mmol) in 1:10 acetic acid-MeOH (110 mL) was stirred at 25° C. for 30 minutes and was cooled to 0° C. Borane 2-methylpyridine complex (4.48 g, 41.9 mmol) was added and the mixture was allowed to reach ambient temperature. The mixture was stirred at ambient temperature for 16 hours and the mixture was concentrated under reduced pressure. The residue was diluted with water (25 mL) and ethyl acetate (25 mL) and stirred for 15 minutes. The organic layer was removed and the aqueous layer was extracted with ethyl acetate (30 mL×2). The organic fractions were combined, dried with anhydrous sodium sulfate, filtered, and concentrated. The residue was purified by silica gel column chromatography (2-5% ethyl acetate in petroleum ether) to give 3-((4-(((tert-butyldimethylsilyl)oxy)methyl)-2-fluorobenzyl)amino)phthalic acid (9.90 g, 81.8% yield) as a white solid. LCMS (ESI) m/z: 434.1 [M+1]$^+$.

4-((4-(((tert-Butyldimethylsilyl)oxy)methyl)-2-fluorobenzyl)amino)-2-(2,6-dioxopiperidin-3-yl)isoindoline-1,3-dione A solution of 3-((4-(((tert-butyldimethylsilyl)oxy)methyl)-2-fluorobenzyl)amino)phthalic acid (11.8 g, 27.2 mmol) and 3-aminopiperidine-2,6-dione hydrochloride (6.72 g, 40.8 mmol) in pyridine (150 mL) was stirred at 120° C. for 12 hours under a nitrogen atmosphere. The mixture was concentrated under reduced pressure and the residue was purified by silica gel column chromatography (2-5% ethyl acetate in petroleum ether) to give 4-((4-(((tert-butyldimethylsilyl)oxy)methyl)-2-fluorobenzyl)amino)-2-(2,6-dioxopiperidin-3-yl)isoindoline-1,3-dione (9.90 g, 69.2% yield) as a yellow solid. LCMS (ESI) m/z: 526.2 [M+1]$^+$.

2-(2,6-Dioxopiperidin-3-yl)-4-((2-fluoro-4-(hydroxymethyl)benzyl)amino)isoindoline-1,3-dione To a solution of 4-((4-(((tert-butyldimethylsilyl)oxy)methyl)-2-fluorobenzyl)amino)-2-(2,6-dioxopiperidin-3-yl)isoindoline-1,3-dione (9.90 g, 18.8 mmol) in THF (100 mL) was added concentrated sulfuric acid (20.0 mL, 368 mmol) and the mixture was stirred at ambient temperature for 12 hours. The mixture was concentrated under vacuum and the residue was treated with 1:5 ethyl acetate-petroleum ether (20 mL). The resulting suspension was stirred for 30 minutes and filtered. The collected solid was washed with 1:5 ethyl acetate-petroleum ether and dried in vacuum to give 2-(2,6-dioxopiperidin-3-yl)-4-((2-fluoro-4-(hydroxymethyl)benzyl)amino)isoindoline-1,3-dione (6.58 g, 85.2% yield) as a yellow solid. MS (ESI) m/z: 412.0 [M+1]$^+$. $^1$H NMR (400 MHz, DMSO-$d_6$) δ ppm 11.12 (s, 1H), 7.54 (dd, J=7.3, 8.4 Hz, 1H), 7.33 (t, J=7.8 Hz, 1H), 7.16-7.07 (m, 3H), 7.05 (d, J=7.0 Hz, 1H), 6.99 (d, J=8.5 Hz, 1H), 5.33-5.25 (m, 1H), 5.07 (dd, J=5.3, 12.9 Hz, 1H), 4.59 (d, J=6.3 Hz, 2H), 4.47 (d, J=5.8 Hz, 2H), 2.95-2.84 (m, 1H), 2.65-2.52 (m, 2H), 2.09-2.01 (m, 1H).

4-((4-(chloromethyl)-2-fluorobenzyl)amino)-2-(2,6-dioxopiperidin-3-yl)isoindoline-1,3-dione A solution of 2-(2,6-dioxopiperidin-3-yl)-4-((2-fluoro-4-(hydroxymethyl)benzyl)amino)isoindoline-1,3-dione (6.58 g, 16.0 mmol) in dichloromethane (200 mL) was cooled to 0° C. and thionyl chloride (20.0 mL, 276 mmol) was added dropwise. After complete addition, the cooling bath was removed and the reaction mixture was stirred at ambient temperature for 2 hours. The mixture was concentrated under vacuum and the residue was purified by silica gel column chromatography (1.00-1.25% MeOH in dichloromethane) to give 4-((4-(chloromethyl)-2-fluorobenzyl)amino)-2-(2,6-dioxopiperidin-3-yl)isoindoline-1,3-dione (3.80 g, 55.4% yield) as a yellow solid. LCMS (ESI) m/z: 430.0 $[M+1]^+$. $^1H$ NMR (400 MHz, DMSO-$d_6$) δ ppm 11.12 (s, 1H), 7.54 (dd, J=7.3, 8.4 Hz, 1H), 7.38 (t, J=7.9 Hz, 1H), 7.32 (dd, J=1.5, 11.0 Hz, 1H), 7.24 (dd, J=1.6, 7.8 Hz, 1H), 7.16 (t, J=6.3 Hz, 1H), 7.06 (d, J=6.9 Hz, 1H), 6.98 (d, J=8.5 Hz, 1H), 5.08 (dd, J=5.3, 12.9 Hz, 1H), 4.74 (s, 2H), 4.63 (d, J=6.3 Hz, 2H), 2.95-2.85 (m, 1H), 2.66-2.53 (m, 2H), 2.09-2.02 (m, 1H).

4-((4-((2-Azaspiro[3.3]heptan-2-yl)methyl)-2-fluorobenzyl)amino)-2-(2,6-dioxopiperidin-3-yl)isoindoline-1,3-dione To a solution of 4-((4-(chloromethyl)-2-fluorobenzyl)amino)-2-(2,6-dioxopiperidin-3-yl)isoindoline-1,3-dione (0.200 g, 0.486 mmol) and 2-azaspiro[3.3]heptane (0.132 g, 0.931 mmol) in dry DMF (1.00 mL) was added DIEA (0.284 mL, 1.63 mmol) and the reaction mixture was stirred at ambient temperature for 24 hours. The reaction was diluted with DMSO (2.0 mL), filtered through a membrane syringe filter (0.45 μm nylon) and the solution was purified using standard methods to afford 2-(2,6-dioxopiperidin-3-yl)-4-((4-((4-ethylpiperidin-yl)methyl)benzyl)amino)isoindoline-1,3-dione (18.6 mg, 8.2% yield). LCMS (ESI) m/z 491.5 $[M+H]^+$.

Example 19: 2-(2,6-Dioxopiperidin-3-yl)-4-((2-fluoro-4-((3-morpholinoazetidin-1-yl)methyl)benzyl)amino)isoindoline-1,3-dione

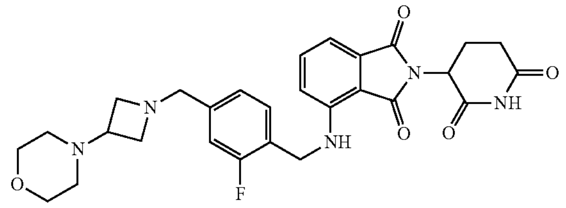

To a solution of 4-((4-(chloromethyl)-2-fluorobenzyl)amino)-2-(2,6-dioxopiperidin-3-yl)isoindoline-1,3-dione (215 mg, 0.500 mmol) (prepared as described herein) and 4-(azetidin-3-yl)morpholine hydrochloride (107 mg, 0.600 mmol) in dry DMSO (1.7 mL) was added DIEA (262 μL, 1.50 mmol) and the mixture stirred at ambient temperature for 48 hours. The reaction mixture was diluted with 20% formic acid in DMSO (2.5 mL) and filtered through a membrane syringe filter (0.45 μm nylon). The solution was purified using standard methods to provide 2-(2,6-dioxopiperidin-3-yl)-4-((2-fluoro-4-((3-morpholinoazetidin-1-yl)methyl)benzyl)amino)isoindoline-1,3-dione (173 mg, 64.6% yield). LCMS (ESI) m/z 536.2 [M+H]+.

Example 20: 6-(4-(4-(((2-(2,6-Dioxopiperidin-3-yl)-1,3-dioxoisoindolin-4-yl)amino)methyl)-3-fluorobenzyl)piperazin-1-yl)nicotinamide

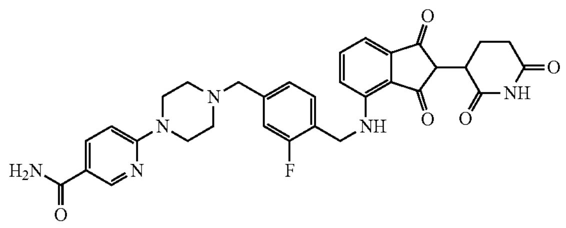 [SMILES: NC(=O)c1ccc(N2CCN(Cc3ccc(CNc4cccc5c4C(=O)C(C4CCC(=O)NC4=O)C5=O)c(F)c3)CC2)nc1]

To a solution of 4-((4-(chloromethyl)-3-fluorobenzyl)amino)-2-(2,6-dioxopiperidin-3-yl)isoindoline-1,3-dione (60.0 mg, 0.140 mmol) and 6-(piperazin-1-yl)nicotinamide (35.0 mg, 0.168 mmol) in dry DMSO (1.0 mL) was added DIEA (0.12 mL, 0.698 mmol) and the reaction mixture was stirred at 60° C. for 5 hours. The reaction was quenched with 10% formic acid in DMSO (1.0 mL), filtered through a membrane syringe filter (0.45 μm nylon) and the solution was purified using standard methods to afford 6-(4-(4-(((2-(2,6-dioxopiperidin-3-yl)-1,3-dioxoisoindolin-4-yl)amino)methyl)-3-fluorobenzyl)piperazin-1-yl)nicotinamide (69.0 mg, 82% yield). LCMS (ESI) m/z 600.2 [M+H]+.

Example 21: 2-(2,6-Dioxopiperidin-3-yl)-4-((4-((4-(ethylsulfonyl)piperidin-1-yl)methyl)-2-fluorobenzyl)amino)isoindoline-1,3-dione

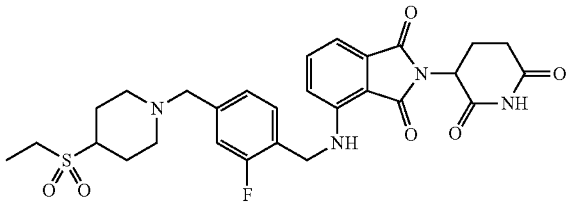 [SMILES: CCS(=O)(=O)C1CCN(Cc2ccc(CNc3cccc4c3C(=O)N(C3CCC(=O)NC3=O)C4=O)c(F)c2)CC1]

To a mixture of 4-((4-(chloromethyl)-2-fluorobenzyl)amino)-2-(2,6-dioxopiperidin-3-yl)isoindoline-1,3-dione (64.5 mg, 0.150 mmol) and 4-(ethylsulfonyl)piperidine hydrochloride (38.5 mg, 0.180 mmol) in dry DMSO (0.5 mL) was added DIEA (105 μL, 0.600 mmol) and the reaction mixture was stirred at ambient temperature for 16 hours. The mixture was diluted with 20% formic acid in DMSO (1 mL), filtered through a membrane syringe filter (0.45 μm nylon) and the solution was purified by standard methods to give 2-(2,6-dioxopiperidin-3-yl)-4-((4-((4-(ethylsulfonyl)piperidin-1-yl)methyl)-2-fluorobenzyl)amino)isoindoline-1,3-dione (58.0 mg, 67.8% yield). LCMS (ESI) m/z 571.4 [M+H]+.

Example 22: 2-(2,6-Dioxopiperidin-3-yl)-4-((2-fluoro-4-((3-(pyridin-2-yl)azetidin-1-yl)methyl)benzyl)amino)isoindoline-1,3-dione

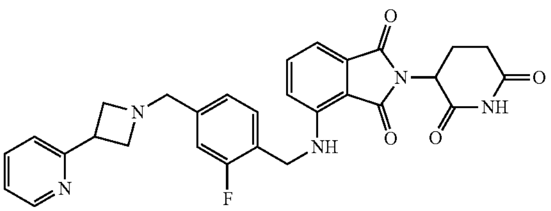 [SMILES: O=C1CCC(N2C(=O)c3cccc(NCc4ccc(CN5CC(c6ccccn6)C5)cc4F)c3C2=O)C(=O)N1]

To a mixture of 4-((4-(chloromethyl)-2-fluorobenzyl)amino)-2-(2,6-dioxopiperidin-3-yl)isoindoline-1,3-dione (64.5 mg, 0.150 mmol) and 2-(azetidin-3-yl)pyridine dihydrochloride (46.6 mg, 0.225 mmol) in dry DMSO (0.5 mL) was added DIEA (105 μL, 0.600 mmol) and the reaction mixture was stirred at ambient temperature for 7 hours. The mixture was diluted with 20% formic acid in DMSO (1 mL), filtered through a membrane syringe filter (0.45 μm nylon) and the solution was purified by standard methods to give 2-(2,6-dioxopiperidin-3-yl)-4-((2-fluoro-4-((3-(pyridin-2-yl)azetidin-1-yl)methyl)benzyl)amino)isoindoline-1,3-dione (34.0 mg, 43.0% yield). LCMS (ESI) m/z 528.2 [M+H]+.

Example 23: 2-(2,6-Dioxopiperidin-3-yl)-4-((2-fluoro-4-((3-(2-oxopyrrolidin-1-yl)azetidin-1-yl)methyl)benzyl)amino)isoindoline-1,3-dione

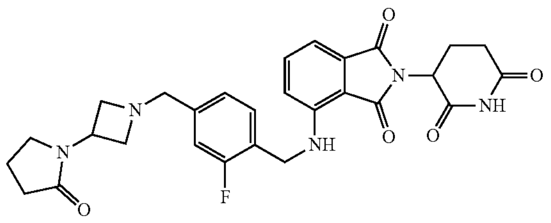 [SMILES: O=C1CCC(N2C(=O)c3cccc(NCc4ccc(CN5CC(N6CCCC6=O)C5)cc4F)c3C2=O)C(=O)N1]

To a mixture of 4-((4-(chloromethyl)-2-fluorobenzyl)amino)-2-(2,6-dioxopiperidin-3-yl)isoindoline-1,3-dione (64.5 mg, 0.150 mmol) and 1-(azetidin-3-yl)pyrrolidin-2-one trifluoracetate (57.2 mg, 0.225 mmol) in dry DMSO (0.5 mL) was added DIEA (105 μL, 0.600 mmol) and the reaction mixture was stirred at ambient temperature for 24 hours. The mixture was diluted with 20% formic acid in DMSO (1 mL), filtered through a membrane syringe filter (0.45 μm nylon) and the solution was purified using standard methods to give 2-(2,6-dioxopiperidin-3-yl)-4-((2-fluoro-4-((3-(2-oxopyrrolidin-1-yl)azetidin-1-yl)methyl)benzyl)amino)isoindoline-1,3-dione (35.0 mg, 43.7% yield). LCMS (ESI) m/z 534.2 [M+H]+.

Example 24: 2-(2,6-Dioxopiperidin-3-yl)-4-((3-fluoro-4-((4-isopropylpiperidin-1-yl)methyl)benzyl)amino)isoindoline-1,3-dione

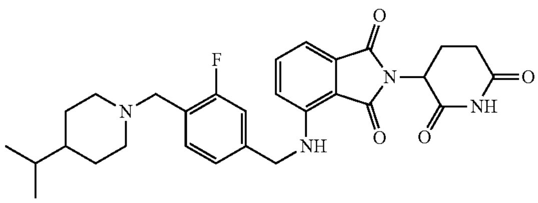 [SMILES: CC(C)C1CCN(Cc2ccc(CNc3cccc4c3C(=O)N(C3CCC(=O)NC3=O)C4=O)cc2F)CC1]

((4-Bromo-2-fluorobenzyl)oxy)(tert-butyl)dimethylsilane

A mixture of (4-bromo-2-fluorophenyl)methanol (30.0 g, 146 mmol) and imidazole (14.9 g, 219 mmol) in dichloromethane (200 mL) was cooled to 0° C. and tert-butylchlorodimethylsilane (24.2 g, 161 mmol) was added. The mixture was stirred for 5 minutes, the cooling bath removed and the mixture was stirred at ambient temperature for 16 hours. The reaction mixture was poured into chilled water (300 mL), mixed and the organic layer was separated. The aqueous layer was extracted with dichloromethane (30 mL×3) and the combined organic layers were washed with saturated NaCl (20 mL×3), dried over $Na_2SO_4$, filtered and concentrated under reduced pressure to give ((4-bromo-2-fluorobenzyl)oxy)(tert-butyl)dimethylsilane (46.0 g, 98.5%) as a yellow oil. $^1H$ NMR (400 MHz, $CDCl_3$) δ ppm 7.40-7.34 (m, 1H), 7.31-7.28 (m, 1H), 7.19 (dd, J=1.8, 9.6 Hz, 1H), 4.74 (s, 2H), 0.97 (s, 9H), 0.16 (s, 6H).

4-(((tert-Butyldimethylsilyl)oxy)methyl)-3-fluorobenzaldehyde

Under a nitrogen atmosphere a solution ((4-bromo-2-fluorobenzyl)oxy)(tert-butyl)dimethylsilane (10.0 g, 31.3 mmol) in THF (30 mL) was cooled to −78° C. and n-butyl lithium (15.0 mL, 37.5 mmol, 2.5 M in hexane) was added. The mixture was stirred at −78° C. for 2 hours and DMF (3.61 mL, 47.0 mmol) was added. The mixture was allowed to reach ambient temperature and was stirred for 30 minutes. The reaction mixture was cooled to 0° C. and quenched with saturated ammonium chloride (15 mL) and diluted with water (30 mL). The mixture was extracted with ethyl acetate (40 mL×3) and the combined organic layers were washed with saturated NaCl (30 mL×2), dried over anhydrous sodium sulfate, filtered and concentrated under reduced pressure to give crude 4-(((tert-butyldimethylsilyl)oxy)methyl)-3-fluorobenzaldehyde as a yellow oil (8.00 g, 95.4% yield). LCMS (ESI) m/z: 269.0 $[M+1]^+$.

Dimethyl 3-((4-(((tert-butyldimethylsilyl)oxy)methyl)-3-fluorobenzyl)amino)phthalate A mixture of crude 4-(((tert-butyldimethylsilyl)oxy)methyl)-3-fluorobenzaldehyde (8.00 g, 29.8 mmol) and dimethyl 3-aminobenzene-1,2-dicarboxylate (6.24 g, 29.8 mmol) in 10:1 MeOH-acetic acid (110 mL) was purged with nitrogen and treated with borane 2-methylpyridine complex (4.78 g, 44.7 mmol). The reaction mixture was stirred for 14 hours at ambient temperature. The reaction mixture was concentrated under reduced pressure to remove the MeOH and was diluted with water (40 mL). The mixture was extracted with ethyl acetate (30 mL×3) and the combined organic fractions were washed with saturated NaCl (20 mL×3), dried over anhydrous sodium sulfate, filtered and concentrated in vacuum. The residue was purified by silica gel column chromatography (5-10% ethyl acetate in petroleum ether) to give dimethyl 3-((4-(((tert-butyldimethylsilyl)oxy)methyl)-3-fluorobenzyl)amino)phthalate (6.30 g, 45.8% yield) as a yellow oil. $^1$H NMR (400 MHz, $CDCl_3$) δ ppm 7.33 (t, J=7.7 Hz, 1H), 7.13-7.09 (m, 1H), 7.00 (d, J=8.0 Hz, 1H), 6.86 (d, J=10.7 Hz, 1H), 6.72 (d, J=7.4 Hz, 1H), 6.57 (d, J=8.5 Hz, 1H), 4.66 (s, 2H), 4.31 (d, J=5.6 Hz, 2H), 3.75 (d, J=7.7 Hz, 6H), 0.83 (s, 9H), 0.02 (s, 6H).

3-((3-Fluoro-4-(hydroxymethyl)benzyl)amino) phthalic acid

To a solution of dimethyl 3-((4-(((tert-butyldimethylsilyl)oxy)methyl)-3-fluorobenzyl)amino)phthalate (13.3 g, 28.8 mmol) in 2:2:1 water-THF-MeOH (100 mL) was added sodium hydroxide (9.21 g, 230 mmol) an the reaction mixture was stirred at ambient temperature for 4 hours. The mixture was cooled to 0° C. and 6 M aqueous hydrochloric acid solution was added until pH=10. The mixture was concentrated to remove the MeOH and THF and the residual aqueous mixture was cooled to 0° C. Subsequently, 6 M hydrochloric acid was added until pH=5 and the resulting precipitate was collected by filtration, washed with $H_2O$ and dried in vacuum to give 3-((3-fluoro-4-(hydroxymethyl)benzyl)amino)phthalic acid (8.90 g, 96.8% yield) as a yellow solid. LCMS (ESI) m/z: 320.0 [M+1]+. $^1$H NMR (400 MHz, DMSO-$d_6$) δ ppm 12.99 (br s, 2H), 7.41 (t, J=7.8 Hz, 1H), 7.22 (t, J=7.9 Hz, 1H), 7.15 (d, J=7.9 Hz, 1H), 7.08 (d, J=11.2 Hz, 1H), 6.75 (d, J=7.1 Hz, 1H), 6.69 (d, J=7.9 Hz, 1H), 5.21 (s, 1H), 4.50 (s, 2H), 4.44 (s, 2H).

2-(2,6-Dioxopiperidin-3-yl)-4-((3-fluoro-4-(hydroxymethyl)benzyl)amino)isoindoline-1,3-dione To a solution of 3-aminopiperidine-2,6-dione hydrochloride (6.88 g, 41.8 mmol) in pyridine (20 mL) was added 3-((3-fluoro-4-(hydroxymethyl)benzyl)amino) phthalic acid (8.90 g, 27.9 mmol) and the mixture was stirred at 120° C. for 5 hours. The reaction mixture was allowed to cool and was concentrated under reduced pressure. The residue was diluted with ethyl acetate (300 mL) and the solution washed with 0.5 M HCl (300 mL) dried over $MgSO_4$ and concentrated. The residual solid was dried in vacuum to give 2-(2,6-dioxopiperidin-3-yl)-4-((3-fluoro-4-(hydroxymethyl)benzyl)amino)isoindoline-1,3-dione (9.00 g, 78.5% yield) as a yellow solid. LCMS (ESI) m/z: 394.0 [MH-18]+. $^1$H NMR (400 MHz, DMSO-$d_6$) δ ppm 11.11 (s, 1H), 7.51 (dd, J=7.2, 8.5 Hz, 1H), 7.42 (t, J=7.8 Hz, 1H), 7.29 (br s, 1H), 7.20 (d, J=7.5 Hz, 1H), 7.14 (d, J=10.6 Hz, 1H), 7.03 (d, J=7.0 Hz, 1H), 6.94 (d, J=8.7 Hz, 1H), 5.08 (dd, J=5.4, 12.9 Hz, 1H), 4.56 (br d, J=5.4 Hz, 2H), 4.50 (s, 2H), 2.93-2.88 (m, 1H), 2.65-2.54 (m, 2H), 2.10-2.05 (m, 1H).

4-((4-(chloromethyl)-3-fluorobenzyl)amino)-2-(2,6-dioxopiperidin-3-yl)isoindoline-1,3-dione A mixture of 2-(2,6-dioxopiperidin-3-yl)-4-((3-fluoro-4-(hydroxymethyl)benzyl)amino)isoindoline-1,3-dione (4.00 g, 9.72 mmol) in dichloromethane (120 mL) was cooled to 0° C. and thionyl chloride (12.0 mL, 165 mmol) was added. The cooling bath was removed and the mixture was stirred at ambient temperature for 22 hours. The reaction mixture was poured into a mixture of ethyl acetate (400 mL) and aqueous saturated sodium bicarbonate (300 mL), mixed and the organic layer was removed. The aqueous layer was treated with saturated sodium bicarbonate to pH=5 and was extracted with dichloromethane (300 mL×3). All organic fractions were combined, dried over anhydrous sodium sulfate and concentrated. The residue was purified by silica gel column chromatography (1:2:8 then 1:1:5 ethyl acetate/petroleum ether/dichloromethane) to provide 4-((4-(chloromethyl)-3-fluorobenzyl)amino)-2-(2,6-dioxopiperidin-3-yl)isoindoline-1,3-dione (3.24 g, 77.6% yield) as a yellow solid. LCMS (ESI) m/z: 430.1 [M+1]+. $^1$H NMR (400 MHz, DMSO-$d_6$) δ ppm 11.12 (s, 1H), 7.50 (q, J=8.1 Hz, 2H), 7.33 (br t, J=6.3 Hz, 1H), 7.29-7.18 (m, 2H), 7.04 (d, J=7.0 Hz, 1H), 6.93 (d, J=8.6 Hz, 1H), 5.08 (dd, J=5.3, 12.9 Hz, 1H), 4.75 (s, 2H), 4.59 (br d, J=6.2 Hz, 2H), 2.97-2.82 (m, 1H), 2.69-2.53 (m, 2H), 2.13-1.98 (m, 1H).

2-(2,6-dioxopiperidin-3-yl)-4-((3-fluoro-4-((4-isopropylpiperidin-1-yl)methyl)benzyl)amino)isoindoline-1,3-dione To a solution of 4-((4-(chloromethyl)-3-fluorobenzyl)amino)-2-(2,6-dioxopiperidin-3-yl)isoindoline-1,3-dione (0.060 g, 0.140 mmol) and 4-isopropylpiperidine hydrochloride (0.023 mg, 0.140 mmol) in dry DMF (1.0 mL) was added DIEA (0.073 mL, 0.419 mmol) and the reaction mixture was stirred at 80° C. for 15 hours. The reaction mixture was cooled to ambient temperature and quenched with 10% formic acid in DMSO (1.0 mL). The mixture was filtered through a membrane syringe filter (0.45 μm nylon) and the solution was purified using standard methods to afford 2-(2,6-dioxopiperidin-3-yl)-4-((3-fluoro-4-(4-isopropylpiperidin-1-yl)methyl)benzyl)amino)isoindoline-1,3-dione (56.0 mg, 77% yield). LCMS (ESI) m/z 521.2 [M+H]$^+$.

Example 25: 4-((4-((2,2-Dimethyl-1-oxa-8-azaspiro[4.5]decan-8-yl)methyl)-3-fluorobenzyl)amino)-2-(2,6-dioxopiperidin-3-yl)isoindoline-1,3-dione

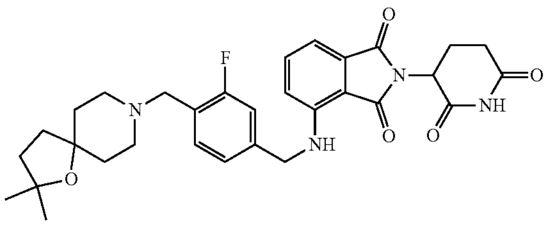 [SMILES: CC1(C)CCC2(CCN(Cc3ccc(CNc4cccc5c4C(=O)N(C4CCC(=O)NC4=O)C5=O)cc3F)CC2)O1]

To a solution of 4-((4-(chloromethyl)-3-fluorobenzyl)amino)-2-(2,6-dioxopiperidin-3-yl)isoindoline-1,3-dione (73.0 mg, 0.170 mmol) and 2,2-dimethyl-1-oxa-8-azaspiro[4.5]decane (37.4 mg, 0.221 mmol) in dry DMSO (0.7 mL) was added DIEA (89.0 μL, 0.510 mmol) and the mixture stirred at 50° C. for 5 hours. The mixture was cooled to ambient temperature, diluted with 20% formic acid in DMSO (1 mL) and filtered through a membrane syringe filter (0.45 μm nylon). The solution was purified using standard methods to provide 4-((4-((2,2-dimethyl-1-oxa-8-azaspiro[4.5]decan-8-yl)methyl)-3-fluorobenzyl)amino)-2-(2,6-dioxopiperidin-3-yl)isoindoline-1,3-dione (36.0 mg, 37.7%). LCMS (ESI) m/z 563.2 [M+H]$^+$.

Example 26: (S)-6-(4-(4-(((2-(2,6-Dioxopiperidin-3-yl)-1,3-dioxoisoindolin-4-yl)amino)methyl)-3-fluorobenzyl)piperazin-1-yl)nicotinamide

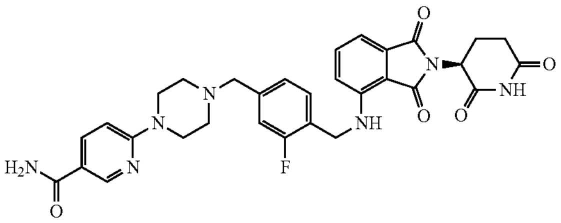 [SMILES: NC(=O)c1ccc(N2CCN(Cc3ccc(CNc4cccc5c4C(=O)N([C@H]4CCC(=O)NC4=O)C5=O)c(F)c3)CC2)nc1]

(S)-2-(2,6-Dioxopiperidin-3-yl)-4-((2-fluoro-4-(hydroxymethyl)benzyl)amino)isoindoline-1,3-dione A suspension of (S)-4-amino-2-(2,6-dioxopiperidin-3-yl)isoindoline-1,3-dione (5.00 g, 18.3 mmol) and 2-fluoro-4-(hydroxymethyl)benzaldehyde (2.82 g, 18.30 mmol) in 2:1 dioxane-MeOH (75 mL) was cooled to 0° C. and $B_{10}H_{14}$ (4.92 g, 40.3 mmol) was added in small portions over 5 minutes. The reaction flask was fitted with a septum and needle vent (pressure) and vigorously stirred for 10 minutes. The mixture was allowed to reach ambient temperature and stirred for 3 hours. The mixture was concentrated and the residue purified by silica gel chromatography (0-10% MeOH-DCM) to provide (S)-2-(2,6-dioxopiperidin-3-yl)-4-((2-fluoro-4-(hydroxymethyl)benzyl)amino)isoindoline-1,3-dione as a yellow solid (4.23 g, 56%). LCMS (ESI) m/z 411.8 $[M+H]^+$.

(S)-4-((4-(Chloromethyl)-2-fluorobenzyl)amino)-2-(2,6-dioxopiperidin-3-yl)isoindoline-1,3-dione A solution of (S)-2-(2,6-dioxopiperidin-3-yl)-4-((2-fluoro-4-(hydroxymethyl)benzyl)amino)isoindoline-1,3-dione (0.727 g, 1.77 mmol) in dry NMP (6 mL) was cooled to 0° C. and methane sulfonyl chloride (0.275 mL, 3.35 mmol) and DIEA (0.617 mL, 3.53 mmol) were added sequentially. The reaction mixture was allowed to reach ambient temperature and was stirred for 18 hours. The reaction mixture was slowly added to $H_2O$ (60 mL) cooled to 0° C. with vigorous mixing. The resulting suspension was filtered and the collected solid was washed with $H_2O$ and $Et_2O$. The solid was dissolved in EtOAc and the solution dried with $MgSO_4$, filtered and concentrated to provide (S)-4-((4-(chloromethyl)-2-fluorobenzyl)amino)-2-(2,6-dioxopiperidin-3-yl)isoindoline-1,3-dione as a yellow solid (0.600 g, 79%). LCMS (ESI) m/z 430.0 $[M+H]^+$.

(S)-6-(4-(4-(((2-(2,6-Dioxopiperidin-3-yl)-1,3-dioxoisoindolin-4-yl)amino)methyl)-3-fluorobenzyl)piperazin-1-yl)nicotinamide To a solution of (S)-4-((4-(chloromethyl)-2-fluorobenzyl)amino)-2-(2,6-dioxopiperidin-3-yl)isoindoline-1,3-dione (300 mg, 0.698 mmol) in dry DMSO (1.0 mL) was added 6-(piperazin-1-yl)nicotinamide (144 mg, 1.00 mmol) and DIEA (0.122 mL, 0.698 mmol). The reaction mixture was stirred at ambient temperature for 18 hours and was diluted with DMSO (1 mL). The solution was purified by chiral reverse-phase chromatography to give (S)-6-(4-(4-(((2-(2,6-dioxopiperidin-3-yl)-1,3-dioxoisoindolin-4-yl)amino)methyl)-3-fluorobenzyl)piperazin-1-yl)nicotinamide (173 mg, 41%, >99% ee), LCMS (ESI) m/z 600.2 $[M+H]^+$.

Example 27: (R)-6-(4-(4-(((2-(2,6-Dioxopiperidin-3-yl)-1,3-dioxoisoindolin-4-yl)amino)methyl)-3-fluorobenzyl)piperazin-1-yl)nicotinamide

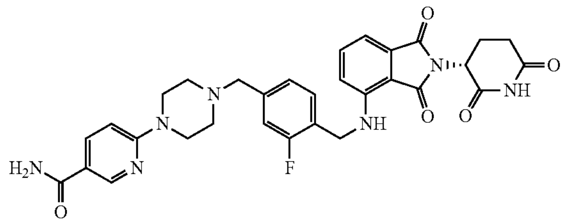 [SMILES: NC(=O)c1ccc(N2CCN(Cc3ccc(CNc4cccc5c4C(=O)N([C@@H]4CCC(=O)NC4=O)C5=O)c(F)c3)CC2)nc1]

The chiral reverse-phase chromatography described in the example 26 additionally provided (R)-6-(4-(4-(((2-(2,6-dioxopiperidin-3-yl)-1,3-dioxoisoindolin-4-yl)amino)methyl)-3-fluorobenzyl)piperazin-1-yl)nicotinamide (3 mg, >99% ee), LCMS (ESI) m/z 600.2 $[M+H]^+$.

Example 28: 4-((4-((4-(tert-Butyl)piperidin-1-yl)methyl)-3-fluorobenzyl)amino)-2-(2,6-dioxopiperidin-3-yl)isoindoline-1,3-dione

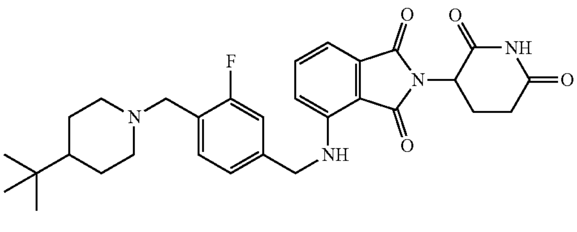 [SMILES: CC(C)(C)C1CCN(Cc2ccc(CNc3cccc4c3C(=O)N(C3CCC(=O)NC3=O)C4=O)cc2F)CC1]

To a solution of 4-((4-(chloromethyl)-3-fluorobenzyl)amino)-2-(2,6-dioxopiperidin-3-yl)isoindoline-1,3-dione (0.050 g, 0.116 mmol) and 4-(tert-butyl)piperidine hydrochloride (0.025 mg, 0.141 mmol) in dry DMF (1.0 mL) was added DIEA (0.10 mL, 0.573 mmol) and the reaction mixture was stirred at 60° C. for 3 hours. The reaction cooled to ambient temperature and was quenched with 10% formic acid in DMSO (1.0 mL). The mixture was filtered through a membrane syringe filter (0.45 μm nylon) and the solution was purified using standard methods to afford 2-(2,6-dioxopiperidin-3-yl)-4-((3-fluoro-4-((4-isopropylpiperidin-1-yl)methyl)benzyl)amino)isoindoline-1,3-dione (49.0 mg, 78%). LCMS (ESI) m/z 535.2 [M+H]+.

Example 29: 4-(1-(4-(((2-(2,6-Dioxopiperidin-3-yl)-1,3-dioxoisoindolin-4-yl)amino)methyl)-3-methylbenzyl)azetidin-3-yl)benzonitrile

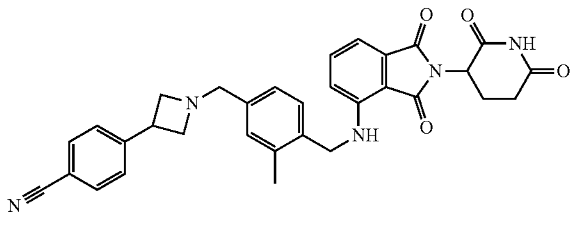 [SMILES: Cc1cc(CN2CC(c3ccc(C#N)cc3)C2)ccc1CNc1cccc2c1C(=O)N(C1CCC(=O)NC1=O)C2=O]

(4-Bromo-3-methyl-phenyl)methanol

A solution of 4-bromo-3-methyl-benzoic acid (50.0 g, 232 mmol) in THF (500 mL) was cooled to 0° C. and borane dimethyl sulfide complex (35.0 mL, 350 mmol, 10M in THF) was added under nitrogen. The reaction mixture was allowed to reach ambient temperature and stirred for 2 hours followed by stirring at 40° C. for 3 hours. The mixture was cooled to 0° C. and was quenched with water (200 mL). The mixture was extracted with ethyl acetate (300 mL) and the organic layer was dried over anhydrous sodium sulfate, filtered and concentrated give (4-bromo-3-methyl-phenyl) methanol (45.0 g, 96.3% yield) as a brown oil. $^1$H NMR ($CDCl_3$, 400 MHz) δ ppm 7.51 (d, J=8.2 Hz, 1H), 7.25 (d, J=1.6 Hz, 1H), 7.05 (dd, J=1.6, 8.2 Hz, 1H), 4.63 (s, 2H), 2.41 (s, 3H).

(4-Bromo-3-methyl-phenyl)methoxy-tert-butyl-dimethyl-silane

To a solution of (4-bromo-3-methyl-phenyl)methanol (45.0 g, 224 mmol) in dichloromethane (500 mL) were sequentially added imidazole (38.1 g, 559 mmol) and tert-butyldimethylsilyl chloride (40.5 g, 269 mmol) and the reaction mixture was stirred at ambient temperature for 15 hours. The mixture was washed with water (2×500 mL), saturated NaCl (500 mL) and dried over anhydrous sodium sulfate. The dried solution was filtered and concentrated to give (4-bromo-3-methyl-phenyl)methoxy-tert-butyl-dimethyl-silane (68.0 g, 96.4% yield) as a brown oil. $^1$H NMR ($CDCl_3$, 400 MHz) δ 7.48 (d, J=8.2 Hz, 1H), 7.19 (d, J=1.1 Hz, 1H), 7.02 (dd, J=1.6, 8.1 Hz, 1H), 4.67 (s, 2H), 2.40 (s, 3H), 0.95 (s, 9H), 0.11 (s, 6H).

4-[[tert-Butyl)dimethyl)silyl]oxymethyl]-2-methyl-benzaldehyde

Under an atmosphere of nitrogen, a solution of (4-bromo-3-methyl-phenyl)methoxy-tert-butyl-dimethyl-silane (63.0 g, 200 mmol) in THF (600 mL) was cooled to −78° C. and n-butyllithium (95.9 mL, 240 mmol, 2.5 M in hexane) was added dropwise. The mixture was stirred at −78° C. for 2 hours and DMF (23.1 mL, 300 mmol) was added dropwise. The mixture was stirred at −78° C. for 30 minutes, allowed to reach ambient temperature and stirred for 1 hour. The mixture was quenched with saturated ammonium chloride (300 mL) and extracted with ethyl acetate (300 mL). The organic phase was washed with saturated NaCl (300 mL), dried over anhydrous sodium sulfate, filtered and concentrated. The residual oil was purified by silica gel column chromatography (petroleum ether) to give 4-[[tert-butyl(dimethyl)silyl]oxymethyl]-2-methyl-benzaldehyde (45.0 g, 85.2% yield) as a brown oil. $^1$H NMR (400 MHz, $CDCl_3$) δ ppm 10.24 (s, 1H), 7.78 (d, J=7.9 Hz, 1H), 7.32 (d, J=7.9 Hz, 1H), 7.22 (s, 1H), 4.77 (s, 2H), 2.68 (s, 3H), 0.96 (s, 9H), 0.12 (s, 6H).

Dimethyl 3-((4-(((tert-butyldimethylsilyl)oxy) methyl)-2-methylbenzyl)amino)phthalate To a solution of 4-[[tert-butyl(dimethyl)silyl]oxymethyl]-2-methyl-benzaldehyde (20.0 g, 75.6 mmol) and dimethyl 3-aminobenzene-1,2-dicarboxylate (15.0 g, 71.8 mmol) in MeOH (200 mL) was added acetic acid (20.0 mL, 350 mmol) and the mixture was stirred at ambient temperature for 6 hours. The mixture was cooled to 0° C. and borane 2-methylpyridine complex (12.1 g, 113 mmol) was added portion-wise. The mixture was allowed to reach ambient temperature and was stirred for 15 hours. The mixture was concentrated and the residue was diluted with water (300 mL) and extracted with ethyl acetate (300 mL). The organic layer was washed with 0.5 M hydrochloric acid (300 mL), saturated NaCl (300 mL) and dried over anhydrous sodium sulfate. The dried solution was filtered, concentrated and the residue was purified by silica gel column chromatography (0-10% ethyl acetate in petroleum ether) to give dimethyl 3-((4-(((tert-butyldimethylsilyl)oxy)methyl)-2-methylbenzyl)amino)phthalate (18.0 g, 43.2% yield) as a colorless oil.

3-((4-(Hydroxymethyl)-2-methylbenzyl)amino) phthalic acid

To a solution of dimethyl 3-((4-(((tert-butyldimethylsilyl) oxy)methyl)-2-methylbenzyl)amino)phthalate (18.0 g, 32.7 mmol) in 1:1 THF-MeOH (200 mL) was added sodium hydroxide (131 g, 327 mmol) in water (50 mL) and the mixture was stirred at ambient temperature for 15 hours. The mixture was concentrated to remove the MeOH and THF and the remaining aqueous mixture was cooled to 0° C. Then 6M hydrochloric acid was added until pH=7 and the resulting precipitate was collected by filtration, washed with water and dried in vacuum to give 3-((4-(hydroxymethyl)-2-methylbenzyl)amino)phthalic acid (5.30 g, 51.4% yield) as a yellow solid. $^1$H NMR (400 MHz, DMSO-$d_6$) δ 8.41 (br t, J=5.3 Hz, 1H), 7.22 (d, J=7.8 Hz, 1H), 7.11 (s, 1H), 7.04 (d, J=7.9 Hz, 1H), 6.91 (t, J=7.8 Hz, 1H), 6.38 (br d, J=7.4 Hz, 1H), 6.30 (d, J=8.0 Hz, 1H), 5.07 (br s, 1H), 4.43 (br s, 2H), 4.19 (br d, J=5.1 Hz, 2H), 2.31 (s, 3H).

2-(2,6-Dioxopiperidin-3-yl)-4-((4-(hydroxymethyl)-2-methylbenzyl)amino)isoindoline-1,3-dione To a solution 3-((4-(hydroxymethyl)-2-methylbenzyl) amino)phthalic acid (5.30 g, 16.8 mmol) in pyridine (60 mL) was added 3-aminopiperidine-2,6-dione hydrochloride (4.15 g, 25.2 mmol) and the mixture was stirred at 120° C. for 10 hours. The mixture was concentrated and the residue was dissolved in ethyl acetate (300 mL). The solution was washed with 0.5 M hydrochloric acid (300 mL), dried over sodium sulfate, filtered and concentrated to 2-(2,6-dioxopiperidin-3-yl)-4-((4-(hydroxymethyl)-2-methylbenzyl) amino)isoindoline-1,3-dione (4.80 g, 70.1% yield) as a yellow solid. $^1$H NMR (400 MHz, DMSO-$d_6$) δ 11.10 (s, 1H), 7.52 (dd, J=7.2, 8.4 Hz, 1H), 7.20-7.12 (m, 2H), 7.10-7.01 (m, 2H), 6.98-6.87 (m, 2H), 5.06 (dd, J=5.4, 12.9 Hz, 1H), 4.50 (br d, J=5.5 Hz, 2H), 4.42 (s, 2H), 2.95-2.79 (m, 1H), 2.64-2.52 (m, 2H), 2.33 (s, 3H), 2.08-1.99 (m, 1H).

4-((4-(Chloromethyl)-2-methylbenzyl)amino)-2-(2,6-dioxopiperidin-3-yl)isoindoline-1,3-dione To a solution of 2-(2,6-dioxopiperidin-3-yl)-4-((4-(hydroxymethyl)-2-methylbenzyl)amino)isoindoline-1,3-dione (9.10 g, 22.3 mmol) in dichloromethane (200 mL) was added thionyl chloride (32.4 mL, 447 mmol) and the mixture was stirred at ambient temperature for 15 hours. The mixture was diluted with dichloromethane (300 mL) and poured into saturated sodium bicarbonate (300 mL) cooled to 0° C. and mixed. The organic phase was separated, dried with anhydrous sodium sulfate, filtered and concentrated. The residue was slurried in 1:1 dichloromethane-petroleum ether (20 mL) and the solid was collected by filtration. The collected solid was purified by silica gel column chromatography (20-100% ethyl acetate in 1:1 petroleum ether-dichloromethane) to give 4-((4-(chloromethyl)-2-methylbenzyl) amino)-2-(2,6-dioxopiperidin-3-yl)isoindoline-1,3-dione (7.40 g, 70.8% yield) as a yellow solid. LCMS (ESI) m/z: 426.1 $[M+1]^+$. $^1$H NMR (400 MHz, DMSO-$d_6$) δ 11.12 (m, 1H), 7.52 (dd, J=7.3, 8.4 Hz, 1H), 7.27 (s, 1H), 7.20 (d, J=1.0 Hz, 2H), 7.07-7.01 (m, 2H), 6.90 (d, J=8.5 Hz, 1H), 5.07 (dd, J=5.5, 12.9 Hz, 1H), 4.69 (s, 2H), 4.53 (d, J=6.0 Hz, 2H), 2.94-2.79 (m, 1H), 2.64-2.52 (m, 2H), 2.34 (s, 3H), 2.09-2.00 (m, 1H).

4-(1-(4-(((2-(2,6-Dioxopiperidin-3-yl)-1,3-dioxoisoindolin-4-yl)amino)methyl)-3-methylbenzyl)azetidin-3-yl)benzonitrile To a mixture of 4-((4-(chloromethyl)-2-methylbenzyl) amino)-2-(2,6-dioxopiperidin-3-yl)isoindoline-1,3-dione (0.060 g, 0.141 mmol) and 4-(azetidin-3-yl)benzonitrile hydrochloride (0.027 mg, 0.141 mmol) in dry DMF (1.0 mL) was added DIEA (0.074 mL, 0.423 mmol) and the reaction mixture was stirred at 80° C. for 15 hours. The reaction was cooled to ambient temperature and quenched with 10% formic acid in DMSO (1.0 mL). The mixture was filtered through a membrane syringe filter (0.45 μm nylon) and the eluted solution was purified using standard methods to afford 2-(2,6-dioxopiperidin-3-yl)-4-((3-fluoro-4-((4-isopropylpiperidin-1-yl)methyl)benzyl)amino)isoindoline-1,3-dione (49.0 mg, 59.9% yield). LCMS (ESI) m/z 548.2 $[M+H]^+$.

Example 30: 4-((4-((4-(tert-Butyl)piperidin-1-yl) methyl)-2-methylbenzyl)amino)-2-(2,6-dioxopiperidin-3-yl)isoindoline-1,3-dione

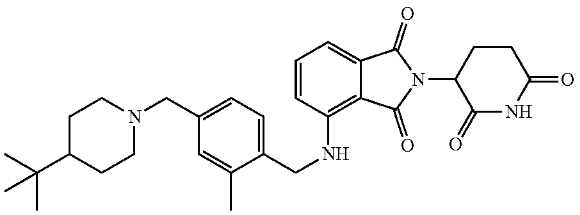 [SMILES: Cc1cc(CN2CCC(C(C)(C)C)CC2)ccc1CNc1cccc2c1C(=O)N(C1CCC(=O)NC1=O)C2=O]

A solution of 4-((4-(chloromethyl)-2-methylbenzyl) amino)-2-(2,6-dioxopiperidin-3-yl)isoindoline-1,3-dione (0.050 g, 0.117 mmol), 4-(tert-butyl)piperidine (0.0249 mL, 0.176 mmol), and DIEA (0.102 mL, 0.585 mmol) in DMF (0.500 mL) was stirred at 60° C. for 3 hours under an atmosphere of $N_2$. The reaction was quenched with 10% formic acid in DMSO (1.0 mL), filtered through a membrane syringe filter (0.45 μm nylon) and the solution was purified using standard methods to afford 4-((4-((4-(tert-butyl)piperidin-1-yl)methyl)-2-methylbenzyl)amino)-2-(2,6-dioxopiperidin-3-yl)isoindoline-1,3-dione (43.0 mg, 69.0%). LCMS (ESI) m/z 531.3 $[M+H]^+$.

Example 31: 4-((4-((4-(2,4-Difluorophenyl)piperazin-1-yl)methyl)-2-methylbenzyl)amino)-2-(2,6-dioxopiperidin-3-yl)isoindoline-1,3-dione

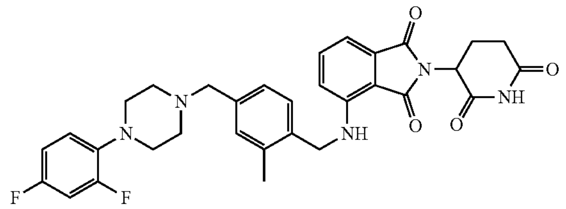 [SMILES: Cc1cc(CN2CCN(c3ccc(F)cc3F)CC2)ccc1CNc1cccc2c1C(=O)N(C1CCC(=O)NC1=O)C2=O]

A solution of 4-((4-(chloromethyl)-2-methylbenzyl) amino)-2-(2,6-dioxopiperidin-3-yl)isoindoline-1,3-dione (0.060 g, 0.141 mmol), difluorophenyl)piperazine (0.031 g, 0.155 mmol), and DIEA (0.074 mL, 1.73 mmol) in DMF (1.00 mL) was stirred at 80° C. for 15 hours under an atmosphere of $N_2$. The reaction was quenched with 10% formic acid in DMSO (1.0 mL), filtered through a membrane syringe filter (0.45 μm nylon) and the solution was purified using standard methods to afford 4-((4-((4-(2,4-difluorophenyl)piperazin-1-yl)methyl)-2-methylbenzyl)amino)-2-(2,6-dioxopiperidin-3-yl)isoindoline-1,3-dione (34.0 mg, 40.9%). LCMS (ESI) m/z 588.2 $[M+H]^+$.

Example 32: (S)-2-(2,6-Dioxopiperidin-3-yl)-4-((2-fluoro-4-((3-morpholinoazetidin-1-yl)methyl)benzyl) amino)isoindoline-1,3-dione

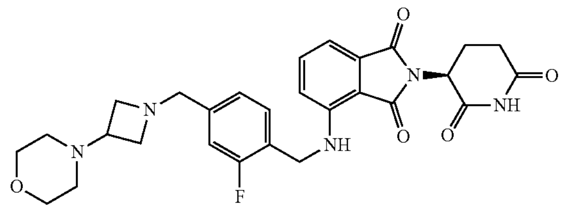 [SMILES: O=C1CC[C@H](N2C(=O)c3cccc(NCc4ccc(CN5CC(N6CCOCC6)C5)cc4F)c3C2=O)C(=O)N1]

To a solution of (S)-4-((4-(chloromethyl)-2-fluorobenzyl) amino)-2-(2,6-dioxopiperidin-3-yl)isoindoline-1,3-dione (300 mg, 0.698 mmol) in dry DMSO (1.0 mL) was added 4-(azetidin-3-yl)morpholine hydrochloride (125 mg, 0.698 mmol) and DIEA (0.122 mL, 0.698 mmol). The reaction mixture was stirred at ambient temperature for 18 hours and was diluted with DMSO (1 mL). The solution was purified by chiral reverse-phase chromatography to give (S)-2-(2,6-dioxopiperidin-3-yl)-4-((2-fluoro-4-((3-morpholinoazetidin-1-yl)methyl)benzyl)amino)isoindoline-1,3-dione (89 mg, 24%, 97% ee) LCMS (ESI) m/z 536.2 $[M+H]^+$.

Example 33: (R)-2-(2,6-Dioxopiperidin-3-yl)-4-((2-fluoro-4-((3-morpholinoazetidin-1-yl)methyl)benzyl)amino)isoindoline-1,3-dione

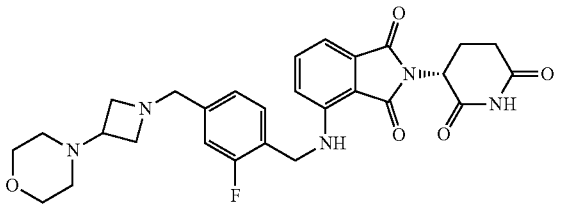 [SMILES: O=C1CC[C@@H](N2C(=O)c3cccc(NCc4ccc(CN5CC(N6CCOCC6)C5)cc4F)c3C2=O)C(=O)N1]

The chiral reverse-phase chromatography described in example 32 additionally provided (R)-2-(2,6-dioxopiperidin-3-yl)-4-((2-fluoro-4-((3-morpholinoazetidin-1-yl)methyl)benzyl)amino)isoindoline-1,3-dione (16 mg, 97% ee) LCMS (ESI) m/z 535.6 $[M+H]^+$.

Example 34: (S)-5-(4-(4-(((2-(2,6-Dioxopiperidin-3-yl)-1,3-dioxoisoindolin-4-yl)amino)methyl)benzyl)piperazin-1-yl)picolinamide

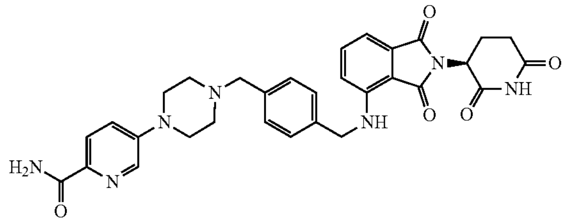 [SMILES: NC(=O)c1ccc(N2CCN(Cc3ccc(CNc4cccc5c4C(=O)N([C@H]4CCC(=O)NC4=O)C5=O)cc3)CC2)cn1]

To a solution of (S)-4-((4-(chloromethyl)benzyl)amino)-2-(2,6-dioxopiperidin-3-yl)isoindoline-1,3-dione (300 mg, 0.619 mmol) in dry DMSO (3.0 mL) was added 5-(piperazin-1-yl)picolinamide (153 mg, 0.743 mmol) and DIEA (0.108 mL, 0.619 mmol) and the mixture was stirred at ambient temperature for 16 hours. The mixture was diluted with 15% formic acid in DMSO (3 mL) and the solution purified by reverse phase chromatography to provide (S)-5-(4-(4-(((2-(2,6-dioxopiperidin-3-yl)-1,3-dioxoisoindolin-4-yl)amino)methyl)benzyl)piperazin-1-yl)picolinamide (255 mg, 71%, 95% ee), LCMS (ESI) m/z 582.2 $[M+H]^+$.

Example 35: ((R)-5-(4-(4-(((2-(2,6-Dioxopiperidin-3-yl)-1,3-dioxoisoindolin-4-yl)amino)methyl)benzyl)piperazin-1-yl)picolinamide

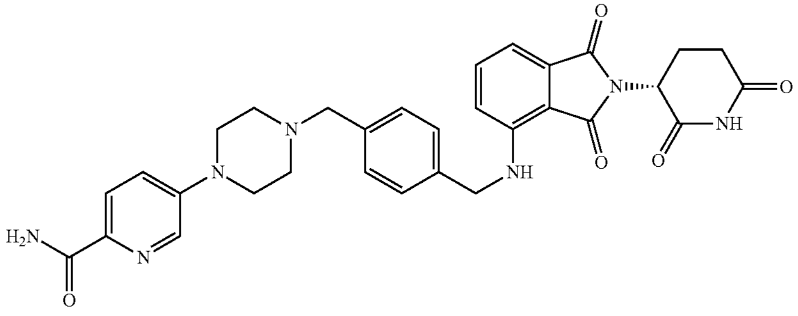 [SMILES: NC(=O)c1ccc(N2CCN(Cc3ccc(CNc4cccc5c4C(=O)N([C@@H]4CCC(=O)NC4=O)C5=O)cc3)CC2)cn1]

Purification by chiral chromatography of the solution obtained in example 34 or the racemic material obtained in example 7 afforded ((R)-5-(4-(4-(((2-(2,6-dioxopiperidin-3-yl)-1,3-dioxoisoindolin-4-yl)amino)methyl)benzyl)piperazin-1-yl)picolinamide, LCMS (ESI) m/z 582.2 $[M+H]^+$.

Assays

Cell Based Assays

SU-DHL-4 Cell Proliferation Assay.

The following is an example of an assay that can be used to determine the anti-proliferative activity of Isoindolinedione Compounds in a DLBCL cell line, for example, the SU-DHL-4 cell line (Deutsche Sammlung von Mikroorganismen and Zellkulturen GmbH [DSMZ]: catalogue number ACC-495) at 120 hours post-treatment. The seeding density for SU-DHL-4 can be optimized to ensure assay linearity in 1536-well plates.

Increasing concentrations of test compounds (0.5 nM to 10 μM) were spotted in a 20-point dilution fashion (unevenly spaced data points) via an acoustic dispenser (EDC ATS-100) into an empty 1536-well plate. The DMSO concentration was kept constant for a final assay concentration of 0.1% DMSO. Prior to testing, SU-DHL-4 cells were grown in RPMI-1640 (Roswell Park Memorial Institute—1640) medium with 10% FBS (fetal bovine serum: HyClone) and expanded in culture flasks to provide sufficient amounts of starting material. Cells were then diluted to 500 cells per well in a 5 μL volume, and added directly to the compound-spotted 1536-well plates. Cells were allowed to grow for 120 hours in 5% $CO_2$ at 37° C. At the time when exposure of cells to compound began (to), initial viable cell number was assessed via Cell Titer-Glo® Luminescent Cell Viability Assay at a 1 vol:2 vol ratio according to manufacturer's instructions (Promega Corporation, Madison, Wis.) by quantifying the level of luminescence generated by adenosine-5'-triphosphate (ATP) present in viable cells. After 120 hours, cell viability of the treated cells was assessed via Cell Titer-Gb® and read for luminescence. All growth inhibition curves were processed and evaluated using Activity Base (IDBS, Alameda, Calif.). Cell viability $IC_{50}$ values were calculated using a four parameter logistic model (sigmoidal dose-response model):

$$y=(A+((B-A)/(1+((C/x)^D))))$$

wherein:
$A=Y_{Min}$
$B=Y_{Max}$
$C=EC_{50}$
D=Hill slope
$IC_{50}$=the concentration of the compound when Y=50% of DMSO control
Y=cell viability measured as luminescence unit, and
x=concentration of compound.

In Vivo Assays

WSU-DLCL2 (GCB-Subtype) Triple-Hit (Myc, Bcl2, Bcl6 rearrangement) DLBCL Xenograft Model.

WSU-DLCL2 cells are derived from a diffuse-large B-cell lymphoma, a type of non-Hodgkin lymphoma. Female SCID mice (Fox Chase SCID®, CB17/Icr-Prkdcscid, Charles River), characterized by severe combined T and B cell immunodeficiency, are 10 weeks old, with body weights ranging from 15.4 to 24.2 g, on day 1 of the study. Female CB17 SCID mice are inoculated with $10\times10^6$ WSU-DLCL2 cells subcutaneously into the flank. Mice are randomized into treatment groups (n=9/group) at the time of treatment initiation and treatments start on day 18 when the tumors are approximately 350 $mm^3$. Test compound (at four dose levels) is administered once daily (QD). MCT (0.5% Methyl Cellulose, 0.25% Tween 80 and 50 mM Citrate pH in PBS) administered QD is used as vehicle control. A single cycle of CHOP therapy (combination of cyclophosphamide—single dose on day 1, doxorubicin-single dose on day 1, vincristine—single dose on day 1 and prednisone—QDx5 on days 1-5) which causes significant body weight loss is used as positive control. The 2 endpoints in this study include tumor volume reduction (TVR) and time to progression (TTP). The TVR is determined at the time of the termination of the vehicle group that reaches the predetermined endpoint of approximately 1400 $mm^3$. Tumor free animals are defined as animals with no palpable tumors or tumors with <50 $mm^3$. The 30 mg/kg, QD-treatment group is followed for TTP to determine the tumor growth delay (TGD), which is defined as the difference in days for treated versus control tumors to reach a specified volume of 1000 $mm^3$. Multiple dosing schedules can be tested. The final tumor volume reduction is determined at the time of the termination of the study when the mean tumor volumes in the vehicle group reach a predetermined endpoint of approximately 1400 $mm^3$.

SU-DHL-6 (GCB Sub-Type) Double Hit DLBCL Xenograft Model.

SU-DHL-6 cells are derived from a diffuse-large B-cell lymphoma, a type of non-Hodgkins lymphoma. SU-DHL-6 cell line is a GCB type "double hit" (Myc in combination with Bcl2 rearrangement) DLBCL. Female SCID mice (Fox Chase SCID®, CB17/Icr-Prkdcscid, Charles River), characterized by severe combined T and B cell immunodeficiency, are 10 weeks old, with body weights ranging from 15.4 to 24.2 g, on day 1 of this study. Female CB17 SCID mice are inoculated with $10\times10^6$ SU-DHL-6 cells subcutaneously into the flank. Mice are randomized into treatment groups (n=7/group) at the time of treatment initiation and treatments are started on day 28 when the tumors are approximately 170 $mm^3$. Three week oral dosing is completed on day 49. The final tumor volume reduction is determined at the time of the termination of the study when the mean tumor volumes in vehicle group reach a predetermined endpoint of approximately 1400 $mm^3$. MCT (0.5% Methyl Cellulose, 0.25% Tween 80 and 50 mM Citrate pH in PBS) administered QD is used as vehicle control. A single cycle of R-CHOP therapy (combination of rituximab—single dose on day 1, cyclophosphamide—single dose on day 1, doxorubicin-single dose on day 1, vincristine—single dose on day 1 and prednisone—QDx5 on days 1-5) which causes significant body weight loss is used as positive control. Endpoint of this study includes tumor volume reduction (TVR). The TVR is determined at the time of the termination of the vehicle group that reaches the predetermined endpoint of approximately 1400 $mm^3$. Tumor free animals are defined as animals with no palpable tumors or tumors with <50 $mm^3$.

OCI-LY10 (ABC Sub-Type) DLBCL Xenograft Model.

OCI-LY10 cells are derived from a diffuse-large B-cell lymphoma, a type of non-Hodgkin lymphoma. Female SCID mice (Fox Chase SCID®, CB17/Icr-Prkdcscid, Charles River), characterized by severe combined T and B cell immunodeficiency, are 10 weeks old, with body weights ranging from 15.4 to 24.2 g, on day 1 of this study. Female CB17 SCID mice are inoculated with $10\times10^6$ OCI-LY10 cells subcutaneously into the flank. Mice are randomized into treatment groups (n=9/group) at the time of treatment initiation and treatments are started on day 9 when the tumors are approximately 100 $mm^3$. The final tumor volume reduction is determined at the time of the termination of the study when the mean tumor volumes in vehicle group reach a predetermined endpoint of approximately 1400 $mm^3$. Rituximab (at one dose level dosed biweekly injected intraperitoneally) was used as positive control. Endpoint of this study includes tumor volume reduction (TVR). The TVR was determined at the time of the termination of the vehicle group that reaches the predetermined endpoint of approximately 1400 $mm^3$. Tumor free animals are defined as animals with no palpable tumors or tumors with <50 $mm^3$.

Cell lines that can be used in the xenograft assays described herein include GCB DLBCL cell lines (for example, Karpas-422, WSU-DLBCL2, SU-DHL-1, SU-DHL-4, SU-DHL-5, SU-DHL-6, SU-DHL-8, SU-DHL-10, HT, Farage, Pfeifer, or OCI-Ly7), ABC DLBCL cell lines (for example, OCI-Ly10, U2932, OCI-Ly3, or RC-$K_8$), or DHIT (double hit, i.e. cMyc and Bcl-2 mutant) or THIT (triple hit, i.e. Myc, Bcl2, Bcl6 rearrangement) cell lines.

Isoindolinedione Compounds have been, or will be tested in the DLBCL xenograft models and have shown, or will be shown, to be effective as treatments of DLBCL in the models.

Activity Tables

Each of the Isoindolinedione Compounds in Table 1, was tested in one or more of the DLBCL cell proliferation assays, for example, the SU-DHL-4 cell proliferation assay, and was found to have activity therein, with all of the compounds having an $IC_{50}$ below 1 μM in the assay, with some compounds having an $IC_{50}$ below 200 nM (activity level D), some an $IC_{50}$ from 200 nM to 500 nM (activity level C), some an $IC_{50}$ from 501 nM to 750 nM (activity level B), and others having an $IC_{50}$ from 751 nM to 1 μM (activity level A).

TABLE 1
| Cpd # | Cpd Structure | Cpd Name | Obs. MH+ | SU-DHL-4 Act |
|---|---|---|---|---|
| 1 | 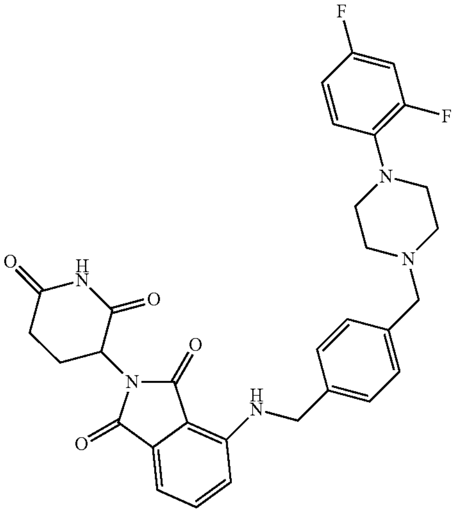 [SMILES: O=C1CCC(N2C(=O)c3cccc(NCc4ccc(CN5CCN(c6ccc(F)cc6F)CC5)cc4)c3C2=O)C(=O)N1] | 4-(4-((4-(2,4-difluorophenyl)piperazin-1-yl)methyl)benzylamino)-2-(2,6-dioxopiperidin-3-yl)isoindoline-1,3-dione | 574.2 | B |
| 2 | 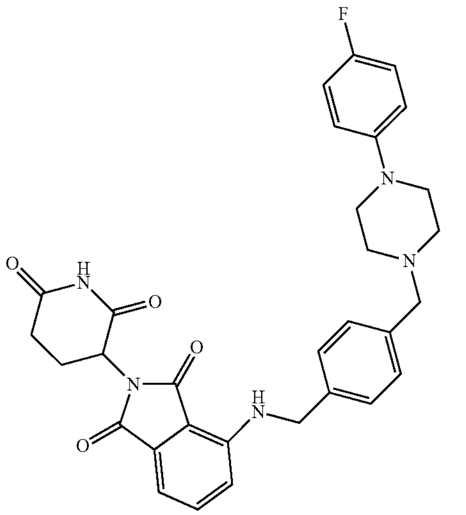 [SMILES: O=C1CCC(N2C(=O)c3cccc(NCc4ccc(CN5CCN(c6ccc(F)cc6)CC5)cc4)c3C2=O)C(=O)N1] | 2-(2,6-dioxopiperidin-3-yl)-4-(4-((4-(4-fluorophenyl)piperazin-1-yl)methyl)benzylamino)isoindoline-1,3-dione | 556.2 | B |
| 3 | 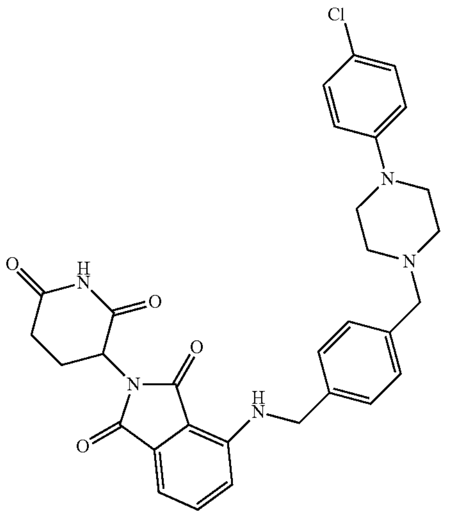 [SMILES: O=C1CCC(N2C(=O)c3cccc(NCc4ccc(CN5CCN(c6ccc(Cl)cc6)CC5)cc4)c3C2=O)C(=O)N1] | 4-(4-((4-(4-chlorophenyl)piperazin-1-yl)metthyl)benzylamino)-2-(2,6-dioxopiperidin-3-yl)isoindoline-1,3-dione | 572.3 | C |

TABLE 1-continued
| Cpd # | Cpd Structure | Cpd Name | Obs. MH+ | SU-DHL-4 Act |
|---|---|---|---|---|
| 4 | 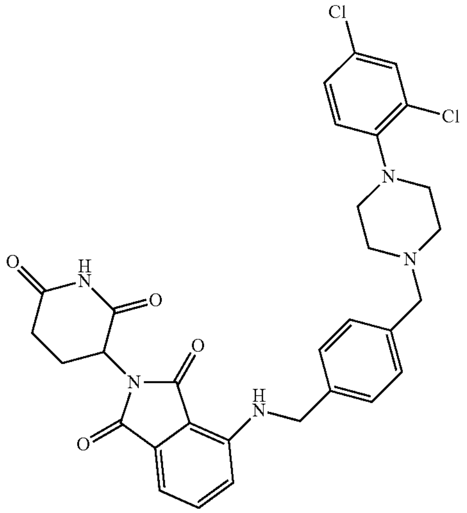 [SMILES: O=C1CCC(N2C(=O)c3cccc(NCc4ccc(CN5CCN(c6ccc(Cl)cc6Cl)CC5)cc4)c3C2=O)C(=O)N1] | 4-(4-((4-(2,4-dichlorophenyl)piperazin-1-yl)methyl)benzylamino)-2-(2,6-dioxopiperidin-3-yl)isoindoline-1,3-dione | 606.2 | B |
| 5 | 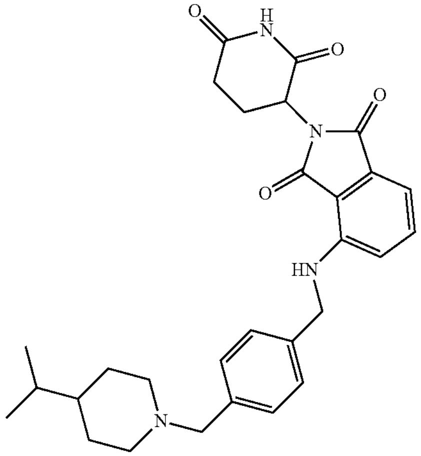 [SMILES: CC(C)C1CCN(Cc2ccc(CNc3cccc4c3C(=O)N(C3CCC(=O)NC3=O)C4=O)cc2)CC1] | 2-(2,6-dioxopiperidin-3-yl)-4-(4-((4-isopropylpiperidin-1-yl)methyl)benzylamino)isoindoline-1,3-dione | 503.3 | D |
| 6 | 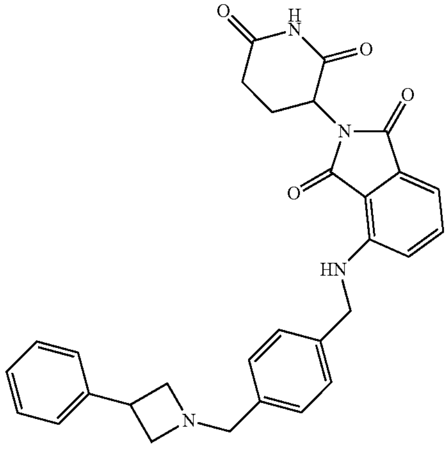 [SMILES: O=C1CCC(N2C(=O)c3cccc(NCc4ccc(CN5CC(c6ccccc6)C5)cc4)c3C2=O)C(=O)N1] | 2-(2,6-dioxopiperidin-3-yl)-4-(4-((3-phenylazetidin-1-yl)methyl)benzylamino)isoindoline-1,3-dione | 509.2 | B |

TABLE 1-continued
| Cpd # | Cpd Structure | Cpd Name | Obs. MH+ | SU-DHL-4 Act |
|---|---|---|---|---|
| 7 | 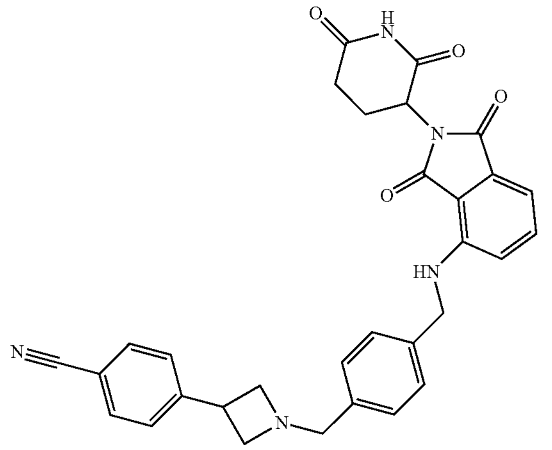 [SMILES: N#Cc1ccc(C2CN(Cc3ccc(CNc4cccc5c4C(=O)N(C4CCC(=O)NC4=O)C5=O)cc3)C2)cc1] | 4-(1-(4-((2-(2,6-dioxopiperidin-3-yl)-1,3-dioxoisoindolin-4-ylamino)methyl)benzyl)azetidin-3-yl)benzonitrile | 534.2 | D |
| 8 | 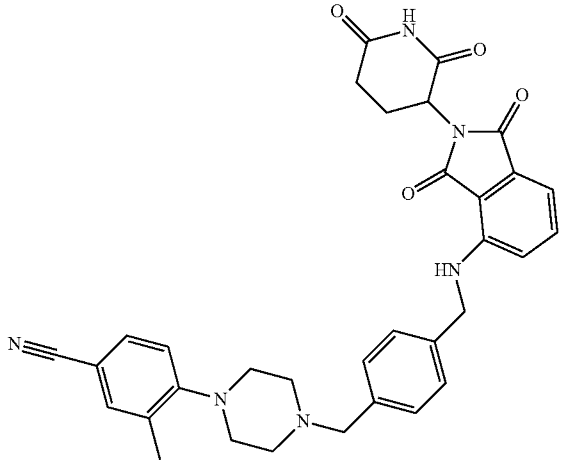 [SMILES: Cc1cc(C#N)ccc1N1CCN(Cc2ccc(CNc3cccc4c3C(=O)N(C3CCC(=O)NC3=O)C4=O)cc2)CC1] | 4-(4-(4-((2-(2,6-dioxopiperidin-3-yl)-1,3-dioxoisoindolin-4-ylamino)methyl)benzyl)piperazin-1-yl)-3-methylbenzonitrile | 577.2 | C |
| 9 | 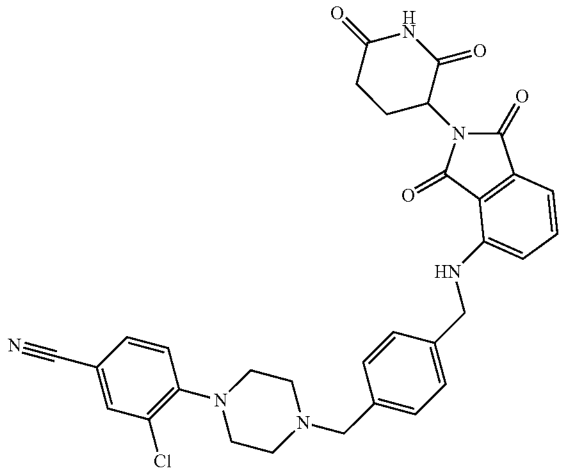 | 3-chloro-4-(4-(4-((2-(2,6-dioxopiperidin-3-yl)-1,3-dioxoisoindolin-4-ylamino)methyl)benzyl)piperazin-1-yl)benzonitrile | 597.2 | D |

TABLE 1-continued
| Cpd # | Cpd Structure | Cpd Name | Obs. MH+ | SU-DHL-4 Act |
|---|---|---|---|---|
| 10 | 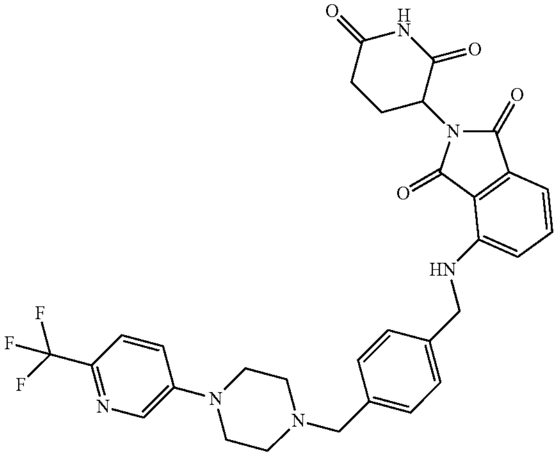 [SMILES: O=C1CCC(N2C(=O)c3cccc(NCc4ccc(CN5CCN(c6ccc(C(F)(F)F)nc6)CC5)cc4)c3C2=O)C(=O)N1] | 2-(2,6-dioxopiperidin-3-yl)-4-(4-((4-(6-(trifluoromethyl)pyridin-3-yl)piperazin-1-yl)methyl)benzylamino)isoindoline-1,3-dione | 607.2 | C |
| 11 | 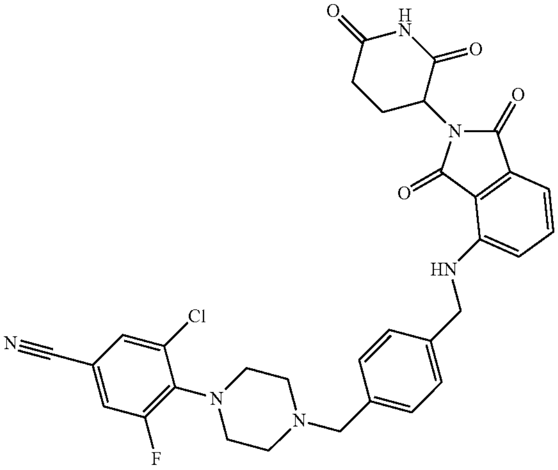 [SMILES: N#Cc1cc(F)c(N2CCN(Cc3ccc(CNc4cccc5c4C(=O)N(C4CCC(=O)NC4=O)C5=O)cc3)CC2)c(Cl)c1] | 3-chloro-4-(4-(4-((2-(2,6-dioxopiperidin-3-yl)-1,3-dioxoisoindolin-4-ylamino)methyl)benzyl)piperazin-1-yl)-5-fluorobenzonitrile | 615.2 | B |
| 12 | 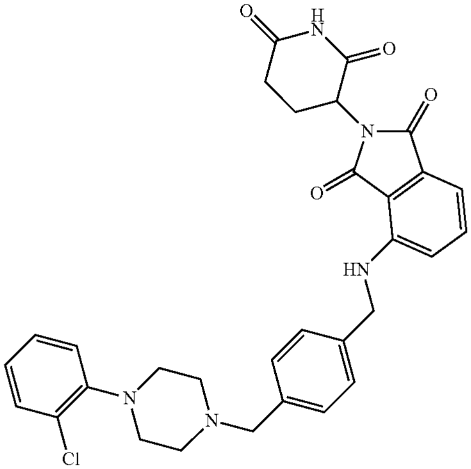 [SMILES: O=C1CCC(N2C(=O)c3cccc(NCc4ccc(CN5CCN(c6ccccc6Cl)CC5)cc4)c3C2=O)C(=O)N1] | 4-(4-((4-(2-chlorophenyl)piperazin-1-yl)methyl)benzylamino)-2-(2,6-dioxopiperidin-3-yl)isoindoline-1,3-dione | 572.2 | C |

TABLE 1-continued
| Cpd # | Cpd Structure | Cpd Name | Obs. MH+ | SU-DHL-4 Act |
|---|---|---|---|---|
| 13 | 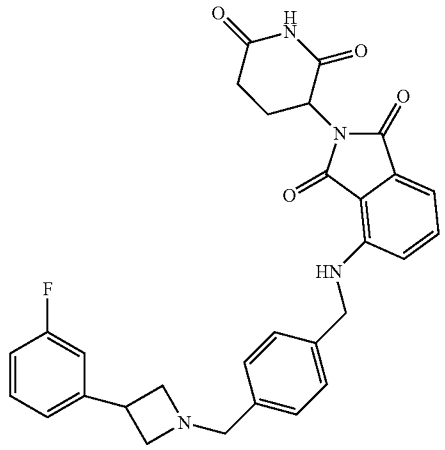 [SMILES: O=C1CCC(N2C(=O)c3cccc(NCc4ccc(CN5CC(c6cccc(F)c6)C5)cc4)c3C2=O)C(=O)N1] | 2-(2,6-dioxopiperidin-3-yl)-4-(4-((3-(3-fluorophenyl)azetidin-1-yl)methyl)benzylamino)isoindoline-1,3-dione | 527.2 | B |
| 14 | 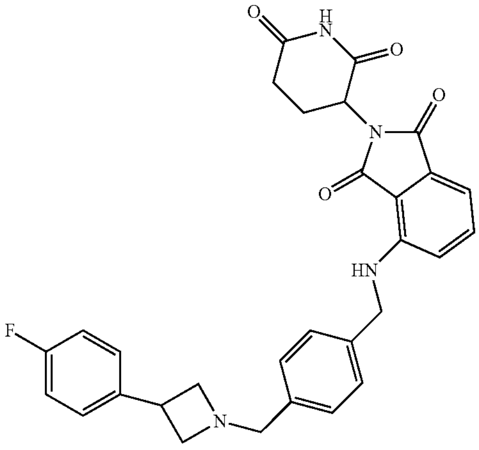 [SMILES: O=C1CCC(N2C(=O)c3cccc(NCc4ccc(CN5CC(c6ccc(F)cc6)C5)cc4)c3C2=O)C(=O)N1] | 2-(2,6-dioxopiperidin-3-yl)-4-(4-((3-(4-fluorophenyl)azetidin-1-yl)methyl)benzylamino)isoindoline-1,3-dione | 527.2 | C |
| 15 | 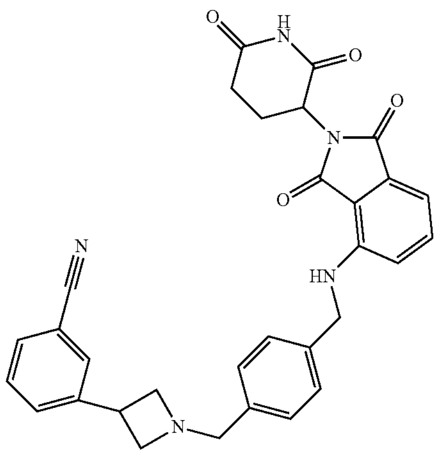 [SMILES: N#Cc1cccc(C2CN(Cc3ccc(CNc4cccc5c4C(=O)N(C4CCC(=O)NC4=O)C5=O)cc3)C2)c1] | 3-(1-(4-((2-(2,6-dioxopiperidin-3-yl)-1,3-dioxoisoindolin-4-ylamino)methyl)benzyl)azetidin-3-yl)benzonitrile | 534.2 | A |

TABLE 1-continued
| Cpd # | Cpd Structure | Cpd Name | Obs. MH+ | SU-DHL-4 Act |
|---|---|---|---|---|
| 16 | 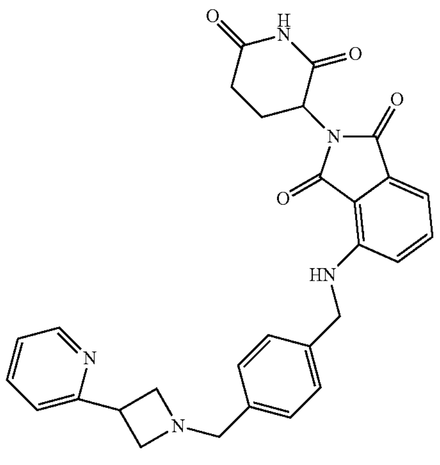 [SMILES: O=C1CCC(N2C(=O)c3cccc(NCc4ccc(CN5CC(c6ccccn6)C5)cc4)c3C2=O)C(=O)N1] | 2-(2,6-dioxopiperidin-3-yl)-4-(4-((3-(pyridin-2-yl)azetidin-1-yl)methyl)benzylamino)isoindoline-1,3-dione | 510.2 | D |
| 17 | 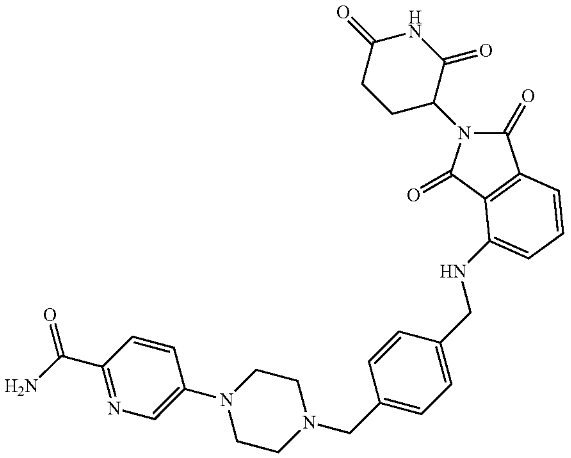 [SMILES: NC(=O)c1ccc(N2CCN(Cc3ccc(CNc4cccc5c4C(=O)N(C4CCC(=O)NC4=O)C5=O)cc3)CC2)cn1] | 5-(4-(4-((2-(2,6-dioxopiperidin-3-yl)-1,3-dioxoisoindolin-4-ylamino)methyl)benzyl)piperazin-1-yl)picolinamide | 582.2 | D |
| 18 | 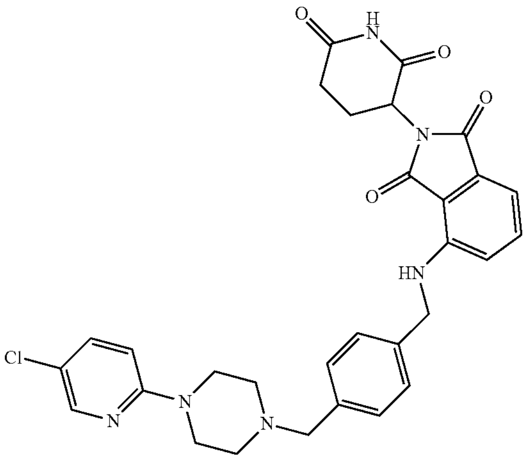 [SMILES: O=C1CCC(N2C(=O)c3cccc(NCc4ccc(CN5CCN(c6ccc(Cl)cn6)CC5)cc4)c3C2=O)C(=O)N1] | 4-(4-((4-(5-chloropyridin-2-yl)piperazin-1-yl)methyl)benzylamino)-2-(2,6-dioxopiperidin-3-yl)isoindoline-1,3-dione | 573.3 | A |

TABLE 1-continued
| Cpd # | Cpd Structure | Cpd Name | Obs. MH+ | SU-DHL-4 Act |
|---|---|---|---|---|
| 19 | 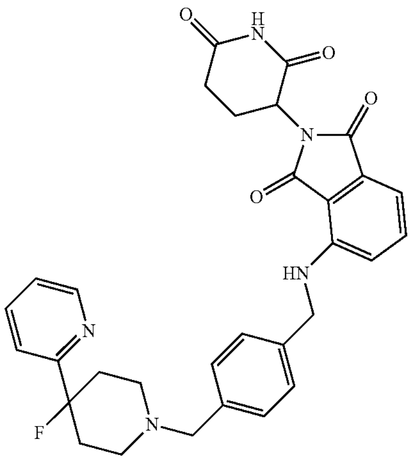 [SMILES: O=C1CCC(N2C(=O)c3cccc(NCc4ccc(CN5CCC(F)(c6ccccn6)CC5)cc4)c3C2=O)C(=O)N1] | 2-(2,6-dioxopiperidin-3-yl)-4-(4-((4-fluoro-4-(pyridin-2-yl)piperidin-1-yl)methyl)benzylamino)isoindoline-1,3-dione | 556.3 | B |
| 20 | 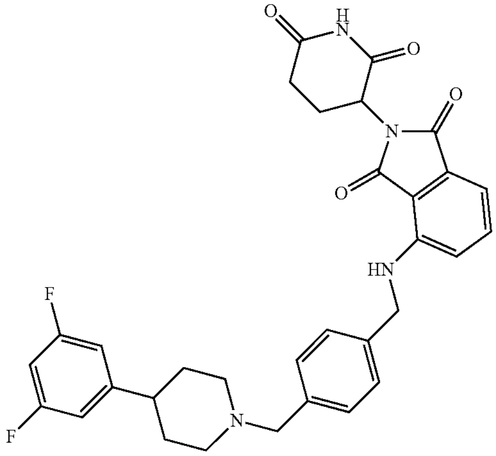 [SMILES: O=C1CCC(N2C(=O)c3cccc(NCc4ccc(CN5CCC(c6cc(F)cc(F)c6)CC5)cc4)c3C2=O)C(=O)N1] | 4-(4-((4-(3,5-difluorophenyl)piperidin-1-yl)methyl)benzylamino)-2-(2,6-dioxopiperidin-3-yl)isoindoline-1,3-dione | 573.3 | C |
| 21 | 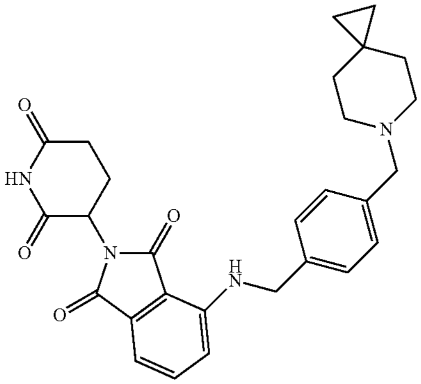 [SMILES: O=C1CCC(N2C(=O)c3cccc(NCc4ccc(CN5CCC6(CC5)CC6)cc4)c3C2=O)C(=O)N1] | 4-(4-(6-azaspiro[2.5]octan-6-ylmethyl)benzylamino)-2-(2,6-dioxopiperidin-3-yl)isoindoline-1,3-dione | 487.2 | B |

TABLE 1-continued
| Cpd # | Cpd Structure | Cpd Name | Obs. MH+ | SU-DHL-4 Act |
|---|---|---|---|---|
| 22 | 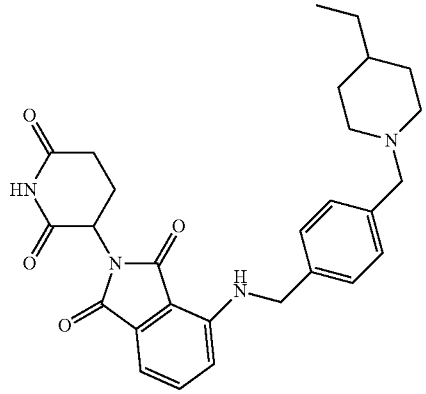 [SMILES: CCC1CCN(Cc2ccc(CNc3cccc4c3C(=O)N(C3CCC(=O)NC3=O)C4=O)cc2)CC1] | 2-(2,6-dioxopiperidin-3-yl)-4-(4-((4-ethylpiperidin-1-yl)methyl)benzylamino)isoindoline-1,3-dione | 489.2 | C |
| 23 | 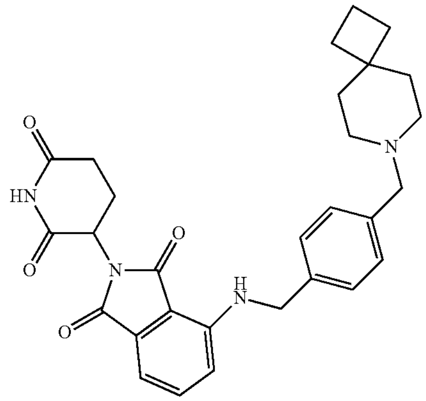 [SMILES: O=C1CCC(N2C(=O)c3cccc(NCc4ccc(CN5CCC6(CCC6)CC5)cc4)c3C2=O)C(=O)N1] | 4-(4-(7-azaspiro[3.5]nonan-7-ylmethyl)benzylamino)-2-(2,6-dioxopiperidin-3-yl)isoindoline-1,3-dione | 501.4 | D |
| 24 | 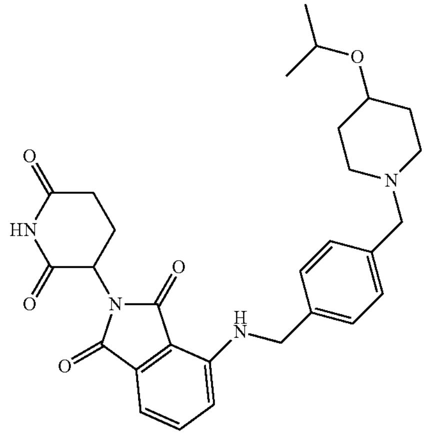 [SMILES: CC(C)OC1CCN(Cc2ccc(CNc3cccc4c3C(=O)N(C3CCC(=O)NC3=O)C4=O)cc2)CC1] | 2-(2,6-dioxopiperidin-3-yl)-4-(4-((4-isopropoxypiperidin-1-yl)methyl)benzylamino)isoindoline-1,3-dione | 519.7 | C |

TABLE 1-continued
| Cpd # | Cpd Structure | Cpd Name | Obs. MH+ | SU-DHL-4 Act |
|---|---|---|---|---|
| 25 | 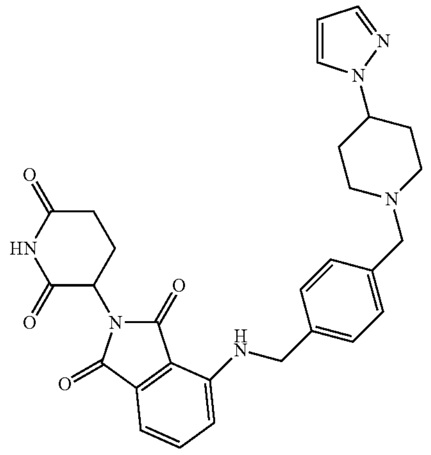 [SMILES: O=C1CCC(N2C(=O)c3cccc(NCc4ccc(CN5CCC(n6cccn6)CC5)cc4)c3C2=O)C(=O)N1] | 4-(4-((4-(1H-pyrazol-1-yl)piperidin-1-yl)methyl)benzylamino)-2-(2,6-dioxopiperidin-3-yl)isoindoline-1,3-dione | 527.6 | C |
| 26 | 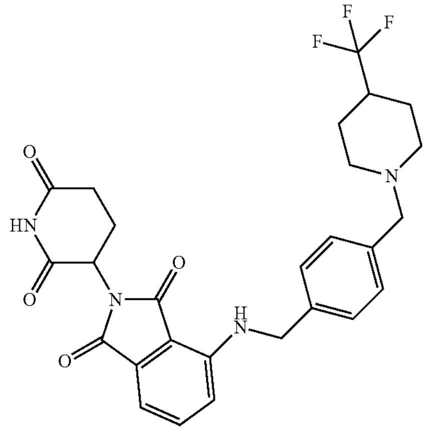 [SMILES: O=C1CCC(N2C(=O)c3cccc(NCc4ccc(CN5CCC(C(F)(F)F)CC5)cc4)c3C2=O)C(=O)N1] | 2-(2,6-dioxopiperidin-3-yl)-4-(4-((4-(trifluoromethyl)piperidin-1-yl)methyl)benzylamino)isoindoline-1,3-dione | 529.5 | C |
| 27 | 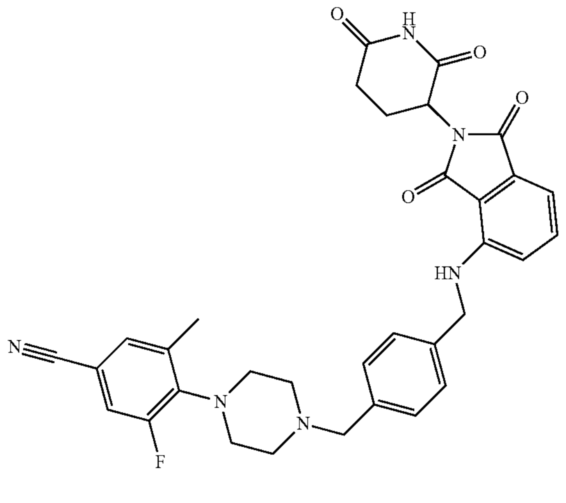 [SMILES: Cc1cc(C#N)cc(F)c1N1CCN(Cc2ccc(CNc3cccc4c3C(=O)N(C3CCC(=O)NC3=O)C4=O)cc2)CC1] | 4-(4-(4-((2-(2,6-dioxopiperidin-3-yl)-1,3-dioxoisoindolin-4-ylamino)methyl)benzyl)piperazin-1-yl)-3-fluoro-5-methylbenzonitrile | 595.3 | C |

TABLE 1-continued
| Cpd # | Cpd Structure | Cpd Name | Obs. MH+ | SU-DHL-4 Act |
|---|---|---|---|---|
| 28 | 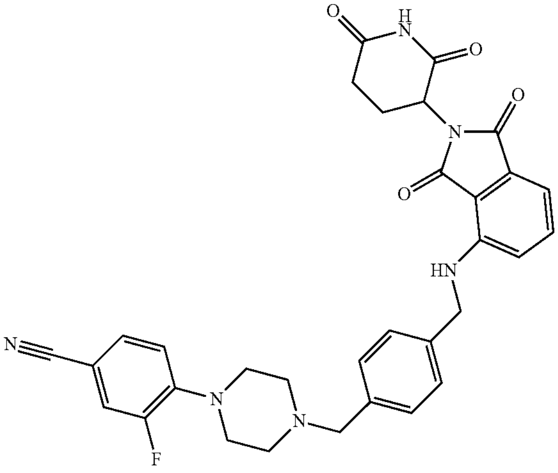 | 4-(4-(4-((2-(2,6-dioxopiperidin-3-yl)-1,3-dioxoisoindolin-4-ylamino)methyl)benzyl)piperazin-1-yl)-3-fluorobenzonitrile | 581.3 | D |
| 29 | 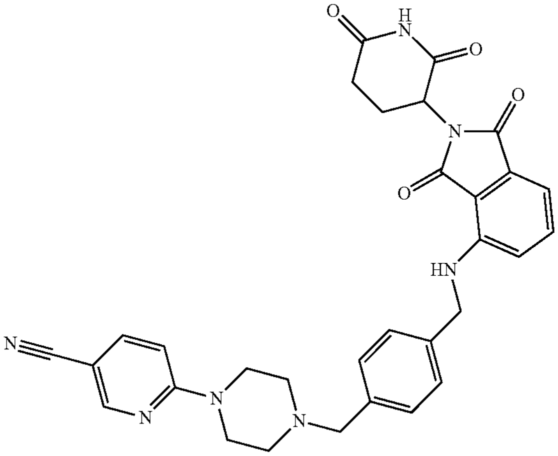 [SMILES: N#Cc1ccc(N2CCN(Cc3ccc(CNc4cccc5c4C(=O)N(C4CCC(=O)NC4=O)C5=O)cc3)CC2)nc1] | 6-(4-(4-((2-(2,6-dioxopiperidin-3-yl)-1,3-dioxoisoindolin-4-ylamino)methyl)benzyl)piperazin-1-yl)nicotinonitrile | 564.3 | C |
| 30 | 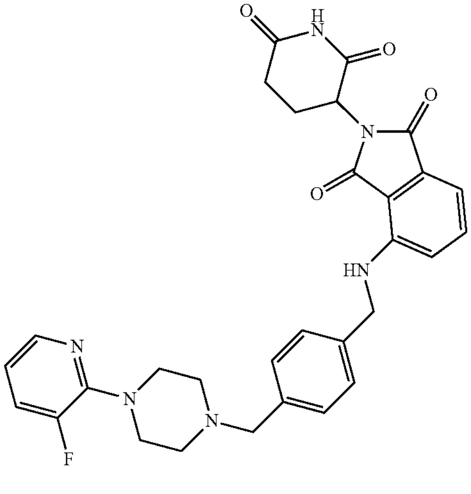 [SMILES: O=C1CCC(N2C(=O)c3cccc(NCc4ccc(CN5CCN(c6ncccc6F)CC5)cc4)c3C2=O)C(=O)N1] | 2-(2,6-dioxopiperidin-3-yl)-4-(4-((4-(3-fluoropyridin-2-yl)piperazin-1-yl)methyl)benzylamino)isoindoline-1,3-dione | 557.3 | D |

TABLE 1-continued
| Cpd # | Cpd Structure | Cpd Name | Obs. MH+ | SU-DHL-4 Act |
|---|---|---|---|---|
| 31 | 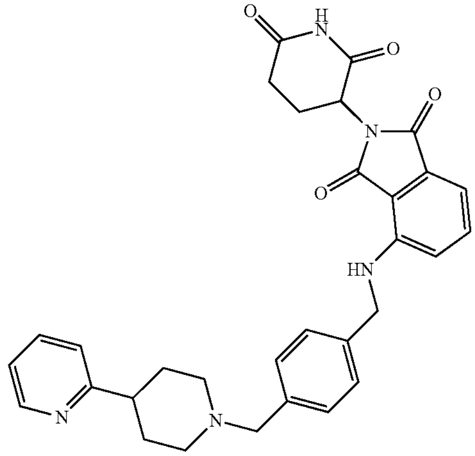 [SMILES: O=C1CCC(N2C(=O)c3cccc(NCc4ccc(CN5CCC(c6ccccn6)CC5)cc4)c3C2=O)C(=O)N1] | 2-(2,6-dioxopiperidin-3-yl)-4-(4-((4-(pyridin-2-yl)piperidin-1-yl)methyl)benzylamino)isoindoline-1,3-dione | 538.2 | C |
| 32 | 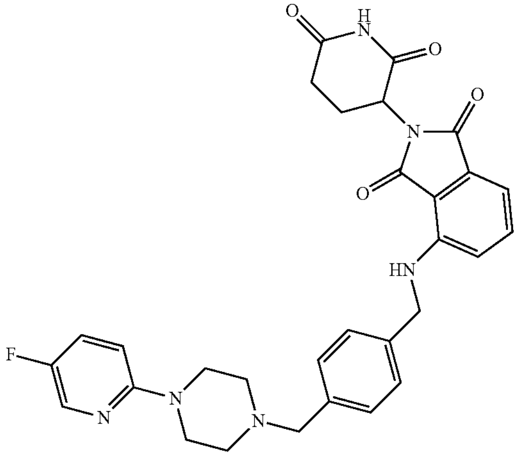 [SMILES: O=C1CCC(N2C(=O)c3cccc(NCc4ccc(CN5CCN(c6ccc(F)cn6)CC5)cc4)c3C2=O)C(=O)N1] | 2-(2,6-dioxopiperidin-3-yl)-4-(4-((4-(5-fluoropyridin-2-yl)piperazin-1-yl)methyl)benzylamino)isoindoline-1,3-dione | 557.3 | C |
| 33 | 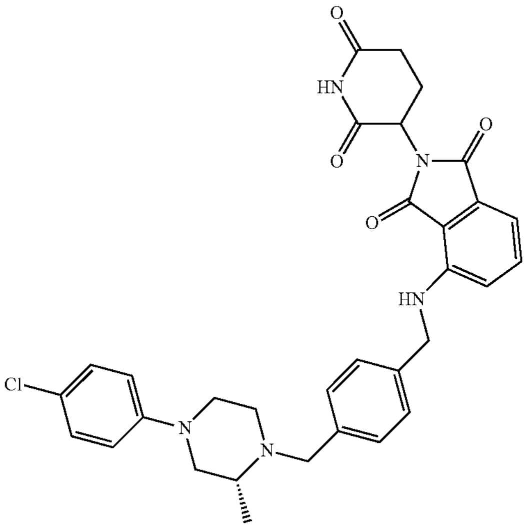 [SMILES: C[C@@H]1CN(c2ccc(Cl)cc2)CCN1Cc1ccc(CNc2cccc3c2C(=O)N(C2CCC(=O)NC2=O)C3=O)cc1] | 4-(4-(((R)-4-(4-chlorophenyl)-2-methylpiperazin-1-yl)methyl)benzylamino)-2-(2,6-dioxopiperidin-3-yl)isoindoline-1,3-dione | 586.2 | C |

TABLE 1-continued
| Cpd # | Cpd Structure | Cpd Name | Obs. MH+ | SU-DHL-4 Act |
|---|---|---|---|---|
| 34 | 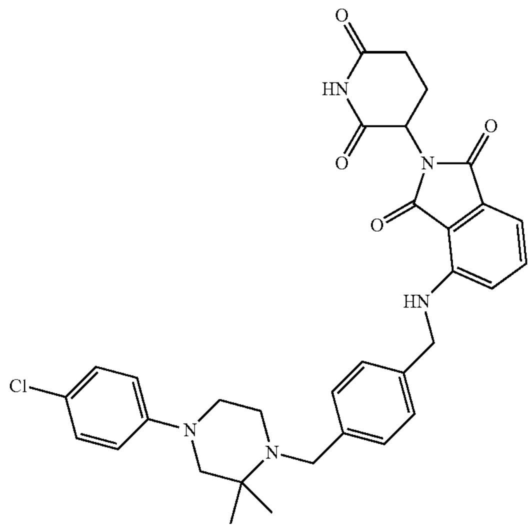 [SMILES: CC1(C)CN(c2ccc(Cl)cc2)CCN1Cc1ccc(CNc2cccc3c2C(=O)N(C2CCC(=O)NC2=O)C3=O)cc1] | 4-(4-((4-(4-chlorophenyl)-2,2-dimethylpiperazin-1-yl)methyl)benzylamino)-2-(2,6-dioxopiperidin-3-yl)isoindoline-1,3-dione | 600.2 | A |
| 35 | 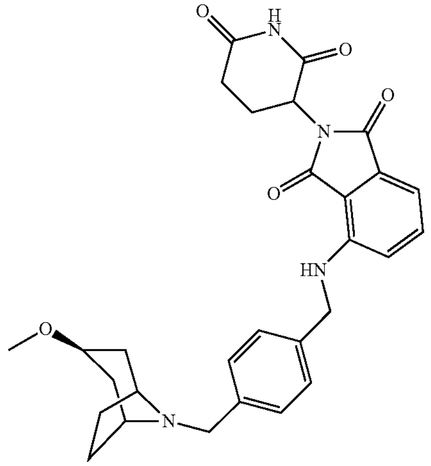 | 2-(2,6-dioxopiperidin-3-yl)-4-(4-(((1R,3r,5S)-3-methoxy-8-azabicyclo[3.2.1]octan-8-yl)methyl)benzylamino)isoindoline-1,3-dione | 517.2 | A |
| 36 | 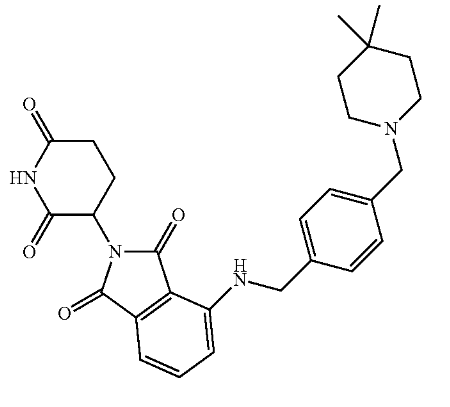 [SMILES: CC1(C)CCN(Cc2ccc(CNc3cccc4c3C(=O)N(C3CCC(=O)NC3=O)C4=O)cc2)CC1] | 4-(4-((4,4-dimethylpiperidin-1-yl)methyl)benzylamino)-2-(2,6-dioxopiperidin-3-yl)isoindoline-1,3-dione | 489.2 | C |

TABLE 1-continued
| Cpd # | Cpd Structure | Cpd Name | Obs. MH+ | SU-DHL-4 Act |
|---|---|---|---|---|
| 37 | 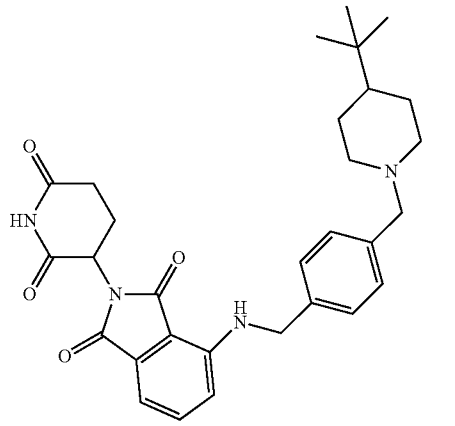 [SMILES: CC(C)(C)C1CCN(Cc2ccc(CNc3cccc4c3C(=O)N(C3CCC(=O)NC3=O)C4=O)cc2)CC1] | 4-(4-((4-tert-butylpiperidin-1-yl)methyl)benzylamino)-2-(2,6-dioxopiperidin-3-yl)isoindoline-1,3-dione | 517.4 | D |
| 38 | 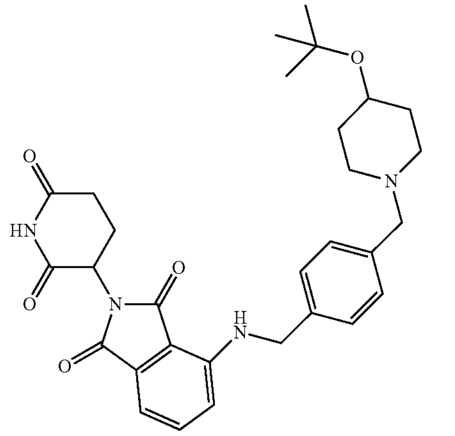 [SMILES: CC(C)(C)OC1CCN(Cc2ccc(CNc3cccc4c3C(=O)N(C3CCC(=O)NC3=O)C4=O)cc2)CC1] | 4-(4-((4-tert-butoxypiperidin-1-yl)methyl)benzylamino)-2-(2,6-dioxopiperidin-3-yl)isoindoline-1,3-dione | 533.3 | D |
| 39 | 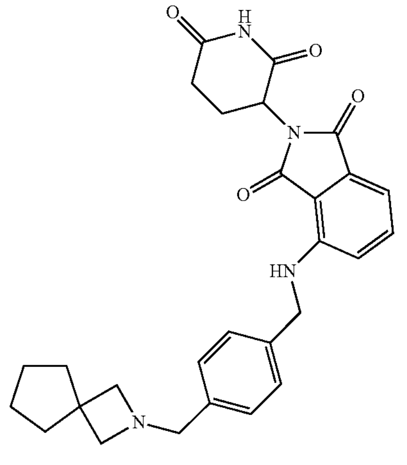 [SMILES: O=C1CCC(N2C(=O)c3cccc(NCc4ccc(CN5CC6(CCCC6)C5)cc4)c3C2=O)C(=O)N1] | 4-(4-(2-azaspiro[3.4]octan-2-ylmethyl)benzylamino)-2-(2,6-dioxopiperidin-3-yl)isoindoline-1,3-dione | 487.2 | D |

TABLE 1-continued

| Cpd # | Cpd Structure | Cpd Name | Obs. MH+ | SU-DHL-4 Act |
|---|---|---|---|---|
| 40 | 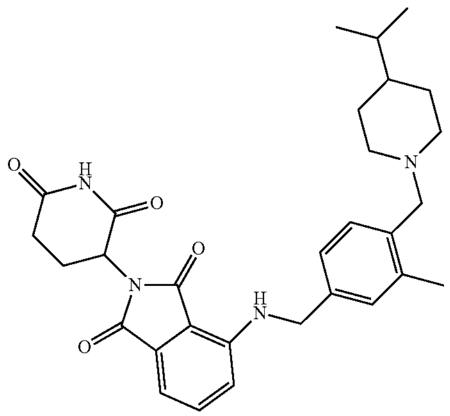 [SMILES: Cc1cc(CNc2cccc3c2C(=O)N(C2CCC(=O)NC2=O)C3=O)ccc1CN1CCC(C(C)C)CC1] | 2-(2,6-dioxopiperidin-3-yl)-4-(4-((4-isopropylpiperidin-1-yl)methyl)-3-methylbenzylamino)isoindoline-1,3-dione | 517.9 | D |
| 41 | 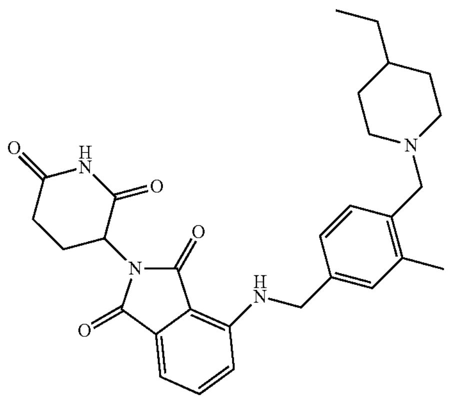 [SMILES: CCC1CCN(Cc2ccc(CNc3cccc4c3C(=O)N(C3CCC(=O)NC3=O)C4=O)cc2C)CC1] | 2-(2,6-dioxopiperidin-3-yl)-4-(4-((4-ethylpiperidin-1-yl)methyl)-3-methylbenzylamino)isoindoline-1,3-dione | 503.6 | D |
| 42 | 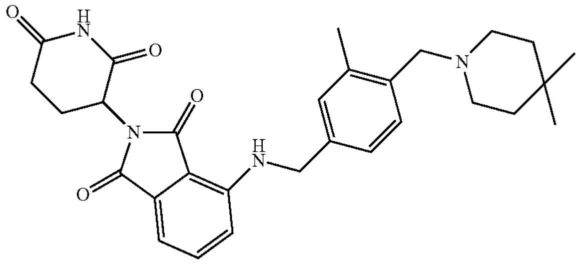 [SMILES: Cc1cc(CNc2cccc3c2C(=O)N(C2CCC(=O)NC2=O)C3=O)ccc1CN1CCC(C)(C)CC1] | 4-(4-((4,4-dimethylpiperidin-1-yl)methyl)-3-methylbenzylamino)-2-(2,6-dioxopiperidin-3-yl)isoindoline-1,3-dione | 503.9 | D |
| 43 | 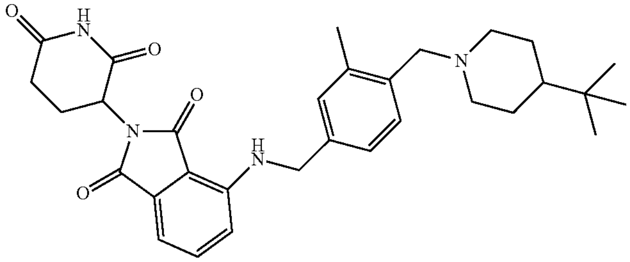 [SMILES: Cc1cc(CNc2cccc3c2C(=O)N(C2CCC(=O)NC2=O)C3=O)ccc1CN1CCC(C(C)(C)C)CC1] | 4-(4-((4-tert-butylpiperidin-1-yl)methyl)-3-methylbenzylamino)-2-(2,6-dioxopiperidin-3-yl)isoindoline-1,3-dione | 531.9 | D |

TABLE 1-continued

| Cpd # | Cpd Structure | Cpd Name | Obs. MH+ | SU-DHL-4 Act |
|---|---|---|---|---|
| 44 | 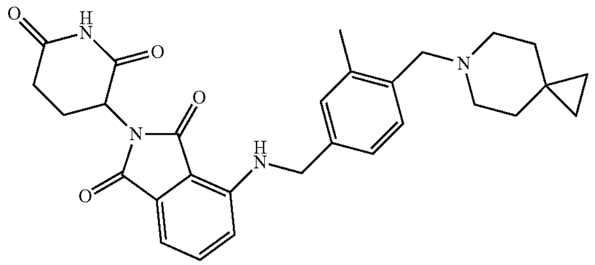 [SMILES: Cc1cc(CNc2cccc3c2C(=O)N(C2CCC(=O)NC2=O)C3=O)ccc1CN1CCC2(CC1)CC2] | 4-(4-(6-azaspiro[2.5]octan-6-ylmethyl)-3-methylbenzylamino)-2-(2,6-dioxopiperidin-3-yl)isoindoline-1,3-dione | 501.6 | D |
| 45 | 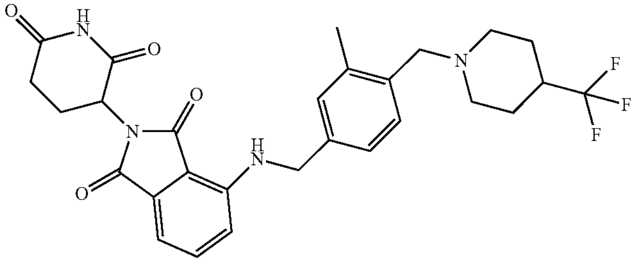 [SMILES: Cc1cc(CNc2cccc3c2C(=O)N(C2CCC(=O)NC2=O)C3=O)ccc1CN1CCC(C(F)(F)F)CC1] | 2-(2,6-dioxopiperidin-3-yl)-4-(3-methyl-4-((4-(trifluoromethyl)piperidin-1-yl)methyl)benzylamino)isoindoline-1,3-dione | 543.9 | D |
| 46 | 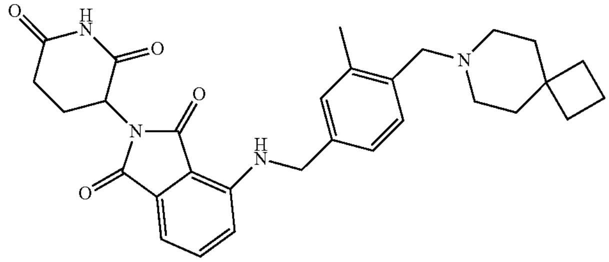 [SMILES: Cc1cc(CNc2cccc3c2C(=O)N(C2CCC(=O)NC2=O)C3=O)ccc1CN1CCC2(CCC2)CC1] | 4-(4-(7-azaspiro[3.5]nonan-7-ylmethyl)-3-methylbenzylamino)-2-(2,6-dioxopiperidin-3-yl)isoindoline-1,3-dione | 515.4 | D |
| 47 | 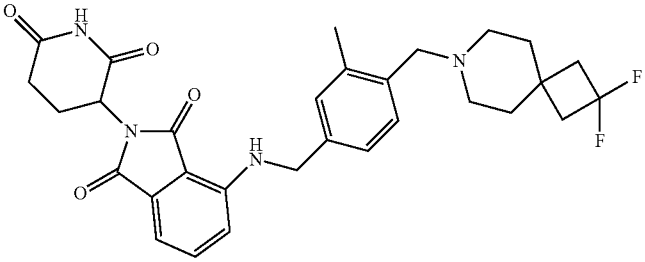 [SMILES: Cc1cc(CNc2cccc3c2C(=O)N(C2CCC(=O)NC2=O)C3=O)ccc1CN1CCC2(CC1)CC(F)(F)C2] | 4-(4-((2,2-difluoro-7-azaspiro[3.5]nonan-7-yl)methyl)-3-methylbenzylamino)-2-(2,6-dioxopiperidin-3-yl)isoindoline-1,3-dione | 551.4 | D |
| 48 | 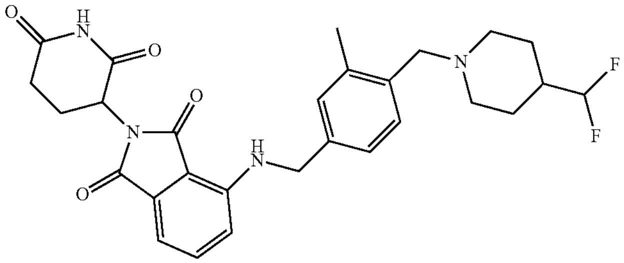 [SMILES: Cc1cc(CNc2cccc3c2C(=O)N(C2CCC(=O)NC2=O)C3=O)ccc1CN1CCC(C(F)F)CC1] | 4-(4-((4-(difluoromethyl)piperidin-1-yl)methyl)-3-methylbenzylamino)-2-(2,6-dioxopiperidin-3-yl)isoindoline-1,3-dione | 525.8 | C |

TABLE 1-continued

| Cpd # | Cpd Structure | Cpd Name | Obs. MH+ | SU-DHL-4 Act |
|---|---|---|---|---|
| 49 | 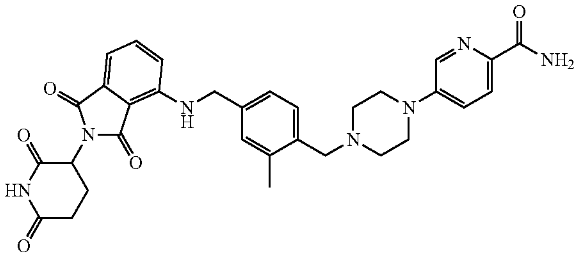 [SMILES: Cc1cc(CNc2cccc3c2C(=O)N(C2CCC(=O)NC2=O)C3=O)ccc1CN1CCN(c2ccc(C(N)=O)nc2)CC1] | 5-(4-(4-((2-(2,6-dioxopiperidin-3-yl)-1,3-dioxoisoindolin-4-ylamino)methyl)-2-methylbenzyl)piperazin-1-yl)picolinamide | 596.6 | D |
| 50 | 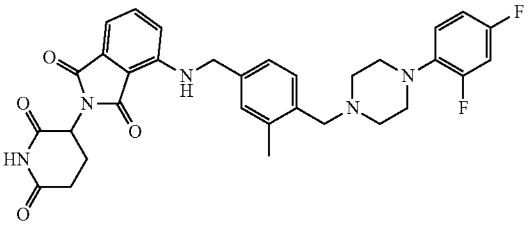 [SMILES: Cc1cc(CNc2cccc3c2C(=O)N(C2CCC(=O)NC2=O)C3=O)ccc1CN1CCN(c2ccc(F)cc2F)CC1] | 4-(4-((4-(2,4-difluorophenyl)piperazin-1-yl)methyl)-3-methylbenzylamino)-2-(2,6-dioxopiperidin-3-yl)isoindoline-1,3-dione | 588.2 | C |
| 51 | 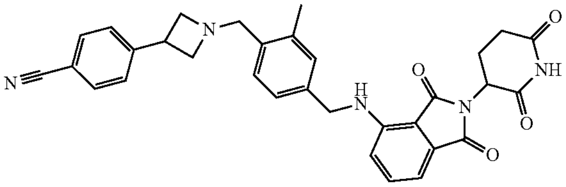 [SMILES: Cc1cc(CNc2cccc3c2C(=O)N(C2CCC(=O)NC2=O)C3=O)ccc1CN1CC(c2ccc(C#N)cc2)C1] | 4-(1-(4-((2-(2,6-dioxopiperidin-3-yl)-1,3-dioxoisoindolin-4-ylamino)methyl)-2-methylbenzyl)aetidin-3-yl)benzonitrile | 548.2 | D |
| 52 | 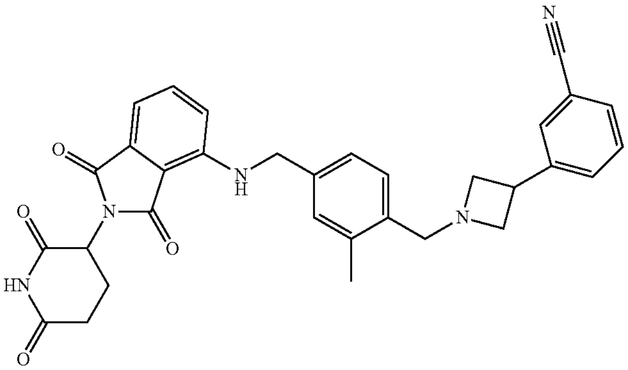 [SMILES: Cc1cc(CNc2cccc3c2C(=O)N(C2CCC(=O)NC2=O)C3=O)ccc1CN1CC(c2cccc(C#N)c2)C1] | 3-(1-(4-((2-(2,6-dioxopiperidin-3-yl)-1,3-dioxoisoindolin-4-ylamino)methyl)-2-mtehylbenzyl)azetidin-3-yl)benzonitrile | 548.2 | D |

TABLE 1-continued
| Cpd # | Cpd Structure | Cpd Name | Obs. MH+ | SU-DHL-4 Act |
|---|---|---|---|---|
| 53 | 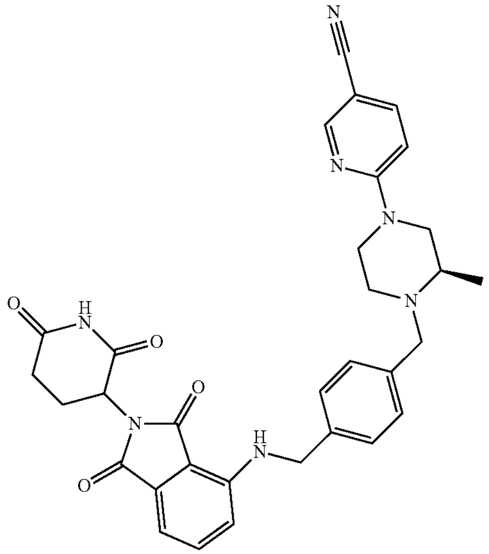 [SMILES: C[C@@H]1CN(c2ccc(C#N)cn2)CCN1Cc1ccc(CNc2cccc3c2C(=O)N(C2CCC(=O)NC2=O)C3=O)cc1] | 6-((3R)-4-(4-((2-(2,6-dioxopiperidin-3-yl)-1,3-dioxoisoindolin-4-ylamino)methyl)benzyl)-3-methylpiperazin-1-yl)nicotinonitrile | 578.3 | D |
| 54 | 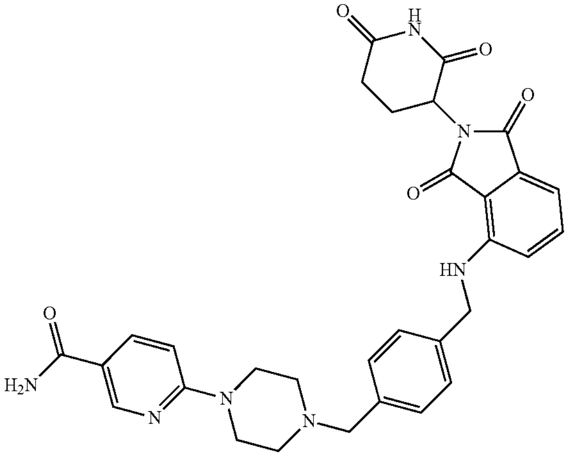 [SMILES: NC(=O)c1ccc(N2CCN(Cc3ccc(CNc4cccc5c4C(=O)N(C4CCC(=O)NC4=O)C5=O)cc3)CC2)nc1] | 6-(4-(4-((2-(2,6-dioxopiperidin-3-yl)-1,3-dioxoisoindolin-4-ylamino)methyl)benzyl)piperazin-1-yl)nicotinamide | 582.3 | C |
| 55 | 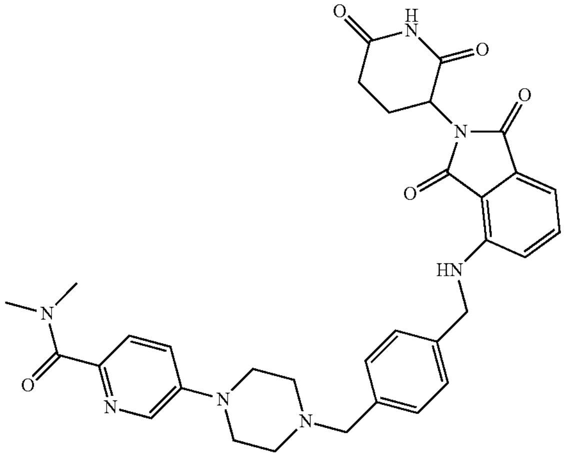 [SMILES: CN(C)C(=O)c1ccc(N2CCN(Cc3ccc(CNc4cccc5c4C(=O)N(C4CCC(=O)NC4=O)C5=O)cc3)CC2)cn1] | 5-(4-(4-((2-(2,6-dioxopiperidin-3-yl)-1,3-dioxoisoindolin-4-ylamino)methyl)benzyl)piperazin-1-yl)-N,N-dimethylpicolinamide | 610.4 | C |

TABLE 1-continued
| Cpd # | Cpd Structure | Cpd Name | Obs. MH+ | SU-DHL-4 Act |
|---|---|---|---|---|
| 56 | 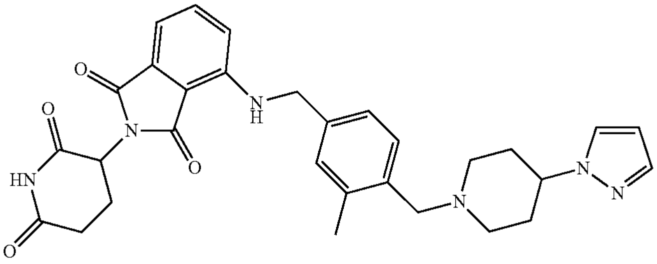 [SMILES: Cc1cc(CNc2cccc3c2C(=O)N(C2CCC(=O)NC2=O)C3=O)ccc1CN1CCC(n2cccn2)CC1] | 4-(4-((4-(1H-pyrazol-1-yl)piperidin-1-yl)methyl)-3-methylbenzylamino)-2-(2,6-dioxopiperidin-3-yl)isoindoline-1,3-dione | 541.2 | D |
| 57 | 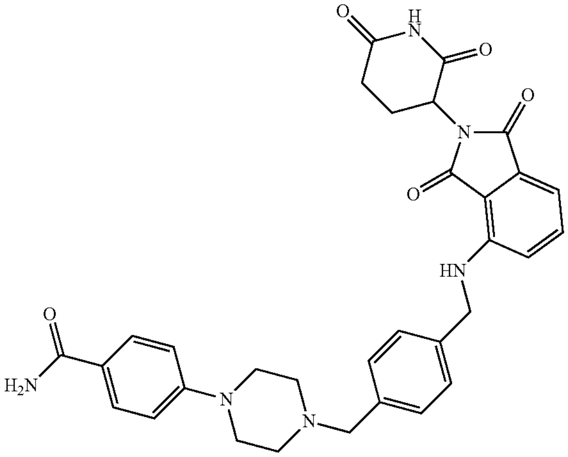 | 4-(4-(4-((2-(2,6-dioxopiperidin-3-yl)-1,3-dioxoisoindolin-4-ylamino)methyl)benzyl)piperazin-1-yl)benzamide | 581.4 | D |
| 58 | 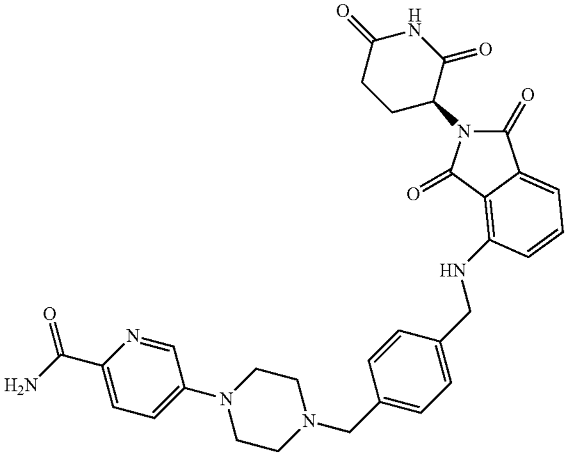 [SMILES: NC(=O)c1ccc(N2CCN(Cc3ccc(CNc4cccc5c4C(=O)N([C@H]4CCC(=O)NC4=O)C5=O)cc3)CC2)cn1] | (S)-5-(4-(4-((2-(2,6-dioxopiperidin-3-yl)-1,3-dioxoisoindolin-4-ylamino)methyl)benzyl)piperazin-1-yl)picolinamide | 582.2 | D |

TABLE 1-continued

| Cpd # | Cpd Structure | Cpd Name | Obs. MH+ | SU-DHL-4 Act |
|---|---|---|---|---|
| 59 | 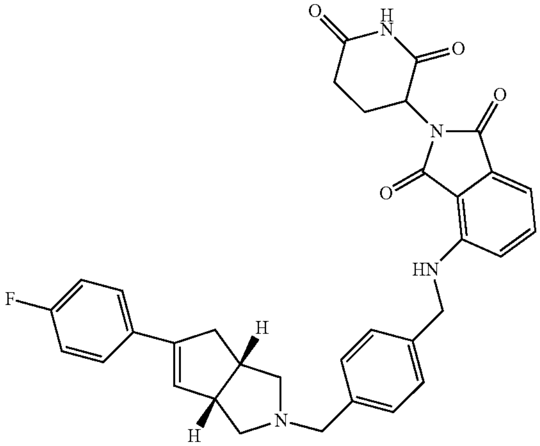 [SMILES: O=C1CCC(N2C(=O)c3cccc(NCc4ccc(CN5C[C@H]6CC(c7ccc(F)cc7)=C[C@H]6C5)cc4)c3C2=O)C(=O)N1] | 2-(2,6-dioxopiperidin-3-yl)-4-(4-(((3aS,6aR)-5-(4-fluorophenyl)-3,3a,6,6a-tetrahydrocyclopenta[c]pyrrol-2(1H)-yl)methyl)benzylamino)isoindoline-1,3-dione | 579.2 | D |
| 60 | 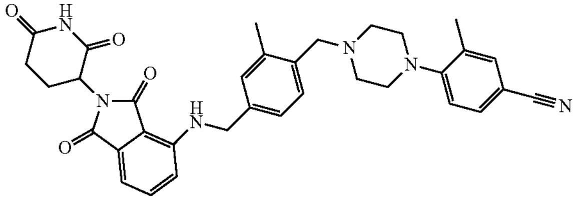 [SMILES: Cc1cc(CNc2cccc3c2C(=O)N(C2CCC(=O)NC2=O)C3=O)ccc1CN1CCN(c2ccc(C#N)cc2C)CC1] | 4-(4-(4-((2-(2,6-dioxopiperidin-3-yl)-1,3-dioxoisoindolin-4-ylamino)methyl)-2-methylbenzyl)piperazin-1-yl)-3-methylbenzonitrile | 591.3 | D |
| 61 | 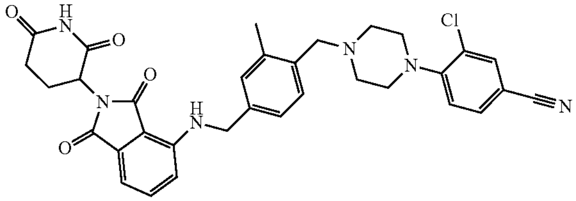 [SMILES: Cc1cc(CNc2cccc3c2C(=O)N(C2CCC(=O)NC2=O)C3=O)ccc1CN1CCN(c2ccc(C#N)cc2Cl)CC1] | 3-chloro-4-(4-(4-((2-(2,6-dioxopiperidin-3-yl)-1,3-dioxoisoindolin-4-ylamino)methyl)-2-methylbenzyl)piperazin-1-yl)benzonitrile | 611.3 | D |
| 62 | 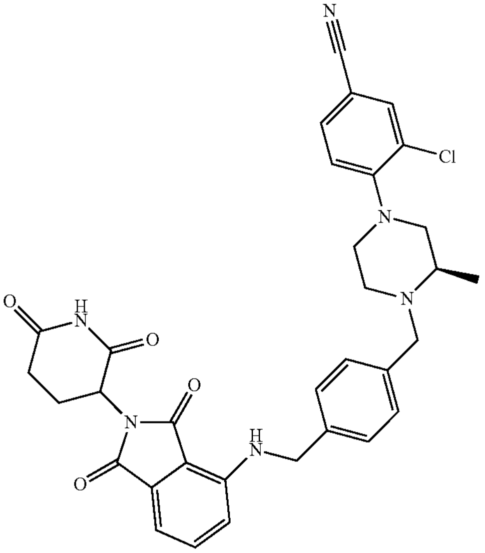 [SMILES: C[C@@H]1CN(c2ccc(C#N)cc2Cl)CCN1Cc1ccc(CNc2cccc3c2C(=O)N(C2CCC(=O)NC2=O)C3=O)cc1] | 3-chloro-4-((3R)-4-(4-((2-(2,6-dioxopiperidin-3-yl)-1,3-dioxoisoindolin-4-ylamino)methyl)benzyl)-3-methylpiperazin-1-yl)benzonitrile | 611.3 | D |

TABLE 1-continued

| Cpd # | Cpd Structure | Cpd Name | Obs. MH+ | SU-DHL-4 Act |
|---|---|---|---|---|
| 63 | 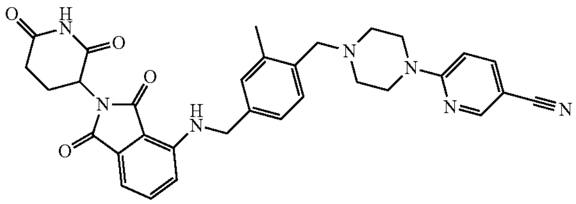 [SMILES: Cc1cc(CNc2cccc3c2C(=O)N(C2CCC(=O)NC2=O)C3=O)ccc1CN1CCN(c2ccc(C#N)cn2)CC1] | 6-(4-(4-((2-(2,6-dioxopiperidin-3-yl)-1,3-dioxoisoindolin-4-ylamino)methyl)-2-methylbenzyl)piperazin-1-yl)nicotinonitrile | 578.3 | D |
| 64 | 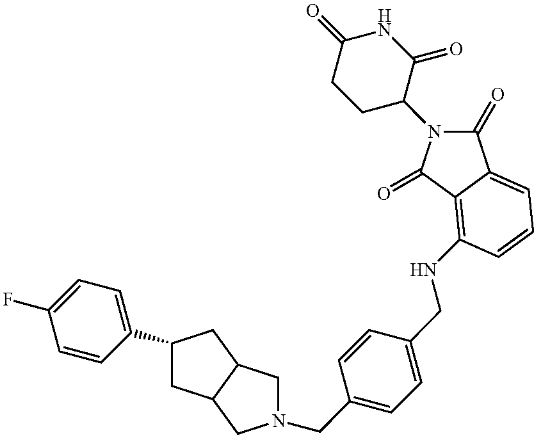 | 2-(2,6-dioxopiperidin-3-yl)-4-(4-(((3aR,5r,6aS)-5-(4-fluorophenyl)hexahydrocyclopenta[c]pyrrol-2-(1H)-yl)methyl)benzylamino)isoindoline-1,3-dione | 581.2 | C |
| 65 | 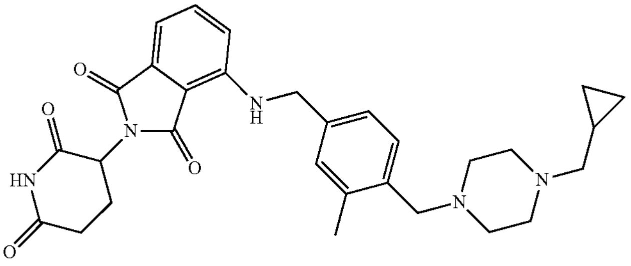 [SMILES: Cc1cc(CNc2cccc3c2C(=O)N(C2CCC(=O)NC2=O)C3=O)ccc1CN1CCN(CC2CC2)CC1] | 4-(4-((4-(cyclopropylmethyl)piperazin-1-yl)methyl)-3-methylbenzylamino)-2-(2,6-dioxopiperidin-3-yl)isoindoline-1,3-dione | 530.3 | C |
| 66 | 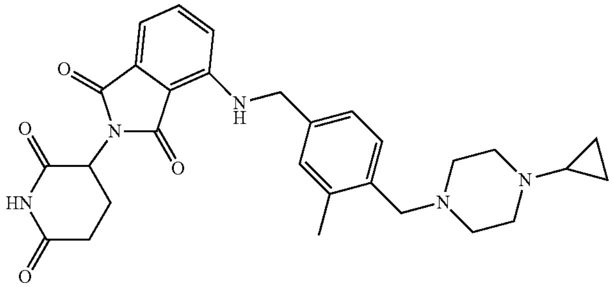 [SMILES: Cc1cc(CNc2cccc3c2C(=O)N(C2CCC(=O)NC2=O)C3=O)ccc1CN1CCN(C2CC2)CC1] | 4-(4-((4-cyclopropylpiperazin-1-yl)methyl)-3-methylbenzylamino)-2-(2,6-dioxopiperidin-3-yl)isoindoline-1,3-dione | 516.2 | D |

TABLE 1-continued

| Cpd # | Cpd Structure | Cpd Name | Obs. MH+ | SU-DHL-4 Act |
|---|---|---|---|---|
| 67 | 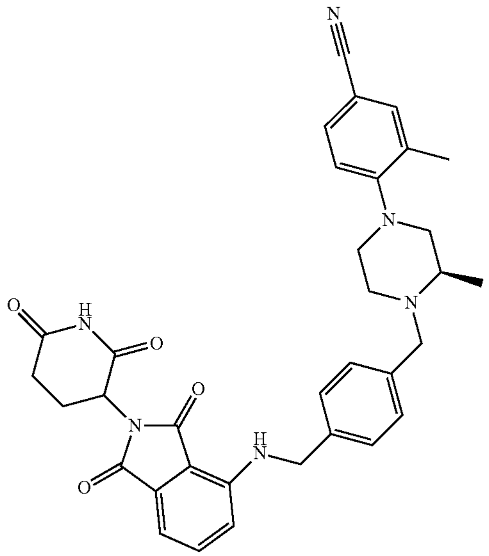 [SMILES: Cc1cc(C#N)ccc1N1CCN(Cc2ccc(CNc3cccc4c3C(=O)N(C3CCC(=O)NC3=O)C4=O)cc2)[C@H](C)C1] | 4-((3R)-4-(4-((2-(2,6-dioxopiperidin-3-yl)-1,3-dioxoisoindolin-4-ylamino)methyl)benzyl)-3-methylpiperazin-1-yl)-3-methylbenzonitrile | 591.2 | D |
| 68 | 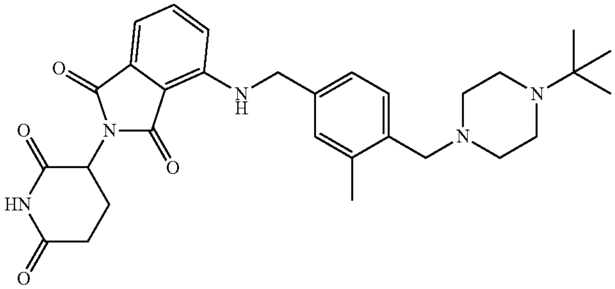 [SMILES: Cc1cc(CNc2cccc3c2C(=O)N(C2CCC(=O)NC2=O)C3=O)ccc1CN1CCN(C(C)(C)C)CC1] | 4-(4-((4-tert-butylpiperazin-1-yl)methyl)-3-methylbenzylamino)-2-(2,6-dioxopiperidin-3-yl)isoindoline-1,3-dione | 532.4 | D |
| 69 | 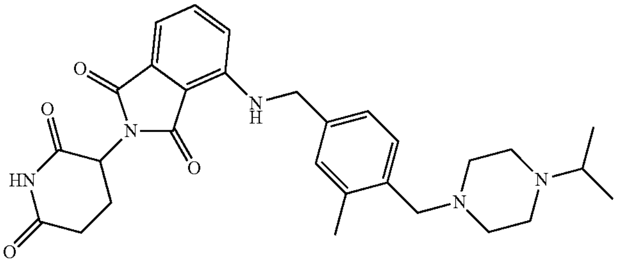 [SMILES: Cc1cc(CNc2cccc3c2C(=O)N(C2CCC(=O)NC2=O)C3=O)ccc1CN1CCN(C(C)C)CC1] | 2-(2,6-dioxopiperidin-3-yl)-4-(4-((4-isopropylpiperazin-1-yl)methyl)-3-methylbenzylamino)isoindoline-1,3-dione | 518.2 | D |
| 70 | 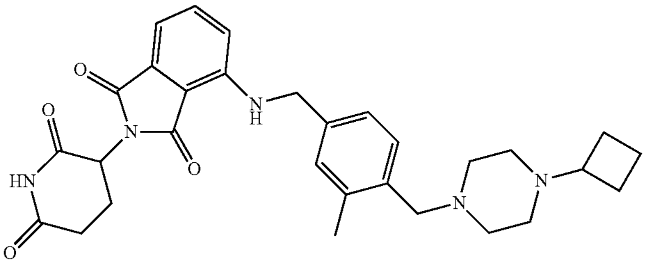 [SMILES: Cc1cc(CNc2cccc3c2C(=O)N(C2CCC(=O)NC2=O)C3=O)ccc1CN1CCN(C2CCC2)CC1] | 4-(4-((4-cyclobutylpiperazin-1-yl)methyl)-3-methylbenzylamino)-2-(2,6-dioxopiperidin-3-yl)isoindoline-1,3-dione | 530.4 | D |

TABLE 1-continued
| Cpd # | Cpd Structure | Cpd Name | Obs. MH+ | SU-DHL-4 Act |
|---|---|---|---|---|
| 71 | 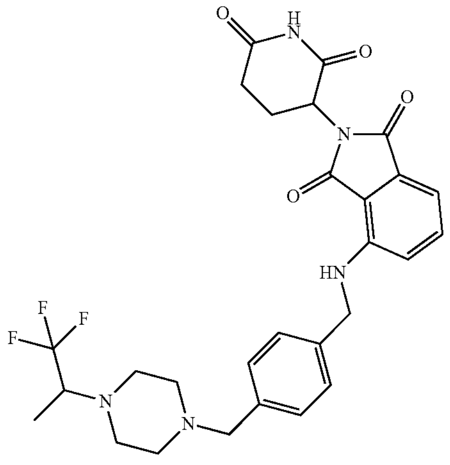 [SMILES: CC(N1CCN(Cc2ccc(CNc3cccc4c3C(=O)N(C3CCC(=O)NC3=O)C4=O)cc2)CC1)C(F)(F)F] | 2-(2,6-dioxopiperidin-3-yl)-4-(4-((4-(1,1,1,-trifluoropropan-2-yl)piperazin-1-yl)methyl)benzylamino)isoindoline-1,3-dione | 558.2 | D |
| 72 | 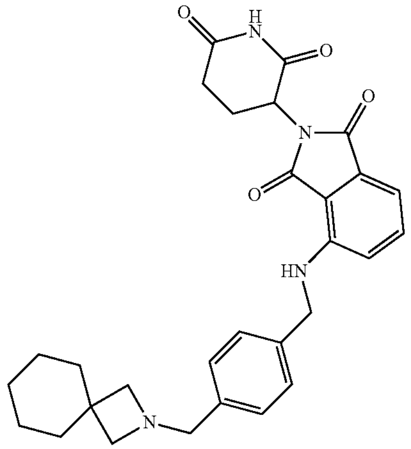 [SMILES: O=C1CCC(N2C(=O)c3cccc(NCc4ccc(CN5CC6(CCCCC6)C5)cc4)c3C2=O)C(=O)N1] | 4-(4-(2-azaspiro[3.5]nonan-2-ylmethyl)benzylamino)-2-(2,6-dioxopiperidin-3-yl)isoindoline-1,3-dione | 501.2 | C |
| 73 | 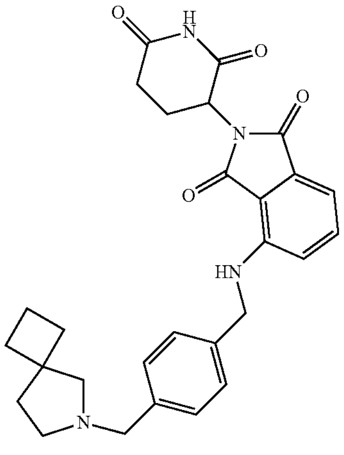 [SMILES: O=C1CCC(N2C(=O)c3cccc(NCc4ccc(CN5CCC6(CCC6)C5)cc4)c3C2=O)C(=O)N1] | 4-(4-(6-azaspiro[3.4]octan-6-ylmethyl)benzylamino)-2-(2,6-dioxopiperidin-3-yl)isoindoline-1,3-dione | 487.2 | A |

TABLE 1-continued
| Cpd # | Cpd Structure | Cpd Name | Obs. MH+ | SU-DHL-4 Act |
|---|---|---|---|---|
| 74 | 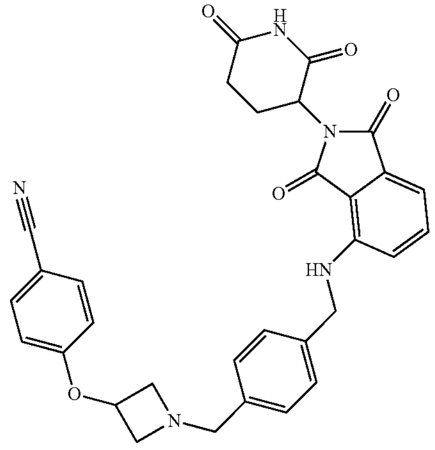 [SMILES: N#Cc1ccc(OC2CN(Cc3ccc(CNc4cccc5c4C(=O)N(C4CCC(=O)NC4=O)C5=O)cc3)C2)cc1] | 4-(1-(4-((2-(2,6-dioxopiperidin-3-yl)-1,3-dioxoisoindolin-4-ylamino)methyl)benzyl)azetidin-3-yloxy)benzonitrile | 550.2 | B |
| 75 | 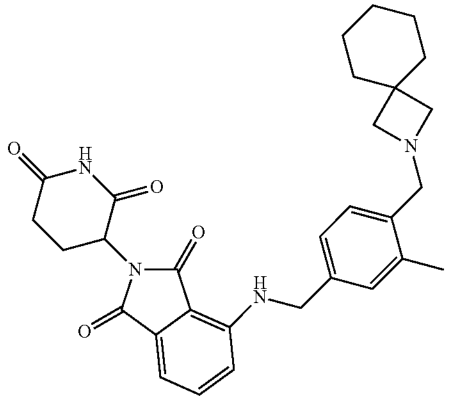 [SMILES: Cc1cc(CNc2cccc3c2C(=O)N(C2CCC(=O)NC2=O)C3=O)ccc1CN1CC2(CCCCC2)C1] | 4-(4-(2-azaspiro[3.5]nonan-2-ylmethyl)-3-methylbenzylamino)-2-(2,6-dioxopiperidin-3-yl)isoindoline-1,3-dione | 515.2 | D |
| 76 | 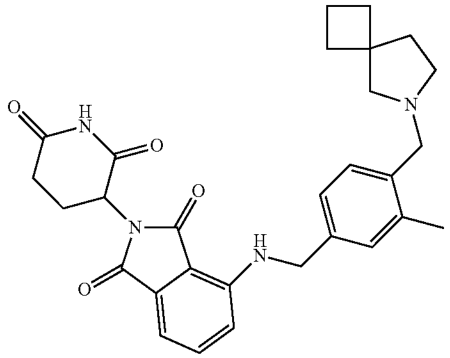 [SMILES: Cc1cc(CNc2cccc3c2C(=O)N(C2CCC(=O)NC2=O)C3=O)ccc1CN1CCC2(CCC2)C1] | 4-(4-(6-azaspiro[3.4]octan-6-ylmethyl)-3-methylbenzylamino)-2-(2,6-dioxopiperidin-3-yl)isoindoline-1,3-dione | 501.2 | C |

TABLE 1-continued
| Cpd # | Cpd Structure | Cpd Name | Obs. MH+ | SU-DHL-4 Act |
|---|---|---|---|---|
| 77 | 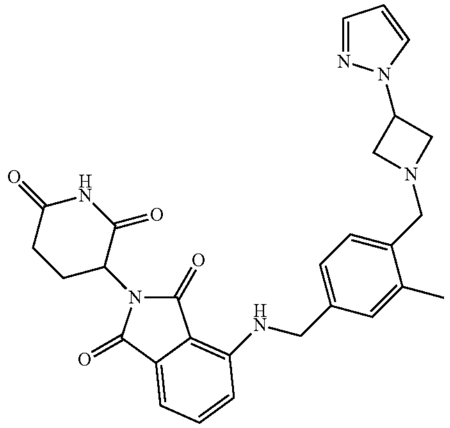 [SMILES: Cc1cc(CNc2cccc3c2C(=O)N(C2CCC(=O)NC2=O)C3=O)ccc1CN1CC(n2cccn2)C1] | 4-(4-((3-(1H-pyrazol-1-yl)azetidin-1-yl)methyl)-3-methylbenzylamino)-2-(2,6-dioxopiperidin-3-yl)isoindoline-1,3-dione | 513.2 | C |
| 78 | 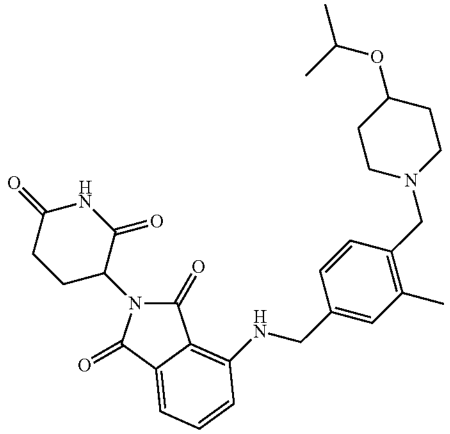 [SMILES: Cc1cc(CNc2cccc3c2C(=O)N(C2CCC(=O)NC2=O)C3=O)ccc1CN1CCC(OC(C)C)CC1] | 2-(2,6-dioxopiperidin-3-yl)-4-(4-((4-isopropoxypiperidin-1-yl)methyl)-3-methylbenzylamino)isoindoline-1,3-dione | 533.6 | D |
| 79 | 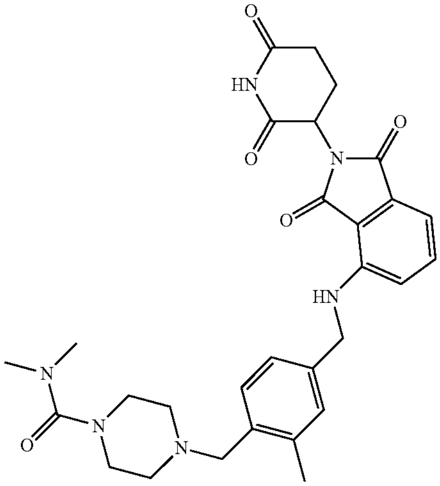 [SMILES: Cc1cc(CNc2cccc3c2C(=O)N(C2CCC(=O)NC2=O)C3=O)ccc1CN1CCN(C(=O)N(C)C)CC1] | 1-(4-((2-(2,6-dioxopiperidin-3-yl)-1,3-dioxoisoindolin-4-ylamino)methyl)-2-methylbenzyl)-N,N-dimethylpiperidine-4-carboxamide | 546.2 | C |

TABLE 1-continued

| Cpd # | Cpd Structure | Cpd Name | Obs. MH+ | SU-DHL-4 Act |
|---|---|---|---|---|
| 80 | 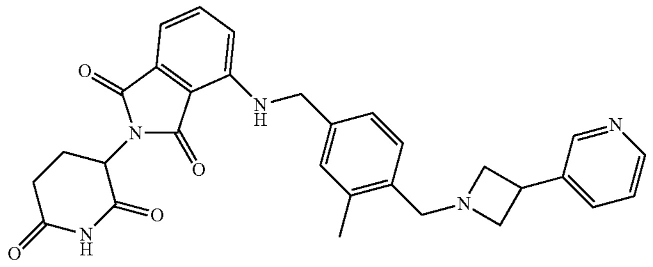 | 2-(2,6-dioxopiperidin-3-yl)-4-(3-methyl-4-((3-(pyridin-3-yl)azetidin-1-yl)methyl)benzylamino)isoindoline-1,3-dione | 524.2 | D |
| 81 | 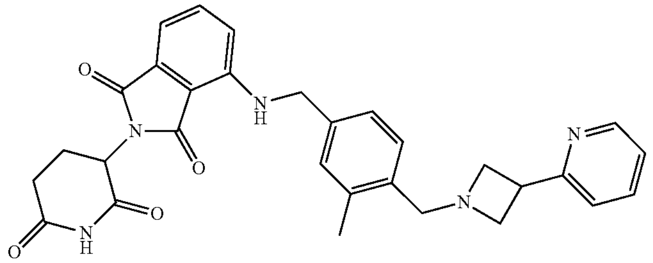 [SMILES: Cc1cc(CNc2cccc3c2C(=O)N(C2CCC(=O)NC2=O)C3=O)ccc1CN1CC(c2ccccn2)C1] | 2-(2,6-dioxopiperidin-3-yl)-4-(3-methyl-4-((3-(pyridin-2-yl)azetidin-1-yl)methyl)benzylamino)isoindoline-1,3-dione | 524.2 | C |
| 82 | 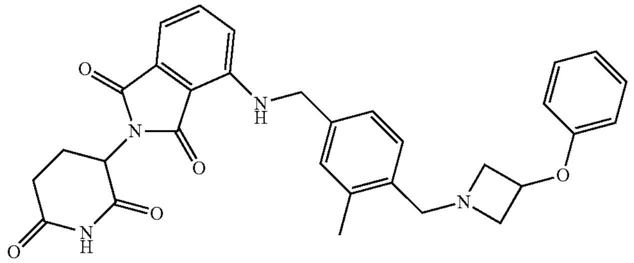 [SMILES: Cc1cc(CNc2cccc3c2C(=O)N(C2CCC(=O)NC2=O)C3=O)ccc1CN1CC(Oc2ccccc2)C1] | 2-(2,6-dioxopiperidin-3-yl)-4-(3-methyl-4-((3-phenoxyazetidin-1-yl)methyl)benzylamino)isoindoline-1,3-dione | 539.2 | B |
| 83 | 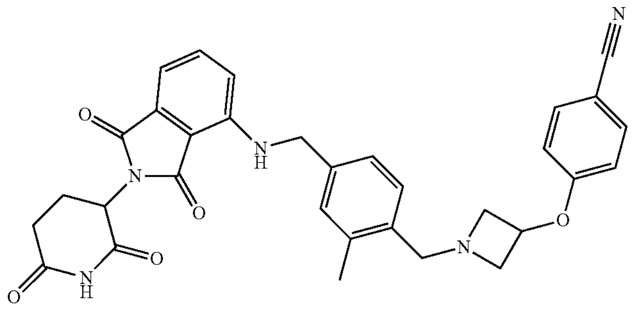 [SMILES: Cc1cc(CNc2cccc3c2C(=O)N(C2CCC(=O)NC2=O)C3=O)ccc1CN1CC(Oc2ccc(C#N)cc2)C1] | 4-(1-(4-((2-(2,6-dioxopiperidin-3-yl)-1,3-dioxoisoindolin-4-ylamino)methyl)-2-methylbenzyl)azetidin-3-yloxy)benzonitrile | 564.2 | D |

TABLE 1-continued

| Cpd # | Cpd Structure | Cpd Name | Obs. MH+ | SU-DHL-4 Act |
|---|---|---|---|---|
| 84 | 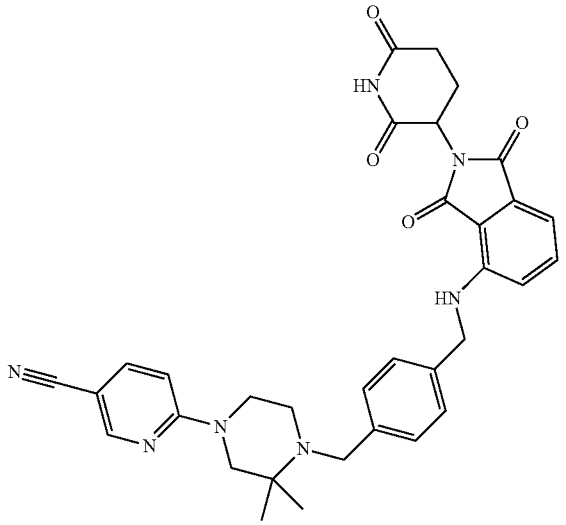 [SMILES: CC1(C)CN(c2ccc(C#N)cn2)CCN1Cc1ccc(CNc2cccc3c2C(=O)N(C2CCC(=O)NC2=O)C3=O)cc1] | 6-(4-(4-((2-(2,6-dioxopiperidin-3-yl)-1,3-dioxoisoindolin-4-ylamino)methyl)benzyl)-3,3-dimethylpiperazin-1-yl)nicotinonitrile | 592.3 | D |
| 85 | 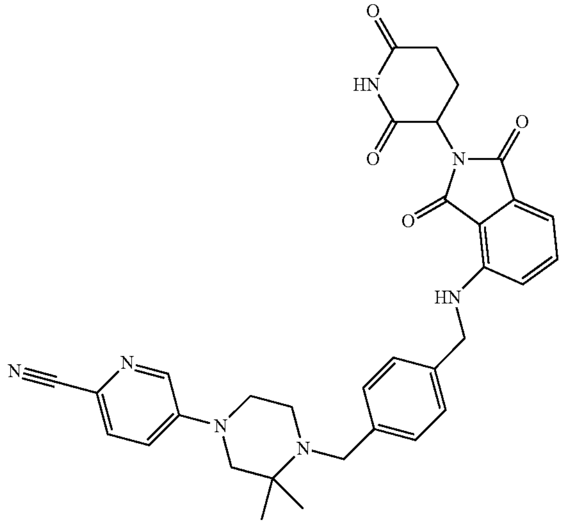 [SMILES: CC1(C)CN(c2ccc(C#N)nc2)CCN1Cc1ccc(CNc2cccc3c2C(=O)N(C2CCC(=O)NC2=O)C3=O)cc1] | 5-(4-(4-((2-(2,6-dioxopiperidin-3-yl)-1,3-dioxoisoindolin-4-ylamino)methyl)benzyl)-3,3-dimethylpiperazin-1-yl)picolinonitrile | 592.3 | D |
| 86 | 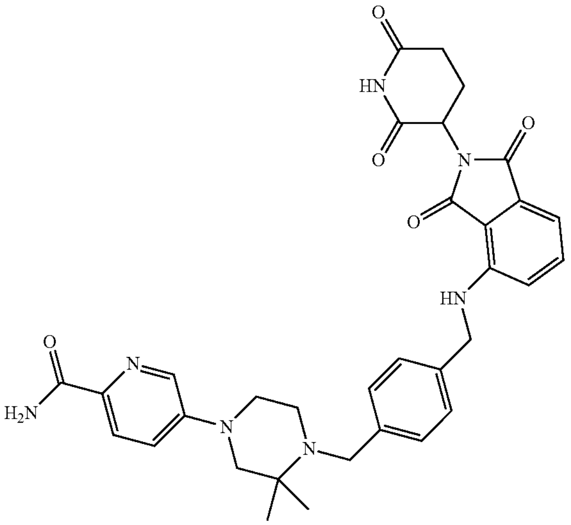 [SMILES: CC1(C)CN(c2ccc(C(N)=O)nc2)CCN1Cc1ccc(CNc2cccc3c2C(=O)N(C2CCC(=O)NC2=O)C3=O)cc1] | 5-(4-(4-((2-(2,6-dioxopiperidin-3-yl)-1,3-dioxoisoindolin-4-ylamino)methyl)benzyl)-3,3-dimethylpiperazin-1-yl)picolinamide | 610.3 | D |

TABLE 1-continued
| Cpd # | Cpd Structure | Cpd Name | Obs. MH+ | SU-DHL-4 Act |
|---|---|---|---|---|
| 87 | 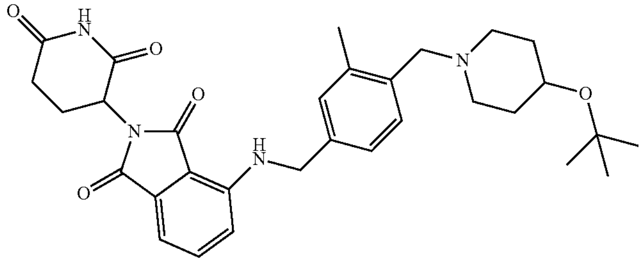 [SMILES: Cc1cc(CNc2cccc3c2C(=O)N(C2CCC(=O)NC2=O)C3=O)ccc1CN1CCC(OC(C)(C)C)CC1] | 4-(4-((4-tert-butoxypiperidin-1-yl)methyl)-3-methylbenzylamino)-2-(2,6-dioxopiperidin-3-yl)isoindoline-1,3-dione | 547.2 | D |
| 88 | 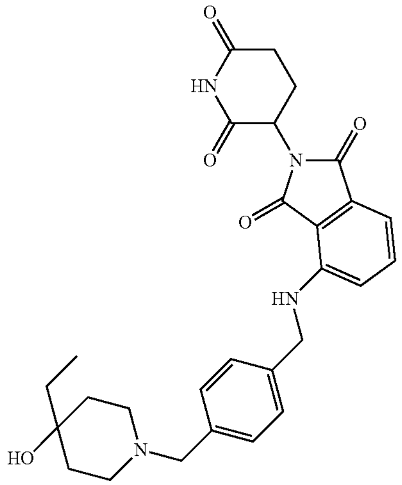 [SMILES: CCC1(O)CCN(Cc2ccc(CNc3cccc4c3C(=O)N(C3CCC(=O)NC3=O)C4=O)cc2)CC1] | 2-(2,6-dioxopiperidin-3-yl)-4-(4-((4-ethyl-4-hydroxypiperidin-1-yl)methyl)benzylamino)isoindoline-1,3-dione | 505.2 | B |
| 89 | 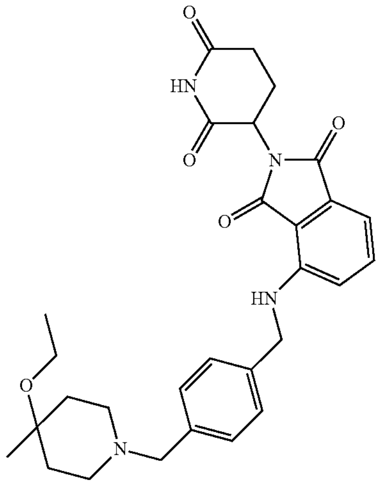 [SMILES: CCOC1(C)CCN(Cc2ccc(CNc3cccc4c3C(=O)N(C3CCC(=O)NC3=O)C4=O)cc2)CC1] | 2-(2,6-dioxopiperidin-3-yl)-4-(4-((4-ethoxy-4-methylpiperidin-1-yl)methyl)benzylamino)isoindoline-1,3-dione | 519.2 | D |

TABLE 1-continued

| Cpd # | Cpd Structure | Cpd Name | Obs. MH+ | SU-DHL-4 Act |
|---|---|---|---|---|
| 90 | 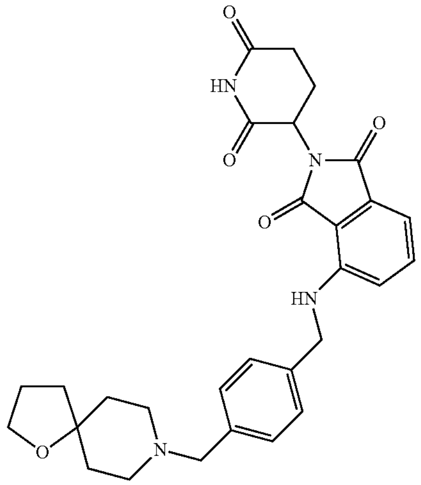 [SMILES: O=C1CCC(N2C(=O)c3cccc(NCc4ccc(CN5CCC6(CCCO6)CC5)cc4)c3C2=O)C(=O)N1] | 4-(4-(1-oxa-8-azaspiro[4.5]decan-8-ylmethyl)benzylamino)-2-(2,6-dioxopiperidin-3-yl)isoindoline-1,3-dione | 517.2 | D |
| 91 | 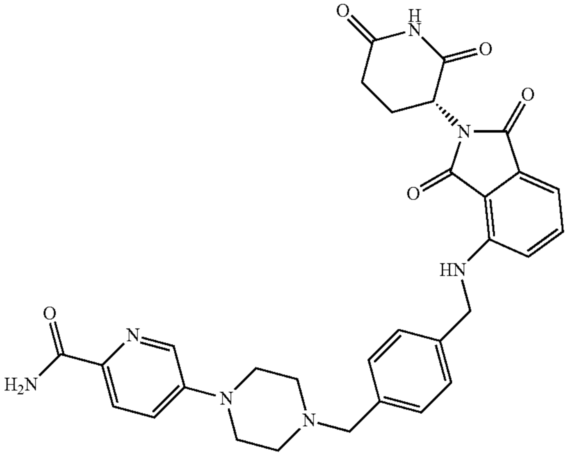 [SMILES: NC(=O)c1ccc(N2CCN(Cc3ccc(CNc4cccc5c4C(=O)N([C@@H]4CCC(=O)NC4=O)C5=O)cc3)CC2)cn1] | (R)-5-(4-(4-((2-(2,6-dioxopiperidin-3-yl)-1,3-dioxoisoindolin-4-ylamino)methyl)benzyl)piperazin-1-yl)picolinamide | 582.5 | D |
| 92 | 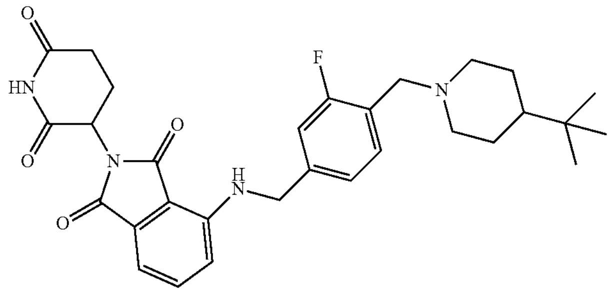 [SMILES: CC(C)(C)C1CCN(Cc2ccc(CNc3cccc4c3C(=O)N(C3CCC(=O)NC3=O)C4=O)cc2F)CC1] | 4-(4-((4-tert-butylpiperidin-1-yl)methyl)-3-fluorobenzylamino)-2-(2,6-dioxopiperidin-3-yl)isoindoline-1,3-dione | 535.2 | D |
| 93 | 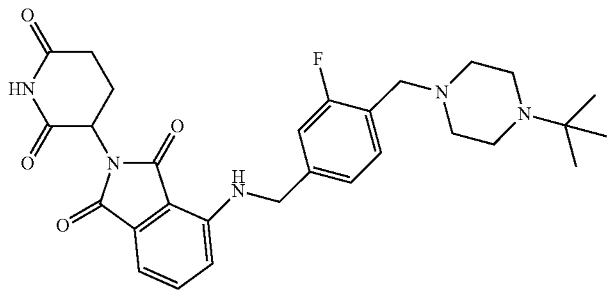 [SMILES: CC(C)(C)N1CCN(Cc2ccc(CNc3cccc4c3C(=O)N(C3CCC(=O)NC3=O)C4=O)cc2F)CC1] | 4-(4-((4-tert-butylpiperazin-1-yl)methyl)-3-fluorobenzylamino)-2-(2,6-dioxopiperidin-3-yl)isoindoline-1,3-dione | 536.2 | D |

TABLE 1-continued

| Cpd # | Cpd Structure | Cpd Name | Obs. MH+ | SU-DHL-4 Act |
|---|---|---|---|---|
| 94 | 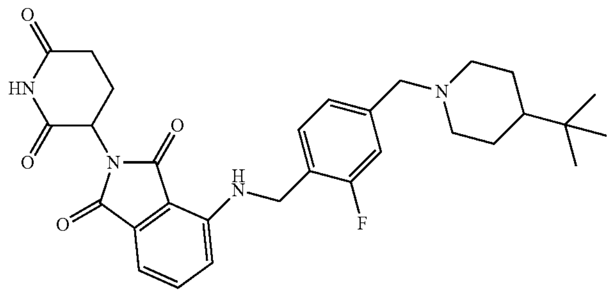 [SMILES: CC(C)(C)C1CCN(Cc2ccc(CNc3cccc4c3C(=O)N(C3CCC(=O)NC3=O)C4=O)c(F)c2)CC1] | 4-(4-((4-tert-butylpiperidin-1-yl)methyl)-2-fluorobenzylamino)-2-(2,6-dioxopiperidin-3-yl)isoindoline-1,3-dione | 535.2 | D |
| 95 | 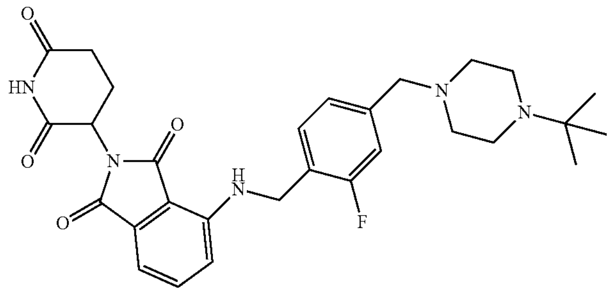 [SMILES: CC(C)(C)N1CCN(Cc2ccc(CNc3cccc4c3C(=O)N(C3CCC(=O)NC3=O)C4=O)c(F)c2)CC1] | 4-(4-((4-tert-butylpiperazin-1-yl)methyl)-2-fluorobenzylamino)-2-(2,6-dioxopiperidin-3-yl)isoindoline-1,3-dione | 536.2 | D |
| 96 | 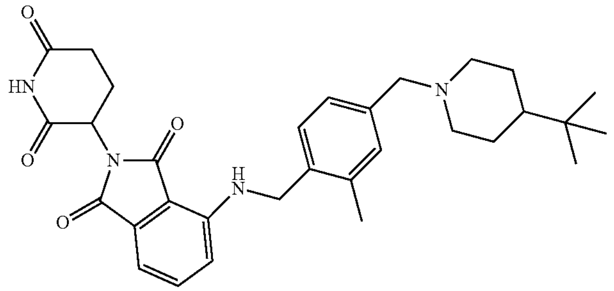 [SMILES: Cc1cc(CN2CCC(C(C)(C)C)CC2)ccc1CNc1cccc2c1C(=O)N(C1CCC(=O)NC1=O)C2=O] | 4-(4-((4-tert-butylpiperidin-1-yl)methyl)-2-methylbenzylamino)-2-(2,6-dioxopiperidin-3-yl)isoindoline-1,3-dione | 531.3 | D |
| 97 | 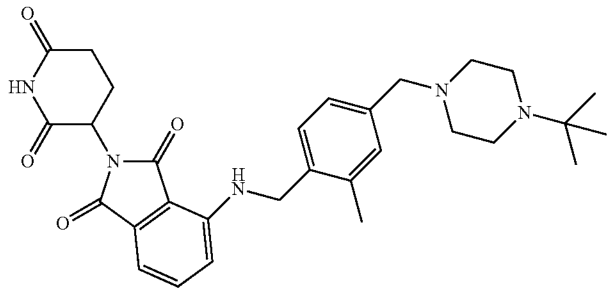 [SMILES: Cc1cc(CN2CCN(C(C)(C)C)CC2)ccc1CNc1cccc2c1C(=O)N(C1CCC(=O)NC1=O)C2=O] | 4-(4-((4-tert-butylpiperazin-1-yl)methyl)-2-methylbenzylamino)-2-(2,6-dioxopiperidin-3-yl)isoindolline-1,3-dione | 532.3 | B |
| 98 | 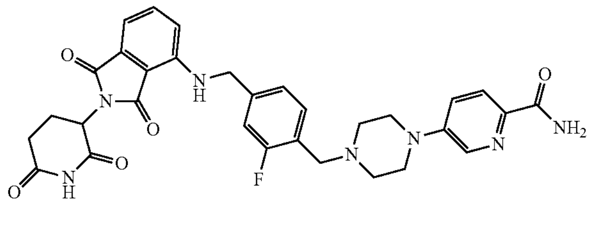 [SMILES: NC(=O)c1ccc(N2CCN(Cc3ccc(CNc4cccc5c4C(=O)N(C4CCC(=O)NC4=O)C5=O)cc3F)CC2)cn1] | 5-(4-(4-((2-(2,6-dioxopiperidin-3-yl)-1,3-dioxoisoindolin-4-ylamino)methyl)-2-fluorobenzyl)piperazin-1-yl)picolinamide | 600.2 | D |

TABLE 1-continued

| Cpd # | Cpd Structure | Cpd Name | Obs. MH+ | SU-DHL-4 Act |
|---|---|---|---|---|
| 99 | 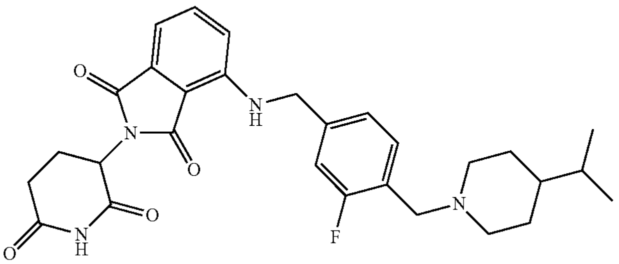 [SMILES: CC(C)C1CCN(Cc2ccc(CNc3cccc4c3C(=O)N(C3CCC(=O)NC3=O)C4=O)cc2F)CC1] | 2-(2,6-dioxopiperidin-3-yl)-4-(3-fluoro-4-((4-isopropylpiperidin-1-yl)methyl)benzylamino)isoindoline-1,3-dione | 521.2 | D |
| 100 | 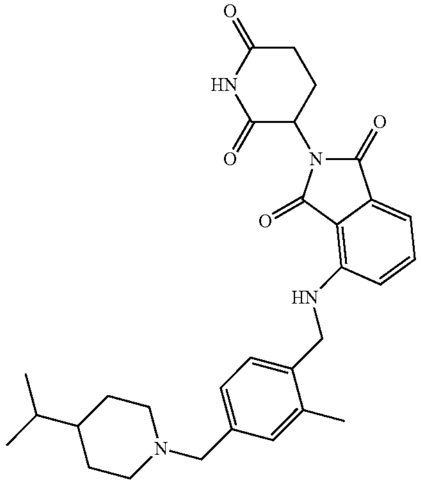 [SMILES: Cc1cc(CN2CCC(C(C)C)CC2)ccc1CNc1cccc2c1C(=O)N(C1CCC(=O)NC1=O)C2=O] | 2-(2,6-dioxopiperidin-3-yl)-4-(4-((4-isopropylpiperidin-1-yl)methyl)-2-methylbenzylamino)isoindoline-1,3-dione | 517.2 | C |
| 101 | 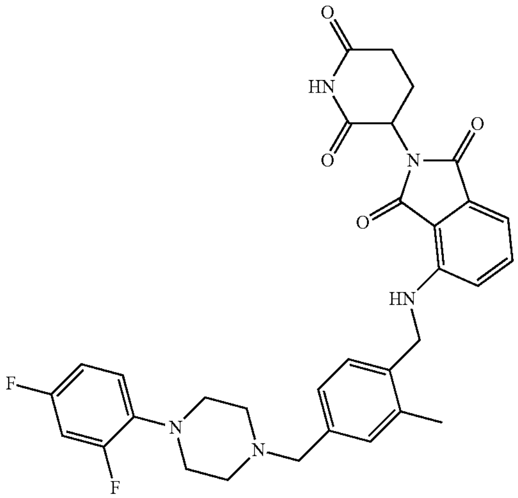 [SMILES: Cc1cc(CN2CCN(c3ccc(F)cc3F)CC2)ccc1CNc1cccc2c1C(=O)N(C1CCC(=O)NC1=O)C2=O] | 4-(4-((4-(2,4-difluorophenyl)piperazin-1-yl)methyl)-2-methylbenzylamino)-2-(2,6-dioxopiperidin-3-yl)isoindoline-1,3-dione | 588.2 | C |
| 102 | 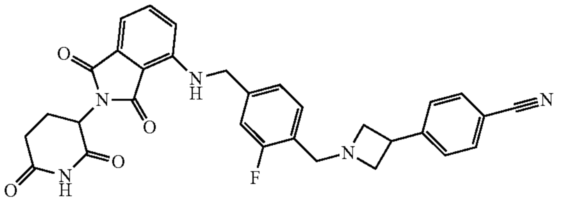 [SMILES: N#Cc1ccc(C2CN(Cc3ccc(CNc4cccc5c4C(=O)N(C4CCC(=O)NC4=O)C5=O)cc3F)C2)cc1] | 4-(1-(4-((2-(2,6-dioxopiperidin-3-yl)-1,3-dioxoisoindolin-4-ylamino)methyl)-2-fluorobenzyl)azetidin-3-yl)benzonitrile | 552.2 | D |

TABLE 1-continued
| Cpd # | Cpd Structure | Cpd Name | Obs. MH+ | SU-DHL-4 Act |
|---|---|---|---|---|
| 103 | 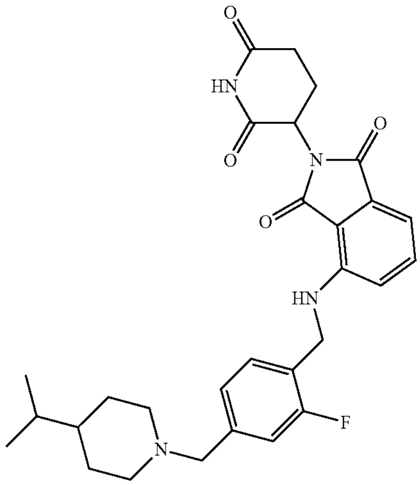 [SMILES: CC(C)C1CCN(Cc2ccc(CNc3cccc4c3C(=O)N(C3CCC(=O)NC3=O)C4=O)c(F)c2)CC1] | 2-(2,6-dioxopiperidin-3-yl)-4-(2-fluoro-4-((4-isopropylpiperidin-1-yl)methyl)benzylamino)isoindoline-1,3-dione | 521.2 | D |
| 104 | 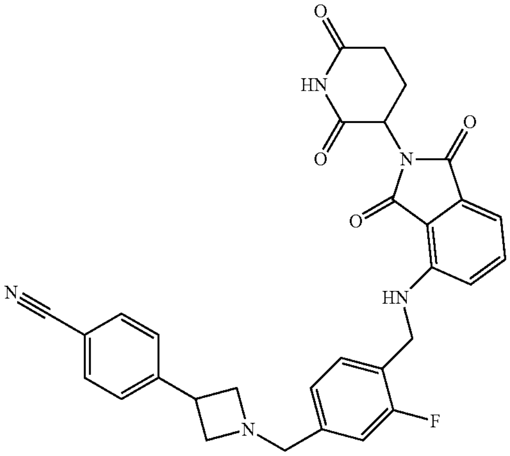 [SMILES: N#Cc1ccc(C2CN(Cc3ccc(CNc4cccc5c4C(=O)N(C4CCC(=O)NC4=O)C5=O)c(F)c3)C2)cc1] | 4-(1-(4-((2-(2,6-dioxopiperidin-3-yl)-1,3-dioxoisoindolin-4-ylamino)methyl)-3-fluorobenzyl)azetidin-3-yl)benzonitrile | 552.2 | D |
| 105 | 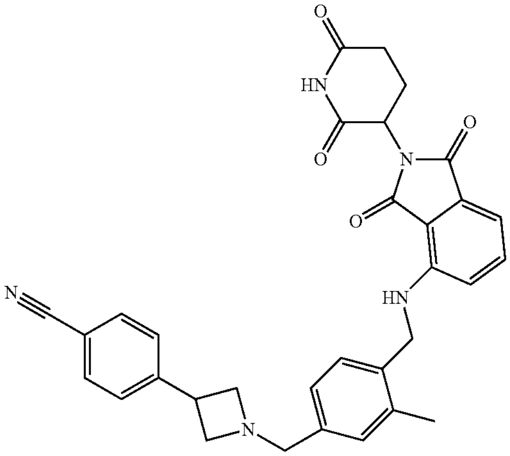 [SMILES: Cc1cc(CN2CC(c3ccc(C#N)cc3)C2)ccc1CNc1cccc2c1C(=O)N(C1CCC(=O)NC1=O)C2=O] | 4-(1-(4-((2-(2,6-dioxopiperidin-3-yl)-1,3-dioxoisoindoliln-4-ylamino)methyl)-3-methylbenzyl)azetidin-3-yl)benzonitrile | 548.2 | D |

TABLE 1-continued

| Cpd # | Cpd Structure | Cpd Name | Obs. MH+ | SU-DHL-4 Act |
|---|---|---|---|---|
| 106 | 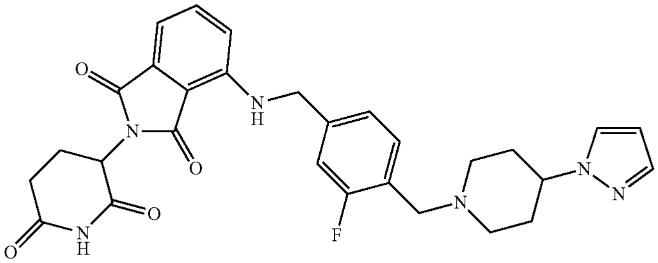 [SMILES: O=C1CCC(N2C(=O)c3cccc(NCc4ccc(CN5CCC(n6cccn6)CC5)c(F)c4)c3C2=O)C(=O)N1] | 4-(4-((4-(1H-pyrazol-1-yl)piperidin-1-yl)methyl)-3-fluorobenzylamino)-2-(2,6-dioxopiperidin-3-yl)isoindoline-1,3-dione | 545.2 | C |
| 107 | 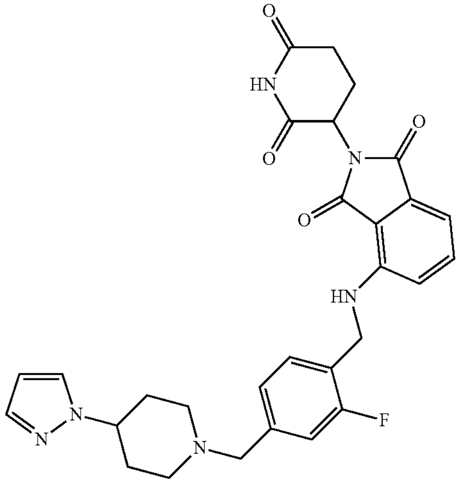 [SMILES: O=C1CCC(N2C(=O)c3cccc(NCc4ccc(CN5CCC(n6cccn6)CC5)cc4F)c3C2=O)C(=O)N1] | 4-(4-((4-(1H-pyrazol-1-yl)piperidin-1-yl)methyl)-2-fluorobenzylamino)-2-(2,6-dioxopiperidin-3-yl)isoindoline-1,3-dione | 545.2 | D |
| 108 | 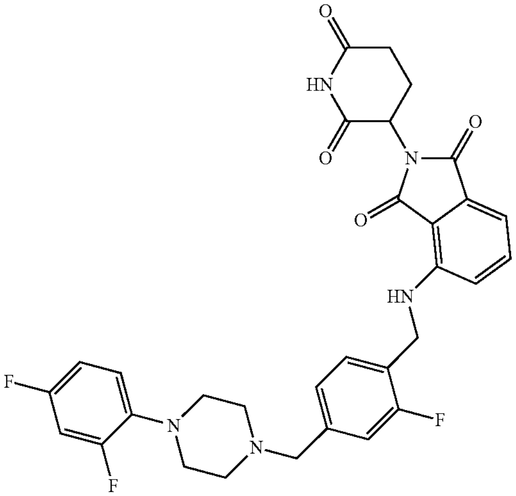 [SMILES: O=C1CCC(N2C(=O)c3cccc(NCc4ccc(CN5CCN(c6ccc(F)cc6F)CC5)cc4F)c3C2=O)C(=O)N1] | 4-(4-((4-(2,4-difluorophenyl)piperazin-1-yl)methyl)-2-fluorobenzylamino)-2-(2,6-dioxopiperidin-3-yl)isoindoline-1,3-dione | 592.2 | D |
| 109 | 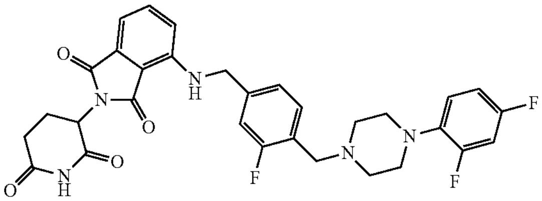 [SMILES: O=C1CCC(N2C(=O)c3cccc(NCc4ccc(CN5CCN(c6ccc(F)cc6F)CC5)c(F)c4)c3C2=O)C(=O)N1] | 4-(4-((4-(2,4-difluorophenyl)piperazin-1-yl)methyl)-3-fluorobenzylamino)-2-(2,6-dioxopiperidin-3-yl)isoindoline-1,3-dione | 592.2 | D |

TABLE 1-continued
| Cpd # | Cpd Structure | Cpd Name | Obs. MH+ | SU-DHL-4 Act |
|---|---|---|---|---|
| 110 | 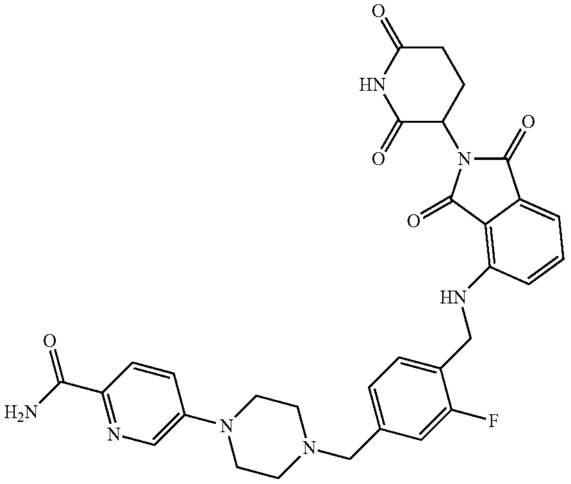 [SMILES: NC(=O)c1ccc(N2CCN(Cc3ccc(CNc4cccc5c4C(=O)N(C4CCC(=O)NC4=O)C5=O)c(F)c3)CC2)cn1] | 5-(4-(4-((2-(2,6-dioxopiperidin-3-yl)-1,3-dioxoisoindolin-4-ylamino)methyl)-3-fluorobenzyl)piperazin-1-yl)picolinamide | 600.2 | D |
| 111 | 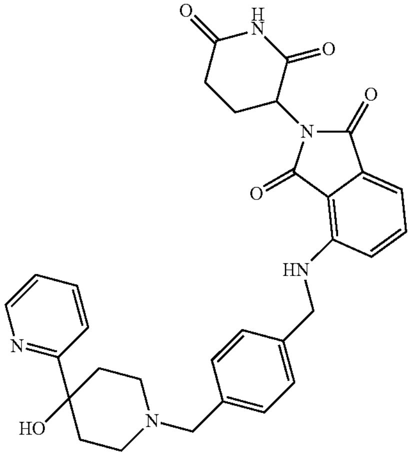 [SMILES: O=C1CCC(N2C(=O)c3cccc(NCc4ccc(CN5CCC(O)(c6ccccn6)CC5)cc4)c3C2=O)C(=O)N1] | 2-(2,6-dioxopiperidin-3-yl)-4-(4-((4-hydroxy-4-(pyridin-2-yl)piperidin-1-yl)methyl)benzylamino)isoindoline-1,3-dione | 554.2 | D |
| 112 | 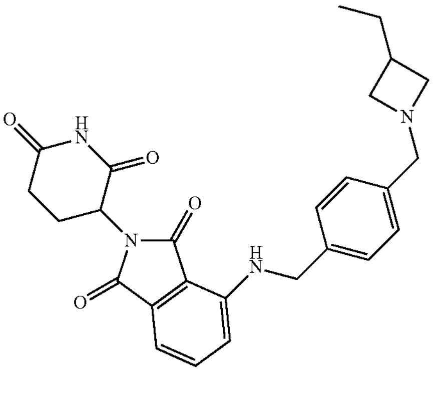 [SMILES: CCC1CN(Cc2ccc(CNc3cccc4c3C(=O)N(C3CCC(=O)NC3=O)C4=O)cc2)C1] | 2-(2,6-dioxopiperidin-3-yl)-4-(4-((3-ethylazetidin-1-yl)methyl)benzylamino)isoindoline-1,3-dione | 461.2 | C |

TABLE 1-continued
| Cpd # | Cpd Structure | Cpd Name | Obs. MH+ | SU-DHL-4 Act |
|---|---|---|---|---|
| 113 | 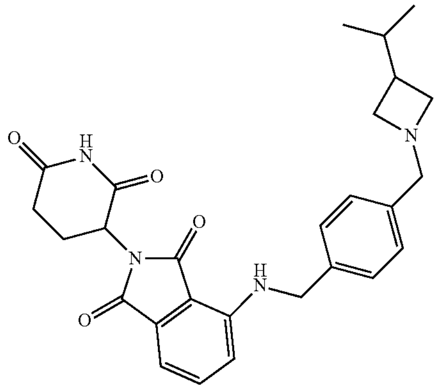 [SMILES: CC(C)C1CN(Cc2ccc(CNc3cccc4c3C(=O)N(C3CCC(=O)NC3=O)C4=O)cc2)C1] | 2-(2,6-dioxopiperidin-3-yl)-4-(4-((3-isopropylazetidin-1-yl)methyl)benzylamino)isoindoline-1,3-dione | 475.2 | C |
| 114 | 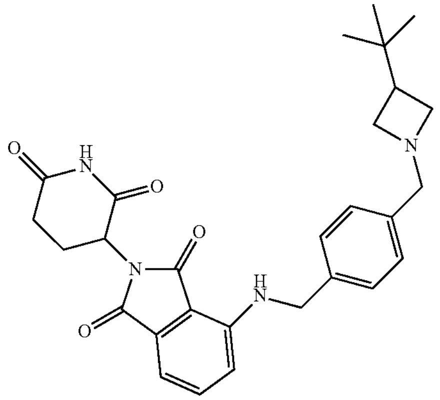 [SMILES: CC(C)(C)C1CN(Cc2ccc(CNc3cccc4c3C(=O)N(C3CCC(=O)NC3=O)C4=O)cc2)C1] | 4-(4-((3-tert-butylazetidin-1-yl)methyl)benzylamino)-2-(2,6-dioxopiperidin-3-yl)isoindoline-1,3-dione | 489.2 | D |
| 115 | 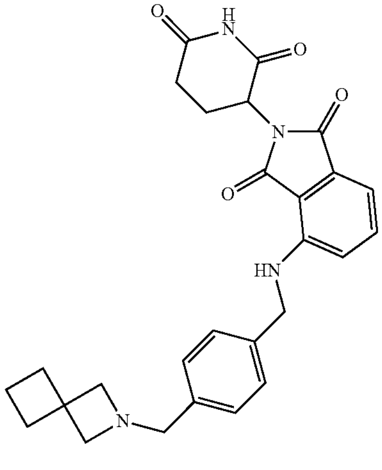 [SMILES: O=C1CCC(N2C(=O)c3cccc(NCc4ccc(CN5CC6(CCC6)C5)cc4)c3C2=O)C(=O)N1] | 4-(4-(2-azaspiro[3.3]heptan-2-ylmethyl)benzylamino)-2-(2,6-dioxopiperidin-3-yl)isoindoline-1,3-dione | 473.2 | D |

TABLE 1-continued
| Cpd # | Cpd Structure | Cpd Name | Obs. MH+ | SU-DHL-4 Act |
|---|---|---|---|---|
| 116 | 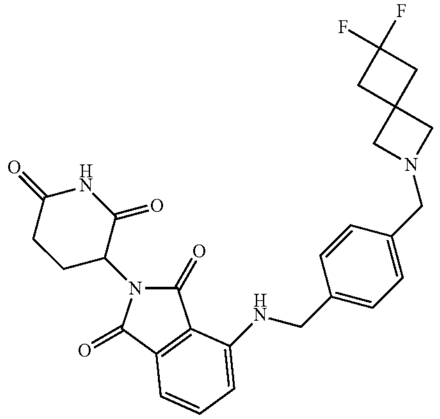 [SMILES: O=C1CCC(N2C(=O)c3cccc(NCc4ccc(CN5CC6(C5)CC(F)(F)C6)cc4)c3C2=O)C(=O)N1] | 4-(4-((6,6-difluoro-2-azaspiro[3.3]heptan-2-yl)methyl)benzylamino)-2-(2,6-dioxopiperidin-3-yl)isoindoline-1,3-dione | 509.2 | A |
| 117 | 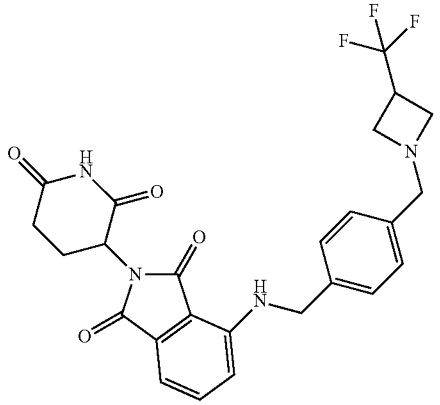 [SMILES: O=C1CCC(N2C(=O)c3cccc(NCc4ccc(CN5CC(C(F)(F)F)C5)cc4)c3C2=O)C(=O)N1] | 2-(2,6-dioxopiperidin-3-yl)-4-(4-((3-(trifluoromethyl)azetidin-1-yl)methyl)benzylamino)isoindoline-1,3-dione | 501.2 | C |
| 118 | 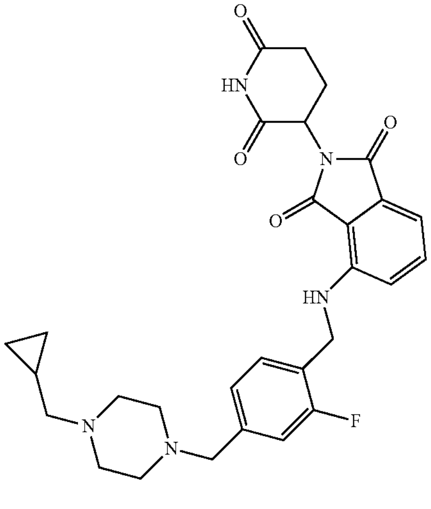 [SMILES: O=C1CCC(N2C(=O)c3cccc(NCc4ccc(CN5CCN(CC6CC6)CC5)cc4F)c3C2=O)C(=O)N1] | 4-(4-((4-(cyclopropylmethyl)piperazin-1-yl)methyl)-2-fluorobenzylamino)-2-(2,6-dioxopiperidin-3-yl)isoindoline-1,3-dione | 534.2 | D |

TABLE 1-continued
| Cpd # | Cpd Structure | Cpd Name | Obs. MH+ | SU-DHL-4 Act |
|---|---|---|---|---|
| 119 | 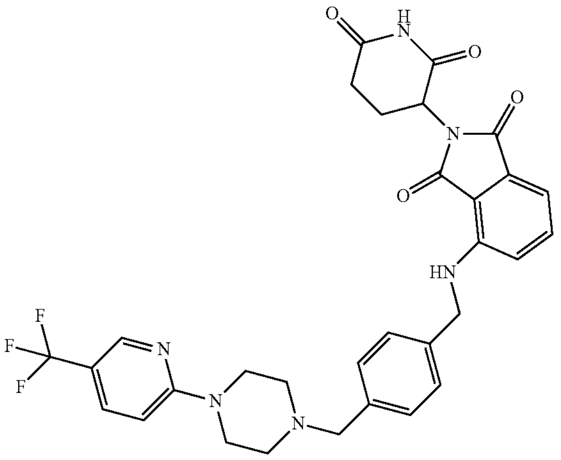 [SMILES: O=C1CCC(N2C(=O)c3cccc(NCc4ccc(CN5CCN(c6ccc(C(F)(F)F)cn6)CC5)cc4)c3C2=O)C(=O)N1] | 2-(2,6-dioxopiperidin-3-yl)-4-(4-((4-(5-(trifluoromethyl)pyridin-2-yl)piperazin-1-yl)methyl)benzylamino)isoindoline-1,3-dione | 607.2 | C |
| 120 | 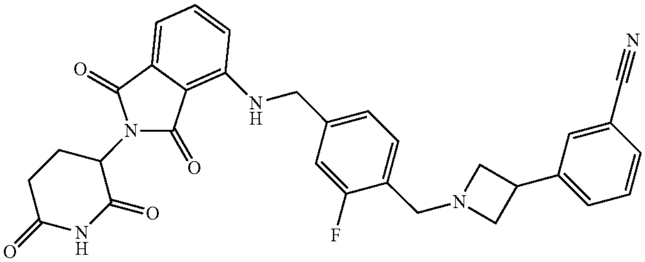 [SMILES: N#Cc1cccc(C2CN(Cc3ccc(CNc4cccc5c4C(=O)N(C4CCC(=O)NC4=O)C5=O)cc3F)C2)c1] | 3-(1-(4-((2-(2,6-dioxopiperidin-3-yl)-1,3-dioxoisoindolin-4-ylamino)methyl)-2-fluorobenzyl)azetidin-3-yl)benzonitrile | 552.2 | D |
| 121 | 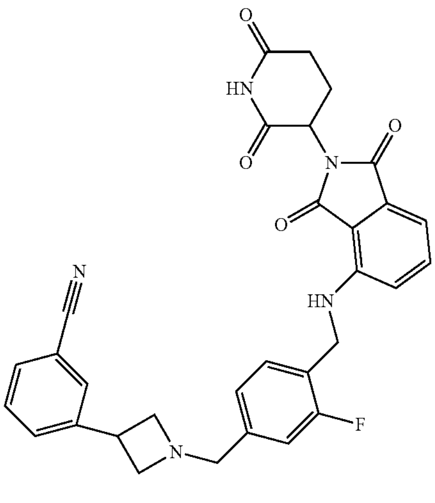 [SMILES: N#Cc1cccc(C2CN(Cc3ccc(CNc4cccc5c4C(=O)N(C4CCC(=O)NC4=O)C5=O)c(F)c3)C2)c1] | 3-(1-(4-((2-(2,6-dioxopiperidin-3-yl)-1,3-dioxoisoindolin-4-ylamino)methyl)-3-fluorobenzyl)azetidin-3-yl)benzonitrile | 552.2 | D |

TABLE 1-continued
| Cpd # | Cpd Structure | Cpd Name | Obs. MH+ | SU-DHL-4 Act |
|---|---|---|---|---|
| 122 | 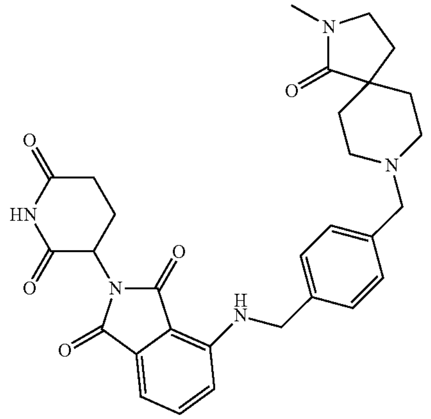 [SMILES: CN1CCC2(CCN(Cc3ccc(CNc4cccc5c4C(=O)N(C4CCC(=O)NC4=O)C5=O)cc3)CC2)C1=O] | 2-(2,6-dioxopiperidin-3-yl)-4-(4-((2-methyl-1-oxo-2,8-diazaspiro[4.5]decan-8-yl)methyl)benzylamino)isoindoline-1,3-dione | 544.2 | C |
| 123 | 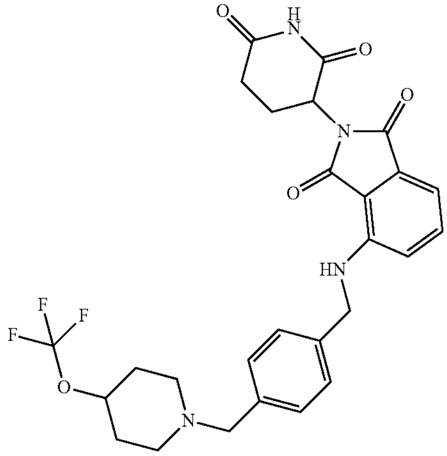 [SMILES: O=C1CCC(N2C(=O)c3cccc(NCc4ccc(CN5CCC(OC(F)(F)F)CC5)cc4)c3C2=O)C(=O)N1] | 2-(2,6-dioxopiperidin-3-yl)-4-(4-((4-(trifluoromethoxy)piperidin-1-yl)methyl)benzylamino)isoindoline-1,3-dione | 545.6 | C |
| 124 | 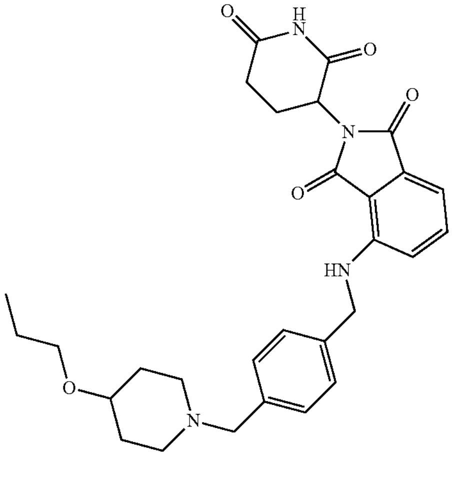 [SMILES: CCCOC1CCN(Cc2ccc(CNc3cccc4c3C(=O)N(C3CCC(=O)NC3=O)C4=O)cc2)CC1] | 2-(2,6-dioxopiperidin-3-yl)-4-(4-((4-propoxypiperidin-1-yl)methyl)benzylamino)isoindoline-1,3-dione | 519.8 | B |

TABLE 1-continued
| Cpd # | Cpd Structure | Cpd Name | Obs. MH+ | SU-DHL-4 Act |
|---|---|---|---|---|
| 125 | 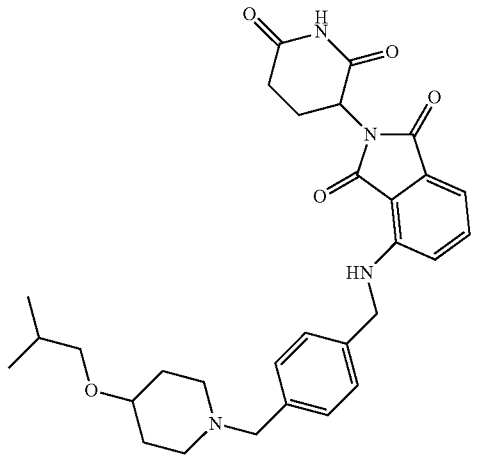 [SMILES: CC(C)COC1CCN(Cc2ccc(CNc3cccc4c3C(=O)N(C3CCC(=O)NC3=O)C4=O)cc2)CC1] | 2-(2,6-dioxopiperidin-3-yl)-4-(4-((4-isobutoxypiperidin-1-yl)methyl)benzylamino)isoindoilne-1,3-dione | 533.8 | C |
| 126 | 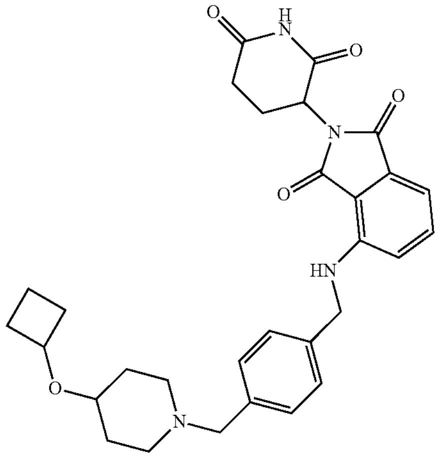 [SMILES: O=C1CCC(N2C(=O)c3cccc(NCc4ccc(CN5CCC(OC6CCC6)CC5)cc4)c3C2=O)C(=O)N1] | 4-(4-((4-cyclobutyoxypiperidin-1-yl)ethyl)benzylamino)-2-(2,6-dioxopiperidin-3-yl)isoindoline-1,3-dione | 531.8 | C |
| 127 | 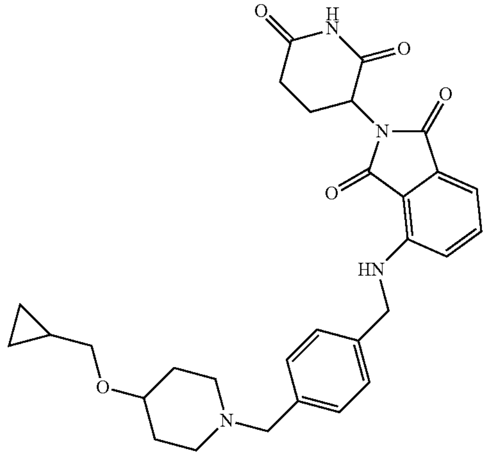 [SMILES: O=C1CCC(N2C(=O)c3cccc(NCc4ccc(CN5CCC(OCC6CC6)CC5)cc4)c3C2=O)C(=O)N1] | 4-(4-((4-(cyclopropylmethoxy)piperidin-1-yl)methyl)benzylamino)-2-(2,6-dioxopiperidin-3-yl)isoindoline-1,3-dione | 531.8 | A |

TABLE 1-continued
| Cpd # | Cpd Structure | Cpd Name | Obs. MH+ | SU-DHL-4 Act |
|---|---|---|---|---|
| 128 | 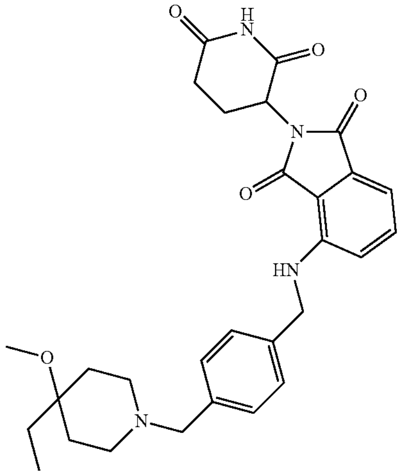 [SMILES: CCC1(OC)CCN(Cc2ccc(CNc3cccc4c3C(=O)N(C3CCC(=O)NC3=O)C4=O)cc2)CC1] | 2-(2,6-dioxopiperidin-3-yl)-4-(4-((4-ethyl-4-methoxypiperidin-1-yl)methyl)benzylamino)isoindoline-1,3-dione | 519.6 | C |
| 129 | 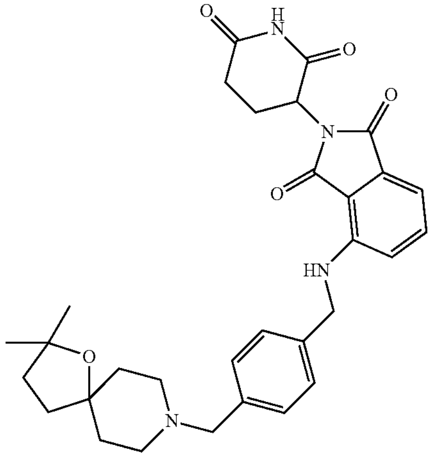 [SMILES: CC1(C)CCC2(CCN(Cc3ccc(CNc4cccc5c4C(=O)N(C4CCC(=O)NC4=O)C5=O)cc3)CC2)O1] | 4-(4-((2,2-dimethyl-1-oxa-8-azaspiro[4.5]decan-8-yl)methyl)benzylamino)-2-(2,6-dioxopiperidin-3-yl)isoindoline-1,3-dione | 545.6 | D |
| 130 | 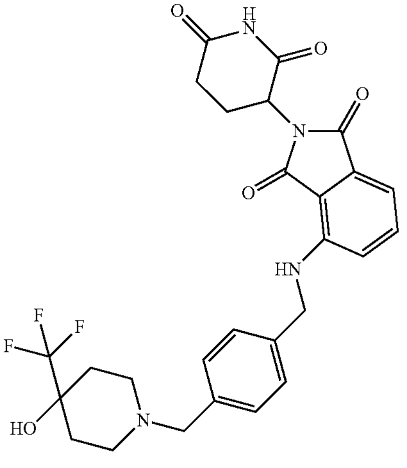 [SMILES: O=C1CCC(N2C(=O)c3cccc(NCc4ccc(CN5CCC(O)(C(F)(F)F)CC5)cc4)c3C2=O)C(=O)N1] | 2-(2,6-dioxopiperidin-3-yl)-4-(4-((4-hydroxy-4-(trifluoromethyl)piperidin-1-yl)methyl)benzylamino)isoindoline-1,3-dione | 545.6 | A |

TABLE 1-continued
| Cpd # | Cpd Structure | Cpd Name | Obs. MH+ | SU-DHL-4 Act |
|---|---|---|---|---|
| 131 | 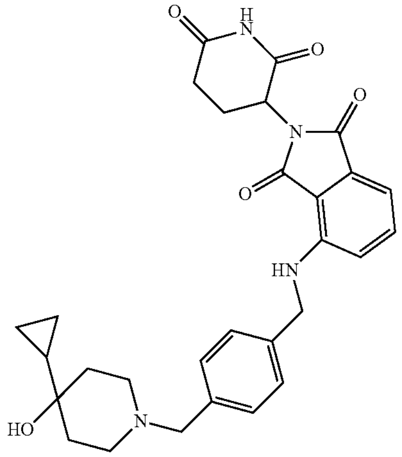 [SMILES: O=C1CCC(N2C(=O)c3cccc(NCc4ccc(CN5CCC(O)(C6CC6)CC5)cc4)c3C2=O)C(=O)N1] | 4-(4-((4-cyclopropyl-4-hydroxypiperidin-1-yl)methyl)benzylamino)-2-(2,6-dioxopiperidin-3-yl)isoindoline-1,3-dione | 517.8 | C |
| 132 | 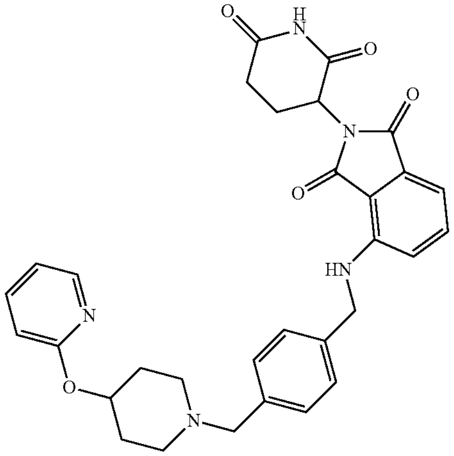 [SMILES: O=C1CCC(N2C(=O)c3cccc(NCc4ccc(CN5CCC(Oc6ccccn6)CC5)cc4)c3C2=O)C(=O)N1] | 2-(2,6-dioxopiperidin-3-yl)-4-(4-((4-(pyridin-2-yloxy)piperidin-1-yl)methyl)benzylamino)isoindoline-1,3-dione | 554.8 | A |
| 133 | 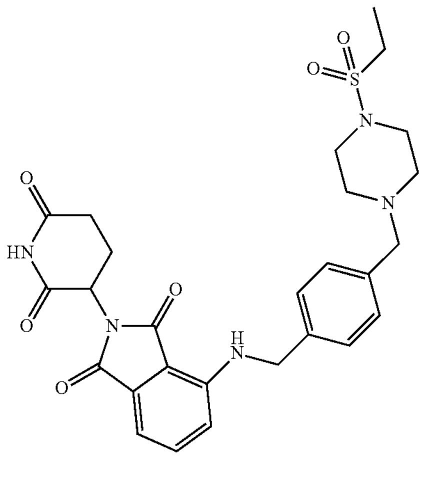 [SMILES: CCS(=O)(=O)N1CCN(Cc2ccc(CNc3cccc4c3C(=O)N(C3CCC(=O)NC3=O)C4=O)cc2)CC1] | 2-(2,6-dioxopiperidin-3-yl)-4-(4-((4-(ethylsulfonyl)piperazin-1-yl)methyl)benzylamino)isoindoline-1,3-dione | 554.2 | C |

TABLE 1-continued

| Cpd # | Cpd Structure | Cpd Name | Obs. MH+ | SU-DHL-4 Act |
|---|---|---|---|---|
| 134 | 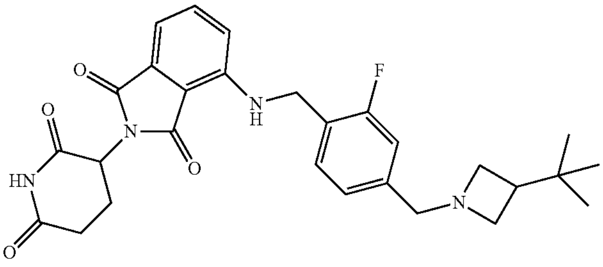 [SMILES: CC(C)(C)C1CN(Cc2ccc(CNc3cccc4c3C(=O)N(C3CCC(=O)NC3=O)C4=O)c(F)c2)C1] | 4-(4-((3-tert-butylazetidin-1-yl)methyl)-2-fluorobenzylamino)-2-(2,6-dioxopiperidin-3-yl)isoindoline-1,3-dione | 507.2 | D |
| 135 | 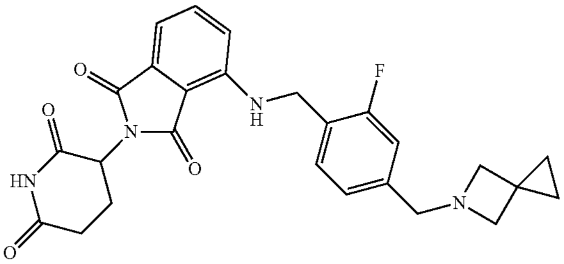 [SMILES: O=C1CCC(N2C(=O)c3cccc(NCc4ccc(CN5CC6(CC6)C5)cc4F)c3C2=O)C(=O)N1] | 4-(4-(5-azaspiro[2.3]hexan-5-ylmethyl)-2-fluorobenzylamino)-2-(2,6-dioxopiperidin-3-yl)isoindoline-1,3-dione | 477.2 | C |
| 136 | 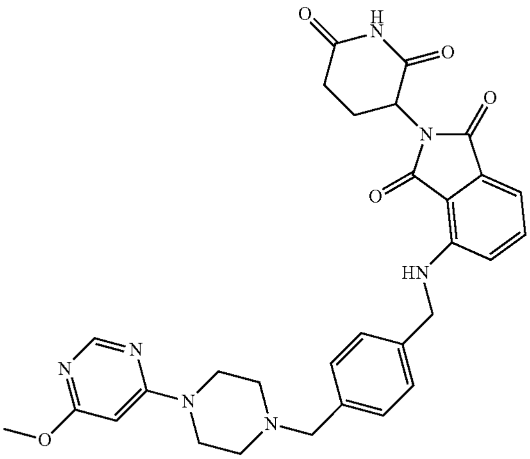 [SMILES: COc1cc(N2CCN(Cc3ccc(CNc4cccc5c4C(=O)N(C4CCC(=O)NC4=O)C5=O)cc3)CC2)ncn1] | 2-(2,6-dioxopiperidin-3-yl)-4-(4-((4-(6-methoxypyrimidin-4-yl)piperazin-1-yl)methyl)benzylamino)isoindoline-1,3-dione | 570.2 | A |
| 137 | 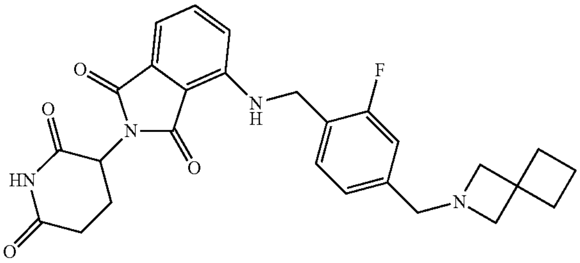 [SMILES: O=C1CCC(N2C(=O)c3cccc(NCc4ccc(CN5CC6(CCC6)C5)cc4F)c3C2=O)C(=O)N1] | 4-(4-(2-azaspiro[3.3]heptan-2-ylmethyl)-2-fluorobenzylamino)-2-(2,6-dioxopiperidin-3-yl)isoindoline-1,3-dione | 491.2 | D |

TABLE 1-continued
| Cpd # | Cpd Structure | Cpd Name | Obs. MH+ | SU-DHL-4 Act |
|---|---|---|---|---|
| 138 | 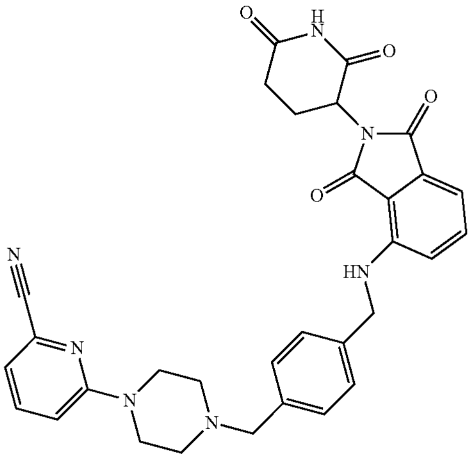 [SMILES: N#Cc1cccc(N2CCN(Cc3ccc(CNc4cccc5c4C(=O)N(C4CCC(=O)NC4=O)C5=O)cc3)CC2)n1] | 6-(4-(4-((2-(2,6-dioxopiperidin-3-yl)-1,3-dioxoisoindolin-4-ylamino)methyl)benzyl)piperazin-1-yl)picolinonitrile | 569.2 | B |
| 139 | 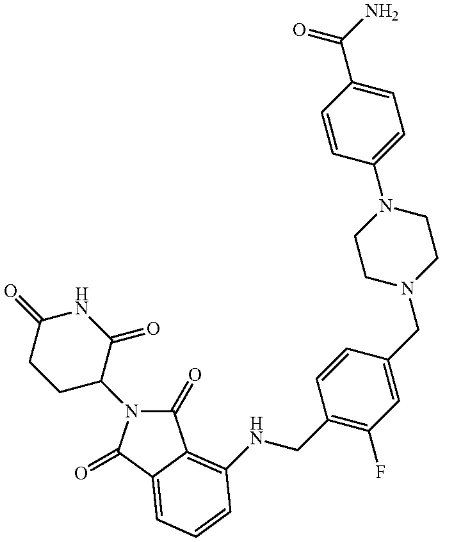 [SMILES: NC(=O)c1ccc(N2CCN(Cc3ccc(CNc4cccc5c4C(=O)N(C4CCC(=O)NC4=O)C5=O)c(F)c3)CC2)cc1] | 4-(4-(4-((2-(2,6-dioxopiperidin-3-yl)-1,3-dioxoisoindolin-4-ylamino)methyl)-3-fluorobenzyl)piperazin-1-yl)benzamide | 599.2 | D |
| 140 | 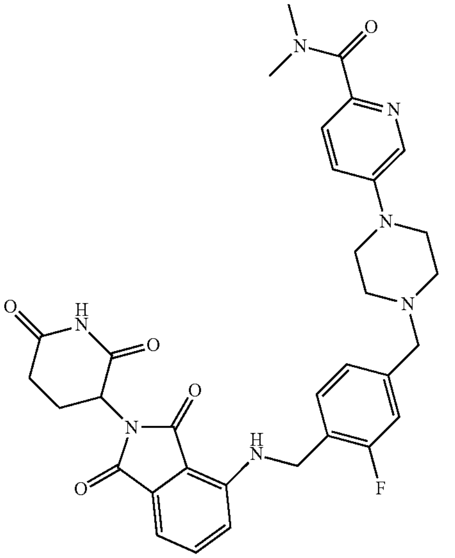 [SMILES: CN(C)C(=O)c1ccc(N2CCN(Cc3ccc(CNc4cccc5c4C(=O)N(C4CCC(=O)NC4=O)C5=O)c(F)c3)CC2)cn1] | 5-(4-(4-((2-(2,6-dioxopiperidin-3-yl)-1,3-dioxoisoindolin-4-ylamino)methyl)-3-fluorobenzyl)piperazin-1-yl)-N,N-dimethylpicolinamide | 628.2 | C |

TABLE 1-continued
| Cpd # | Cpd Structure | Cpd Name | Obs. MH+ | SU-DHL-4 Act |
|---|---|---|---|---|
| 141 | 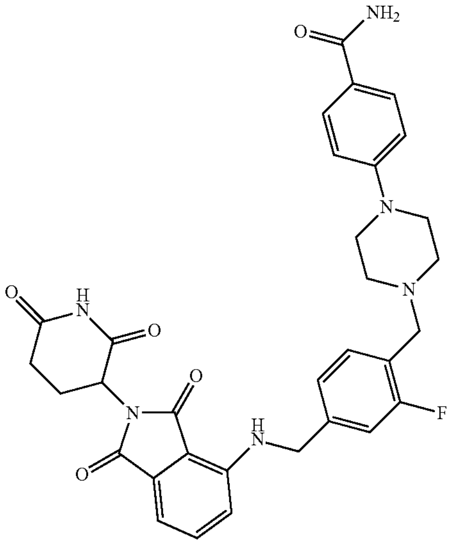 [SMILES: NC(=O)c1ccc(N2CCN(Cc3ccc(CNc4cccc5c4C(=O)N(C4CCC(=O)NC4=O)C5=O)cc3F)CC2)cc1] | 4-(4-(4-((2-(2,6-dioxopiperidin-3-yl)-1,3-dioxoisoindolin-4-ylamino)methyl)-2-fluorobenzyl)piperazin-1-yl)benzamide | 599.2 | D |
| 142 | 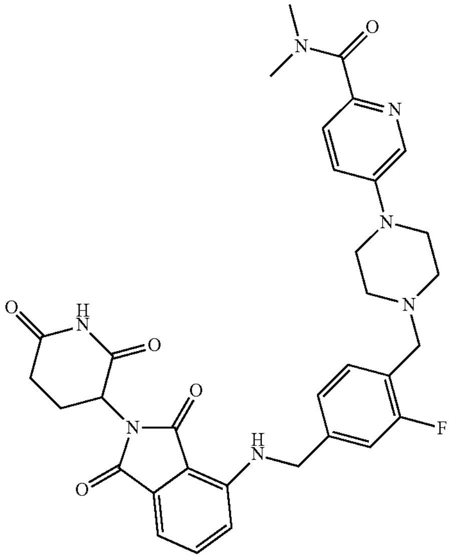 [SMILES: CN(C)C(=O)c1ccc(N2CCN(Cc3ccc(CNc4cccc5c4C(=O)N(C4CCC(=O)NC4=O)C5=O)cc3F)CC2)cn1] | 5-(4-(4-((2-(2,6-dioxopiperidin-3-yl)-1,3-dioxoisoindolin-4-ylamino)methyl)-2-fluorobenzyl)piperazin-1-yl)-N,N-dimethylpicolinamide | 628.3 | B |
| 143 | 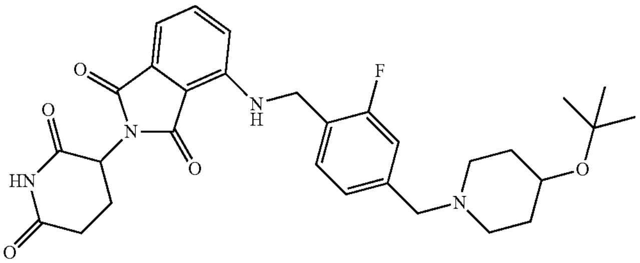 [SMILES: CC(C)(C)OC1CCN(Cc2ccc(CNc3cccc4c3C(=O)N(C3CCC(=O)NC3=O)C4=O)c(F)c2)CC1] | 4-(4-((4-tert-butyoxypiperidin-1-yl)methyl)-2-fluorobenzylamino)-2-(2,6-dioxopiperidin-3-yl)isoindoline-1,3-dione | 551.2 | D |

TABLE 1-continued

| Cpd # | Cpd Structure | Cpd Name | Obs. MH+ | SU-DHL-4 Act |
|---|---|---|---|---|
| 144 | 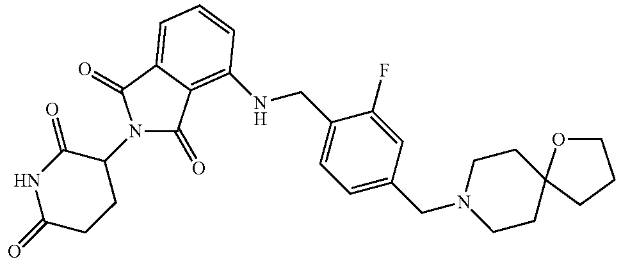 [SMILES: O=C1CCC(N2C(=O)c3cccc(NCc4ccc(CN5CCC6(CCCO6)CC5)cc4F)c3C2=O)C(=O)N1] | 4-(4-(1-oxa-8-azaspiro[4.5]decan-8-ylmethyl)-2-fluorobenzylamino)-2-(2,6-dioxopiperidin-3-yl)isoindoline-1,3-dione | 535.2 | D |
| 145 | 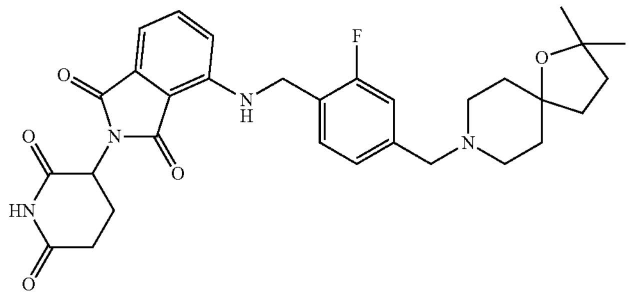 [SMILES: CC1(C)CCC2(CCN(Cc3ccc(CNc4cccc5c4C(=O)N(C4CCC(=O)NC4=O)C5=O)c(F)c3)CC2)O1] | 4-(4-((2,2-dimethyl-1-oxa-8-azaspiro[4.5]decan-8-yl)methyl)-2-fluorobenzylamino)-2-(2,6-dioxopiperidin-3-yl)isoindoline-1,3-dione | 563.2 | D |
| 146 | 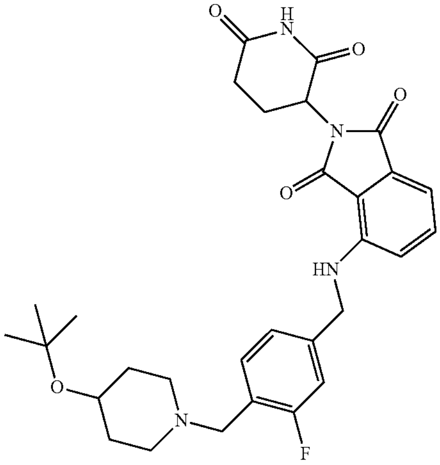 [SMILES: CC(C)(C)OC1CCN(Cc2ccc(CNc3cccc4c3C(=O)N(C3CCC(=O)NC3=O)C4=O)cc2F)CC1] | 4-(4-((4-tert-butoxypiperidin-1-yl)methyl)-3-fluorobenzylamino)-2-(2,6-dioxopiperidin-3-yl)isoindoline-1,3-dione | 551.2 | D |
| 147 | 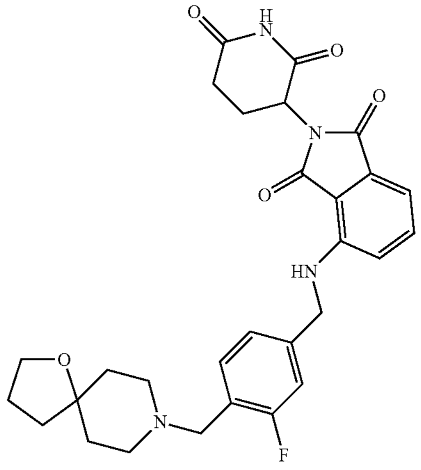 [SMILES: O=C1CCC(N2C(=O)c3cccc(NCc4ccc(CN5CCC6(CCCO6)CC5)c(F)c4)c3C2=O)C(=O)N1] | 4-(4-(1-oxa-8-azaspiro[4.5]decan-8-ylmethyl)-3-fluorobenzylamino)-2-(2,6-dioxopiperidin-3-yl)isoindoline-1,3-dione | 535.2 | C |

TABLE 1-continued
| Cpd # | Cpd Structure | Cpd Name | Obs. MH+ | SU-DHL-4 Act |
|---|---|---|---|---|
| 148 | 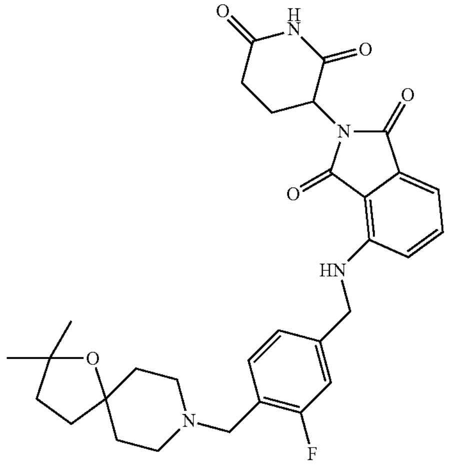 [SMILES: CC1(C)CCC2(CCN(Cc3ccc(CNc4cccc5c4C(=O)N(C4CCC(=O)NC4=O)C5=O)cc3F)CC2)O1] | 4-(4-((2,2-dimethyl-1-oxa-8-azaspiro[4.5]decan-8-yl)methyl)-3-fluorobenzylamino)-2-(2,6-dioxopiperidin-3-yl)isoindoline-1,3-dione | 563.2 | D |
| 149 | 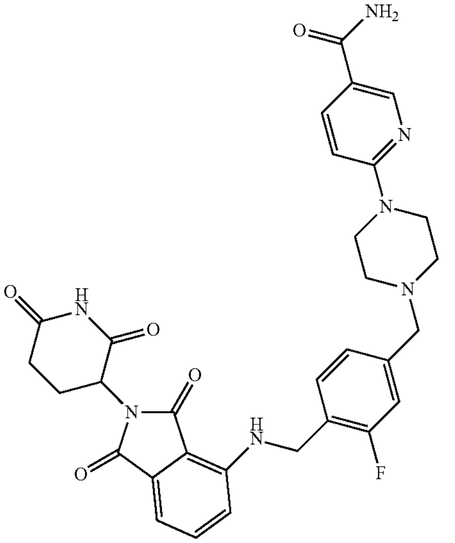 [SMILES: NC(=O)c1ccc(N2CCN(Cc3ccc(CNc4cccc5c4C(=O)N(C4CCC(=O)NC4=O)C5=O)c(F)c3)CC2)nc1] | 6-(4-(4-((2-(2,6-dioxopiperidin-3-yl)-1,3-dioxoisoindolin-4-ylamino)methyl)-3-fluorobenzyl)piperazin-1-yl)nicotinamide | 600.2 | D |
| 150 | 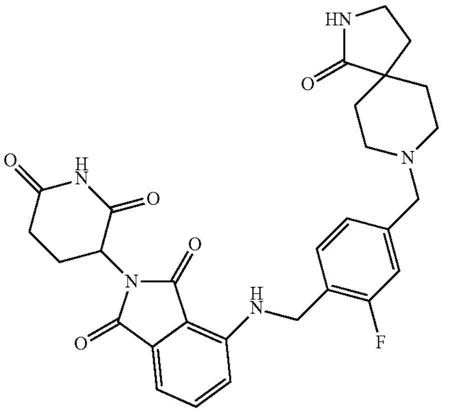 [SMILES: O=C1CCC(N2C(=O)c3cccc(NCc4ccc(CN5CCC6(CCNC6=O)CC5)cc4F)c3C2=O)C(=O)N1] | 2-(2,6-dioxopiperidin-3-yl)-4-(2-fluoro-4-((1-oxo-2,8-diazaspiro[4.5]decan-8-yl)methyl)benzylamino)isoindoline-1,3-dione | 548.2 | D |

TABLE 1-continued
| Cpd # | Cpd Structure | Cpd Name | Obs. MH+ | SU-DHL-4 Act |
|---|---|---|---|---|
| 151 | 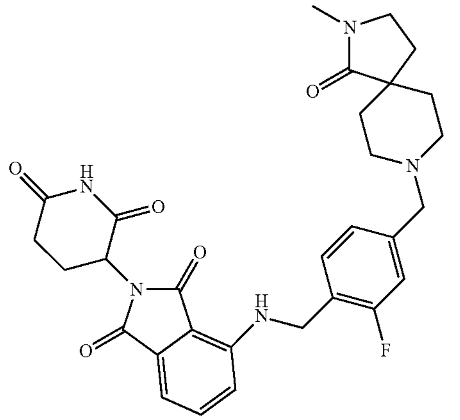 [SMILES: CN1CCC2(CCN(Cc3ccc(CNc4cccc5c4C(=O)N(C4CCC(=O)NC4=O)C5=O)c(F)c3)CC2)C1=O] | 2-(2,6-dioxopiperidin-3-yl)-4-(2-fluoro-4-((2-methyl-1-oxo-2,8-diazaspiro[4.5]decan-8-yl)methyl)benzylamino)isoindoline-1,3-dione | 562.2 | D |
| 152 | 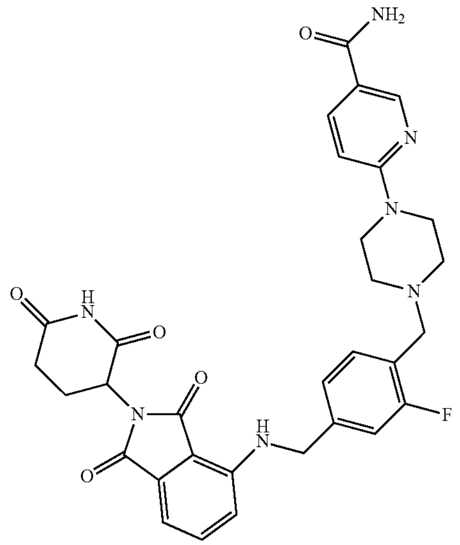 [SMILES: NC(=O)c1ccc(N2CCN(Cc3ccc(CNc4cccc5c4C(=O)N(C4CCC(=O)NC4=O)C5=O)cc3F)CC2)nc1] | 6-(4-(4-((2-(2,6-dioxopiperidin-3-yl)-1,3-dioxoisoindolin-4-ylamino)methyl)-2-fluorobenzyl)piperazin-1-yl)nicotinamide | 600.2 | B |
| 153 | 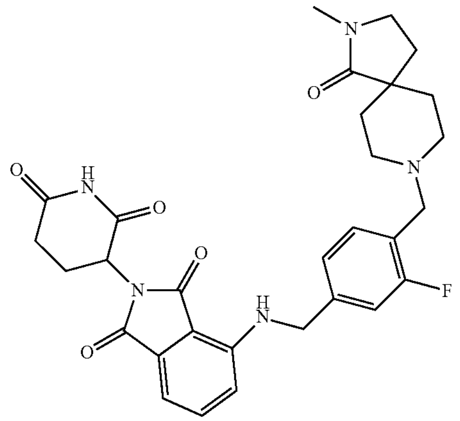 [SMILES: CN1CCC2(CCN(Cc3ccc(CNc4cccc5c4C(=O)N(C4CCC(=O)NC4=O)C5=O)cc3F)CC2)C1=O] | 2-(2,6-dioxopiperidin-3-yl)-4-(3-fluoro-4-((2-methyl-1-oxo-2,8-diazaspior[4.5]decan-8-yl)methyl)benzylamino)isoindoline-1,3-dione | 562.2 | B |

TABLE 1-continued

| Cpd # | Cpd Structure | Cpd Name | Obs. MH+ | SU-DHL-4 Act |
|---|---|---|---|---|
| 154 | 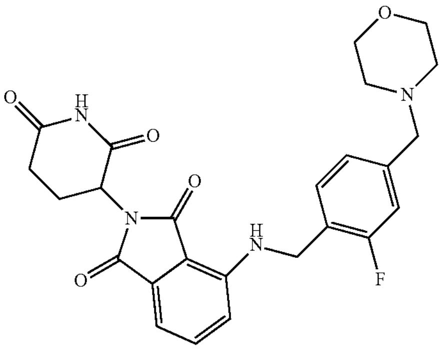 [SMILES: O=C1CCC(N2C(=O)c3cccc(NCc4ccc(CN5CCOCC5)cc4F)c3C2=O)C(=O)N1] | 2-(2,6-dioxopiperidin-3-yl)-4-(2-fluoro-4-(morpholinomethyl)benzylamino) isoindoline-1,3-dione | 481.2 | C |
| 155 | 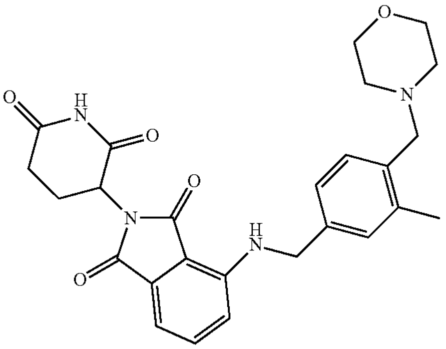 [SMILES: Cc1cc(CNc2cccc3c2C(=O)N(C2CCC(=O)NC2=O)C3=O)ccc1CN1CCOCC1] | 2-(2,6-dioxopiperidin-3-yl)-4-(3-methyl-4-(morpholinomethyl)benzylamino) isoindoline-1,3-dione | 477.2 | A |
| 156 | 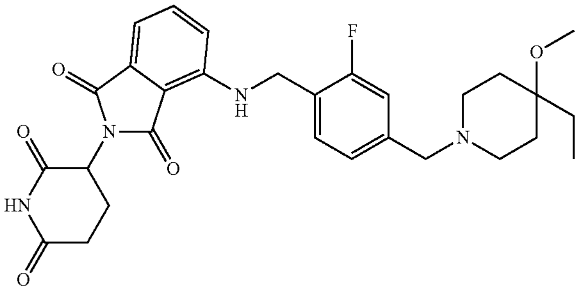 [SMILES: CCC1(OC)CCN(Cc2ccc(CNc3cccc4c3C(=O)N(C3CCC(=O)NC3=O)C4=O)c(F)c2)CC1] | 2-(2,6-dioxopiperidin-3-yl)-4-(4-((4-ethyl-4-methoxypiperidin-1-yl)methyl)-2-fluorobenzylamino)isoindoline-1,3-dione | 537.2 | D |
| 157 | 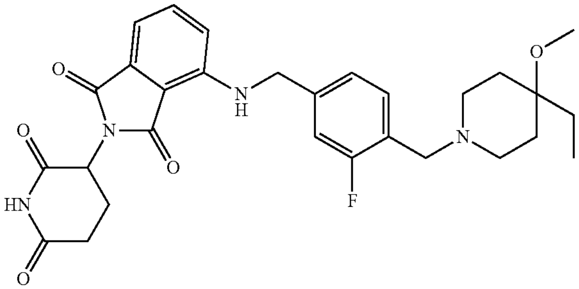 [SMILES: CCC1(OC)CCN(Cc2ccc(CNc3cccc4c3C(=O)N(C3CCC(=O)NC3=O)C4=O)cc2F)CC1] | 2-(2,6-dioxopiperidin-3-yl)-4-(4-((4-ethyl-4-methoxypiperidin-1-yl)methyl)-3-fluorobenzylamino)isoindoline-1,3-dione | 537.2 | D |
| 158 | 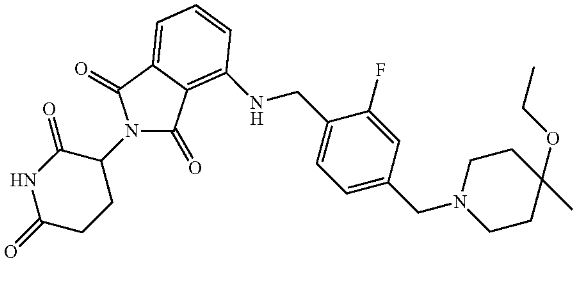 [SMILES: CCOC1(C)CCN(Cc2ccc(CNc3cccc4c3C(=O)N(C3CCC(=O)NC3=O)C4=O)c(F)c2)CC1] | 2-(2,6-dioxopiperidin-3-yl)-4-(4-((4-ethoxy-4-methylpiperidin-1-yl)methyl)-2-fluorobenzylamino)isoindoline-1,3-dione | 537.2 | D |

TABLE 1-continued

| Cpd # | Cpd Structure | Cpd Name | Obs. MH+ | SU-DHL-4 Act |
|---|---|---|---|---|
| 159 | 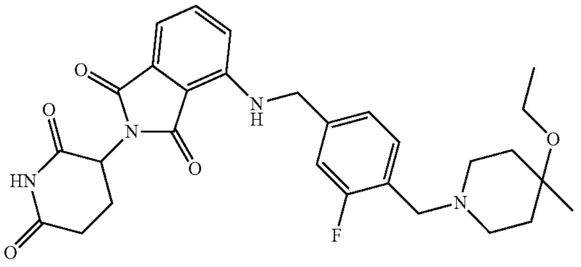 [SMILES: CCOC1(C)CCN(Cc2ccc(CNc3cccc4c3C(=O)N(C3CCC(=O)NC3=O)C4=O)cc2F)CC1] | 2-(2,6-dioxopiperidin-3-yl)-4-(4-((4-ethoxy-4-methylpiperidin-1-yl)methyl)-3-fluorobenzylamino)isoindoline-1,3-dione | 537.2 | D |
| 160 | 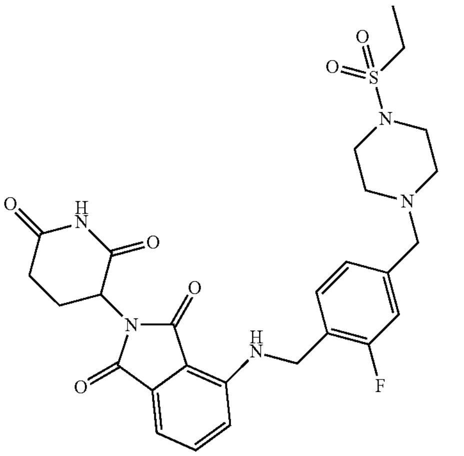 [SMILES: CCS(=O)(=O)N1CCN(Cc2ccc(CNc3cccc4c3C(=O)N(C3CCC(=O)NC3=O)C4=O)c(F)c2)CC1] | 2-(2,6-dioxopiperidin-3-yl)-4-(4-((4-(ethylsulfonyl)piperazin-1-yl)methyl)-2-fluorobenzylamino)isoindoline-1,3-dione | 572.2 | D |
| 161 | 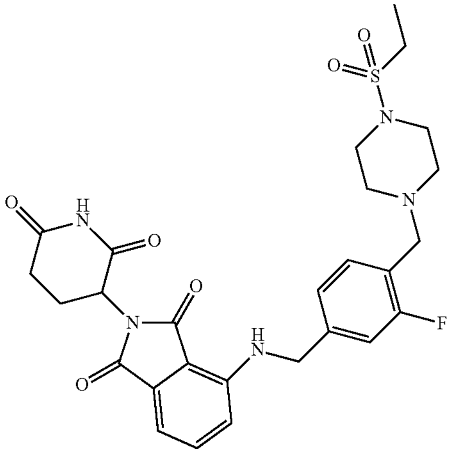 [SMILES: CCS(=O)(=O)N1CCN(Cc2ccc(CNc3cccc4c3C(=O)N(C3CCC(=O)NC3=O)C4=O)cc2F)CC1] | 2-(2,6-dioxopiperidin-3-yl)-4-(4-((4-(ethylsulfonyl)piperazin-1-yl)methyl)-3-fluorobenzylamino)isoindoline-1,3-dione | 572.2 | D |
| 162 | 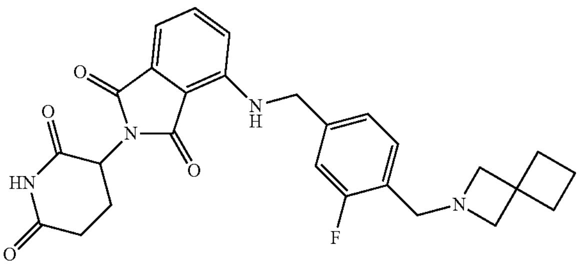 [SMILES: O=C1CCC(N2C(=O)c3cccc(NCc4ccc(CN5CC6(CCC6)C5)c(F)c4)c3C2=O)C(=O)N1] | 4-(4-(2-azaspiro[3.3]heptan-2-ylmethyl)-3-fluorobenzylamino)-2-(2,6-dioxopiperidin-3-yl)isoindoline-1,3-dione | 491.4 | C |

TABLE 1-continued

| Cpd # | Cpd Structure | Cpd Name | Obs. MH+ | SU-DHL-4 Act |
|---|---|---|---|---|
| 163 | 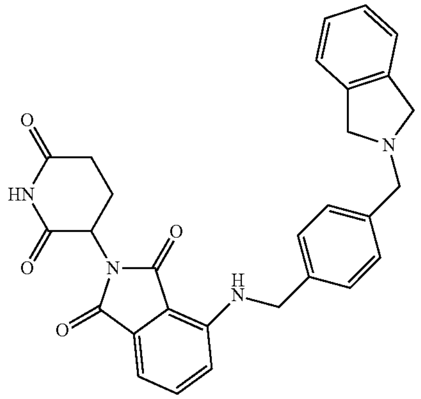 [SMILES: O=C1CCC(N2C(=O)c3cccc(NCc4ccc(CN5Cc6ccccc6C5)cc4)c3C2=O)C(=O)N1] | 2-(2,6-dioxopiperidin-3-yl)-4-(4-(isoindolin-2-ylmethyl)benzylamino)isoindoline-1,3-dione | 495.2 | D |
| 164 | 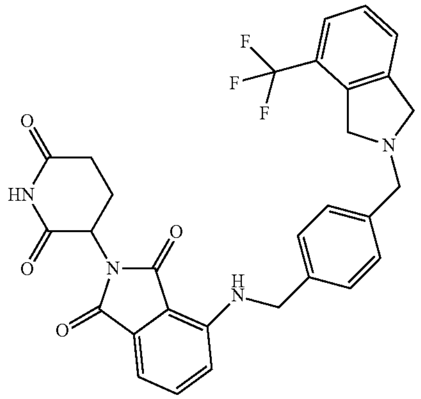 [SMILES: O=C1CCC(N2C(=O)c3cccc(NCc4ccc(CN5Cc6cccc(C(F)(F)F)c6C5)cc4)c3C2=O)C(=O)N1] | 2-(2,6-dioxopiperidin-3-yl)-4-(4-((4-(trifluoromethyl)isoindolin-2-yl)methyl)benzylamino)isoindoline-1,3-dione | 563.2 | C |
| 165 | 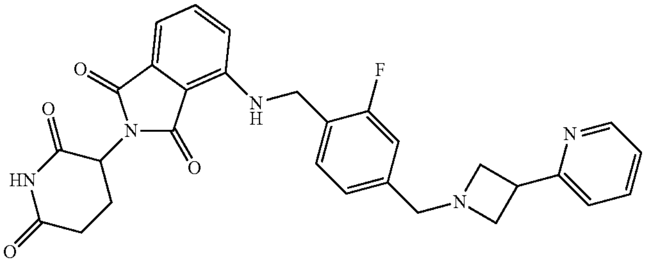 [SMILES: O=C1CCC(N2C(=O)c3cccc(NCc4ccc(CN5CC(c6ccccn6)C5)cc4F)c3C2=O)C(=O)N1] | 2-(2,6-dioxopiperidin-3-yl)-4-(2-fluoro-4-((3-(pyridin-2-yl)azetidin-1-yl)methyl)benzylamino)isoindoline-1,3-dione | 528.2 | D |
| 166 | 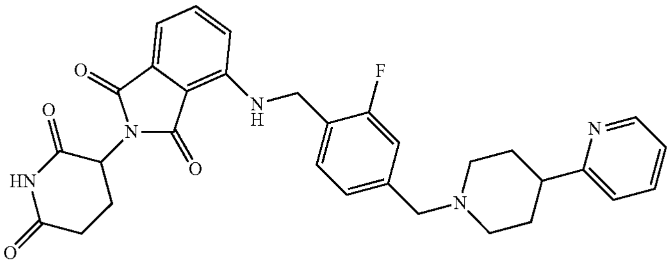 [SMILES: O=C1CCC(N2C(=O)c3cccc(NCc4ccc(CN5CCC(c6ccccn6)CC5)cc4F)c3C2=O)C(=O)N1] | 2-(2,6-dioxopiperidin-3-(4-(2-fluoro-4-((4-(pyridin-2-yl)piperidin-1-yl)methyl)benzylamino)isoindoline-1,3-dione | 556.2 | D |

TABLE 1-continued

| Cpd # | Cpd Structure | Cpd Name | Obs. MH+ | SU-DHL-4 Act |
|---|---|---|---|---|
| 167 | 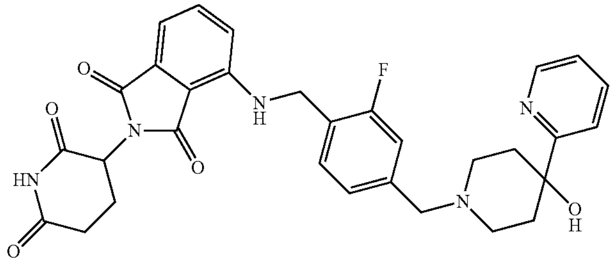 [SMILES: O=C1CCC(N2C(=O)c3cccc(NCc4ccc(CN5CCC(O)(c6ccccn6)CC5)cc4F)c3C2=O)C(=O)N1] | 2-(2,6-dioxopiperidin-3-yl)-4-(2-fluoro-4-((4-hydroxy-4-(pyridin-2-yl)piperidin-1-yl)methyl)benzylamino)isoindoline-1,3-dione | 572.2 | D |
| 168 | 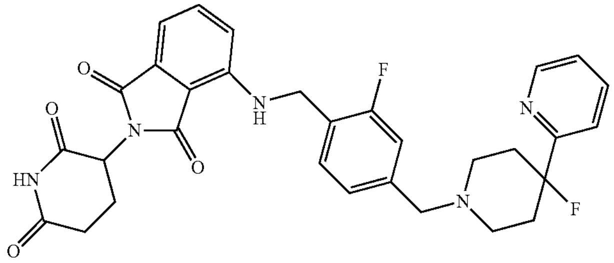 [SMILES: O=C1CCC(N2C(=O)c3cccc(NCc4ccc(CN5CCC(F)(c6ccccn6)CC5)cc4F)c3C2=O)C(=O)N1] | 2-(2,6-dioxopiperidin-3-yl)-4-(2-fluoro-4-((4-fluoro-4-(pyridin-2-yl)piperidin-1-yl)methyl)benzylamino)isoindoline-1,3-dione | 574.2 | D |
| 169 | 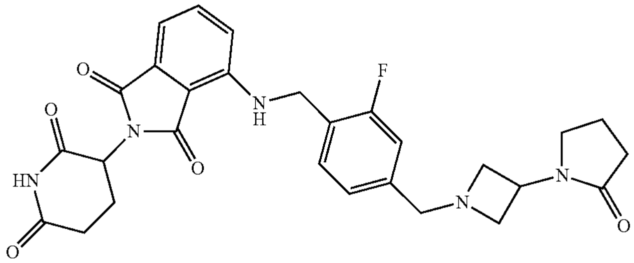 [SMILES: O=C1CCC(N2C(=O)c3cccc(NCc4ccc(CN5CC(N6CCCC6=O)C5)cc4F)c3C2=O)C(=O)N1] | 2-(2,6-dioxopiperidin-3-yl)-4-(2-fluoro-4-((3-(2-oxopyrrolidin-1-yl)azetidin-1-yl)methyl)benzylamino)isoindoline-1,3-dione | 534.2 | D |
| 170 | 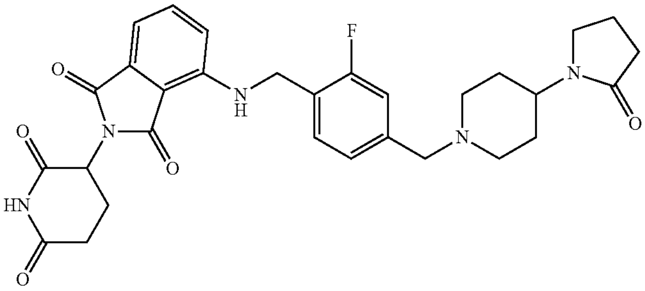 [SMILES: O=C1CCC(N2C(=O)c3cccc(NCc4ccc(CN5CCC(N6CCCC6=O)CC5)cc4F)c3C2=O)C(=O)N1] | 2-(2,6-dioxopiperidin-3-yl)-4-(2-fluoro-4-((4-(2-oxopyrrolidin-1-yl)piperidin-1-yl)methyl)benzylamino)isoindoline-1,3-dione | 562.2 | D |
| 171 | 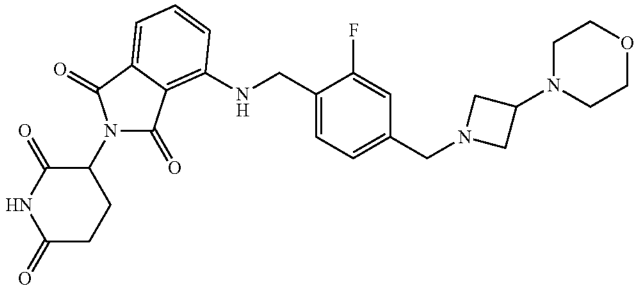 [SMILES: O=C1CCC(N2C(=O)c3cccc(NCc4ccc(CN5CC(N6CCOCC6)C5)cc4F)c3C2=O)C(=O)N1] | 2-(2,6-dioxopiperidin-3-yl)-4-(2-fluoro-4-((3-morpholinoazetidin-1-yl)methyl)benzylamino)isoindoline-1,3-dione | 536.2 | D |

TABLE 1-continued

| Cpd # | Cpd Structure | Cpd Name | Obs. MH+ | SU-DHL-4 Act |
|---|---|---|---|---|
| 172 | 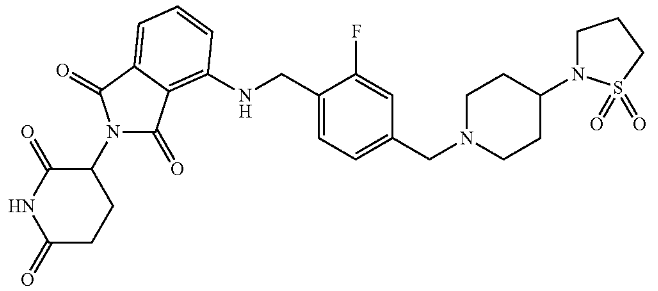 [SMILES: O=C1CCC(N2C(=O)c3cccc(NCc4ccc(CN5CCC(N6CCCS6(=O)=O)CC5)cc4F)c3C2=O)C(=O)N1] | 4-((4-((4-(1,1-dioxidoisothiazolidin-2-yl)piperidin-1-yl)methyl)-2-fluorobenzyl)amino)-2-(2,6-dioxopiperidin-3-yl)isoindoline-1,3-dione | 598.2 | D |
| 173 | 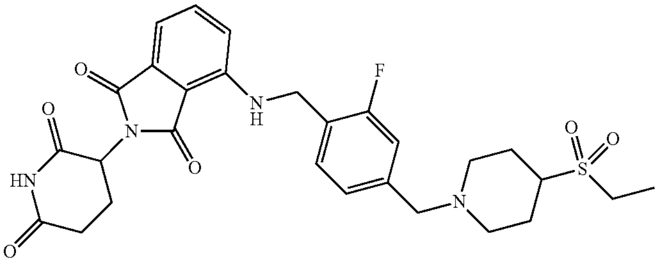 [SMILES: CCS(=O)(=O)C1CCN(Cc2ccc(CNc3cccc4c3C(=O)N(C3CCC(=O)NC3=O)C4=O)c(F)c2)CC1] | 2-(2,6-dioxopiperidin-3-yl)-4-(4-((4-ethylsulfonyl)piperidin-1-yl)methyl)-2-fluorobenzylamino)isoindoline-1,3-dione | 571.4 | D |
| 174 | 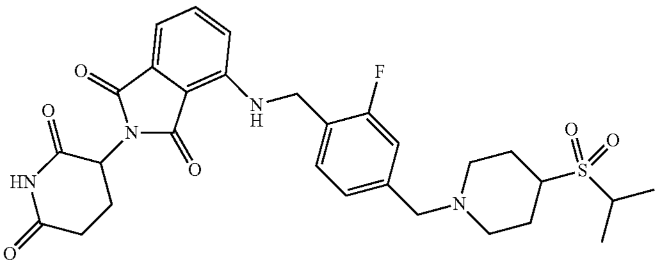 [SMILES: CC(C)S(=O)(=O)C1CCN(Cc2ccc(CNc3cccc4c3C(=O)N(C3CCC(=O)NC3=O)C4=O)c(F)c2)CC1] | 2-(2,6-dioxopiperidin-3-yl)-4-(2-fluoro-4-((4-(isopropylsulfonyl)piperidin-1-yl)methyl)benzylamino)isoindoline-1,3-dione | 585.4 | D |
| 175 | 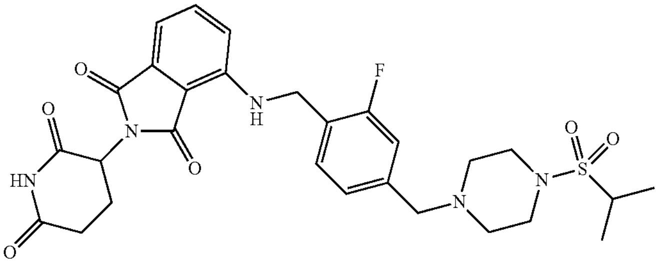 [SMILES: CC(C)S(=O)(=O)N1CCN(Cc2ccc(CNc3cccc4c3C(=O)N(C3CCC(=O)NC3=O)C4=O)c(F)c2)CC1] | 2-(2,6-dioxopiperidin-3-yl)-4-(2-fluoro-4-((4-(isopropylsulfonyl)piperazin-1-yl)methyl)benzylamino)isoindoline-1,3-dione | 586.4 | D |
| 176 | 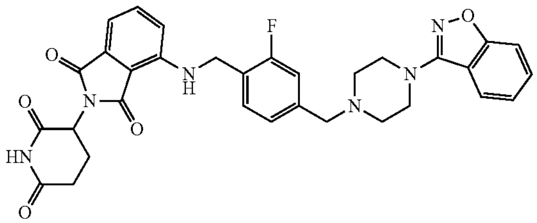 [SMILES: O=C1CCC(N2C(=O)c3cccc(NCc4ccc(CN5CCN(c6noc7ccccc67)CC5)cc4F)c3C2=O)C(=O)N1] | 4-(4-((4-(benzo[d]isoxazol-3-yl)piperazin-1-yl)methyl)-2-fluorobenzylamino)-2-(2,6-dioxopiperidin-3-yl)isoindoline-1,3-dione | 597.4 | D |
| 177 | 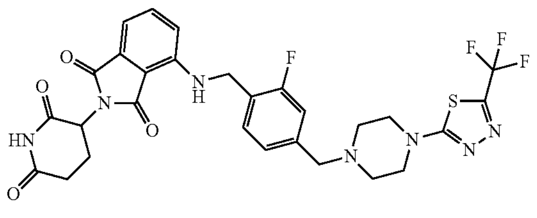 [SMILES: O=C1CCC(N2C(=O)c3cccc(NCc4ccc(CN5CCN(c6nnc(C(F)(F)F)s6)CC5)cc4F)c3C2=O)C(=O)N1] | 2-(2,6-dioxopiperidin-3-yl)-4-(2-fluoro-4-((4-(5-(trifluoromethyl)-1,3,4-thiadiazol-2-yl)piperazin-1-yl)methyl)benzylamino)isoindoline-1,3-dione | 632.4 | D |

TABLE 1-continued

| Cpd # | Cpd Structure | Cpd Name | Obs. MH+ | SU-DHL-4 Act |
| --- | --- | --- | --- | --- |
| 178 | 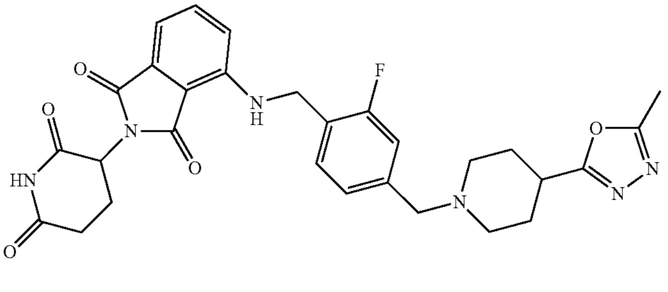 [SMILES: Cc1nnc(C2CCN(Cc3ccc(CNc4cccc5c4C(=O)N(C4CCC(=O)NC4=O)C5=O)c(F)c3)CC2)o1] | 2-(2,6-dioxopiperidin-3-yl)-4-(2-fluoro-4-((4-(5-methyl-1,3,4-oxadiazol-2-yl)piperidin-1-yl)methyl)benzylamino)isoindoline-1,3-dione | 561.4 | C |
| 179 | 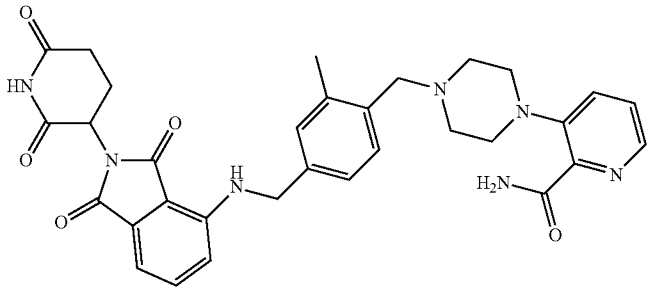 [SMILES: Cc1cc(CNc2cccc3c2C(=O)N(C2CCC(=O)NC2=O)C3=O)ccc1CN1CCN(c2cccnc2C(N)=O)CC1] | 3-(4-(4-((2-(2,6-dioxopiperidin-3-yl)-1,3-dioxoisoindolin-4-ylamino)methyl)-2-methylbenzyl)piperazin-1-yl)picolinamide | 596.6 | A |
| 180 | 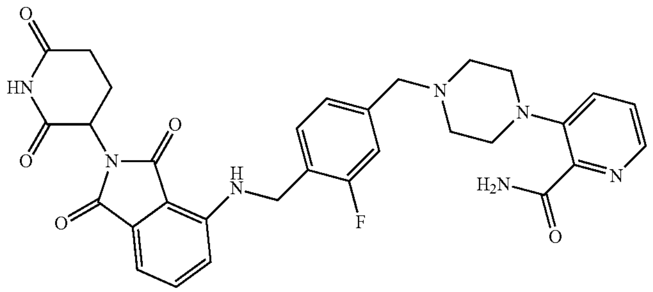 [SMILES: NC(=O)c1ncccc1N1CCN(Cc2ccc(CNc3cccc4c3C(=O)N(C3CCC(=O)NC3=O)C4=O)c(F)c2)CC1] | 3-(4-(4-((2-(2,6-dioxopiperidin-3-yl)-1,3-dioxoisoindolin-4-ylamino)methyl)-3-fluorobenzyl)piperazin-1-yl)picolinamide | 600.4 | C |
| 181 | 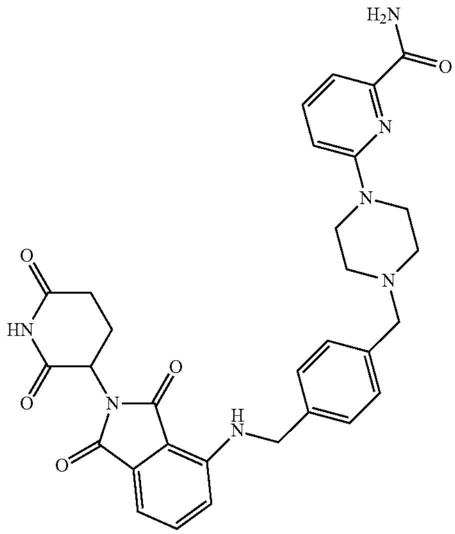 [SMILES: NC(=O)c1cccc(N2CCN(Cc3ccc(CNc4cccc5c4C(=O)N(C4CCC(=O)NC4=O)C5=O)cc3)CC2)n1] | 6-(4-(4-((2-(2,6-dioxopiperidin-3-yl)-1,3-dioxoisoindolin-4-ylamino)methyl)benzyl)piperazin-1-yl)picolinamide | 582.6 | D |

TABLE 1-continued

| Cpd # | Cpd Structure | Cpd Name | Obs. MH+ | SU-DHL-4 Act |
|---|---|---|---|---|
| 182 | 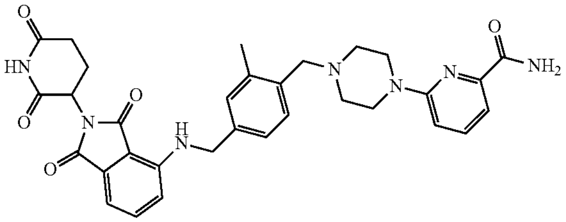 [SMILES: Cc1cc(CNc2cccc3c2C(=O)N(C2CCC(=O)NC2=O)C3=O)ccc1CN1CCN(c2cccc(C(N)=O)n2)CC1] | 6-(4-(4-((2-(2,6-dioxopiperidin-3-yl)-1,3-dioxoisoindolin-4-ylamino)methyl)-2-methylbenzyl)piperazin-1-yl)picolinamide | 596.5 | D |
| 183 | 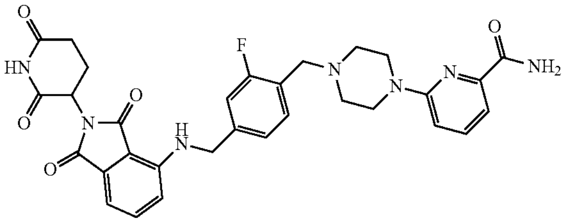 [SMILES: NC(=O)c1cccc(N2CCN(Cc3ccc(CNc4cccc5c4C(=O)N(C4CCC(=O)NC4=O)C5=O)cc3F)CC2)n1] | 6-(4-(4-((2-(2,6-dioxopiperidin-3-yl)-1,3-dioxoisoindolin-4-ylamino)methyl)-2-fluorobenzyl)piperazin-1-yl)picolinamide | 600.4 | D |
| 184 | 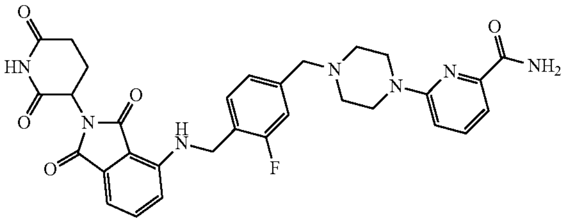 [SMILES: NC(=O)c1cccc(N2CCN(Cc3ccc(CNc4cccc5c4C(=O)N(C4CCC(=O)NC4=O)C5=O)c(F)c3)CC2)n1] | 6-(4-(4-((2-(2,6-dioxopiperidin-3-yl)-1,3-dioxoisoindolin-4-ylamino)methyl)-3-fluorobenzyl)piperazin-1-yl)picolinamide | 600.4 | D |
| 185 | 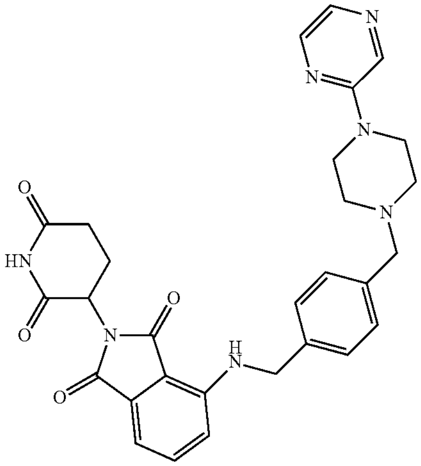 [SMILES: O=C1CCC(N2C(=O)c3cccc(NCc4ccc(CN5CCN(c6cnccn6)CC5)cc4)c3C2=O)C(=O)N1] | 2-(2,6-dioxopiperidin-3-yl)-4-(4-((4-(pyrazin-2-yl)piperazin-1-yl)methyl)benzylamino)isoindoline-1,3-dione | 540.7 | C |

TABLE 1-continued
| Cpd # | Cpd Structure | Cpd Name | Obs. MH+ | SU-DHL-4 Act |
|---|---|---|---|---|
| 186 | 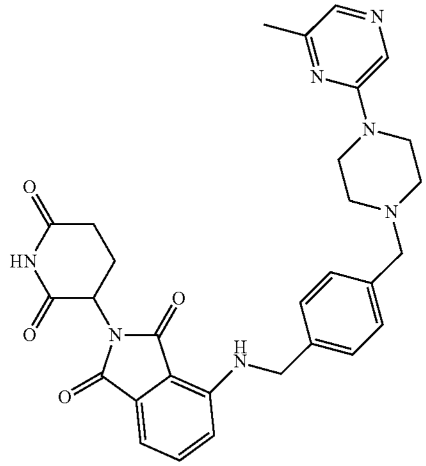 [SMILES: Cc1cncc(N2CCN(Cc3ccc(CNc4cccc5c4C(=O)N(C4CCC(=O)NC4=O)C5=O)cc3)CC2)n1] | 2-(2,6-dioxopiperidin-3-yl)-4-(4-((4-(6-methylpyrazin-2-yl)piperazin-1-yl)methyl)benzylamino)isoindoline-1,3-dione | 554.6 | A |
| 187 | 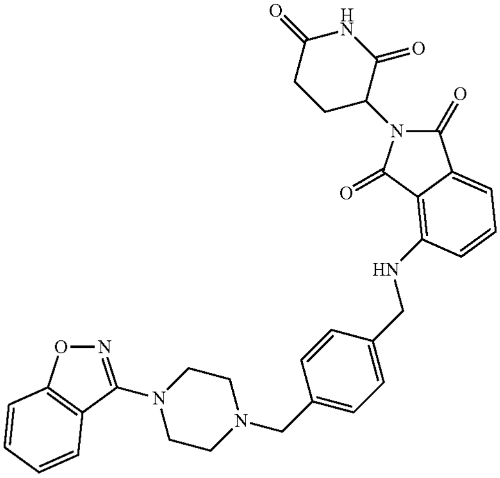 [SMILES: O=C1CCC(N2C(=O)c3cccc(NCc4ccc(CN5CCN(c6noc7ccccc67)CC5)cc4)c3C2=O)C(=O)N1] | 4-(4-((4-(benzo[d]isoxazol-3-yl)piperazin-1-yl)methyl)benzylamino)-2-(2,6-dioxopiperidin-3-yl)isoindoline-1,3-dione | 579.8 | C |
| 188 | 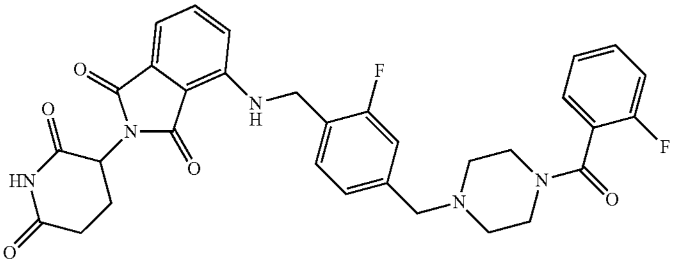 [SMILES: O=C1CCC(N2C(=O)c3cccc(NCc4ccc(CN5CCN(C(=O)c6ccccc6F)CC5)cc4F)c3C2=O)C(=O)N1] | 2-(2,6-dioxopiperidin-3-yl)-4-(2-fluoro-4-((4-(2-fluorobenzoyl)piperazin-1-yl)methyl)benzylamino)isoindoline-1,3-dione | 602.2 | A |

TABLE 1-continued

| Cpd # | Cpd Structure | Cpd Name | Obs. MH+ | SU-DHL-4 Act |
|---|---|---|---|---|
| 189 | 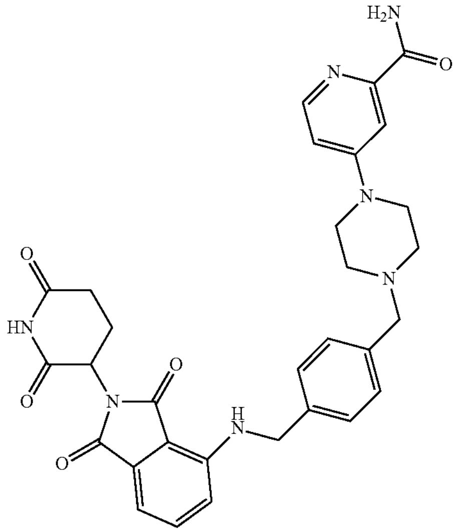 [SMILES: NC(=O)c1cc(N2CCN(Cc3ccc(CNc4cccc5c4C(=O)N(C4CCC(=O)NC4=O)C5=O)cc3)CC2)ccn1] | 4-(4-(4-((2-(2,6-dioxopiperidin-3-yl)-1,3-dioxoisoindolin-4-ylamino)methyl)benzyl)piperazin-1-yl)picolinamide | 582.2 | C |
| 190 | 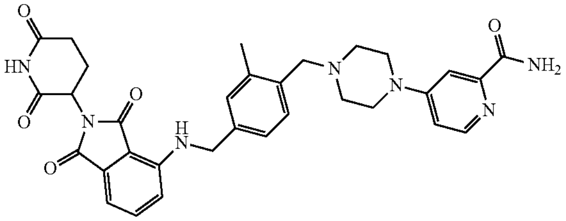 [SMILES: Cc1cc(CNc2cccc3c2C(=O)N(C2CCC(=O)NC2=O)C3=O)ccc1CN1CCN(c2ccnc(C(N)=O)c2)CC1] | 4-(4-(4-((2-(2,6-dioxopiperidin-3-yl)-1,3-dioxoisoindolin-4-ylamino)methyl)-2-methylbenzyl)piperazin-1-yl)picolinamide | 596.2 | C |
| 191 | 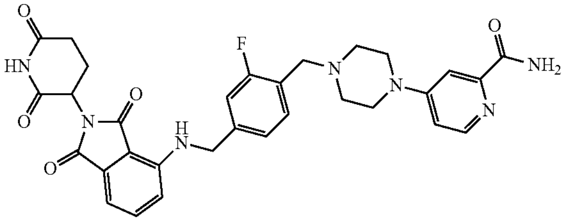 [SMILES: NC(=O)c1cc(N2CCN(Cc3ccc(CNc4cccc5c4C(=O)N(C4CCC(=O)NC4=O)C5=O)cc3F)CC2)ccn1] | 4-(4-(4-((2-(2,6-dioxopiperidin-3-yl)-1,3-dioxoisoindolin-4-ylamino)methyl)-2-fluorobenzyl)piperazin-1-yl)picolinamide | 600.2 | B |
| 192 | 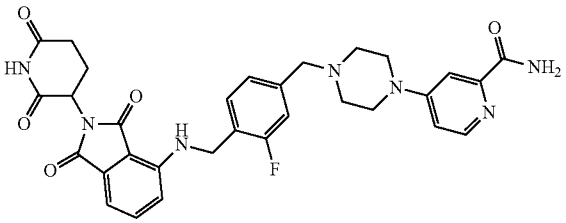 [SMILES: NC(=O)c1cc(N2CCN(Cc3ccc(CNc4cccc5c4C(=O)N(C4CCC(=O)NC4=O)C5=O)c(F)c3)CC2)ccn1] | 4-(4-(4-((2-(2,6-dioxopiperidin-3-yl)-1,3-dioxoisoindolin-4-ylamino)methyl)-3-fluorobenzyl)piperazin-1-yl)picolinamide | 600.2 | D |

TABLE 1-continued
| Cpd # | Cpd Structure | Cpd Name | Obs. MH+ | SU-DHL-4 Act |
|---|---|---|---|---|
| 193 | 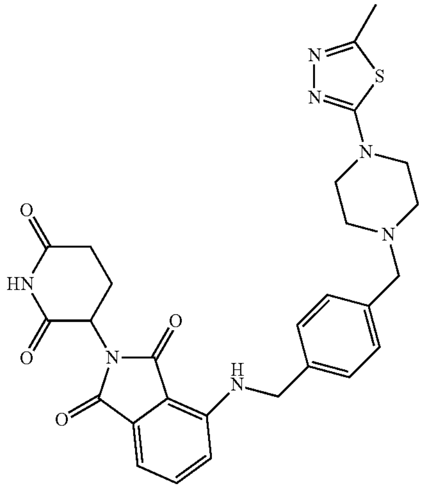 [SMILES: Cc1nnc(N2CCN(Cc3ccc(CNc4cccc5c4C(=O)N(C4CCC(=O)NC4=O)C5=O)cc3)CC2)s1] | 2-(2,6-dioxopiperidin-3-yl)-4-(4-((4-(5-methyl-1,3,4-thiadiazol-2-yl)piperazin-1-yl)methyl)benzylamino)isoindoline-1,3-dione | 560.2 | C |
| 194 | 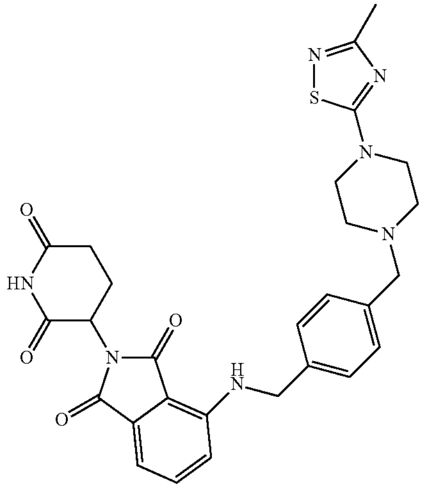 [SMILES: Cc1nsc(N2CCN(Cc3ccc(CNc4cccc5c4C(=O)N(C4CCC(=O)NC4=O)C5=O)cc3)CC2)n1] | 2-(2,6-dioxopiperidin-3-yl)-4-(4-((4-(3-methyl-1,2,4-thiadiazol-5-yl)piperazin-1-yl)methyl)benzylamino)isoindoline-1,3-dione | 560.2 | D |
| 195 | 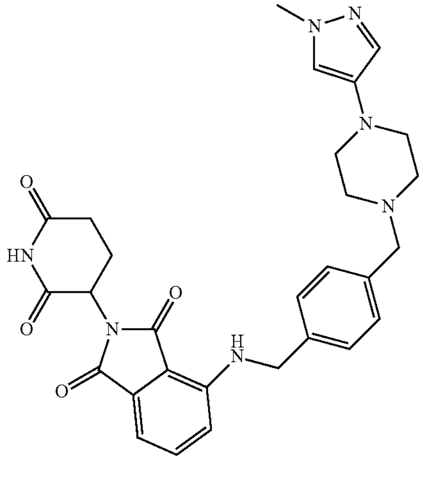 [SMILES: Cn1cc(N2CCN(Cc3ccc(CNc4cccc5c4C(=O)N(C4CCC(=O)NC4=O)C5=O)cc3)CC2)cn1] | 2-(2,6-dioxopiperidin-3-yl)-4-(4-((4-(1-methyl-1H-pyrazol-4-yl)piperazin-1-yl)methyl)benzylamino)isoindoline-1,3-dione | 542.2 | C |

TABLE 1-continued
| Cpd # | Cpd Structure | Cpd Name | Obs. MH+ | SU-DHL-4 Act |
|---|---|---|---|---|
| 196 | 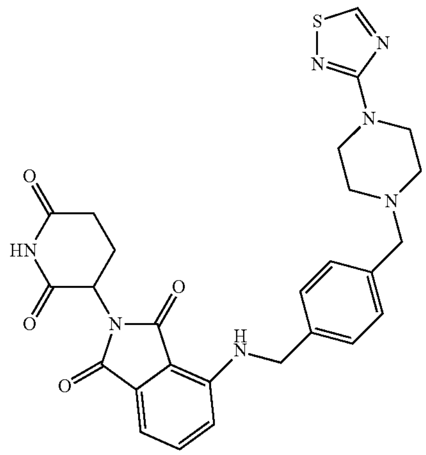 [SMILES: O=C1CCC(N2C(=O)c3cccc(NCc4ccc(CN5CCN(c6ncsn6)CC5)cc4)c3C2=O)C(=O)N1] | 4-(4-((4-(1,2,4,-thiadiazol-3-yl)piperazin-1-yl)methyl)benzylamino)-2-(2,6-dioxopiperidin-3-yl)isoindoline-1,3-dione | 546.2 | D |
| 197 | 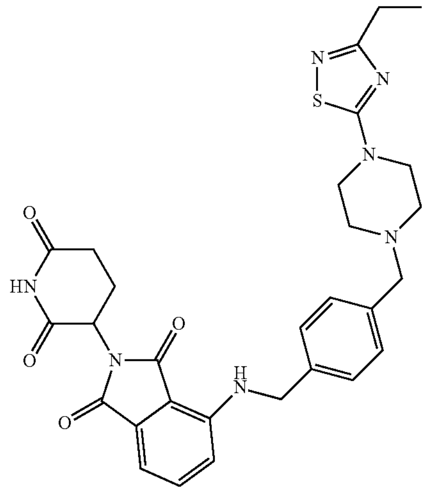 [SMILES: CCc1nsc(N2CCN(Cc3ccc(CNc4cccc5c4C(=O)N(C4CCC(=O)NC4=O)C5=O)cc3)CC2)n1] | 2-(2,6-dioxopiperidin-3-yl)-4-(4-((4-(3-ethyl-1,2,4-thiadiazol-5-yl)piperazin-1-yl)methyl)benzylamino)isoindoline-1,3-dione | 574.2 | D |
| 198 | 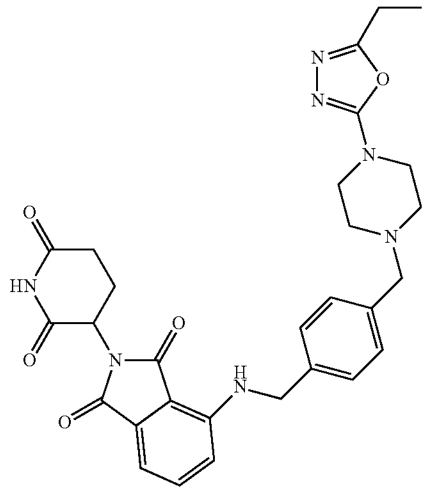 [SMILES: CCc1nnc(N2CCN(Cc3ccc(CNc4cccc5c4C(=O)N(C4CCC(=O)NC4=O)C5=O)cc3)CC2)o1] | 2-(2,6-dioxopiperidin-3-yl)-4-(4-((4-(5-ethyl-1,3,4-oxadiazol-2-yl)piperazin-1-yl)methyl)benzylamino)isoindoline-1,3-dione | 558.2 | A |

TABLE 1-continued

| Cpd # | Cpd Structure | Cpd Name | Obs. MH+ | SU-DHL-4 Act |
|---|---|---|---|---|
| 199 | 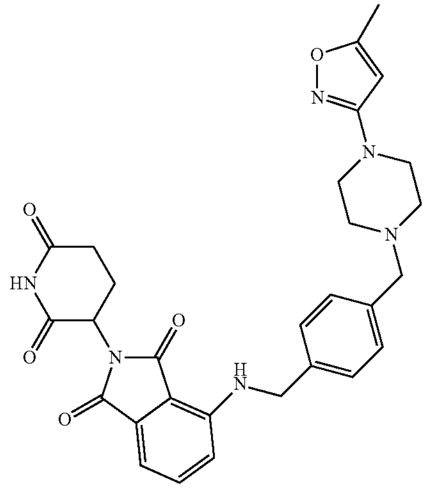 [SMILES: Cc1cc(N2CCN(Cc3ccc(CNc4cccc5c4C(=O)N(C4CCC(=O)NC4=O)C5=O)cc3)CC2)no1] | 2-(2,6-dioxopiperidin-3-yl)-4-(4-((4-(5-methylisoxazol-3-yl)piperazin-1-yl)methyl)benzylamino)isoindoline-1,3-dione | 543.2 | D |
| 200 | 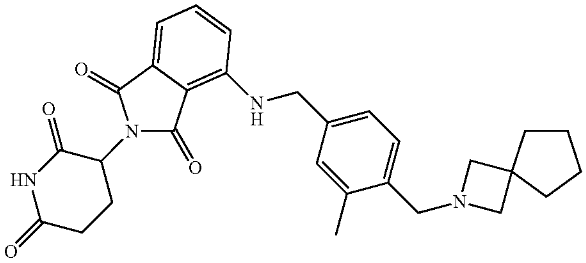 [SMILES: Cc1cc(CNc2cccc3c2C(=O)N(C2CCC(=O)NC2=O)C3=O)ccc1CN1CC2(CCCC2)C1] | 4-(4-(2-azaspiro[3.4]octan-2-ylmethyl)-3-methylbenzylamino)-2-(2,6-dioxopiperidin-3-yl)isoindoline-1,3-dione | 501.2 | D |
| 201 | 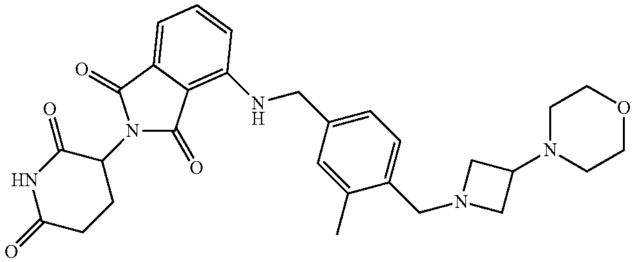 [SMILES: Cc1cc(CNc2cccc3c2C(=O)N(C2CCC(=O)NC2=O)C3=O)ccc1CN1CC(N2CCOCC2)C1] | 2-(2,6-dioxopiperidin-3-yl)-4-(3-methyl-4-((3-morpholinoazetidin-1-yl)methyl)benzylamino)isoindoline-1,3-dione | 532.2 | D |
| 202 | 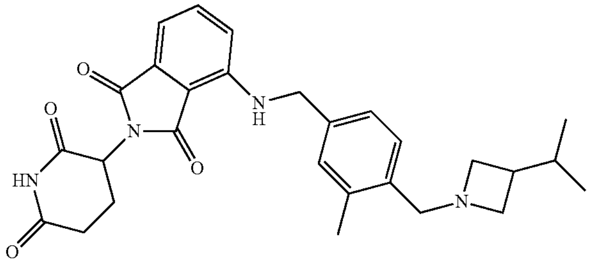 [SMILES: Cc1cc(CNc2cccc3c2C(=O)N(C2CCC(=O)NC2=O)C3=O)ccc1CN1CC(C(C)C)C1] | 2-(2,6-dioxopiperidin-3-yl)-4-(4-((3-isopropylazetidin-1-yl)methyl)-3-methylbenzylamino)isoindoline-1,3-dione | 489.2 | D |

TABLE 1-continued

| Cpd # | Cpd Structure | Cpd Name | Obs. MH+ | SU-DHL-4 Act |
| --- | --- | --- | --- | --- |
| 203 | 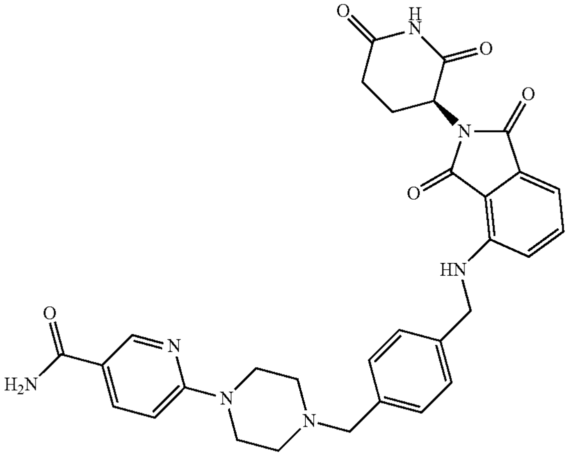 [SMILES: NC(=O)c1ccc(N2CCN(Cc3ccc(CNc4cccc5c4C(=O)N([C@H]4CCC(=O)NC4=O)C5=O)cc3)CC2)nc1] | (S)-6-(4-(4-((2-(2,6-dioxopiperidin-3-yl)-1,3-dioxoisoindolin-4-ylamino)methyl)benzyl)piperazin-1-yl)nicotinamide | 582.2 | D |
| 204 | 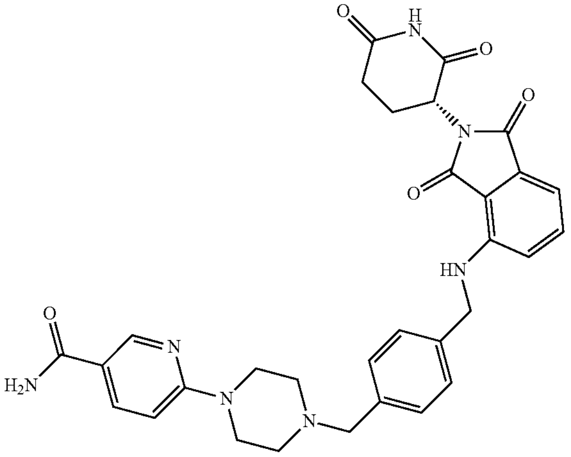 [SMILES: NC(=O)c1ccc(N2CCN(Cc3ccc(CNc4cccc5c4C(=O)N([C@@H]4CCC(=O)NC4=O)C5=O)cc3)CC2)nc1] | (R)-6-(4-(4-((2-(2,6-dioxopiperidin-3-yl)-1,3-dioxoisoindolin-4-ylamino)methyl)benzyl)piperazin-1-yl)nicotinamide | 582.2 | D |
| 205 | 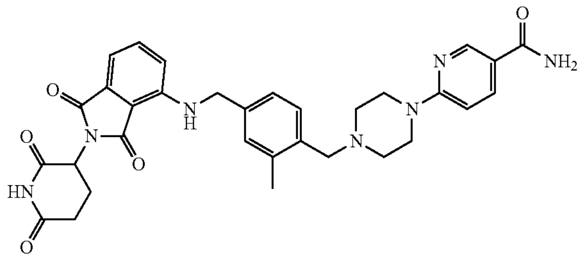 [SMILES: Cc1cc(CNc2cccc3c2C(=O)N(C2CCC(=O)NC2=O)C3=O)ccc1CN1CCN(c2ccc(C(N)=O)cn2)CC1] | 6-(4-(4-((2-(2,6-dioxopiperidin-3-yl)-1,3-dioxoisoindolin-4-ylamino)methyl)-2-methylbenzyl)piperazin-1-yl)nicotinamide | 596.2 | D |
| 206 | 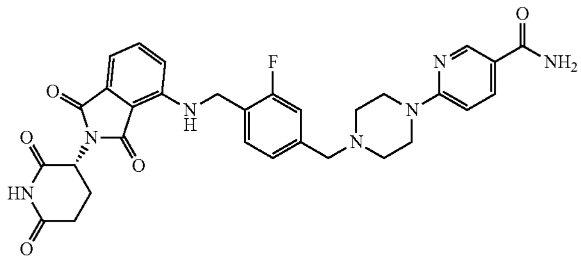 [SMILES: NC(=O)c1ccc(N2CCN(Cc3ccc(CNc4cccc5c4C(=O)N([C@@H]4CCC(=O)NC4=O)C5=O)c(F)c3)CC2)nc1] | (R)-6-(4-(4-((2-(2,6-dioxopiperidin-3-yl)-1,3-dioxoisoindolin-4-ylamino)methyl)-3-fluorobenzyl)piperazin-1-yl)nicotinamide | 600.2 | D |

TABLE 1-continued

| Cpd # | Cpd Structure | Cpd Name | Obs. MH+ | SU-DHL-4 Act |
|---|---|---|---|---|
| 207 | 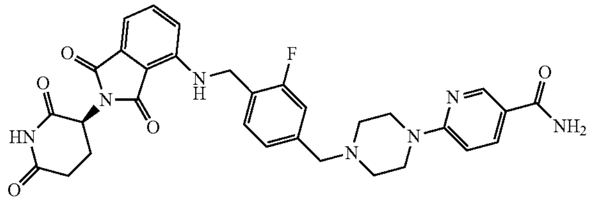 [SMILES: NC(=O)c1ccc(N2CCN(Cc3ccc(CNc4cccc5c4C(=O)N([C@H]4CCC(=O)NC4=O)C5=O)c(F)c3)CC2)nc1] | (S)-6-(4-(4-((2-(2,6-dioxopiperidin-3-yl)-1,3-dioxoisoindolin-4-ylamino)methyl)-3-fluorobenzyl)piperazin-1-yl)nicotinamide | 600.2 | D |
| 208 | 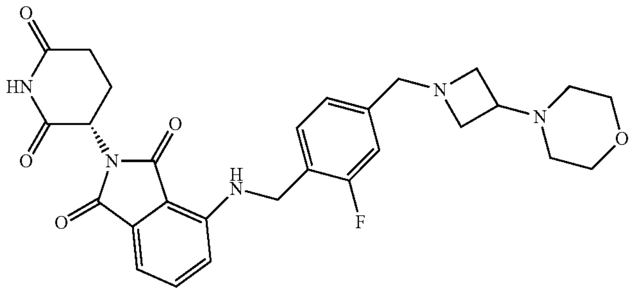 [SMILES: O=C1CC[C@H](N2C(=O)c3cccc(NCc4ccc(CN5CC(N6CCOCC6)C5)cc4F)c3C2=O)C(=O)N1] | (S)-2-(2,6-dioxopiperidin-3-yl)-4-(2-fluoro-4-((3-morpholinoazetidin-1-yl)methyl)benzylamino)isoindoline-1,3-dione | 536.2 | D |
| 209 | 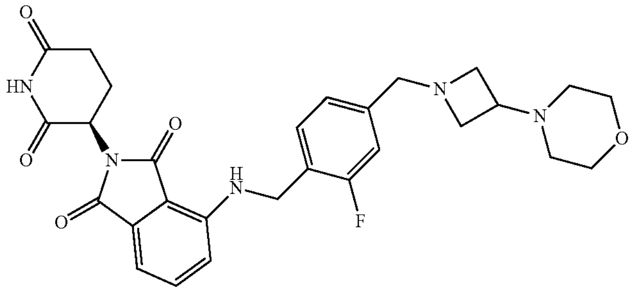 [SMILES: O=C1CC[C@@H](N2C(=O)c3cccc(NCc4ccc(CN5CC(N6CCOCC6)C5)cc4F)c3C2=O)C(=O)N1] | (R)-2-(2,6-dioxopiperidin-3-yl)-4-(2-fluoro-4-((3-morpholinoazetidin-1-yl)methyl)benzylamino)isoindoline-1,3-dione | 535.6 | D |
| 210 | 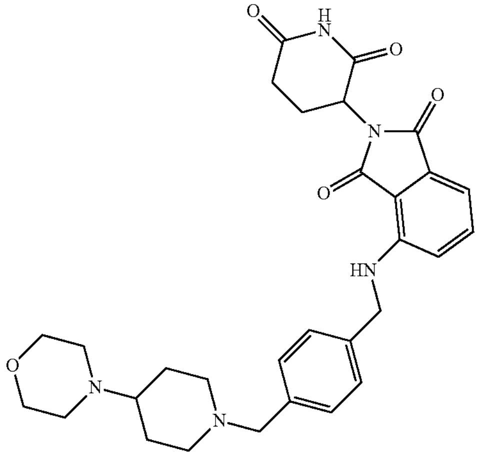 [SMILES: O=C1CCC(N2C(=O)c3cccc(NCc4ccc(CN5CCC(N6CCOCC6)CC5)cc4)c3C2=O)C(=O)N1] | 2-(2,6-dioxopiperidin-3-yl)-4-(4-((4-morpholinopiperidin-1-yl)methyl)benzylamino)isoindoline-1,3-dione | 546.6 | C |
| 211 | 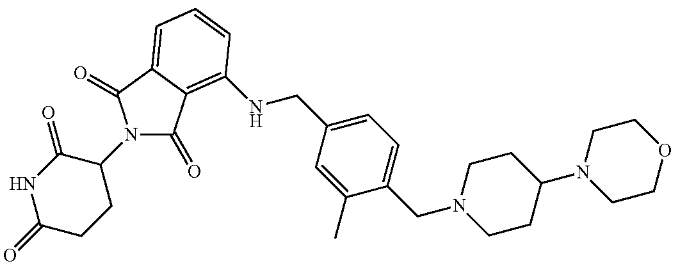 [SMILES: Cc1cc(CNc2cccc3c2C(=O)N(C2CCC(=O)NC2=O)C3=O)ccc1CN1CCC(N2CCOCC2)CC1] | 2-(2,6-dioxopiperidin-3-yl)-4-(3-methyl-4-((4-morpholinopiperidin-1-yl)methyl)benzylamino)isoindoline-1,3-dione | 560.4 | C |

TABLE 1-continued

| Cpd # | Cpd Structure | Cpd Name | Obs. MH+ | SU-DHL-4 Act |
|---|---|---|---|---|
| 212 | 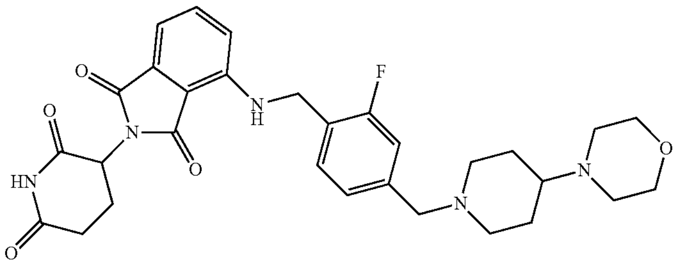 [SMILES: O=C1CCC(N2C(=O)c3cccc(NCc4ccc(CN5CCC(N6CCOCC6)CC5)cc4F)c3C2=O)C(=O)N1] | 2-(2,6-dioxopiperidin-4-yl)-4-(2-fluoro-4-((4-morpholinopiperidin-1-yl)methyl)benzylamino)isoindoline-1,3-dione | 564.5 | D |
| 213 | 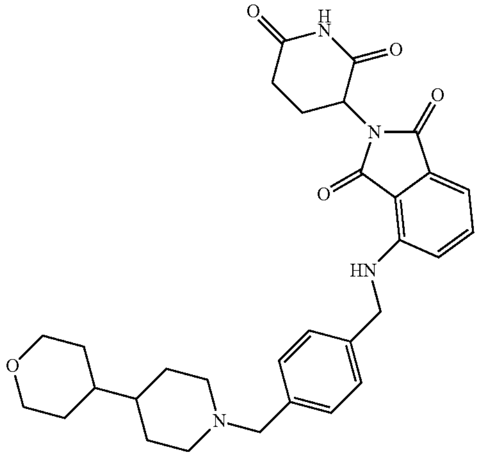 [SMILES: O=C1CCC(N2C(=O)c3cccc(NCc4ccc(CN5CCC(C6CCOCC6)CC5)cc4)c3C2=O)C(=O)N1] | 2-(2,6-dioxopiperidin-3-yl)-4-(4-((4-(tetrahydro-2H-pyran-4-yl)piperridin-1-yl)methyl)benzylamino)isoindoline-1,3-dione | 544.8 | D |
| 214 | 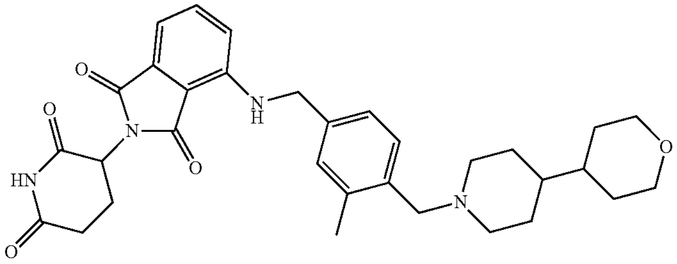 [SMILES: Cc1cc(CNc2cccc3c2C(=O)N(C2CCC(=O)NC2=O)C3=O)ccc1CN1CCC(C2CCOCC2)CC1] | 2-(2,6-dioxopiperidin-3-yl)-4-(3-methyl-4-((4-(tetrahydro-2H-pyran-4-yl)piperidin-1-yl)methyl)benzylamino)isoindoline-1,3-dione | 558.8 | D |
| 215 | 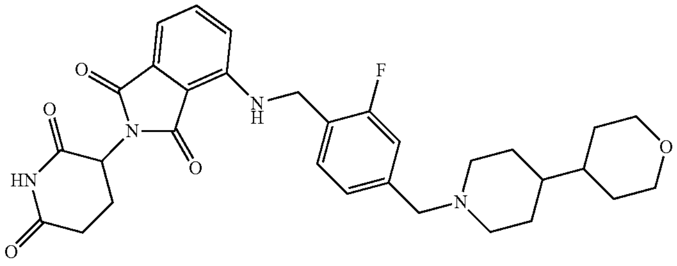 [SMILES: O=C1CCC(N2C(=O)c3cccc(NCc4ccc(CN5CCC(C6CCOCC6)CC5)cc4F)c3C2=O)C(=O)N1] | 2-(2,6-dioxopiperidin-3-yl)-4-(2-fluoro-4-((4-(tetrahydro-2H-pyran-4-yl)piperidin-1-yl)methyl)benzylamino)isoindoline-1,3-dione | 562.6 | D |

TABLE 1-continued

| Cpd # | Cpd Structure | Cpd Name | Obs. MH+ | SU-DHL-4 Act |
|---|---|---|---|---|
| 216 | 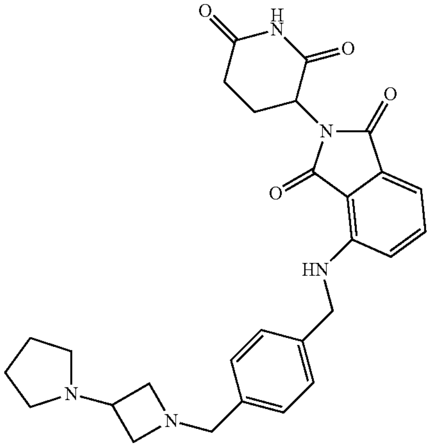 [SMILES: O=C1CCC(N2C(=O)c3cccc(NCc4ccc(CN5CC(N6CCCC6)C5)cc4)c3C2=O)C(=O)N1] | 2-(2,6-dioxopiperidin-3-yl)-4-(4-((3-(pyrrolidin-1-yl)azetidin-1-yl)methyl)benzylamino)isoindoline-1,3-dione | 501.7 | D |
| 217 | 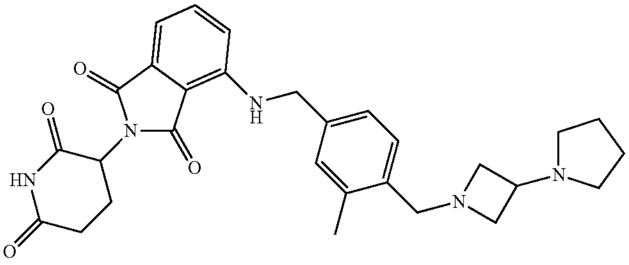 [SMILES: Cc1cc(CNc2cccc3c2C(=O)N(C2CCC(=O)NC2=O)C3=O)ccc1CN1CC(N2CCCC2)C1] | 2-(2,6-dioxopiperidin-3-yl)-4-(3-methyl-4-((3-(pyrrolidin-1-yl)azetidin-1-yl)methyl)benzylamino)isoindoline-1,3-dione | 515.8 | D |
| 218 | 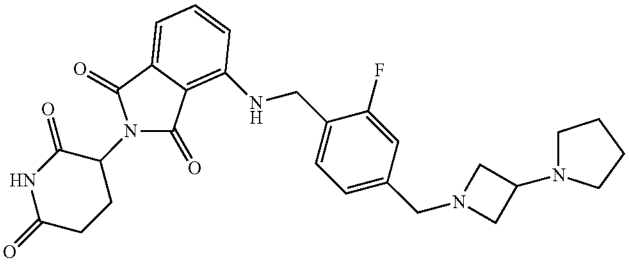 [SMILES: O=C1CCC(N2C(=O)c3cccc(NCc4ccc(CN5CC(N6CCCC6)C5)cc4F)c3C2=O)C(=O)N1] | 2-(2,6-dioxopiperidin-3-yl)-4-(2-fluoro-4-((3-(pyrrolidin-1-yl)azetidin-1-yl)methyl)benzylamino)isoindoline-1,3-dione | 519.7 | D |
| 219 | 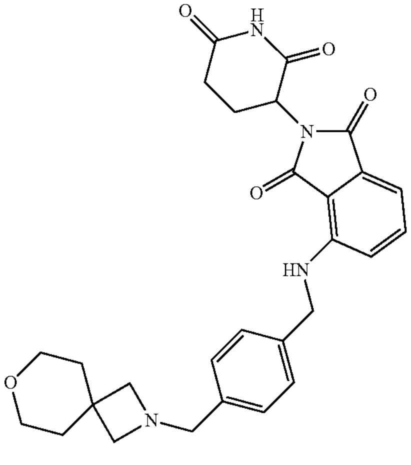 [SMILES: O=C1CCC(N2C(=O)c3cccc(NCc4ccc(CN5CC6(CCOCC6)C5)cc4)c3C2=O)C(=O)N1] | 4-(4-(7-oxa-2-azaspiro[3.5]nonan-2-ylmethyl)benzylamino)-2-(2,6-dioxopiperidin-3-yl)isoindoline-1,3-dione | 503.2 | D |

TABLE 1-continued

| Cpd # | Cpd Structure | Cpd Name | Obs. MH+ | SU-DHL-4 Act |
|---|---|---|---|---|
| 220 | 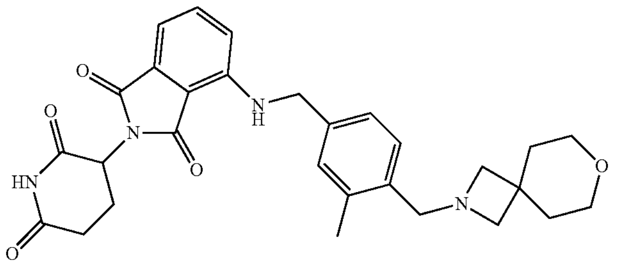 [SMILES: Cc1cc(CNc2cccc3c2C(=O)N(C2CCC(=O)NC2=O)C3=O)ccc1CN1CC2(CCOCC2)C1] | 4-(4-(7-oxa-2-azaspiro[3.5]nonan-2-ylmethyl)-3-methylbenzylamino)-2-(2,6-dioxopiperidin-3-yl)isoindoline-1,3-dione | 517.2 | D |
| 221 | 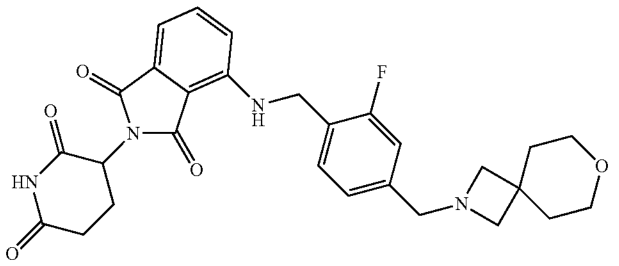 [SMILES: O=C1CCC(N2C(=O)c3cccc(NCc4ccc(CN5CC6(CCOCC6)C5)cc4F)c3C2=O)C(=O)N1] | 4-(4-(7-oxa-2-azaspiro[3.5]nonan-2-ylmethyl)-2-fluorobenzylamino)-2-(2,6-dioxopiperidin-3-yl)isoindoline-1,3-dione | 521.2 | D |
| 222 | 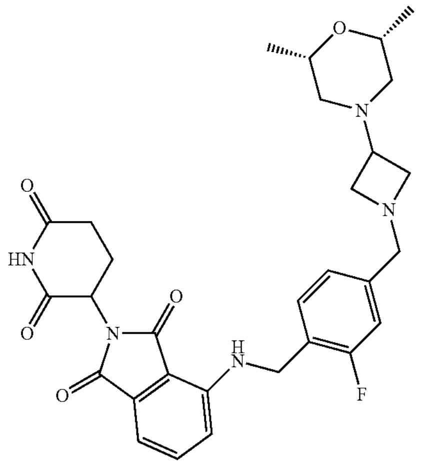 [SMILES: C[C@@H]1CN(C2CN(Cc3ccc(CNc4cccc5c4C(=O)N(C4CCC(=O)NC4=O)C5=O)c(F)c3)C2)C[C@H](C)O1] | 4-(4-((3-((2R,6S)-2,6-dimethylmorpholino)azetidin-1-yl)methyl)-2-fluorobenzylamino)-2-(2,6-dioxopiperidin-3-yl)isoindoline-1,3-dione | 564.2 | C |
| 223 | 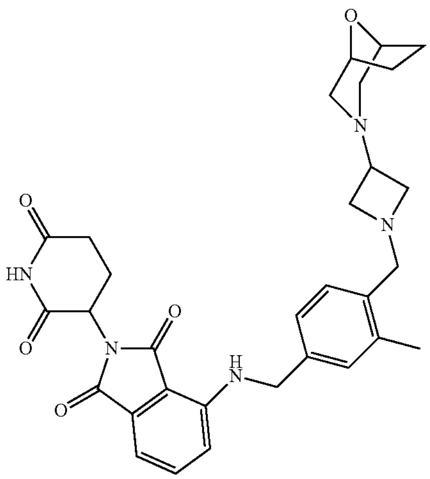 [SMILES: Cc1cc(CNc2cccc3c2C(=O)N(C2CCC(=O)NC2=O)C3=O)ccc1CN1CC(N2CC3CCC(C2)O3)C1] | 4-(4-((3-(8-oxa-3-azabicyclo[3.2.1]octan-3-yl)azetidin-1-yl)methyl)-3-methylbenzylamino)-2-(2,6-dioxopiperidin-3-yl)isoindoline-1,3-dione | 558.3 | D |

TABLE 1-continued

| Cpd # | Cpd Structure | Cpd Name | Obs. MH+ | SU-DHL-4 Act |
|---|---|---|---|---|
| 224 | 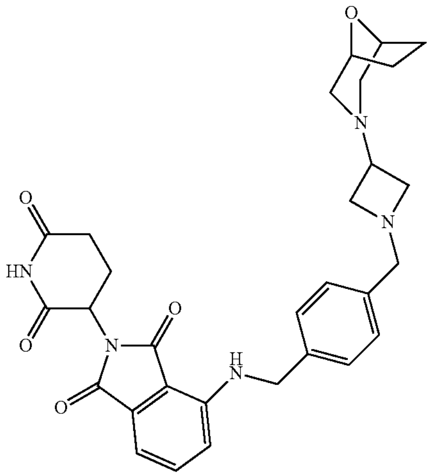 [SMILES: O=C1CCC(N2C(=O)c3cccc(NCc4ccc(CN5CC(N6CC7CCC(C6)O7)C5)cc4)c3C2=O)C(=O)N1] | 4-(4-((3-(8-oxa-3-azabicyclo[3.2.1]octan-3-yl)azetidin-1-yl)methyl)benzylamino)-2-(2,6-dioxopiperidin-3-yl)isoindoline-1,3-dione | 544.1 | D |
| 225 | 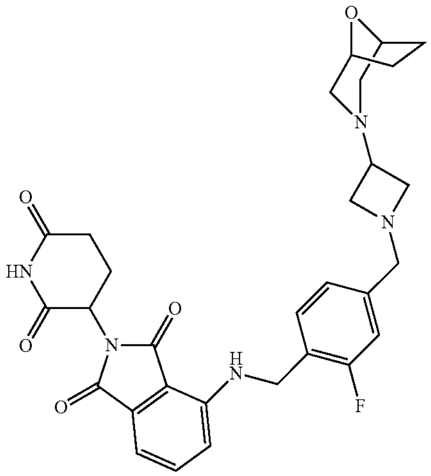 [SMILES: O=C1CCC(N2C(=O)c3cccc(NCc4ccc(CN5CC(N6CC7CCC(C6)O7)C5)cc4F)c3C2=O)C(=O)N1] | 4-(4-((3-(8-oxa-3-azabicyclo[3.2.1]octan-3-yl)azetidin-1-yl)methyl)-2-fluorobenzylamino)-2-(2,6-dioxopiperidin-3-yl)isoindoline-1,3-dione | 562.2 | D |
| 226 | 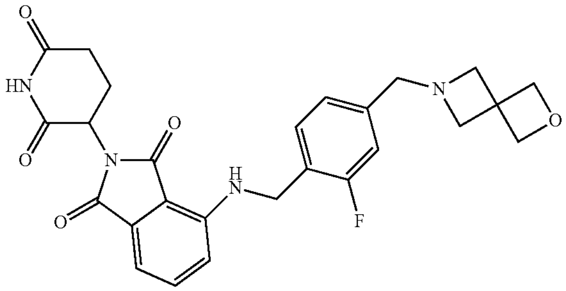 [SMILES: O=C1CCC(N2C(=O)c3cccc(NCc4ccc(CN5CC6(COC6)C5)cc4F)c3C2=O)C(=O)N1] | 4-(4-(2-oxa-6-azaspiro[3.3]heptan-6-ylmethyl)-2-fluorobenzylamino)-2-(2,6-dioxopiperidin-3-yl)isoindoline-1,3-dione | 493.2 | C |
| 227 | 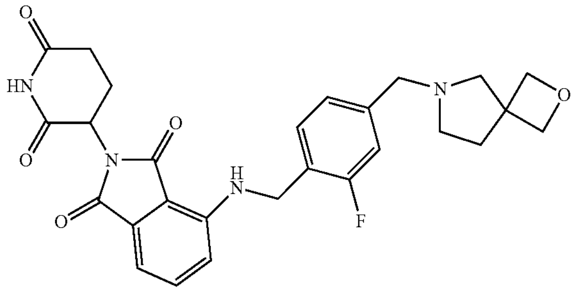 [SMILES: O=C1CCC(N2C(=O)c3cccc(NCc4ccc(CN5CCC6(COC6)C5)cc4F)c3C2=O)C(=O)N1] | 4-(4-(2-oxa-6-azaspiro[3.4]octan-6-ylmethyl)-2-fluorobenylamino)-2-(2,6-dioxopiperidin-3-yl)isoindoline-1,3-dione | 507.2 | D |

TABLE 1-continued

| Cpd # | Cpd Structure | Cpd Name | Obs. MH+ | SU-DHL-4 Act |
|---|---|---|---|---|
| 228 | 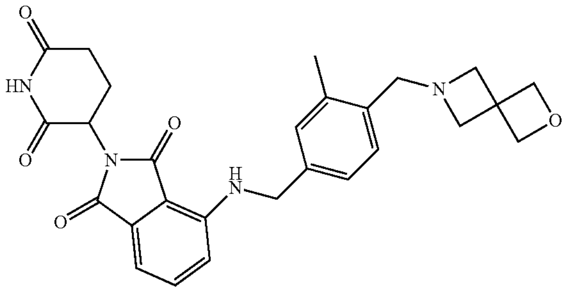 [SMILES: Cc1cc(CNc2cccc3c2C(=O)N(C2CCC(=O)NC2=O)C3=O)ccc1CN1CC2(COC2)C1] | 4-(4-(2-oxa-6-aaspiro[3.3]heptan-6-ylmethyl)-3-methylbenzylamino)-2-(2,6-dioxopiperidin-3-yl)isoindoline-1,3-dione | 489.2 | C |
| 229 | 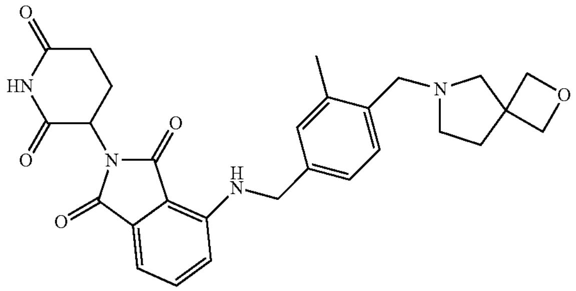 [SMILES: Cc1cc(CNc2cccc3c2C(=O)N(C2CCC(=O)NC2=O)C3=O)ccc1CN1CCC2(COC2)C1] | 4-(4-(2-oxa-6-azaspiro[3.4]octan-6-ylmethyl)-3-methylbenzylamino)-2-(2,6-dioxopiperidin-3-yl)isoindoline-1,3-dione | 503.2 | B |
| 230 | 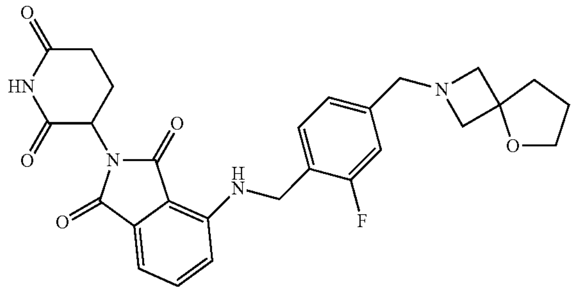 [SMILES: O=C1CCC(N2C(=O)c3cccc(NCc4ccc(CN5CC6(CCCO6)C5)cc4F)c3C2=O)C(=O)N1] | 4-(4-(5-oxa-2-azaspiro[3.4]octan-2-ylmethyl)-2-fluorobenzylamino)-2-(2,6-dioxopiperidin-3-yl)isoindoline-1,3-dione | 507.2 | D |
| 231 | 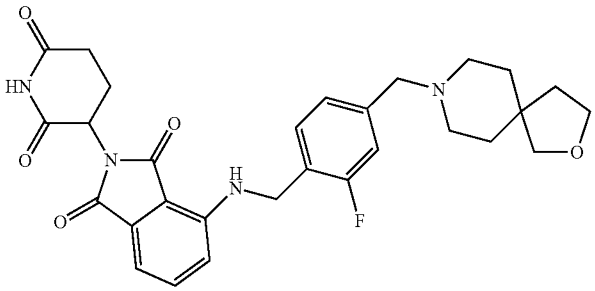 [SMILES: O=C1CCC(N2C(=O)c3cccc(NCc4ccc(CN5CCC6(CCOC6)CC5)cc4F)c3C2=O)C(=O)N1] | 4-(4-(2-oxa-8-azaspiro[4.5]decan-8-ylmethyl)-2-fluorobenzylamino)-2-(2,6-dioxopiperidin-3-yl)isoindoline-1,3-dione | 535.2 | D |
| 232 | 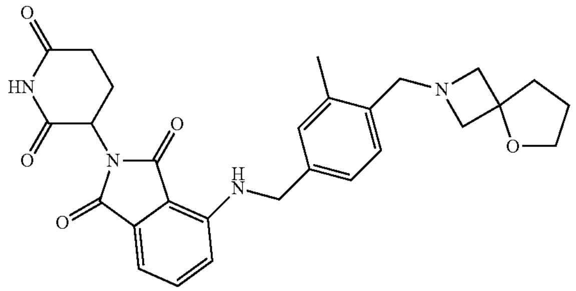 [SMILES: Cc1cc(CNc2cccc3c2C(=O)N(C2CCC(=O)NC2=O)C3=O)ccc1CN1CC2(CCCO2)C1] | 4-(4-(5-oxa-2-azaspiro[3.4]octan-2-ylmethyl)-3-methylbenzylamino)-2-(2,6-dioxopiperidin-3-yl)isoindoline-1,3-dione | 503.2 | D |

TABLE 1-continued

| Cpd # | Cpd Structure | Cpd Name | Obs. MH+ | SU-DHL-4 Act |
|---|---|---|---|---|
| 233 | 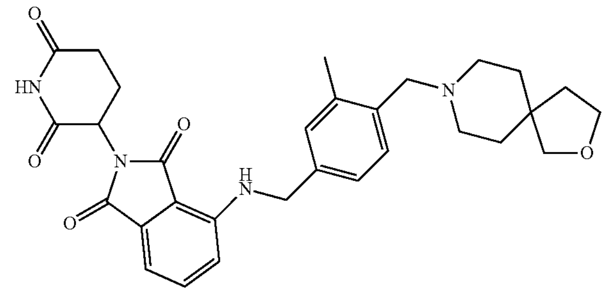 [SMILES: Cc1cc(CNc2cccc3c2C(=O)N(C2CCC(=O)NC2=O)C3=O)ccc1CN1CCC2(CCOC2)CC1] | 4-(4-(2-oxa-8-azaspiro[4.5]decan-8-ylmethyl)-3-methylbenzylamino)-2-(2,6-dioxopiperidin-3-yl)isoindoline-1,3-dione | 531.2 | D |
| 234 | 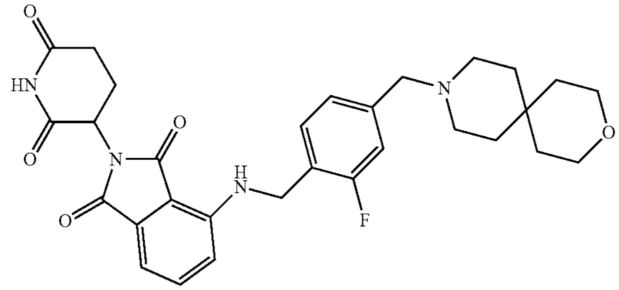 [SMILES: O=C1CCC(N2C(=O)c3cccc(NCc4ccc(CN5CCC6(CCOCC6)CC5)cc4F)c3C2=O)C(=O)N1] | 4-(4-(3-oxa-9-azaspiro[5.5]undecan-9-ylmethyl)-2-fluorobenzylamino)-2-(2,6-dioxopiperidin-3-yl)isoindoline-1,3-dione | 549.2 | D |
| 235 | 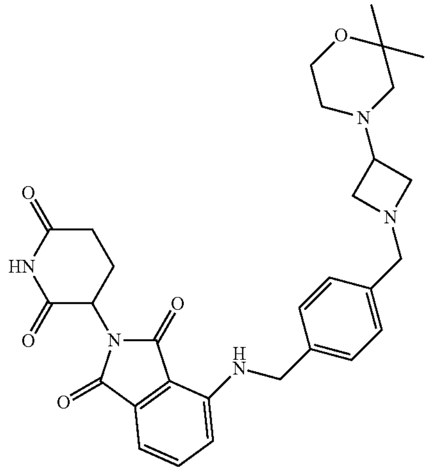 [SMILES: CC1(C)CN(C2CN(Cc3ccc(CNc4cccc5c4C(=O)N(C4CCC(=O)NC4=O)C5=O)cc3)C2)CCO1] | 4-(4-((3-(2,2-dimethylmorpholino)azetidin-1-yl)methyl)benzylamino)-2-(2,6-dioxopiperidin-3-yl)isoindoline-1,3-dione | 546.2 | B |
| 236 | 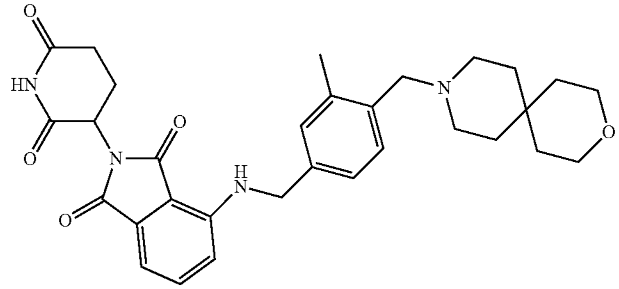 [SMILES: Cc1cc(CNc2cccc3c2C(=O)N(C2CCC(=O)NC2=O)C3=O)ccc1CN1CCC2(CCOCC2)CC1] | 4-(4-(3-oxa-9-azaspiro[5.5]undecan-9-ylmethyl)-3-methylbenzylamino)-2-(2,6-dioxopiperidin-3-yl)isoindoline-1,3-dione | 545.2 | D |

TABLE 1-continued
| Cpd # | Cpd Structure | Cpd Name | Obs. MH+ | SU-DHL-4 Act |
|---|---|---|---|---|
| 237 | 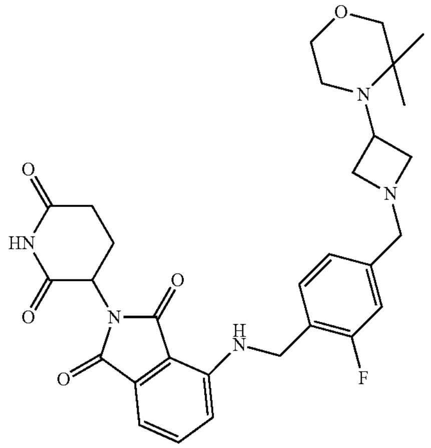 [SMILES: CC1(C)COCCN1C1CN(Cc2ccc(CNc3cccc4c3C(=O)N(C3CCC(=O)NC3=O)C4=O)c(F)c2)C1] | 4-(4-((3-(3,3-dimethylmorpholino)azetidin-1-yl)methyl)-2-fluorobenzylamino)-2-(2,6-dioxopiperidin-3-yl)isoindoline-1,3-dione | 564.2 | D |
| 238 | 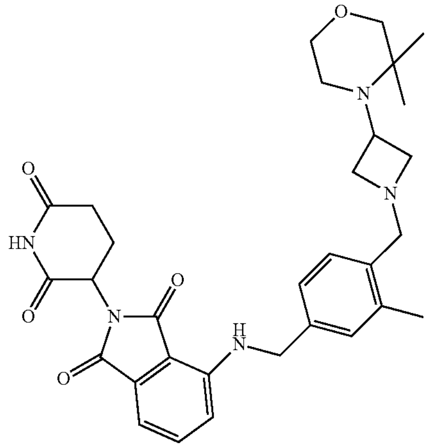 [SMILES: Cc1cc(CNc2cccc3c2C(=O)N(C2CCC(=O)NC2=O)C3=O)ccc1CN1CC(N2CCOCC2(C)C)C1] | 4-(4-((3-(3,3-dimethylmorpholino)azetidin-1-yl)methyl)-3-methylbenzylamino)-2-(2,6-dioxopiperidin-3-yl)isoindoline-1,3-dione | 560.1 | D |
| 239 | 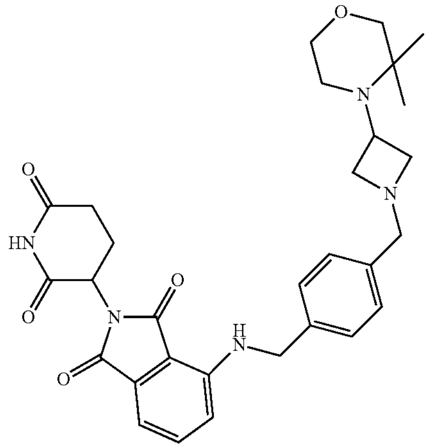 [SMILES: CC1(C)COCCN1C1CN(Cc2ccc(CNc3cccc4c3C(=O)N(C3CCC(=O)NC3=O)C4=O)cc2)C1] | 4-(4-((3-(3,3-dimethylmorpholino)azetidin-1-yl)methyl)benzylamino)-2-(2,6-dioxopiperidin-3-yl)isoindoline-1,3-dione | 546.1 | B |

TABLE 1-continued

| Cpd # | Cpd Structure | Cpd Name | Obs. MH+ | SU-DHL-4 Act |
|---|---|---|---|---|
| 240 | 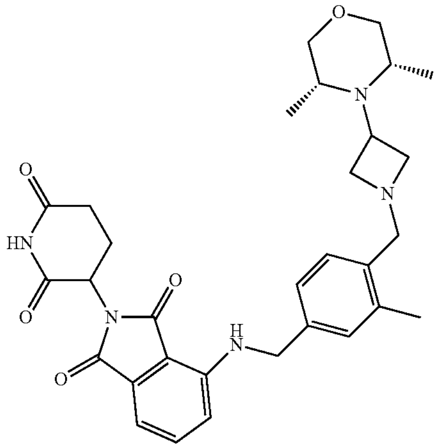 [SMILES: Cc1cc(CNc2cccc3c2C(=O)N(C2CCC(=O)NC2=O)C3=O)ccc1CN1CC(N2[C@H](C)COC[C@@H]2C)C1] | 4-(4-((3-((3S,5R)-3,5-dimethylmorpholino)azetidin-1-yl)methyl)-3-methylbenzylamino)-2-(2,6-dioxopiperidin-3-yl)isoindolinne-1,3-dione | 560.1 | C |
| 241 | 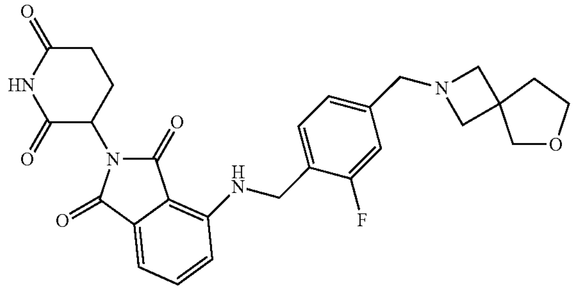 [SMILES: O=C1CCC(N2C(=O)c3cccc(NCc4ccc(CN5CC6(CCOC6)C5)cc4F)c3C2=O)C(=O)N1] | 4-(4-(6-oxa-2-azaspiro[3.4]octan-2-ylmethyl)-2-fluorobenzylamino)-2-(2,6-dioxopiperidin-3-yl)isoindoline-1,3-dione | 507.2 | D |
| 242 | 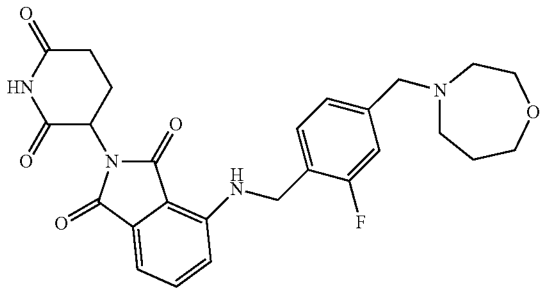 [SMILES: O=C1CCC(N2C(=O)c3cccc(NCc4ccc(CN5CCCOCC5)cc4F)c3C2=O)C(=O)N1] | 4-(4-((1,4-oxazepan-4-yl)methyl)-2-fluorobenzylamino)-2-(2,6-dioxopiperidin-3-yl)isoindoline-1,3-dione | 495.2 | C |
| 243 | 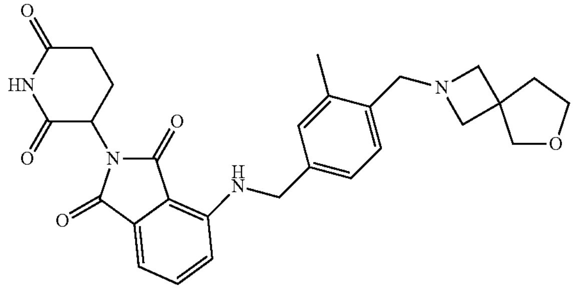 [SMILES: Cc1cc(CNc2cccc3c2C(=O)N(C2CCC(=O)NC2=O)C3=O)ccc1CN1CC2(CCOC2)C1] | 4-(4-(6-oxa-2-azaspiro[3.4]octan-2-ylmethyl)-3-methylbenzylamino)-2-(2,6-dioxopiperidin-3-yl)isoindoine-1,3-dione | 503.2 | D |

TABLE 1-continued
| Cpd # | Cpd Structure | Cpd Name | Obs. MH+ | SU-DHL-4 Act |
|---|---|---|---|---|
| 244 | 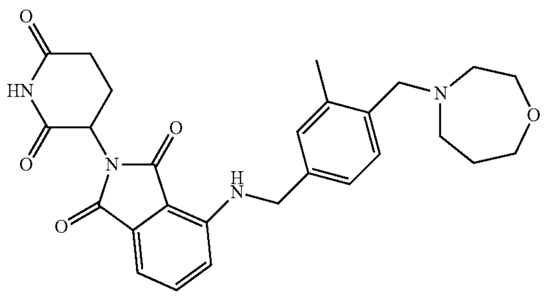 [SMILES: Cc1cc(CNc2cccc3c2C(=O)N(C2CCC(=O)NC2=O)C3=O)ccc1CN1CCCOCC1] | 4-(4-((1,4-oxazepan-4-yl)methyl)-3-methylbenzylamino)-2-(2,6-dioxopiperidin-3-yl)isoindoline-1,3-dione | 491.2 | B |
| 245 | 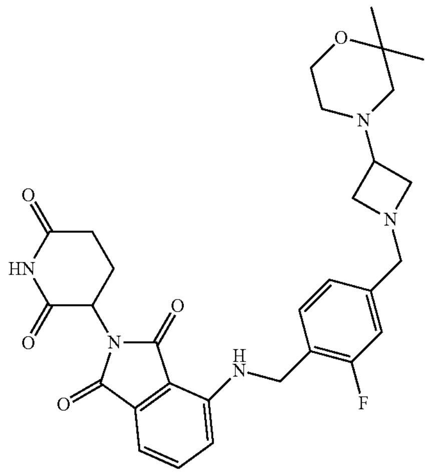 [SMILES: CC1(C)CN(C2CN(Cc3ccc(CNc4cccc5c4C(=O)N(C4CCC(=O)NC4=O)C5=O)c(F)c3)C2)CCO1] | 4-(4-((3-(2,2-dimethylmorpholino)azetidin-1-yl)methyl)-2-fluorobenzylamino)-2-(2,6-dioxopiperidin-3-yl)isoindoline-1,3-dione | 564.3 | D |
| 246 | 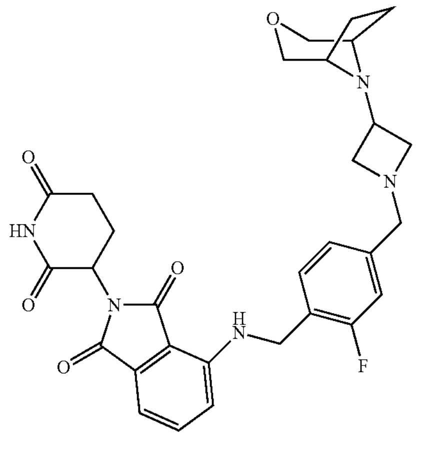 [SMILES: O=C1CCC(N2C(=O)c3cccc(NCc4ccc(CN5CC(N6C7CCC6COC7)C5)cc4F)c3C2=O)C(=O)N1] | 4-(4-((3-(3-oxa-8-azabicyclo[3.2.1]octan-8-yl)azetidin-1-yl)methyl)-2-fluorobenzylamino)-2-(2,6-dioxopiperidin-3-yl)isoindoline-1,3-dione | 562.2 | D |

TABLE 1-continued

| Cpd # | Cpd Structure | Cpd Name | Obs. MH+ | SU-DHL-4 Act |
|---|---|---|---|---|
| 247 | 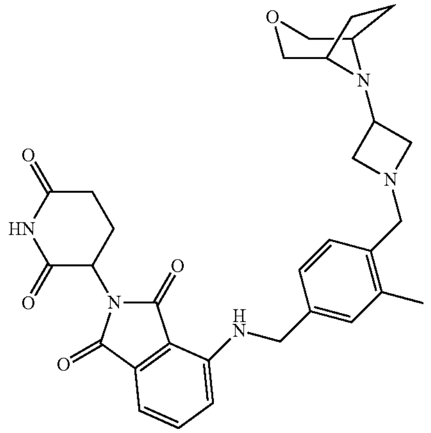 [SMILES: Cc1cc(CNc2cccc3c2C(=O)N(C2CCC(=O)NC2=O)C3=O)ccc1CN1CC(N2C3CCC2COC3)C1] | 4-(4-((3-(3-oxa-8-azabicyclo[3.2.1]octan-8-yl)azetidin-1-yl)methyl)-3-methylbenzylamino)-2-(2,6-dioxopiperidin-3-yl)isoindoline-1,3-dione | 558.3 | D |
| 248 | 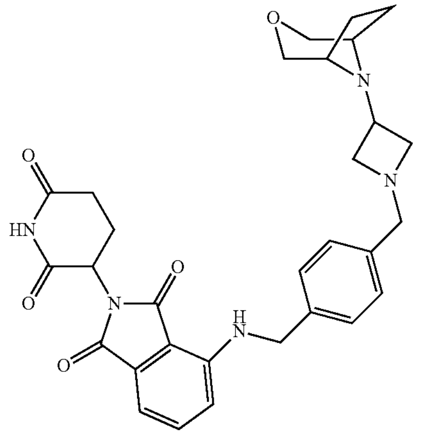 [SMILES: O=C1CCC(N2C(=O)c3cccc(NCc4ccc(CN5CC(N6C7CCC6COC7)C5)cc4)c3C2=O)C(=O)N1] | 4-(4-((3-(3-oxa-8-azabicyclo[3.2.1]octan-8-yl)azetidin-1-yl)methyl)benzylamino)-2-(2,6-dioxopiperidin-3-yl)isoindoline-1,3-dione | 544.2 | D |
| 249 | 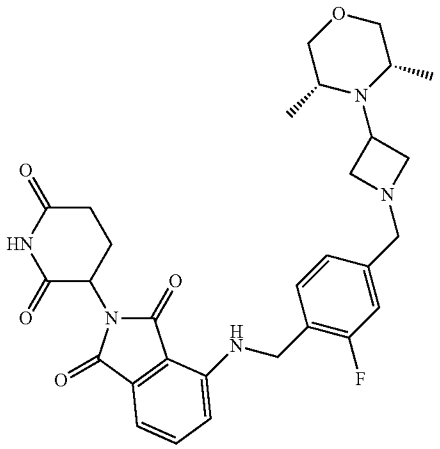 [SMILES: C[C@@H]1COC[C@H](C)N1C1CN(Cc2ccc(CNc3cccc4c3C(=O)N(C3CCC(=O)NC3=O)C4=O)c(F)c2)C1] | 4-(4-((3-((3S,5R)-3,5-dimethylmorpholino)azetidin-1-yl)methyl)-2-fluorobenzylamino)-2-(2,6-dioxopiperidin-3-yl)isoindoline-1,3-dione | 564.3 | D |

A number of references have been cited, the disclosures of which are incorporated herein by reference in their entirety.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A compound of formula (I):

(I)

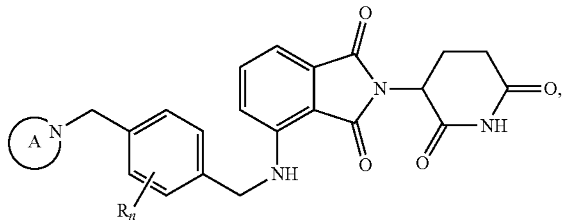

or a pharmaceutically acceptable salt, tautomer, or stereoisomer thereof, wherein:

Ring A is a piperazinyl optionally substituted with one or more substituents independently selected from halogen, $C_{1-6}$ alkyl, $OR^1$, $CON(R^2)_2$, $SO_2(C_{1-4}$ alkyl), $N(R^2)SO_2(C_{1-4}$ alkyl), —($C_{0-3}$ alkyl)-($C_{3-7}$ cycloalkyl), (non-aromatic heterocyclyl), aryl, heteroaryl, O-aryl, O-heteroaryl, and C(O)aryl; wherein the alkyl, cycloalkyl, heterocyclyl, aryl, or heteroaryl are optionally substituted with one or more substituents independently selected from halogen, alkyl optionally substituted with one or more of halogen, oxo, amido, and cyano; wherein $R^1$ is H, $C_{1-6}$ alkyl optionally substituted with one or more of halogen, or —($C_{0-3}$ alkyl)-($C_{3-7}$ cycloalkyl); and each $R^2$ is independently H, or $C_{1-6}$ alkyl;

each R is independently $C_{1-3}$ alkyl optionally substituted with one or more of halogen, or halogen; and n is 0, 1, 2, 3 or 4.

2. The compound of claim 1, wherein the compound is a compound of formula (II):

(II)

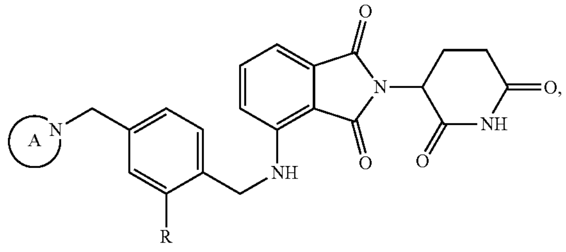

or a pharmaceutically acceptable salt, tautomer, or stereoisomer thereof.

3. The compound of claim 1, wherein the compound is a compound of formula (III):

(III)

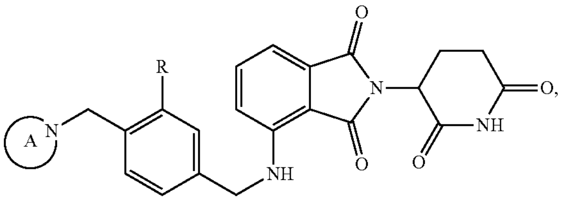

or a pharmaceutically acceptable salt, tautomer, or stereoisomer thereof.

4. The compound of claim 1, wherein the compound is a compound of formula (IV):

(IV)

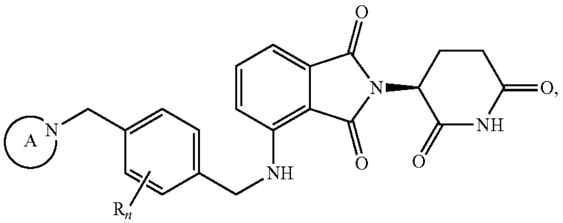

or a pharmaceutically acceptable salt or tautomer thereof.

5. The compound of claim 4, wherein the compound is a compound of formula (V):

(V)

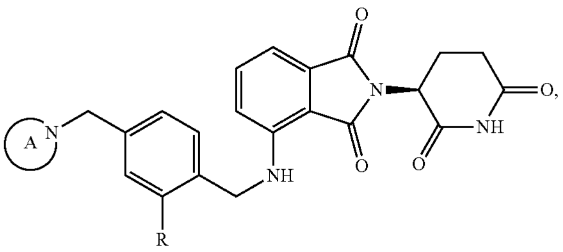

or a pharmaceutically acceptable salt or tautomer thereof.

6. The compound of claim 4, wherein the compound is a compound of formula (VI):

(VI)

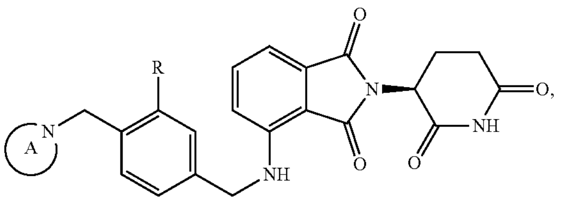

or a pharmaceutically acceptable salt or tautomer thereof.

7. The compound of claim 1, wherein the compound is a compound of formula (VII):

(VII)

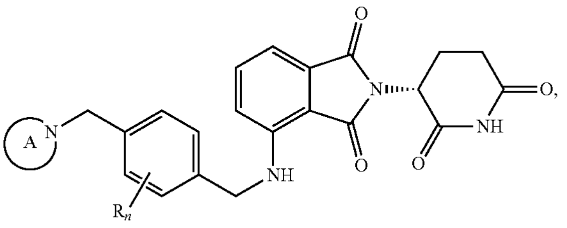

or a pharmaceutically acceptable salt or tautomer thereof.

8. The compound of claim 7, wherein the compound is a compound of formula (VIII):

(VIII)

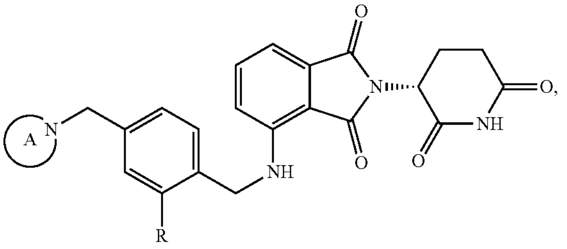

or a pharmaceutically acceptable salt or tautomer thereof.

9. The compound of claim 7, wherein the compound is a compound of formula (IX):

(IX)

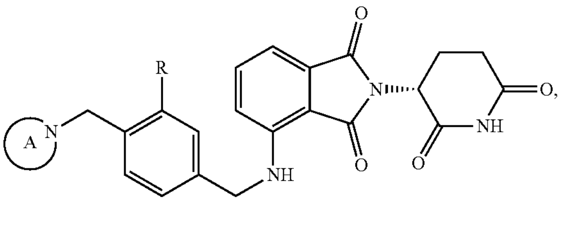

or a pharmaceutically acceptable salt or tautomer thereof.

10. The compound of claim 1, wherein Ring A is

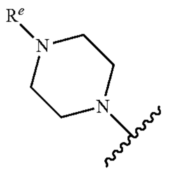

wherein $R^e$ is $C_{1-6}$ alkyl, $SO_2(C_{1-4}$ alkyl), —($C_{0-3}$ alkyl)-($C_{3-7}$ cycloalkyl), aryl, heteroaryl or CO-aryl; wherein the alkyl, cycloalkyl, aryl, or heteroaryl are optionally substituted with one or more substituents independently selected from halogen, alkyl optionally substituted with one or more of halogen, oxo, amido, and cyano.

11. The compound of claim 1, wherein Ring A is substituted with one or more substituents independently selected from halogen, $C_{1-6}$ alkyl, $OR^1$, $CON(R^2)_2$, $SO_2(C_{1-4}$ alkyl), $N(R^2)SO_2(C_{1-4}$ alkyl), —($C_{0-3}$ alkyl)-($C_{3-7}$ cycloalkyl), (non-aromatic heterocyclyl), aryl, heteroaryl, O-aryl, O-heteroaryl, and C(O)aryl; wherein the alkyl, cycloalkyl, heterocyclyl, aryl, or heteroaryl are optionally substituted with one or more substituents independently selected from halogen, alkyl optionally substituted with one or more of halogen, oxo, amido, and cyano; wherein $R^1$ is H, $C_{1-6}$ alkyl optionally substituted with one or more of halogen, or —($C_{0-3}$ alkyl)-($C_{3-7}$ cycloalkyl); and each $R^2$ is independently H, or $C_{1-6}$ alkyl.

12. The compound of claim 1, wherein Ring A is substituted with one or more substituents independently selected from F, Cl, Br, $CH_3$, $CH_2CH_3$, n-propyl, isopropyl, n-butyl, sec-butyl, isobutyl, t-butyl, n-pentyl, isopentyl, $CH_2F$, $CHF_2$, $CF_3$, $CH_2CH_2F$, $CH_2CHF_2$, $CH_2CF_3$, $CH(CH_3)CF_3$, $CH_2CH_2CF_3$, OH, $OCH_3$, $OCH_2CH_3$, O-isopropyl, O-n-propyl, O-n-butyl, O-isobutyl, O-t-butyl, $OCF_3$, O-cyclopropyl, O-cyclobutyl, $OCH_2$-cyclopropyl, $OCH_2$-cyclobutyl, $CONH_2$, $CONH(CH_3)$, $CON(CH_3)_2$, $SO_2CH_3$, $SO_2CH_2CH_3$, $SO_2$-isopropyl, cyclopropyl, cyclobutyl, $CH_2$-cyclopropyl, $CH_2$-cyclobutyl; (non-aromatic heterocyclyl) selected from azetidyl, pyrrolidyl, pyrrolidonyl, isothiazolidyl, isothiazolidine 1,1-dioxidyl, piperidyl, piperazinyl, morpholinyl, 3-oxa-8-azabicyclo[3.2.1]octyl, or 8-oxa-3-azabicyclo[3.2.1]octyl, wherein the heterocyclyl is optionally substituted with one or more substituents independently selected from $CH_3$, $CH_2CH_3$, or $CF_3$; phenyl, 0-phenyl or C(O)-phenyl, wherein the phenyl is optionally substituted with one or more substituents independently selected from F, Cl, $CH_3$, CN, or $CONH_2$; heteroaryl selected from pyrazolyl, imidazolyl, oxazolyl, isoxazolyl, oxadiazolyl, thiadiazolyl, pyridyl, pyrazinyl, pyridazinyl, pyrimidyl, or benzoisoxazolyl, wherein the heteroaryl is optionally substituted with one or more substituents independently selected from F, Cl, $CF_3$, CN, $CONH_2$, $CONH(CH_3)$ or $CON(CH_3)_2$; O-pyridyl, and O-pyrimidyl.

13. The compound of claim 1, wherein Ring A is substituted with one or more substituents independently selected from F, $CH_3$, $CH_2CH_3$, isopropyl, t-butyl, $CH_2F$, $CF_3$, $CH(CH_3)CF_3$, OH, $OCH_3$, $OCH_2CH_3$, O-isopropyl, O-n-propyl, O-isobutyl, O-t-butyl, $OCF_3$, O-cyclobutyl, $OCH_2$-cyclopropyl, $CON(CH_3)_2$, $SO_2CH_2CH_3$, $SO_2$-isopropyl, cyclopropyl, cyclobutyl, $CH_2$-cyclopropyl; (non-aromatic heterocyclyl) selected from pyrrolidyl, pyrrolidonyl, isothiazolidine 1,1-dioxidyl, morpholinyl, 3-oxa-8-azabicyclo[3.2.1]octyl, or 8-oxa-3-azabicyclo[3.2.1]octyl, wherein the heterocyclyl is optionally substituted with one or more $CH_3$; phenyl, O-phenyl or C(O)-phenyl, wherein the phenyl is optionally substituted with one or more substituents independently selected from F, Cl, $CH_3$, CN, or $CONH_2$; heteroaryl selected from pyrazolyl, oxazolyl, oxadiazolyl, thiadiazolyl, pyridyl, pyrazinyl, pyrimidyl or benzoisoxazolyl, wherein the heteroaryl is optionally substituted with one or more substituents independently selected from F, Cl, $CF_3$, CN, $CONH_2$, $CON(CH_3)_2$; O-pyridyl, and O-pyrimidyl.

14. The compound of claim 1, wherein Ring A is piperazinyl, substituted with one or more substituents independently selected from $C_{1-6}$ alkyl, $SO_2(C_{1-4}$ alkyl), —($C_{0-3}$ alkyl)-($C_{3-7}$ cycloalkyl), aryl, heteroaryl and CO-aryl; wherein the alkyl, cycloalkyl, aryl, or heteroaryl are optionally substituted with one or more substituents independently selected from halogen, alkyl optionally substituted with one or more of halogen, oxo, amido, and cyano.

15. The compound of claim 1, wherein Ring A is piperazinyl, substituted with one or more substituents independently selected from $CH_3$, $CH_2CH_3$, n-propyl, isopropyl, n-butyl, sec-butyl, isobutyl, t-butyl, $CF_3$, $CH_2CF_3$, $CH(CH_3)CF_3$, $SO_2CH_3$, $SO_2CH_2CH_3$, $SO_2$-isopropyl, cyclopropyl, cyclobutyl, ($CH_2$)cyclopropyl, ($CH_2$)cyclobutyl, phenyl, optionally substituted with one or more Cl, F, CN, $CH_3$, $CONH_2$; pyrazolyl, optionally substituted with $CH_3$ or $CH_2CH_3$; oxazolyl, optionally substituted with $CH_3$ or $CH_2CH_3$; oxadiazolyl, optionally substituted with $CH_3$ or $CH_2CH_3$; thiadiazolyl, optionally substituted with $CH_3$, $CH_2CH_3$, or $CF_3$; 2-pyridyl, 3-pyridyl, or 4-pyridyl, each optionally substituted with Cl, F, $CF_3$, CN, $CONH_2$, $CONH(CH_3)$ or $CON(CH_3)_2$; pyrazinyl, optionally substituted with $CH_3$ or $CH_2CH_3$; pyrimidyl, optionally substituted with $OCH_3$; benzoisoxazolyl; and CO(phenyl), wherein the phenyl is optionally fluorinated.

16. The compound of claim 1, wherein Ring A is piperazinyl, substituted with one or more substituents independently selected from $CH_3$, isopropyl, t-butyl, $CH(CH_3)CF_3$, $SO_2CH_2CH_3$, $SO_2$-isopropyl, cyclopropyl, cyclobutyl, ($CH_2$)cyclopropyl, phenyl, optionally substituted with one or more Cl, F, CN, $CH_3$, $CONH_2$; pyrazolyl, optionally substituted with $CH_3$; oxazolyl, optionally substituted with $CH_3$; oxadiazolyl, optionally substituted with $CH_2CH_3$; thiadiazolyl, optionally substituted with $CH_3$, or $CH_2CH_3$; 2-pyridyl, optionally substituted with Cl, F, $CF_3$, CN, or $CONH_2$; 3-pyridyl, optionally substituted with $CF_3$, CN, $CONH_2$, or $CON(CH_3)_2$; 4-pyridyl, optionally substituted with $CONH_2$; pyrazinyl, optionally substituted with $CH_3$; pyrimidyl, optionally substituted with $OCH_3$; benzoisoxazolyl; and CO(phenyl), wherein the phenyl is optionally fluorinated.

17. The compound of claim 1, wherein R is F.

18. The compound of claim 1, wherein R is $CH_3$.

19. The compound of claim 1, wherein n is 1.

20. A compound, which is:

Compound 1

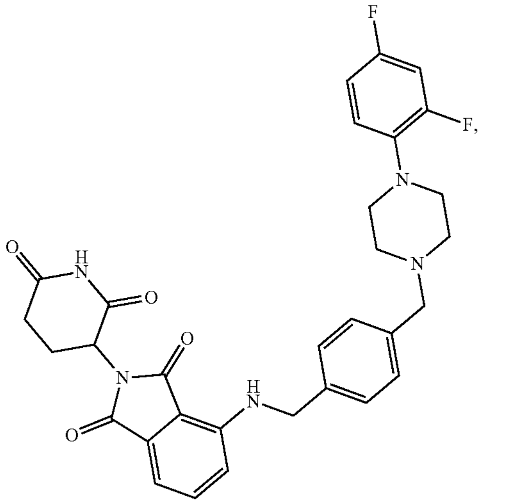
,

Compound 2

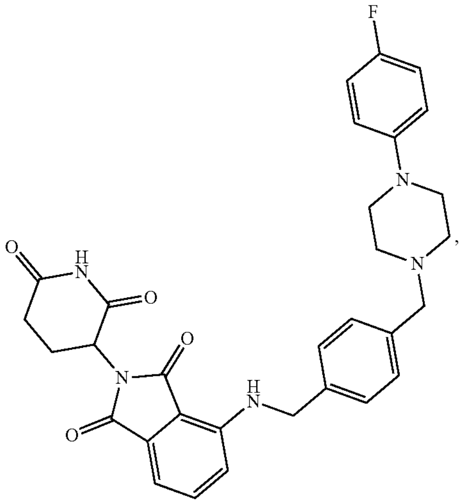
,

Compound 3

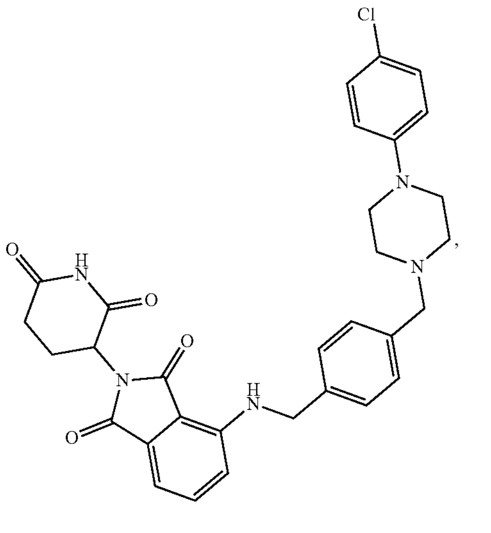
,

Compound 4

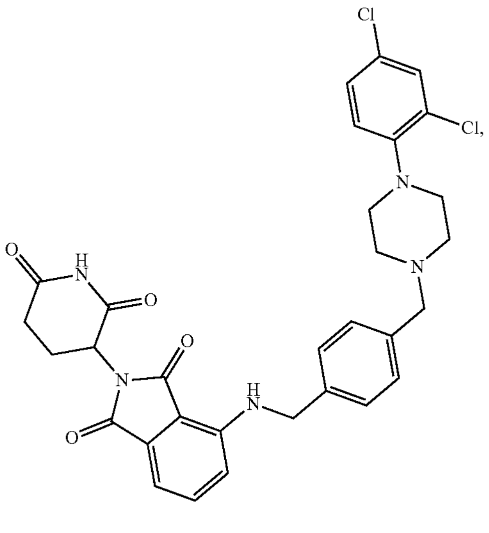
,

-continued
Compound 8
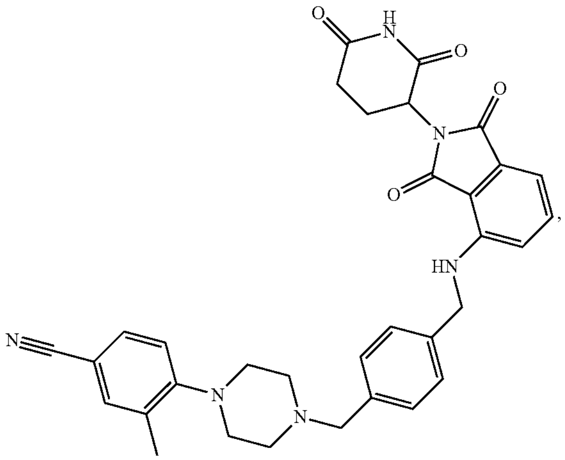
Compound 9
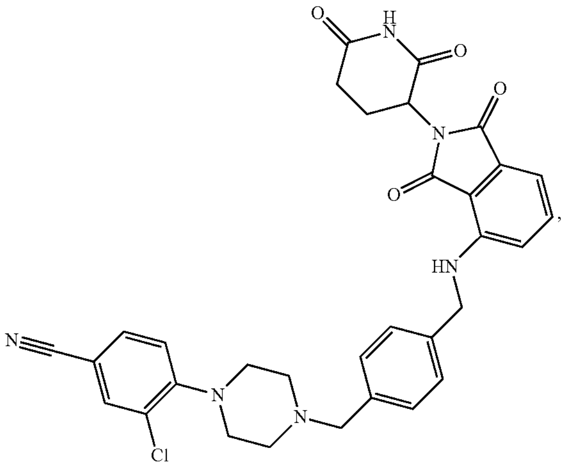
Compound 10
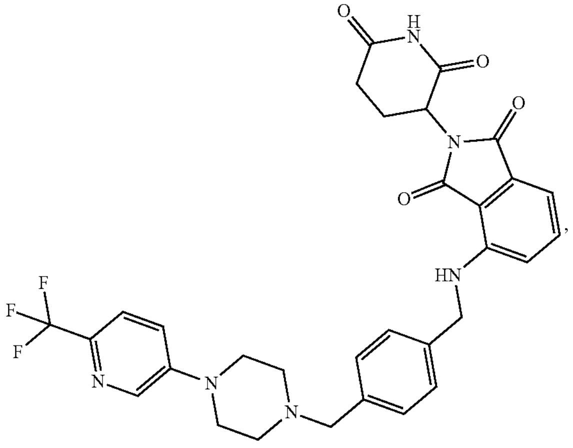
Compound 11
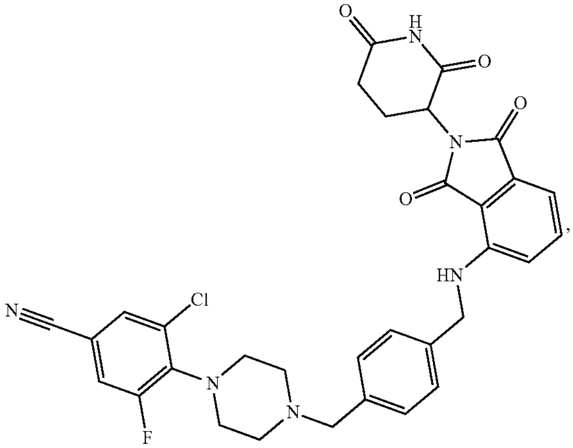
Compound 12
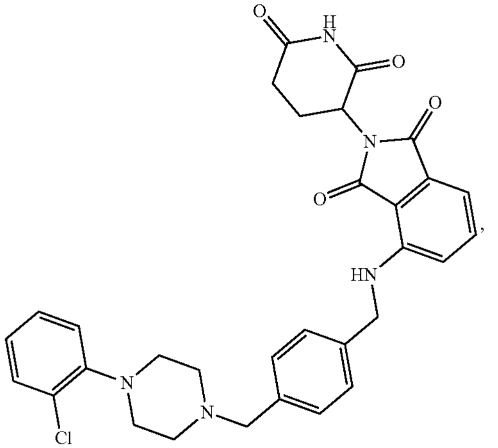
Compound 17
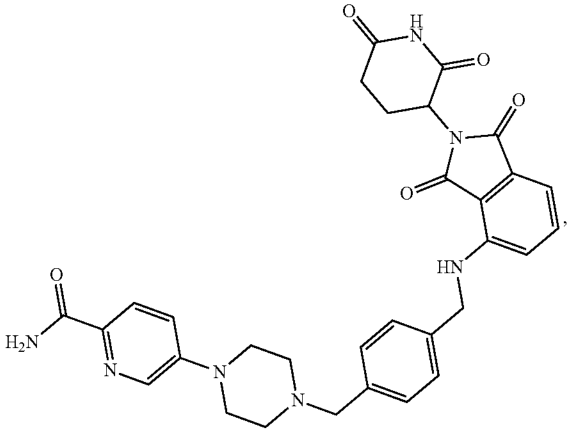

-continued
Compound 18
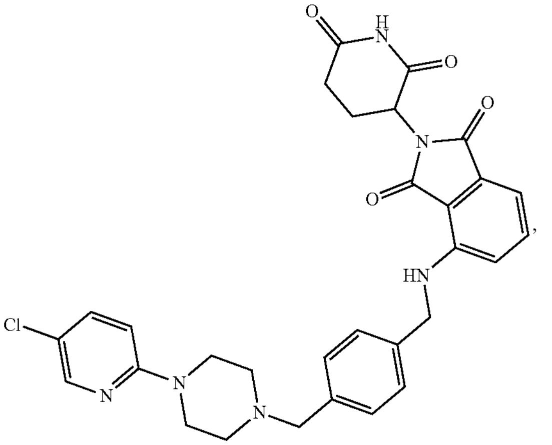
Compound 27
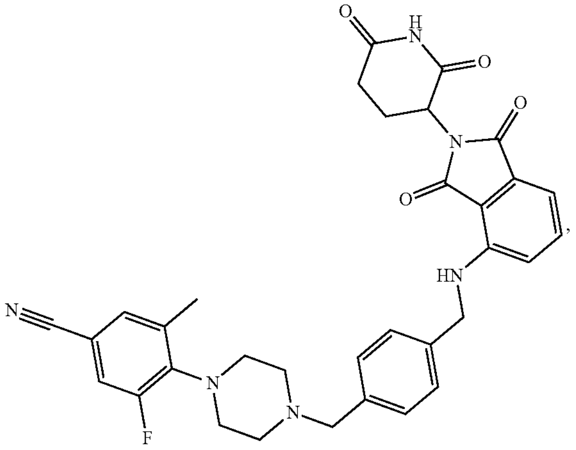
Compound 28
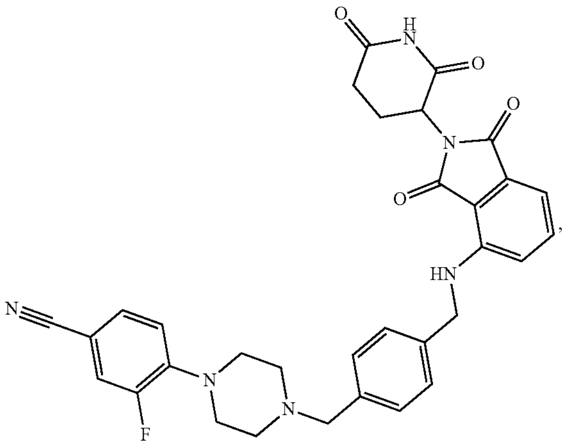
Compound 29
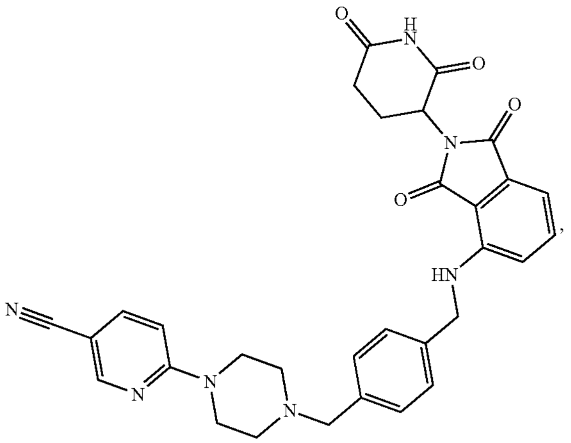
Compound 30
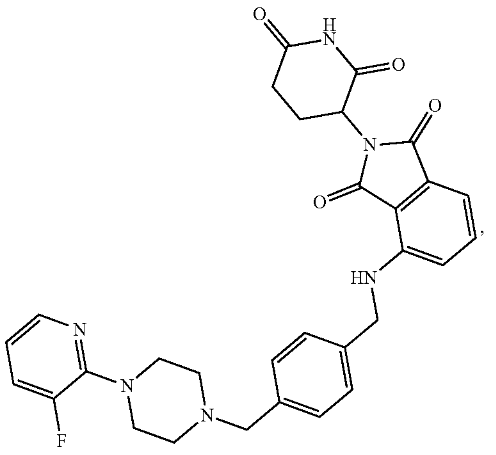
Compound 32
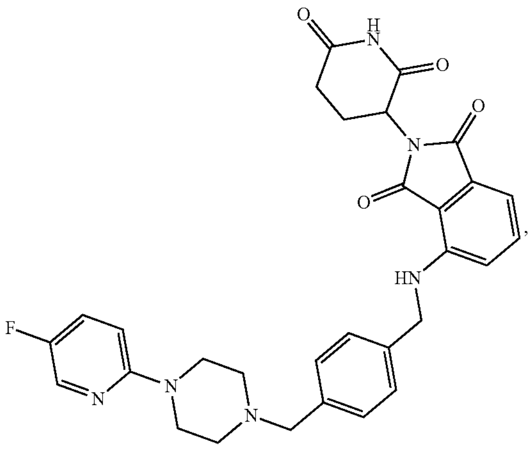

-continued
Compound 33
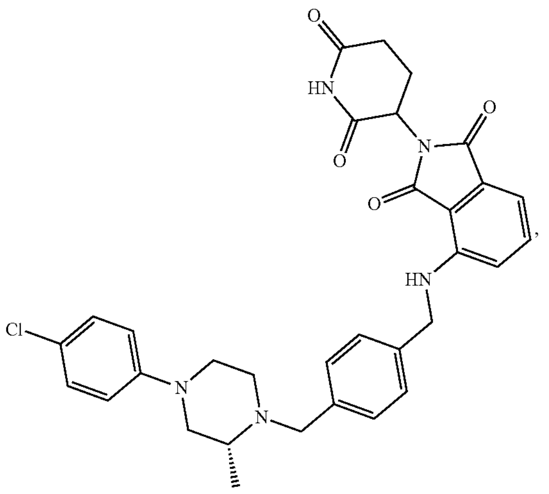,
Compound 34
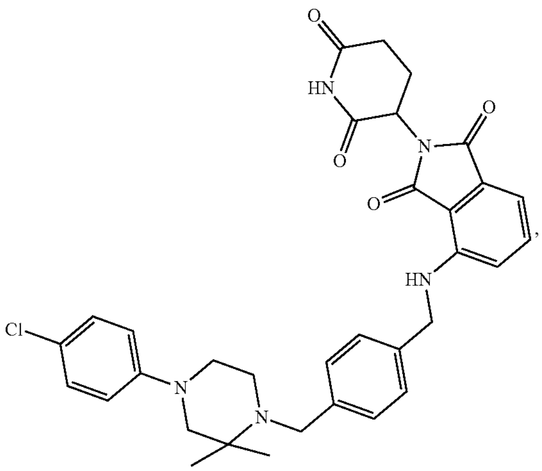,
Compound 49
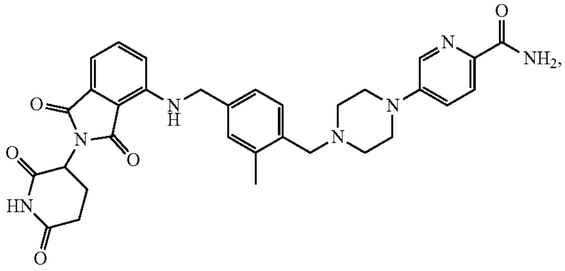,
Compound 50
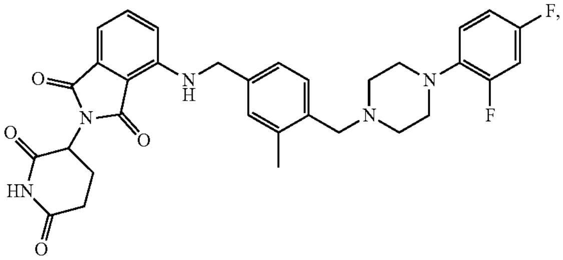,
Compound 53
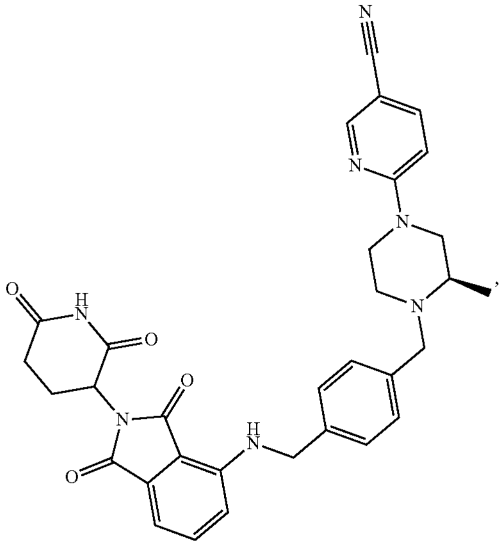,
Compound 54
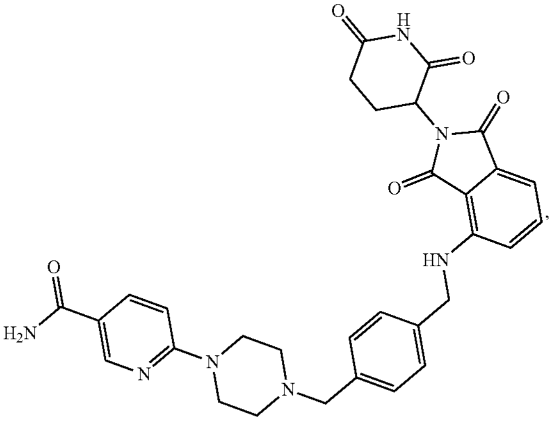, -continued
Compound 55
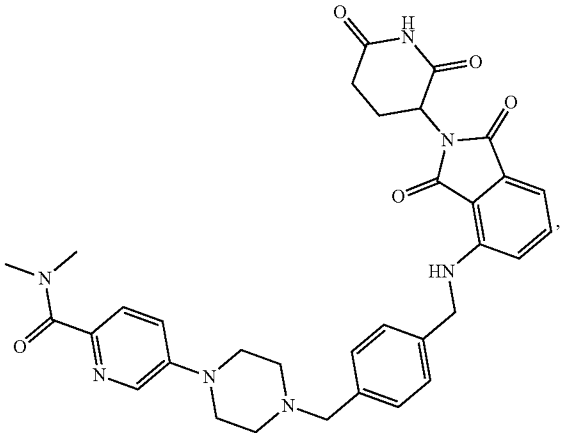
Compound 57
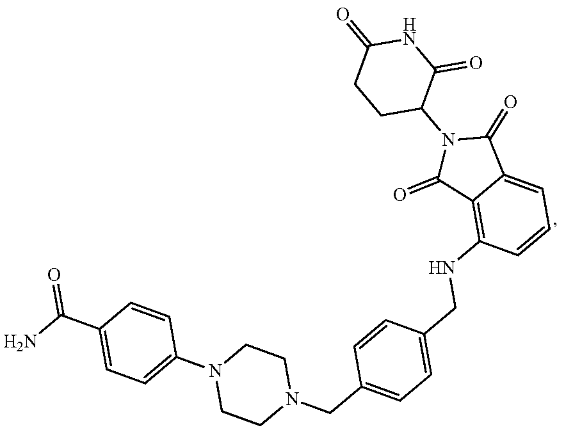
Compound 58
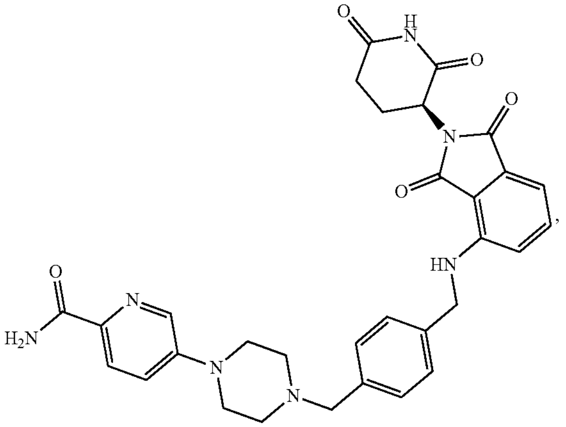
Compound 60
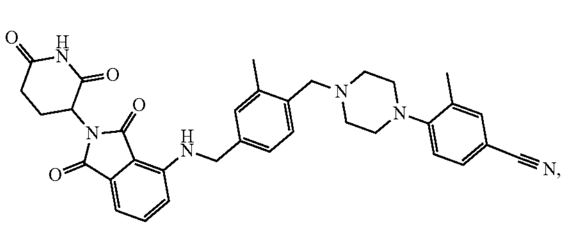
Compound 61
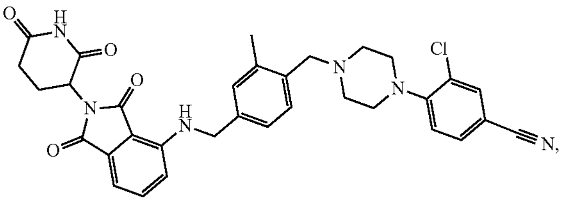
Compound 62
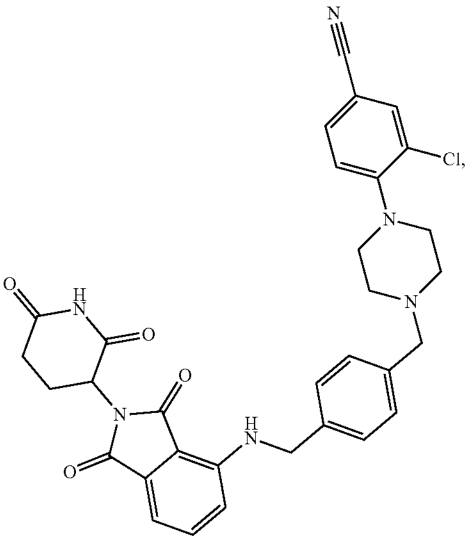

-continued
Compound 63
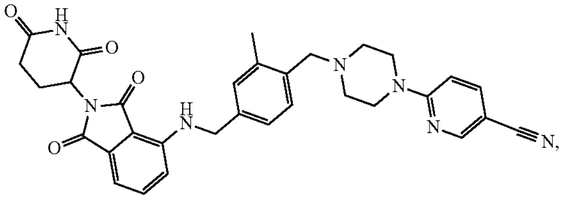
Compound 65
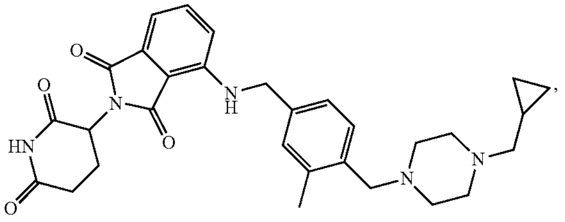
Compound 66
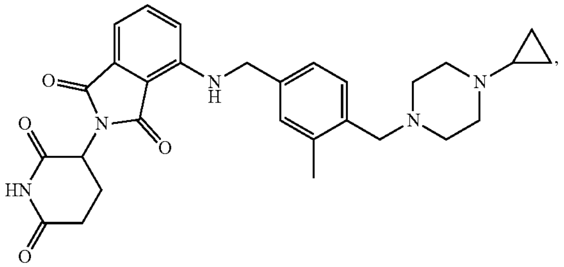
Compound 67
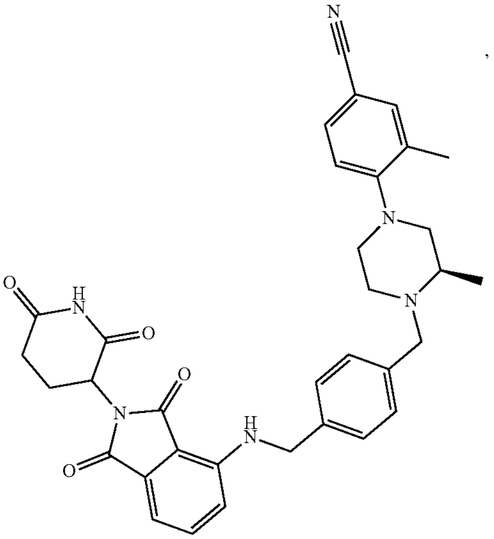
Compound 68
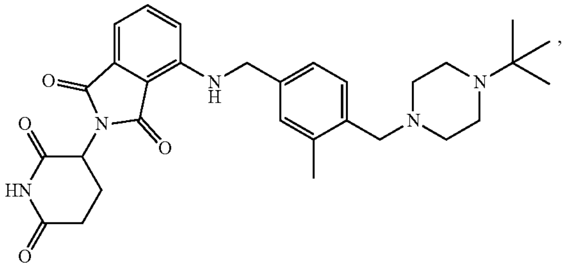
Compound 69
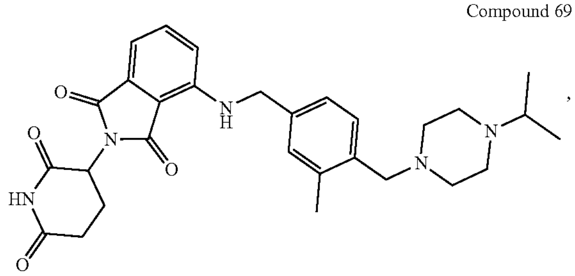
Compound 70
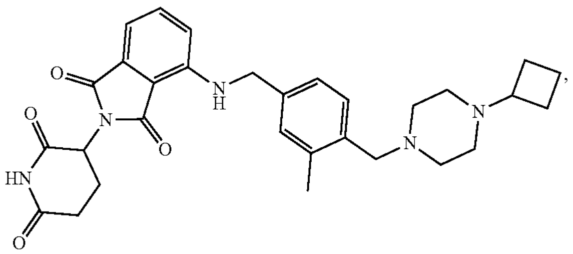
Compound 71
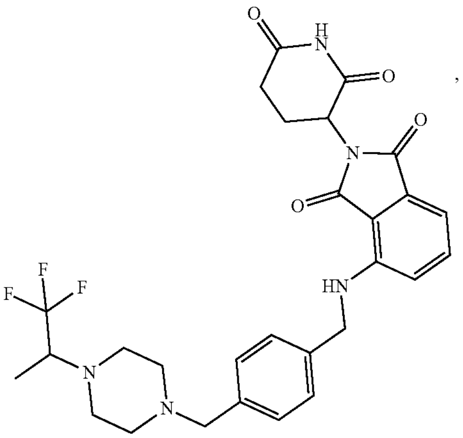

-continued
Compound 84
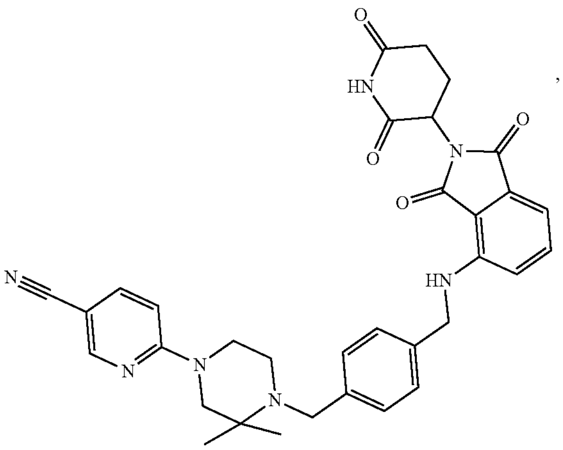
,
Compound 85
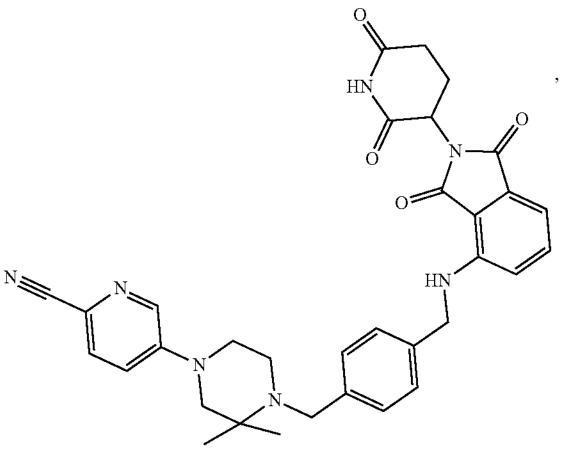
,
Compound 86
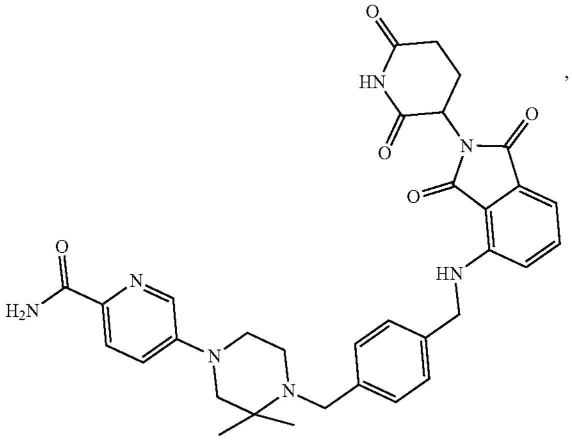
,
Compound 91
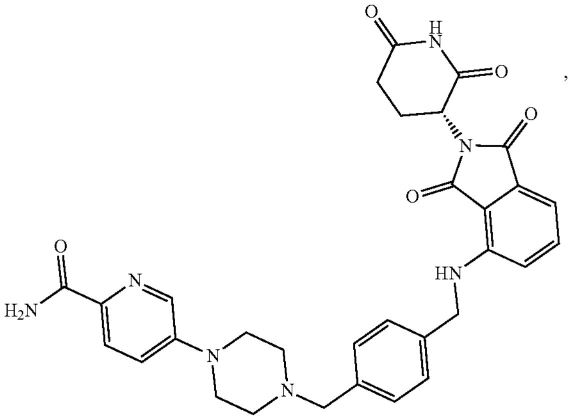
,
Compound 93
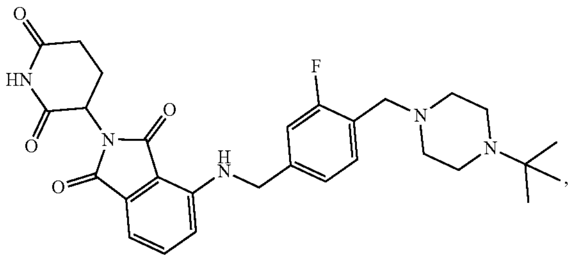
,
Compound 95
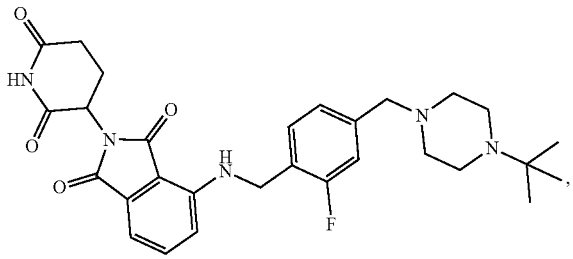
,
Compound 97
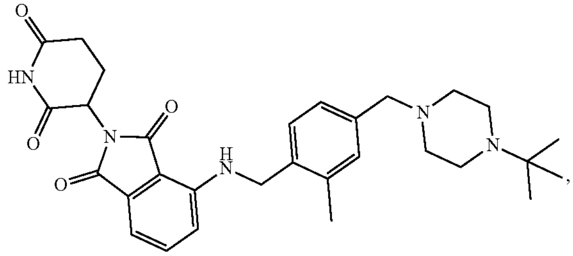
, -continued
Compound 98
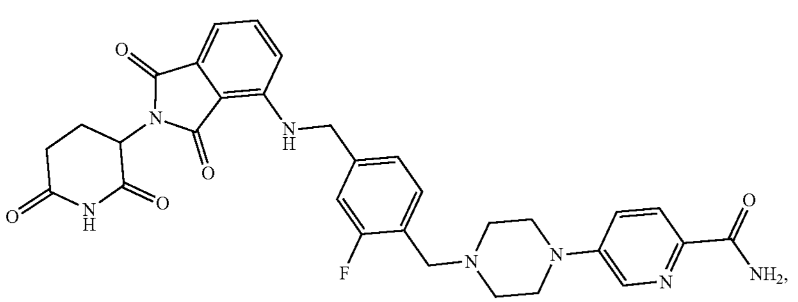
Compound 101
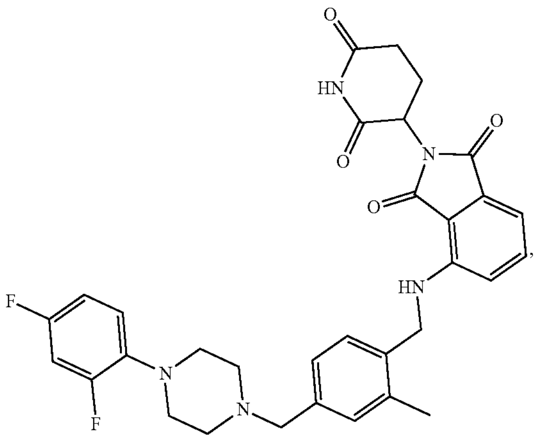
Compound 108
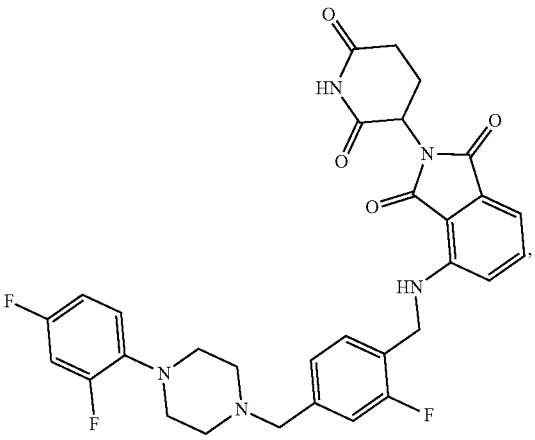
Compound 109
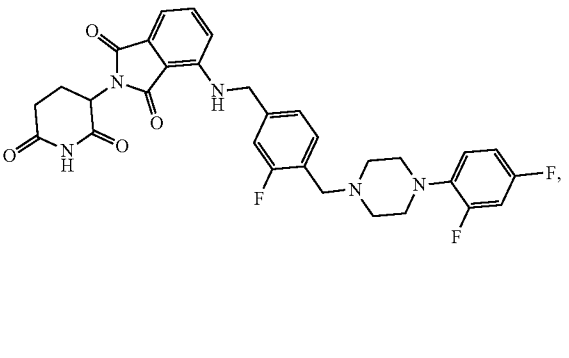
Compound 110
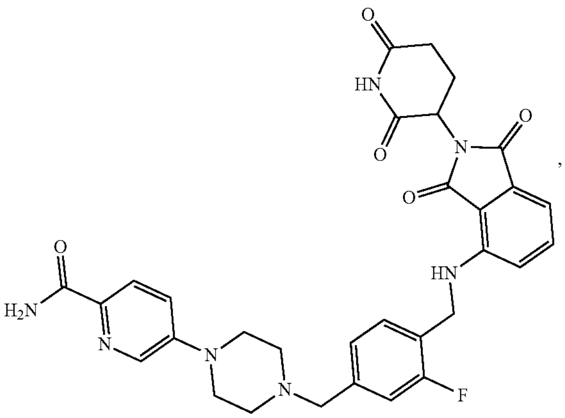

-continued
Compound 118
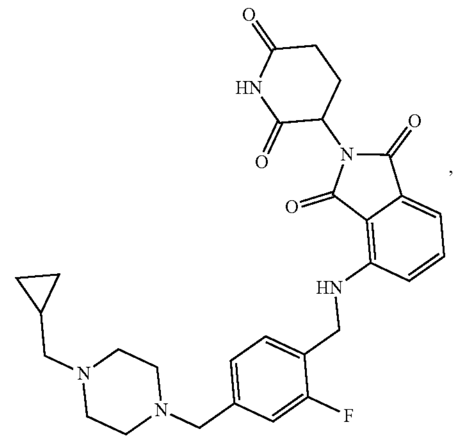
,
Compound 119
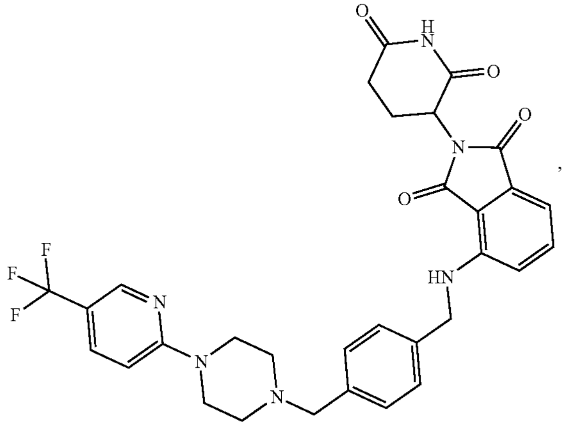
,
Compound 133
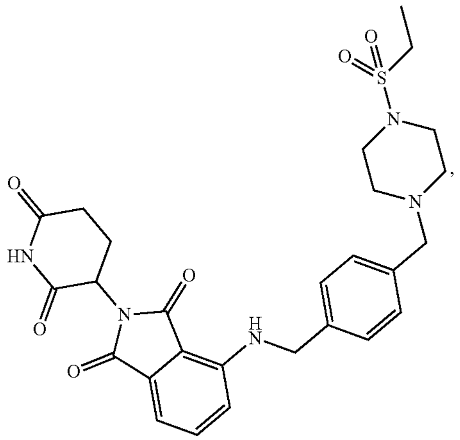
,
Compound 136
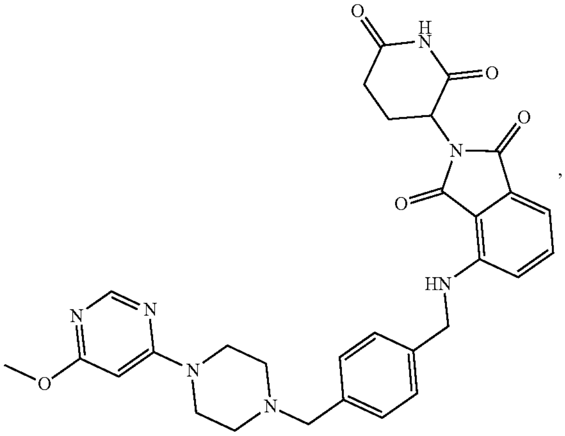
,
Compound 138
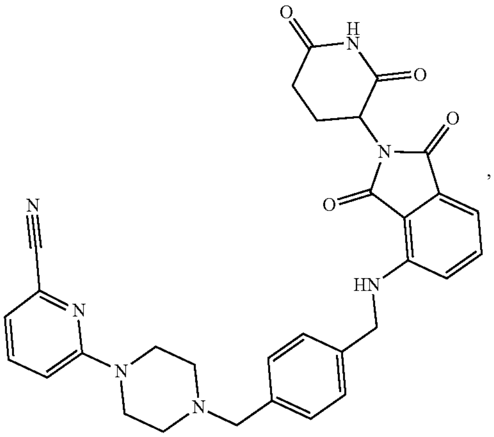
,
Compound 139
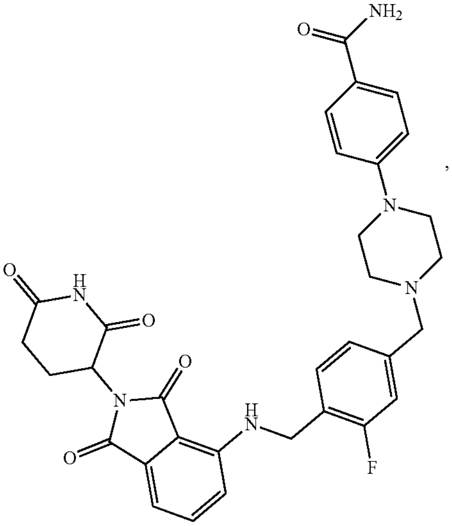
, -continued
Compound 140
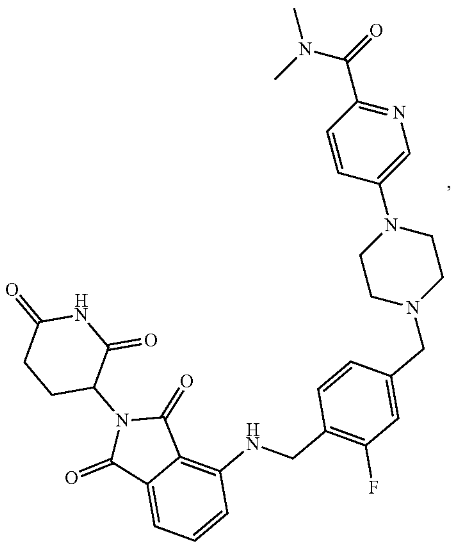
,
Compound 141
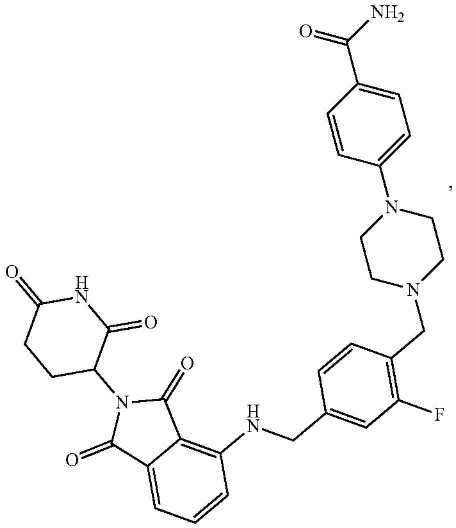
,
Compound 142
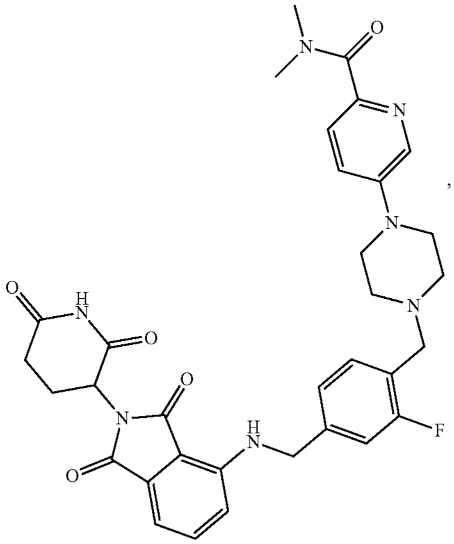
,
Compound 149
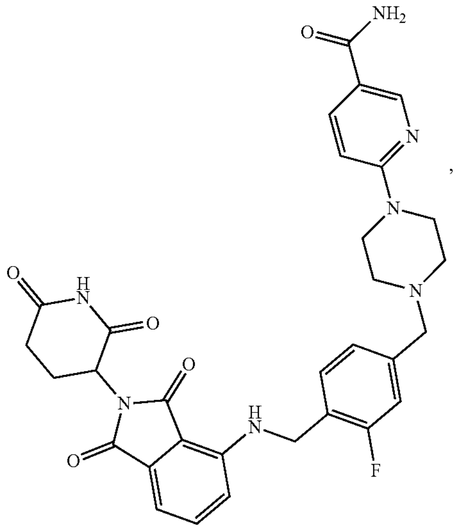
, -continued
Compound 149
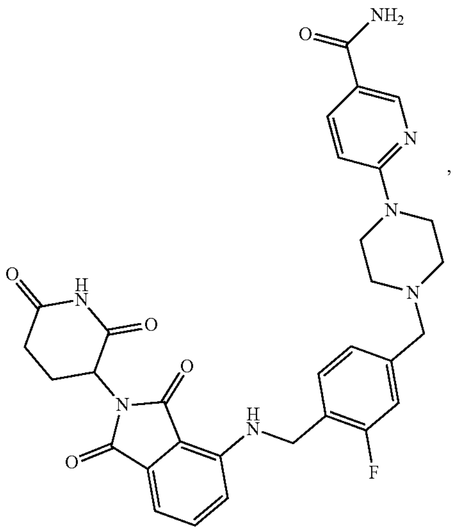
,
Compound 152
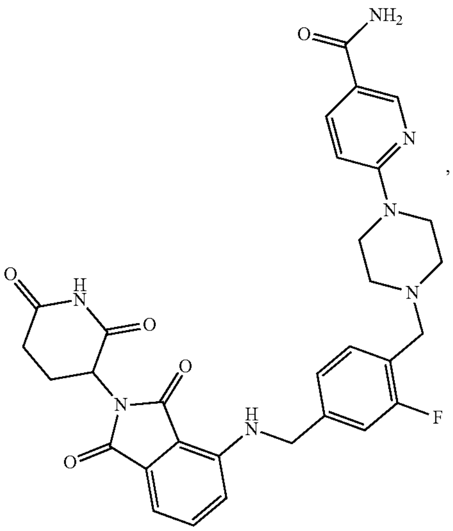
,
Compound 160
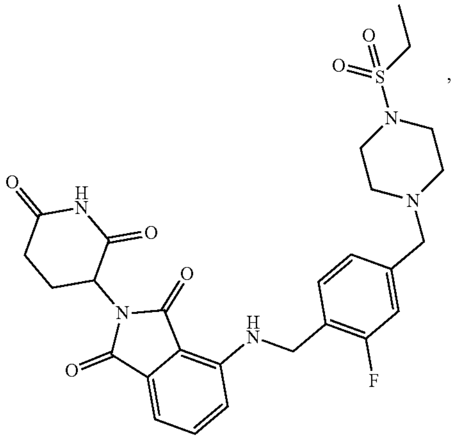
,
Compound 161
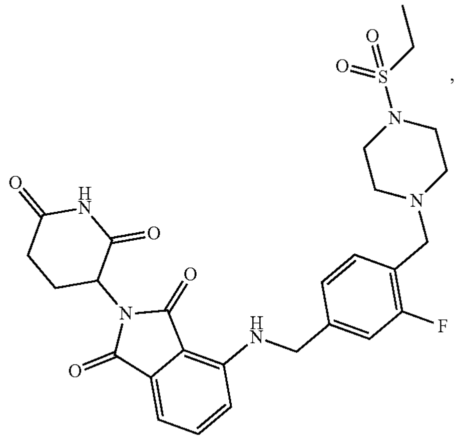
,
Compound 175
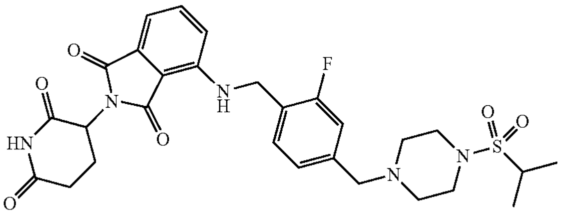
, -continued
Compound 176
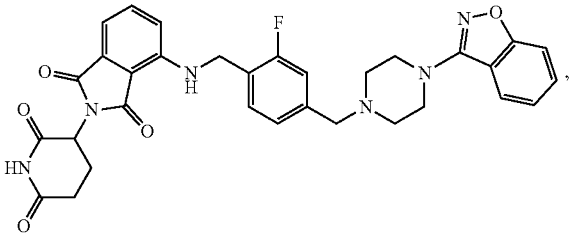
Compound 177
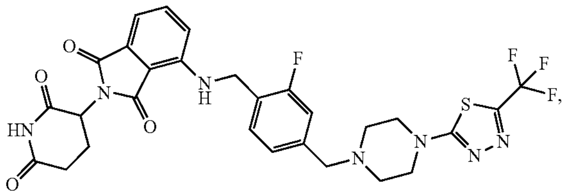
Compound 179
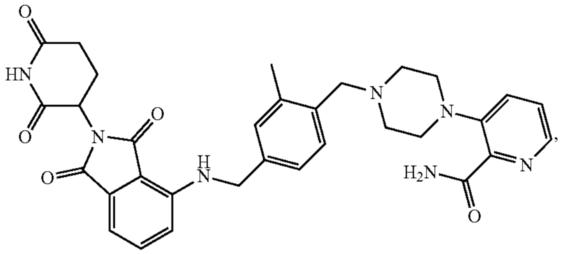
Compound 180
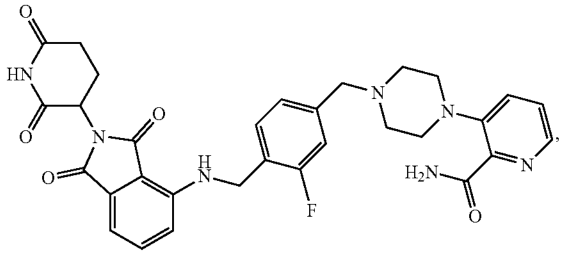
Compound 181
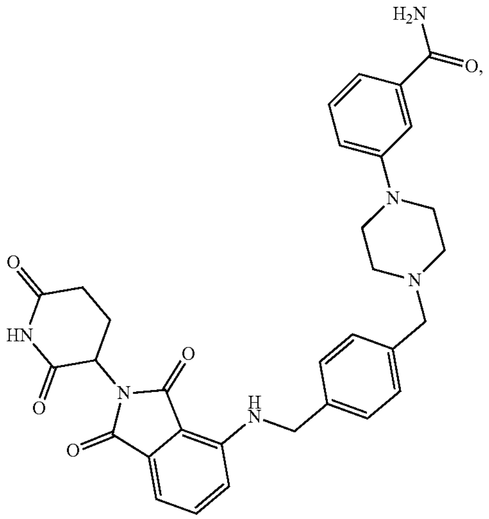
Compound 182
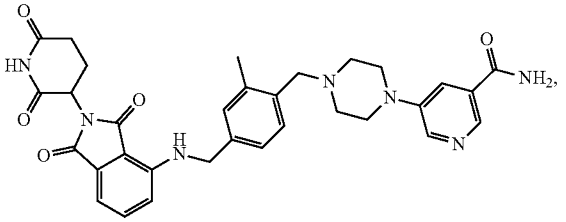
Compound 183
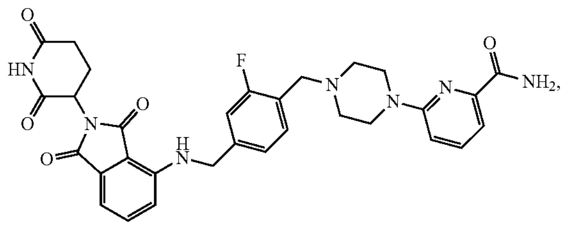
Compound 184
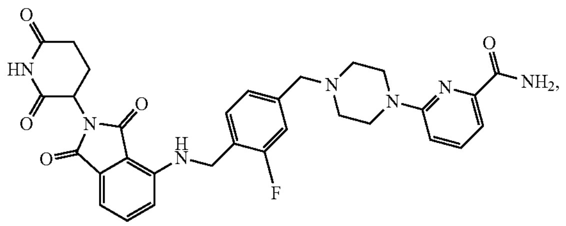

-continued
Compound 185
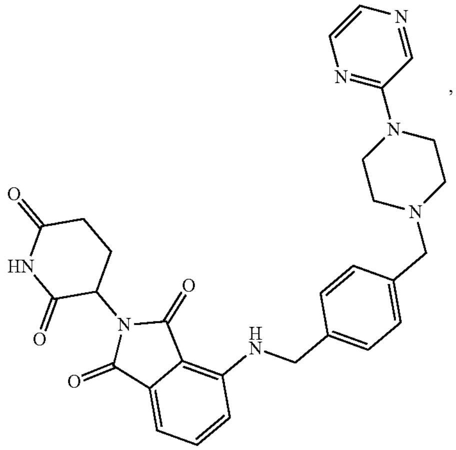
,
Compound 186
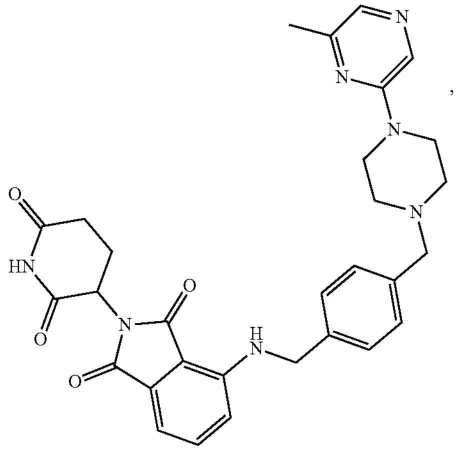
,
Compound 187
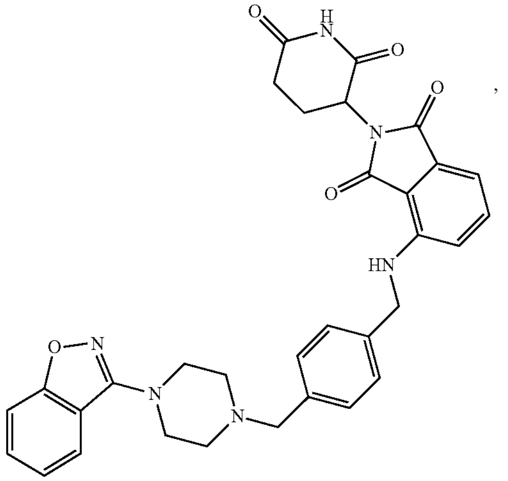
,
Compound 188
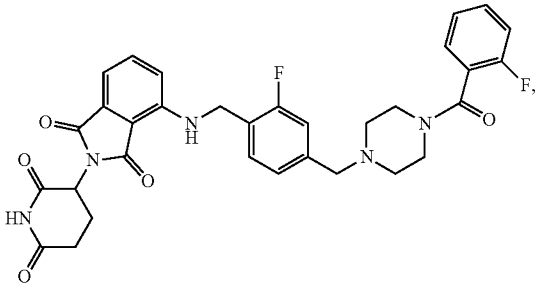
,
Compound 189
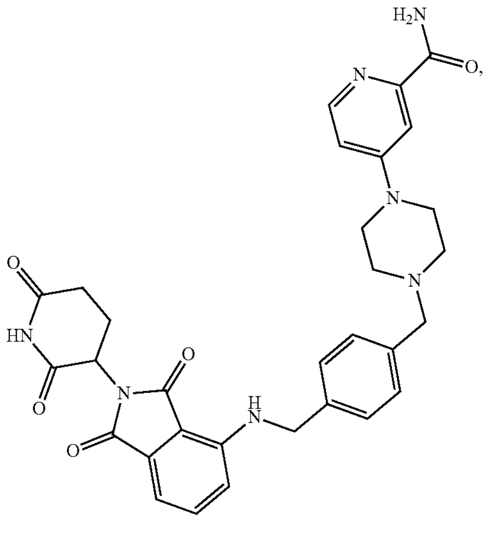
,
Compound 190
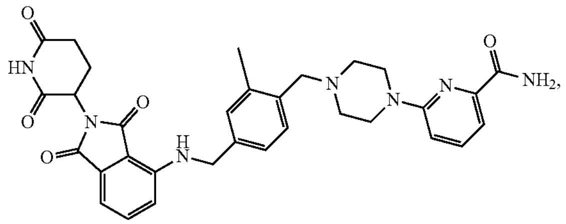
, -continued
Compound 191
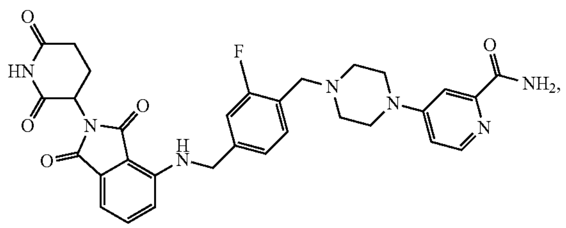
Compound 192
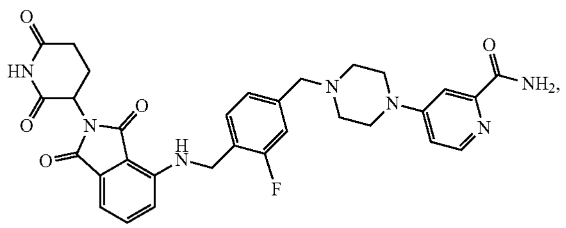
Compound 193
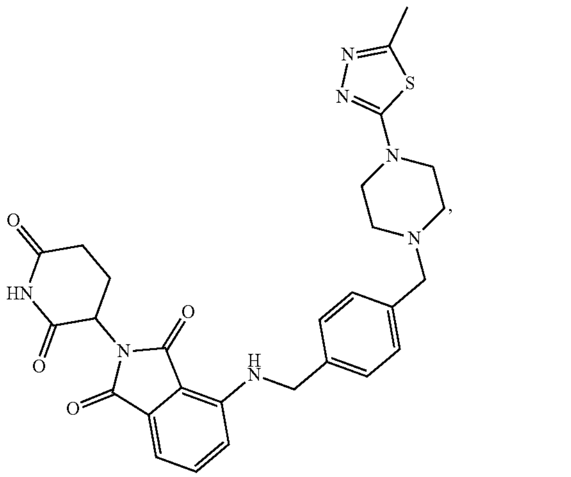
Compound 194
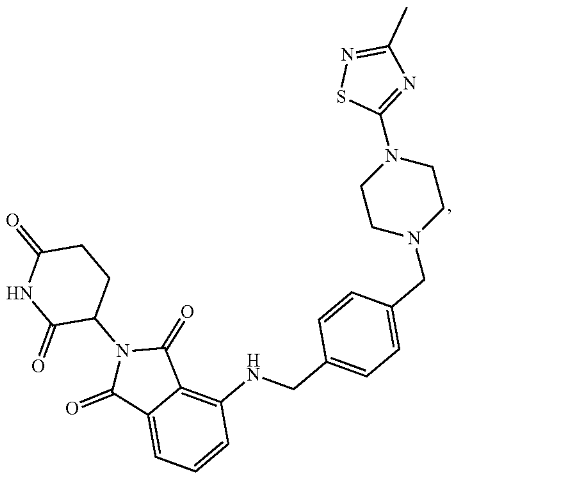
Compound 195
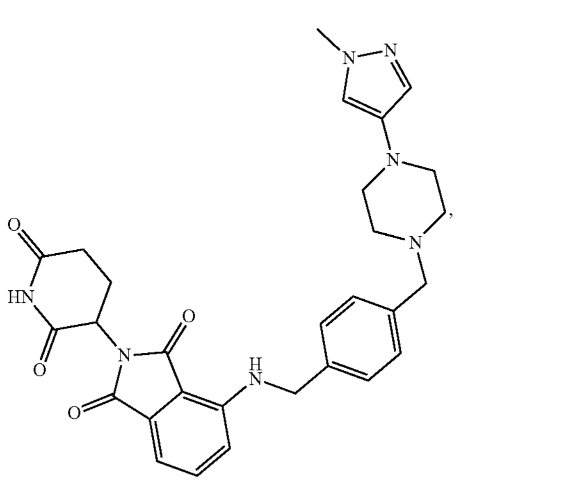
Compound 196
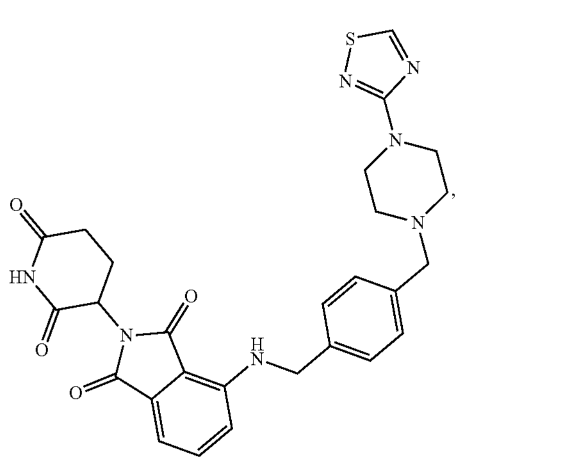

-continued
Compound 197
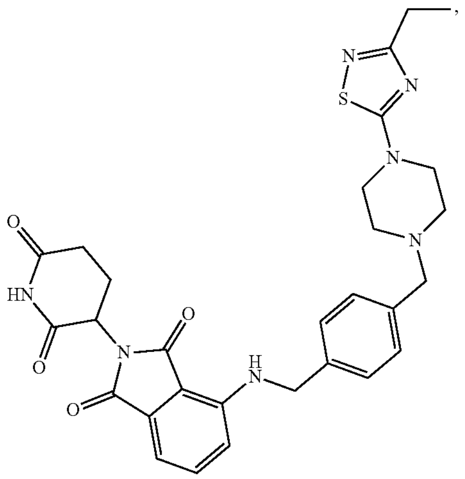
Compound 198
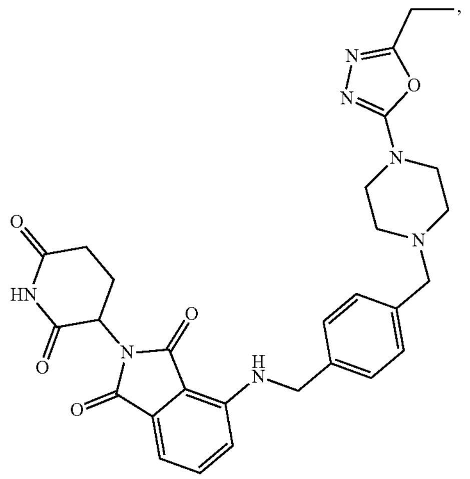
Compound 199
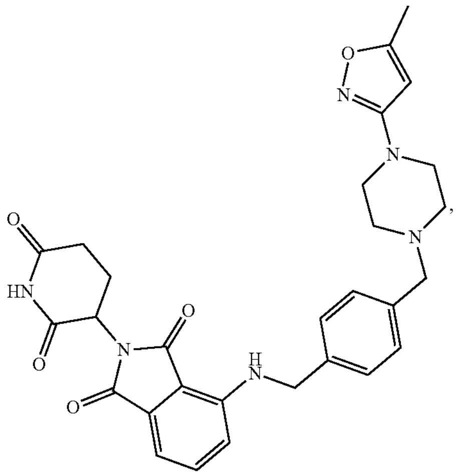
Compound 203
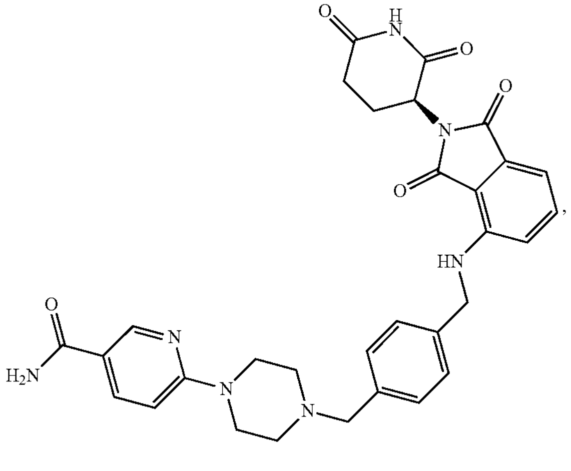
Compound 204
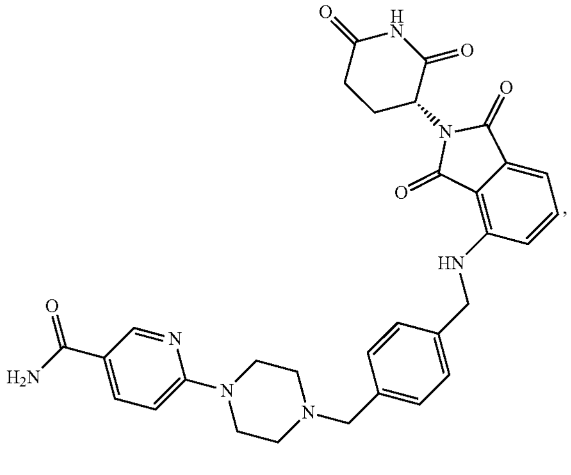
Compound 205
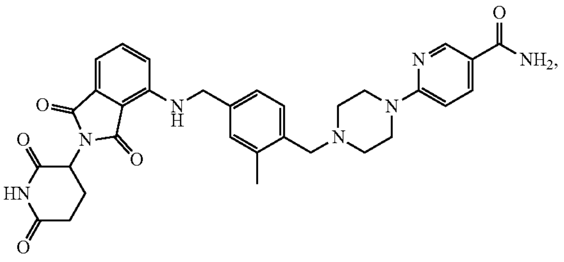

-continued
Compound 206
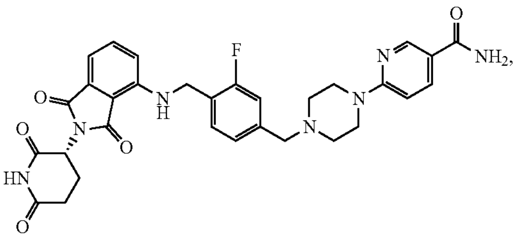
or
Compound 207
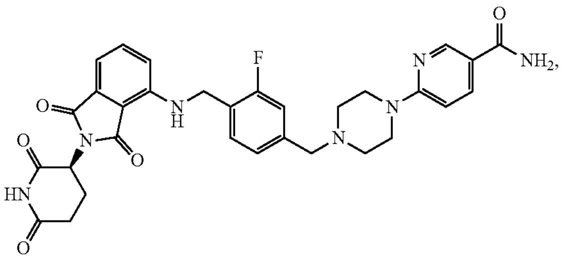
or a pharmaceutically acceptable salt thereof.
21. A pharmaceutical composition comprising a compound of claim 1, or a pharmaceutically acceptable salt, tautomer, or stereoisomer thereof, and a pharmaceutically acceptable carrier, excipient or vehicle.
* * * * *

UNITED STATES PATENT AND TRADEMARK OFFICE

CERTIFICATE OF CORRECTION

PATENT NO. : 11,358,952 B2
APPLICATION NO. : 16/390815
DATED : June 14, 2022
INVENTOR(S) : Alexander et al.

It is certified that error appears in the above-identified patent and that said Letters Patent is hereby corrected as shown below:

In the Claims

In Column 226 (part of Claim 20), replace the chemical structure of Compound 62 with:

-- 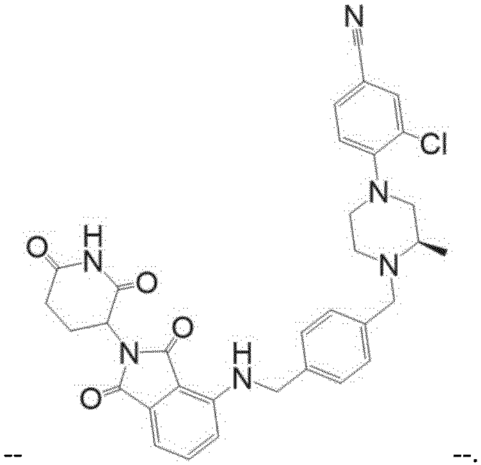 --.

In Column 237 (part of Claim 20), remove "Compound 149" and its chemical structure.

In Column 242 (part of Claim 20), replace the chemical structure of Compound 190 with:

-- 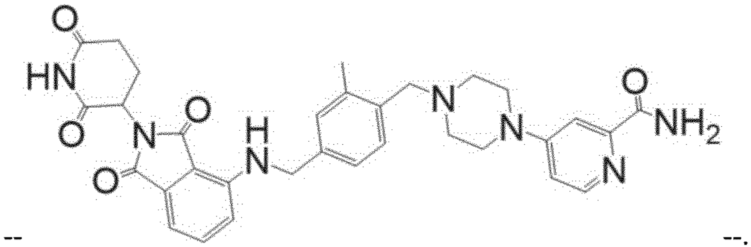 --.

Signed and Sealed this
Thirteenth Day of September, 2022

Katherine Kelly Vidal

Katherine Kelly Vidal
*Director of the United States Patent and Trademark Office*